United States Patent
Jung et al.

(10) Patent No.: US 10,730,872 B2
(45) Date of Patent: Aug. 4, 2020

(54) PESTICIDALLY ACTIVE HETEROCYCLIC DERIVATIVES WITH SULPHUR CONTAINING SUSTITUTENTS

(71) Applicant: SYNGENTA PARTICIPATIONS AG, Basel (CH)

(72) Inventors: Pierre Joseph Marcel Jung, Stein (CH); Andrew Edmunds, Stein (CH); Michel Muehlebach, Stein (CH); André Jeanguenat, Stein (CH); Daniel Emery, Stein (CH); Roger Graham Hall, Stein (CH); Vikas Sikervar, Goa (IN); Jagadish Pabba, Goa (IN)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/775,582

(22) PCT Filed: Nov. 3, 2016

(86) PCT No.: PCT/EP2016/076493
§ 371 (c)(1),
(2) Date: May 11, 2018

(87) PCT Pub. No.: WO2017/084879
PCT Pub. Date: May 26, 2017

(65) Prior Publication Data
US 2018/0354942 A1    Dec. 13, 2018

(30) Foreign Application Priority Data
Nov. 16, 2015 (IN) .......................... 3735/DEL/2015
Aug. 24, 2016 (IN) ............................. 201611028887

(51) Int. Cl.
C07D 471/04 (2006.01)
A01N 43/90 (2006.01)
A01N 47/20 (2006.01)
A01N 53/00 (2006.01)

(52) U.S. Cl.
CPC ........... *C07D 471/04* (2013.01); *A01N 43/90* (2013.01); *A01N 47/20* (2013.01); *A01N 53/00* (2013.01)

(58) Field of Classification Search
CPC ...... C07D 471/04; A01N 43/90; A01N 47/20; A01N 53/00
See application file for complete search history.

(56) References Cited

U.S. PATENT DOCUMENTS

| | | | | |
|---|---|---|---|---|
| 4,696,931 A | * | 9/1987 | Hauel | C07D 235/18 514/263.1 |
| 5,389,641 A | * | 2/1995 | Naka | C07D 401/06 514/243 |
| 5,814,651 A | * | 9/1998 | Duplantier | C07C 17/2632 514/394 |

FOREIGN PATENT DOCUMENTS

| | | |
|---|---|---|
| EP | 2 862 853 A1 | 4/2015 |
| WO | 2015/000715 A1 | 1/2015 |
| WO | 2016/023954 A2 | 2/2016 |
| WO | 2016/058928 A1 | 4/2016 |

OTHER PUBLICATIONS

Notification of Transmittal of the International Search Report and the Written Opinion of the International Searching Authority, or the Declaration, dated Jan. 4, 2017 in International Application No. PCT/EP2016/076493 (10 pages).

* cited by examiner

*Primary Examiner* — John Pak
(74) *Attorney, Agent, or Firm* — Baker & Hostetler, LLP; Toni-Junell Herbert

(57) ABSTRACT

Compounds of formula (I) wherein the substituents are as defined in claim 1, and the agrochemically acceptable salts salts, stereoisomers, enantiomers, tautomers and N-oxides of those compounds, can be used as insecticides and can be prepared in a manner known per se.

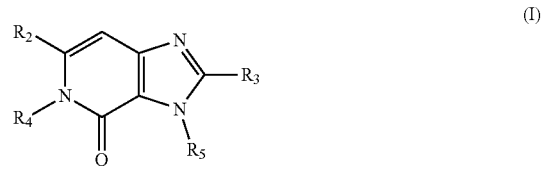

(I)

14 Claims, No Drawings

PESTICIDALLY ACTIVE HETEROCYCLIC DERIVATIVES WITH SULPHUR CONTAINING SUSTITUTENTS

CROSS-REFERENCE TO RELATED APPLICATIONS

This application is a 371 National Stage application of International Application No. PCT/EP2016/076493, filed Nov. 3, 2016, which claims priority to Indian Patent Application No. 3735/DEL/2015, filed Nov. 16, 2015 and Indian Patent Application No. 201611028887, filed Aug. 24, 2016, the entire contents of which are hereby incorporated by reference.

The present invention relates to pesticidally active, in particular insecticidally active heterocyclic derivatives containing sulphur substituents, to processes for their preparation, to compositions comprising those compounds, and to their use for controlling animal pests, including arthropods and in particular insects or representatives of the order Acarina.

Heterocyclic compounds with pesticidal action are known and described, for example, in WO 2010/125985 and WO 2013/018928. There have now been found novel pesticidally active heterocyclic triazole derivatives with sulphur containing amino derivative substituents.

The present invention accordingly relates to compounds of formula I,

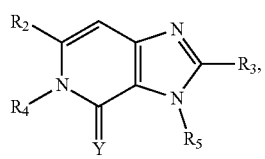

(I)

Wherein
Y is O or S;
$R_2$ is hydrogen, halogen, $C_1$-$C_6$haloalkyl or $C_1$-$C_6$alkyl; or $R_2$ is $C_1$-$C_6$haloalkylsulfanyl, $C_1$-$C_6$haloalkylsulfinyl, $C_1$-$C_6$haloalkylsulfonyl, $C_1$-$C_6$alkylsulfanyl, $C_1$-$C_6$alkylsulfinyl, $C_1$-$C_6$alkylsulfonyl, $C_1$-$C_6$alkoxy, $C_1$-$C_6$haloalkoxy, $C_1$-$C_4$haloalkoxy$C_1$-$C_4$alkyl, $C_1$-$C_4$alkoxy$C_1$-$C_4$alkyl, $SF_5$, cyano, $C_3$-$C_6$cycloalkyl$C_1$-$C_4$alkyl or —C(O)$C_1$-$C_6$haloalkyl; or
$R_2$ is $C_3$-$C_6$ cycloalkyl, which can be mono- or polysubstituted by substituents selected from $R_6$;
$R_4$ is hydrogen, $C_1$-$C_6$alkyl, $C_1$-$C_6$haloalkyl, or is $C_3$-$C_6$cycloalkyl which can be mono- or polysubstituted by $R_{20}$; or is $C_3$-$C_6$cycloalkyl-$C_1$-$C_4$alkyl which can be mono- or polysubstituted by $R_{20}$; or
$R_4$ is $C_1$-$C_4$alkyl substituted by $R_7$; or
$R_4$ is $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_4$alkoxy $C_1$-$C_4$alkyl, $C_1$-$C_6$alkylsulfanyl, $C_1$-$C_4$alkylsulfonyl, $C_1$-$C_6$alkylsulfinyl, $C_1$-$C_6$haloalkylsulfanyl, $C_1$-$C_6$haloalkylsulfonyl, $C_1$-$C_6$haloalkylsulfinyl, amine or hydroxyl;
$R_4$ is $C_2$-$C_6$alkenyl substituted by $R_7$, or is $C_2$-$C_6$alkynyl substituted by $R_7$;
$R_5$ is hydrogen, $C_1$-$C_6$alkyl, $C_1$-$C_6$haloalkyl or $C_1$-$C_4$alkyl substituted by $C_1$-$C_4$alkylsulfanyl;
$R_6$ and $R_{20}$, independently from each other, are selected from the group consisting of cyano, halogen, $C_1$-$C_6$alkyl and $C_1$-$C_4$haloalkyl;
$R_7$ is cyano, halogen, $C_1$-$C_4$alkylsulfanyl, $C_1$-$C_4$alkylsulfonyl, $C_1$-$C_4$alkylsulfinyl, $C_1$-$C_4$alkoxy, $C_1$-$C_4$alkoxy$C_1$-$C_4$ alkoxy or phenyl which itself can be mono- or polysubstituted by substituents selected from $R_8$;
$R_8$ is halogen, cyano, $C_1$-$C_4$alkyl, $C_1$-$C_4$haloalkyl or $C_1$-$C_4$alkoxy;
$R_3$ is a radical selected from the group consisting of formula $Q_1$, $Q_2$, $Q_3$, $Q_4$, $Q_5$, $Q_6$, $Q_7$, $Q_8$, $Q_9$, $Q_{10}$, $Q_{11}$, $Q_{12}$, $Q_{13}$ and $Q_{14}$;

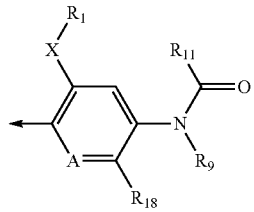

$Q_1$

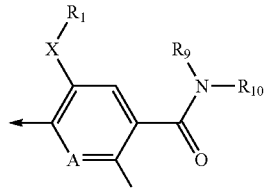

$Q_2$

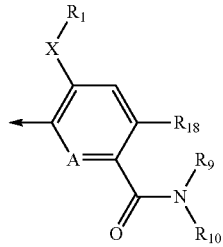

$Q_3$

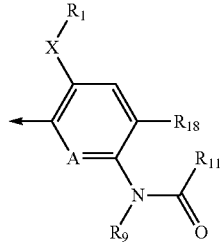

$Q_4$

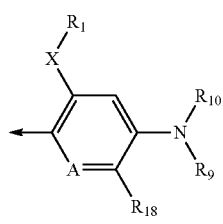

$Q_5$

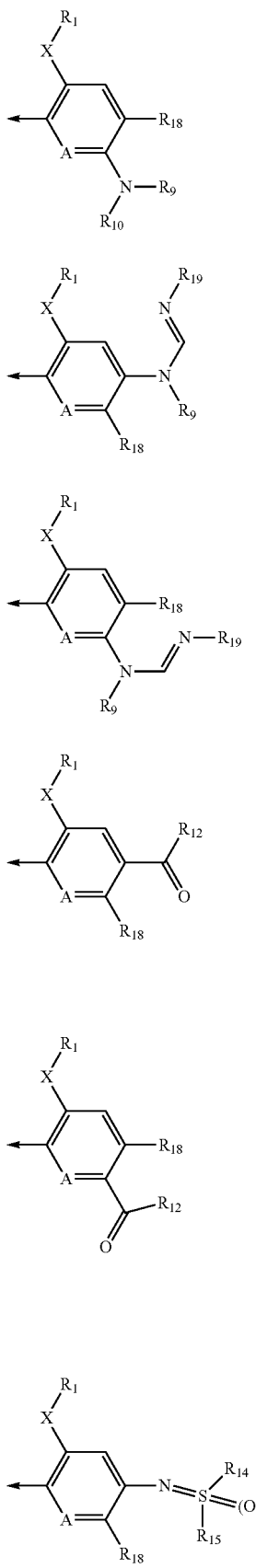

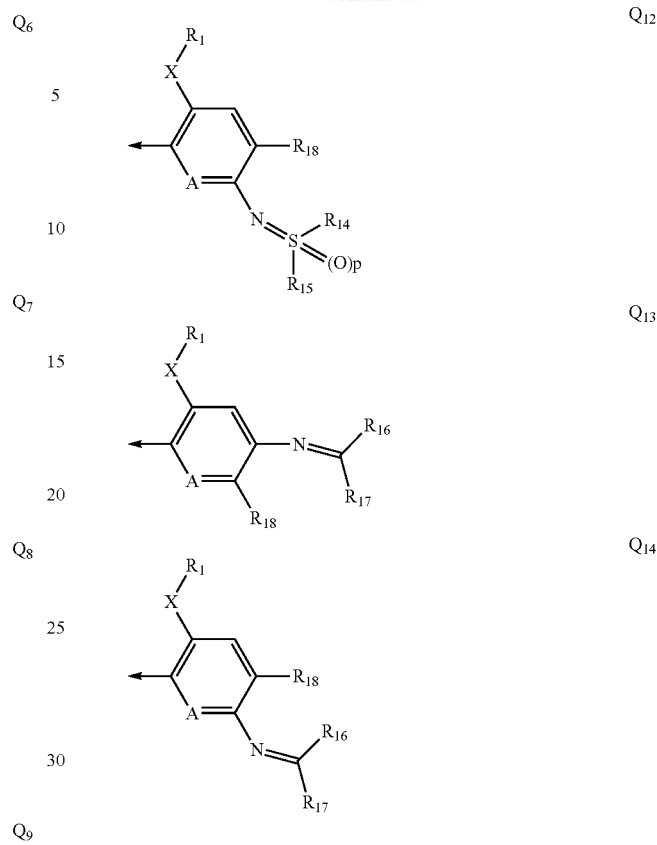

wherein the arrow denotes the point of attachment to the imidazole ring;

A represents CH or N;

X is S, SO or $SO_2$;

$R_1$ is $C_1$-$C_4$alkyl or $C_1$-$C_4$haloalkyl; or $R_1$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_1$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;

$R_9$ is hydrogen, $C_1$-$C_6$alkyl, $C_1$-$C_6$haloalkyl, $C_1$-$C_4$alkoxy$C_1$-$C_4$alkyl, hydroxyl, $C_1$-$C_6$alkoxy or $S(O)m_1R_{21}$; or $R_9$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_9$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl; or $R_9$ is $C_3$-$C_6$ cycloalkylcarbonyl;

$R_{10}$ is hydrogen, $C_1$-$C_6$alkyl, cyano, $C_1$-$C_6$alkoxy, $C_1$-$C_6$haloalkoxy, $C_2$-$C_6$alkynyl, $C_2$-$C_6$alkenyl, amino, NH—CN, N—($C_1$-$C_4$alkyl)amino, N—($C_1$-$C_4$ alkyl)N—($C_1$-$C_4$ alkyl)amino, N—($C_3$-$C_6$cycloalkyl)amino, N—($C_1$-$C_4$alkyl)N—($C_3$-$C_6$cycloalkyl)amino, N—($C_1$-$C_4$alkylcarbonyl)amino, N—($C_1$-$C_4$alkyl)N—($C_1$-$C_4$alkylcarbonyl)amino, N—($C_1$-$C_4$alkyl)N—($C_3$-$C_6$cycloalkylcarbonyl)amino, N—($C_3$-$C_6$cycloalkylcarbonyl)amino, N—($C_1$-$C_4$alkylcarbonyl)N—($C_3$-$C_6$cycloalkyl)amino or —$S(O)mR_{13}$; or $R_{10}$ is $C_1$-$C_4$alkyl mono- or polysubstituted by substituents independently selected from the group Z; or $R_{10}$ is a five- to six-membered aromatic or heteroaromatic ring system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five- to six-membered ring system can be mono- or polysubstituted by substituents independently selected from the group V;

$R_{11}$ is hydrogen, $C_1$-$C_6$alkyl, $C_1$-$C_6$alkoxy, $C_1$-$C_6$haloalkoxy, amino, N—$C_1$-$C_4$alkylamino, N—($C_1$-$C_4$ alkyl)N—($C_3$-$C_6$ cycloalkyl)amino, N—($C_3$-$C_6$cycloalkyl)amino or N—($C_1$-$C_4$alkyl)N—($C_1$-$C_4$alkyl)amino; or $R_{11}$ is $C_1$-$C_4$alkyl mono- or polysubstituted by substituents independently selected from the group Z; or $R_{11}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{11}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl; or $R_{11}$ is a five- to six-membered aromatic or heteroaromatic ring system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five- to six-membered aromatic or heteroaromatic ring system can be mono- or polysubstituted by substituents independently selected from the group V;

$R_{12}$ is hydrogen, $C_1$-$C_6$ alkyl, $C_1$-$C_6$alkoxy, hydroxy or $C_1$-$C_6$haloalkoxy; or $R_{12}$ is $C_1$-$C_4$alkyl mono- or polysubstituted by substituents independently selected from the group Z; or $R_{12}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{12}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;

$R_{13}$ is $C_1$-$C_4$alkyl, $C_1$-$C_4$haloalkyl, N—$C_1$-$C_4$alkylamino, N,N—($C_1$-$C_4$ alkyl)$_2$amino or phenyl; said phenyl can be mono- or polysubstituted by substituents selected from the group consisting of halogen, $C_1$-$C_4$alkyl, cyano, $C_1$-$C_4$haloalkyl and $C_1$-$C_4$alkoxy; or $R_{13}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{13}$ is $C_3$-$C_6$cycloalkyl$C_1$-$C_4$alkyl which can be mono- or polysubstituted by substituents selected from the group consisting of halogen, $C_1$-$C_4$haloalkyl, cyano and $C_1$-$C_4$alkyl;

$R_{21}$ is $C_1$-$C_4$alkyl, $C_1$-$C_4$haloalkyl, N—$C_1$-$C_4$alkylamino, N,N—($C_1$-$C_4$ alkyl)$_2$amino or phenyl; said phenyl can be mono- or polysubstituted by substituents selected from the group consisting of halogen, $C_1$-$C_4$alkyl, cyano, $C_1$-$C_4$haloalkyl and $C_1$-$C_4$alkoxy; or $R_{21}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{21}$ is $C_3$-$C_6$cycloalkyl$C_1$-$C_4$alkyl which can be mono- or polysubstituted by substituents selected from the group consisting of halogen, $C_1$-$C_4$haloalkyl, cyano and $C_1$-$C_4$alkyl;

m is 0, 1 or 2;

$m_1$ is 0, 1 or 2;

$R_{14}$ is hydrogen or $C_1$-$C_6$ alkyl;

$R_{15}$ is hydrogen, $C_1$-$C_6$ alkyl, $C_1$-$C_6$alkoxy, $C_1$-$C_6$haloalkoxy, amino, N—$C_1$-$C_4$alkylamino or N,N—($C_1$-$C_4$ alkyl)$_2$amino; or $R_{15}$ is $C_1$-$C_4$alkyl mono- or polysubstituted by substituents independently selected from the group Z; or $R_{15}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{15}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;

p is 0 or 1;

$R_{16}$ is hydrogen or $C_1$-$C_6$ alkyl;

$R_{17}$ is hydrogen, $C_1$-$C_6$alkyl, $C_1$-$C_6$haloalkyl, $C_1$-$C_6$alkoxy or $C_1$-$C_6$ haloalkoxy; or $R_{17}$ is amino which can be mono- or disubstituted by substituents selected from the group consisting of cyano, $C_1$-$C_6$alkyl, $C_1$-$C_6$alkoxy, $C_1$-$C_6$haloalkoxy, $C_3$-$C_6$cycloalkyl and $C_3$-$C_6$cycloalkyl-$C_1$-$C_4$alkyl, said $C_3$-$C_6$cycloalkyl and $C_3$-$C_6$cycloalkyl-$C_1$-$C_4$alkyl groups itself can be mono- or polysubstituted by substituents selected from the group consisting of halogen, $C_1$-$C_4$haloalkyl, cyano and $C_1$-$C_4$alkyl; or $R_{17}$ is $C_1$-$C_4$alkyl mono- or polysubstituted by substituents independently selected from Z; or $R_{17}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{17}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl; or $R_{17}$ is a five- to six-membered ring aromatic or heteroaromatic ring system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five- to six-membered aromatic or heteroaromatic ring system can be mono- to polysubstituted by substituents independently selected from V;

$R_{18}$ is hydrogen, halogen, amino, cyano, $C_1$-$C_4$alkyl, $C_3$-$C_6$cycloalkyl, $C_1$-$C_4$haloalkyl or $C_3$-$C_6$cycloalkyl substituted by cyano, $C_1$-$C_3$ haloalkyl, $C_1$-$C_3$ alkyl and halogen;

$R_{19}$ is hydrogen, $C_1$-$C_6$alkyl, $C_1$-$C_6$alkoxy, $C_1$-$C_6$haloalkoxy, $C_3$-$C_6$cycloalkyl$C_1$-$C_4$alkyl, $C_3$-$C_6$cycloalkyl;

Z is cyano, halogen, hydroxy, —SH, amino, nitro, $C_1$-$C_4$alkoxy, $C_1$-$C_4$haloalkoxy, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl or phenyl; said phenyl can be mono- or polysubstituted by substituents selected from the group consisting of halogen, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; or Z is pyridyl; said pyridyl can be mono- or polysubstituted by substituents selected from the group consisting of halogen, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; or Z is pyrimidyl; said pyrimidyl can be mono- or polysubstituted by substituents selected from the group consisting of halogen, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; and V is cyano, halogen, $C_1$-$C_4$alkyl, $C_3$-$C_6$ cycloalkyl, $C_1$-$C_4$alkoxy, $C_1$-$C_4$alkoxy$C_1$-$C_4$ alkyl, $C_1$-$C_4$haloalkyl, $C_1$-$C_4$haloalkoxy, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl or $C_1$-$C_4$haloalkylsulfonyl; and agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

The cycloalkyl groups preferably have from 3 to 6 ring carbon atoms, for example cyclopropyl, cyclobutyl, cyclopentyl and cyclohexyl.

Haloalkoxy groups preferably have a chain length of from 1 to 4 carbon atoms. Haloalkoxy is, for example, difluoromethoxy, trifluoromethoxy or 2,2,2-trifluoroethoxy.

Haloalkylsulfanyl groups preferably have a chain length of from 1 to 4 carbon atoms. Haloalkylsulfanyl is, for example, difluoromethylsulfanyl, trifluoromethylsulfanyl or 2,2,2-trifluoroethylsulfanyl. Similar considerations apply to the radicals $C_1$-$C_4$haloalkylsulfinyl and $C_1$-$C_4$haloalkylsulfonyl, which may be, for example, trifluoromethylsulfinyl, trifluoromethylsulfonyl or 2,2,2-trifluoroethylsulfonyl.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

The compounds of formula I according to the invention also include hydrates which may be formed during the salt formation.

According to the present invention, a five- to six-membered aromatic or heteroaromatic ring system, which can contain 1 to 4 hetero atoms selected from the group consisting of nitrogen, oxygen and sulfur, it not being possible for each ring system to contain more than 2 oxygen atoms and more than 2 sulfur atoms, are preferably selected from the group consisting of the following aromatic or heteroaromatic groups: phenyl, pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl, pyranyl; (1H-pyrrol-1-yl)-; (1H-pyrrol-2-yl)-; (1H-pyrrol-3-yl)-; (1H-pyrazol-1-yl)-; (1H-pyrazol-3-yl)-; (3H-pyrazol-3-yl)-; (1H-pyrazol-4-yl)-; (3-isoxazolyl)-; (5-isoxazolyl)-; (2-furanyl)-; (3-furanyl)-; (2-thienyl)-; (3-thienyl)-; (1H-imidazol-2-yl)-; (1H-imidazol-4-yl)-; (1H-imidazol-5-yl)-; (2-oxazol-2-yl)-; (oxazol-4-yl)-; (oxazol-5-yl)-; (thiazol-2-yl)-; (thiazol-4-yl)-; (thiazol-5-yl)-; (isothiazol-3-yl)-; (isothiazol-5-yl)-; (1H-1,2,3-triazol-1-yl)-; (1H-1,2,4-triazol-3-yl)-; (4H-1,2,4-triazol-4-yl)-; (1H-1,2,4-triazol-1-yl)-; (1,2,3-oxadiazol-2-yl)-; (1,2,4-oxadiazol-3-yl)-; (1,2,4-oxadiazol-4-yl)-; (1,2,4-oxadiazol-5-yl)-; (1,2,3-thiadiazol-2-yl)-; (1,2,4-thiadiazol-3-yl)-; (1,2,4-thiadiazol-4-yl)-; (1,3,4-thiadiazol-5-yl)-; (1H-tetrazol-1-yl)-; (1H-tetrazol-5-yl)-; (2H-tetrazol-5-yl)-; (2-pyridyl)-; (3-pyridyl)-; (4-pyridyl)-; (2-pyrimidinyl)-; (4-pyrimidinyl)-; (5-pyrimidinyl)-; (2-pyrazinyl)-; (3-pyridazinyl)-; (4-pyridazinyl)-; (1,3,5-triazin-2-yl)-; (1,2,4-triazin-5-yl)-; (1,2,4-triazin-6-yl)-; (1,2,4-triazin-3-yl)- and (furazan-3-yl)-.

Preferably R$_7$ is cyano, C$_1$-C$_4$alkylsulfanyl, C$_1$-C$_4$alkylsulfonyl, C$_1$-C$_4$alkylsulfinyl, C$_1$-C$_4$alkoxy, C$_1$-C$_4$alkoxyC$_1$-C$_4$ alkoxy or phenyl which itself can be mono- or polysubstituted by substituents selected from R$_8$;

R$_9$ is hydrogen, C$_1$-C$_6$alkyl, C$_1$-C$_6$haloalkyl, C$_1$-C$_4$alkoxyC$_1$-C$_4$alkyl, hydroxyl or C$_1$-C$_6$alkoxy; or R$_9$ is C$_3$-C$_6$cycloalkyl which can be mono- or polysubstituted by substituents selected from the group consisting of halogen, C$_1$-C$_4$haloalkyl, cyano and C$_1$-C$_4$alkyl; or R$_9$ is C$_3$-C$_6$cycloalkyl-C$_1$-C$_4$alkyl which can be mono- or polysubstituted by substituents selected from the group consisting of halogen, C$_1$-C$_4$haloalkyl, cyano and C$_1$-C$_4$alkyl; and R$_{18}$ is hydrogen, halogen, amino, cyano, C$_1$-C$_4$alkyl or C$_1$-C$_4$haloalkyl;

A preferred group of compounds of formula I is represented by the compounds of formula I-1

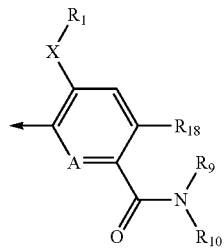
(I-1)

wherein R$_3$ is a radical selected from the group consisting of formulae Q$_1$, Q$_2$, Q$_3$, Q$_4$, Q$_5$, Q$_6$, Q$_7$, Q$_8$, Q$_9$, Q$_{10}$, Q$_{11}$, Q$_{12}$, Q$_{13}$ and Q$_{14}$

Q$_1$

Q$_2$

Q$_3$

-continued

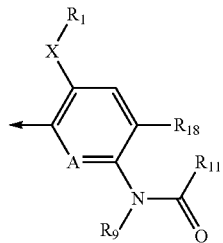
Q$_4$

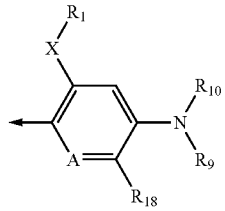
Q$_5$

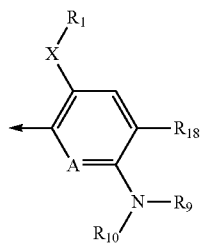
Q$_6$

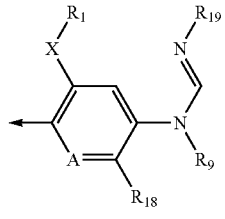
Q$_7$

Q$_8$

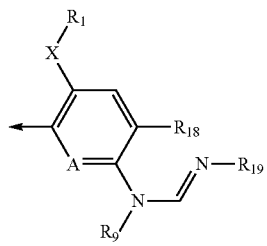

Q$_9$

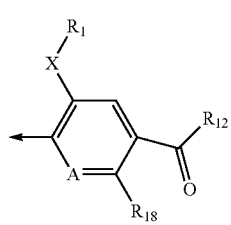

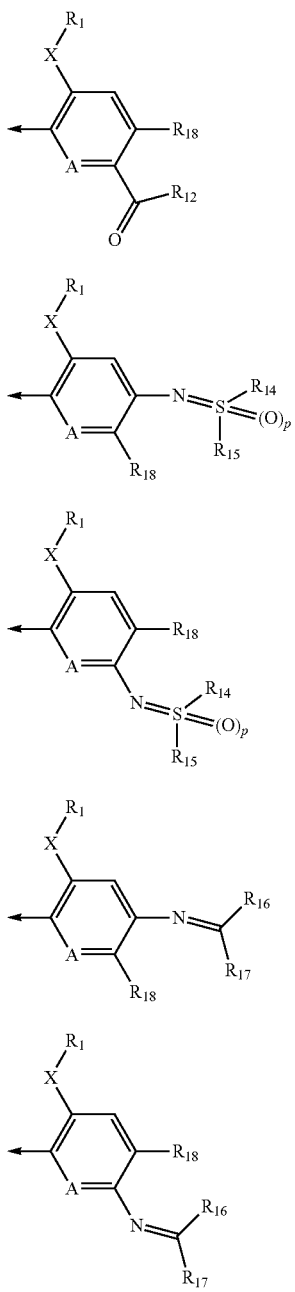

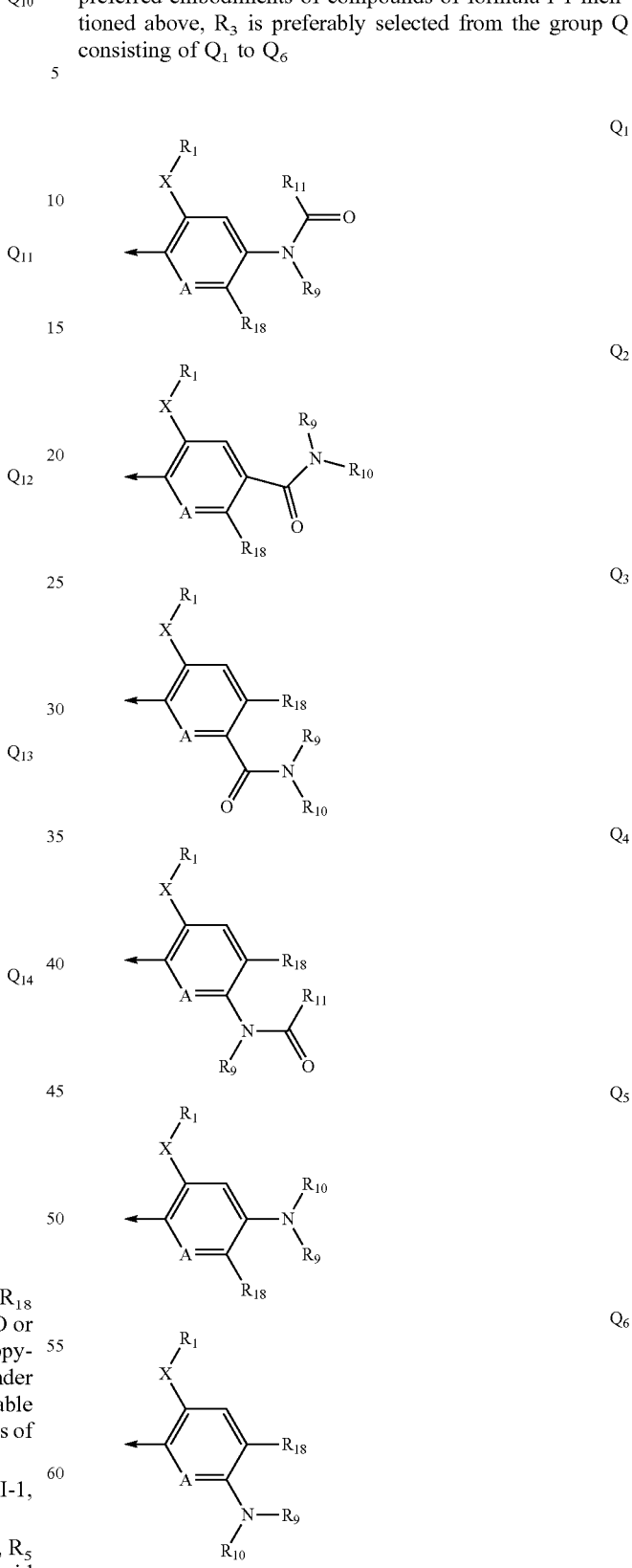

In compounds of formula I, of formula I-1 and all of the preferred embodiments of compounds of formula I-1 mentioned above, $R_3$ is preferably selected from the group Q consisting of $Q_1$ to $Q_6$ wherein A, $R_2$, $R_4$, $R_9$, $R_{10}$, $R_{11}$, $R_{12}$, $R_{14}$, $R_{15}$, $R_{16}$, $R_{17}$, $R_{18}$ and $R_{19}$ are as defined under formula I above; X is S, SO or $SO_2$; $R_1$ is methyl, ethyl, n-propyl, i-propyl or cyclopropylmethyl, preferably ethyl; and $R_5$ is as defined above under formula I, preferably methyl, and agrochemically acceptable salts, stereoisomers, enantiomers, tautomers and N-oxides of those compounds.

A further preferred group of compounds of formula I-1, wherein $R_4$ is methyl, ethyl, cyclopropyl.

In said preferred groups of compounds of formula I-1, $R_5$ is preferably methyl. A further preferred embodiment of said preferred groups of compounds of formula I-1 comprises compounds of formula I-1, wherein A is preferably N; X is preferably S or $SO_2$ and $R_1$ is preferably ethyl.

wherein $R_{18}$ is hydrogen; A, $R_9$, $R_{10}$ and $R_{11}$ are as defined under formula I above; X is S, SO or $SO_2$; $R_1$ is methyl, ethyl, n-propyl, i-propyl or cyclopropylmethyl, preferably ethyl; and $R_5$ is as defined above under formula I, preferably methyl, and agrochemically acceptable salts, stereoisomers, enantiomers, tautomers and N-oxides of those compounds.

A further preferred embodiment of the invention comprises compounds of formula I represented by the compounds of formula I-1 wherein $R_2$ is $C_1$-$C_4$ haloalkyl, in particular trifluoromethyl;

$R_4$ is $C_1$-$C_4$ alkyl or $C_3$-$C_6$ cycloalkyl, in particular methyl, ethyl or cyclopropyl;

$R_5$ is $C_1$-$C_4$ alkyl, in particular methyl;

$R_3$ is selected from the group consisting of $Q_1$ to $Q_6$

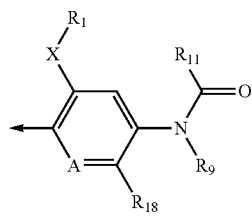
Q₁

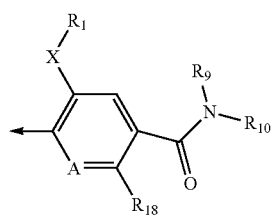
Q₂

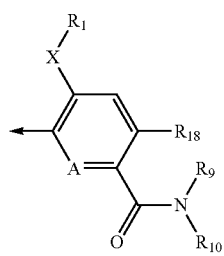
Q₃

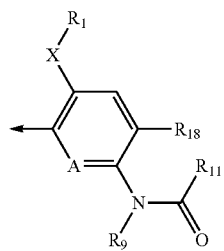
Q₄

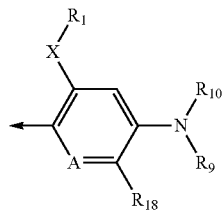
Q₅

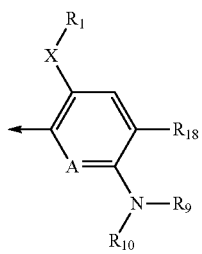
Q₆

-continued wherein $R_1$ is $C_1$-$C_4$ alkyl, in particular ethyl;

X is S, SO or $SO_2$, in particular S or $SO_2$;

$R_9$, $R_{10}$ and $R_{11}$ are as defined under formula I above;

$R_{18}$ is hydrogen; and

A is N or CH; and agrochemically acceptable salts, stereoisomers, enantiomers, tautomers and N-oxides of the compounds of formula I-1.

More preferred are compounds of formula I-1, wherein

A is N or CH;

$R_2$ is $C_1$-$C_4$ haloalkyl, in particular trifluoromethyl;

X is S, SO or $SO_2$, in particular S or $SO_2$;

$R_3$ is selected from the group consisting of $Q_1$ to $Q_6$

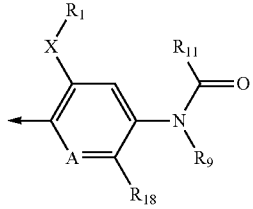
Q₁

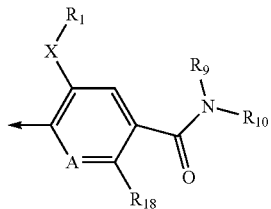
Q₂

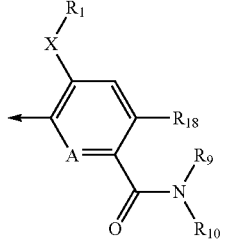
Q₃

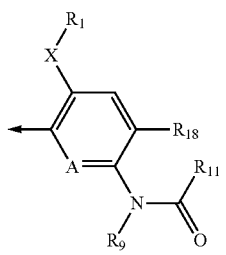
Q₄

-continued

Q5
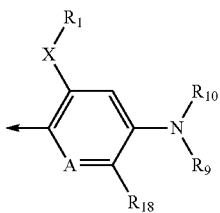

Q6
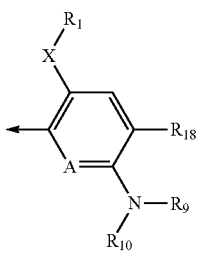

wherein R$_{18}$ is hydrogen; R$_1$ is C$_1$-C$_4$ alkyl, in particular ethyl;

R$_4$ is C$_1$-C$_4$ alkyl or C$_3$-C$_6$ cycloalkyl, in particular methyl, ethyl or cyclopropyl;

R$_5$ is C$_1$-C$_4$ alkyl, in particular methyl;

R$_9$ is hydrogen or C$_1$-C$_4$alkyl; or

R$_9$ is C$_3$-C$_6$cycloalkyl which can be mono- or polysubstituted by substituents selected from the group consisting of halogen, C$_1$-C$_4$haloalkyl, cyano and C$_1$-C$_4$alkyl;

R$_{10}$ is hydrogen, C$_1$-C$_6$alkyl, cyano, N—(C$_1$-C$_4$ alkyl)N—(C$_3$-C$_6$cycloalkylcarbonyl)amino, N—C$_3$-C$_6$cycloalkylcarbonylamino or —S(O)$_2$R$_{13}$; or R$_{10}$ is C$_1$-C$_4$alkyl mono- or disubstituted by a group selected from cyano and halogen; or R$_{10}$ is phenyl, pyridinyl or pyrazolyl; said phenyl, pyridinyl or pyrazolyl can be mono to polysubstituted by substituents independently selected from C$_1$-C$_4$haloalkyl and halogen;

R$_{11}$ is C$_1$-C$_4$alkyl, N—C$_1$-C$_4$alkylamino or N,N—(C$_1$-C$_4$alkyl)$_2$amino;

and agrochemically acceptable salts, stereoisomers, enantiomers, tautomers and N-oxides of the compounds of formula I-1.

Even more preferred compounds of formula I-1, are those, wherein

A is N or CH;

R$_2$ is C$_1$-C$_4$haloalkyl, in particular trifluoromethyl;

X is S, SO or SO$_2$, in particular S or SO$_2$;

R$_3$ is selected from the group consisting of Q$_1$ to Q$_6$

Q$_1$
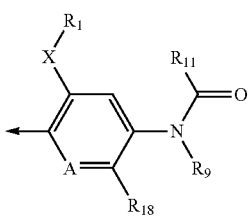

Q$_2$
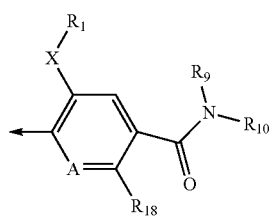

Q$_3$
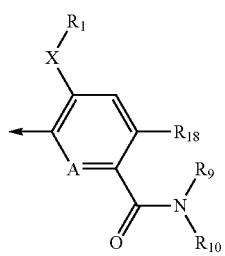

Q$_4$
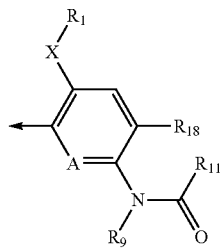

Q$_5$
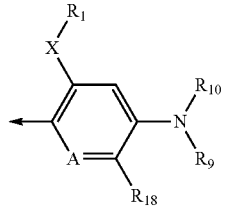

Q$_6$
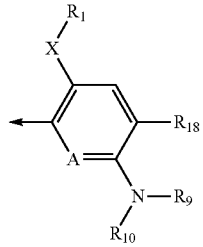

wherein R$_{18}$ is hydrogen; R$_1$ is C$_1$-C$_4$ alkyl, in particular ethyl;

R$_4$ is C$_1$-C$_4$ alkyl or C$_3$-C$_6$ cycloalkyl, in particular methyl, ethyl or cyclopropyl;

R$_5$ is C$_1$-C$_4$ alkyl, in particular methyl;

R$_9$ is hydrogen, C$_1$-C$_4$alkyl or C$_3$-C$_6$cycloalkyl, in particular hydrogen, methyl or cyclopropyl;

R$_{10}$ is hydrogen, C$_1$-C$_6$alkyl; in particular hydrogen and methyl;

R$_{11}$ is C$_1$-C$_6$alkyl or C$_3$-C$_6$cycloalkyl, or C$_1$-C$_6$alkyl or C$_3$-C$_6$cycloalkyl mono- or polysubstituted by substituents selected from the group consisting of hydrogen, halogen, C$_1$-C$_4$haloalkyl, cyano and C$_1$-C$_4$alkyl; in particular hydrogen, methyl and cyclopropyl.

Even more preferred compounds of formula I-1 are those, wherein

Y is O;
$R_2$ is $C_1$-$C_2$ haloalkyl;
$R_4$ is $C_1$-$C_3$ alkyl or cyclopropyl;
$R_5$ is $C_1$-$C_3$ alkyl;
$R_3$ is selected from the group consisting of $Q_1$ to $Q_7$, $Q_9$, $Q_{10}$ and $Q_{11}$

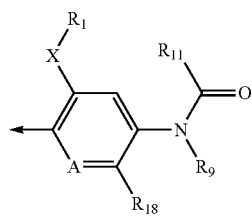
Q1

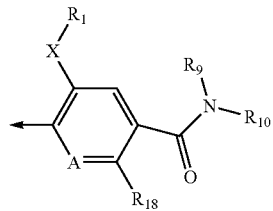
Q2

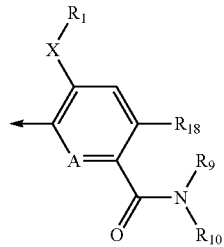
Q3

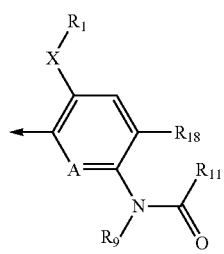
Q4

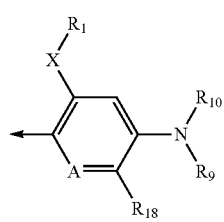
Q5

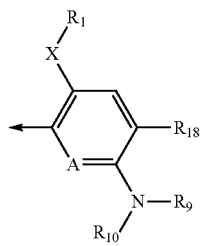
Q6

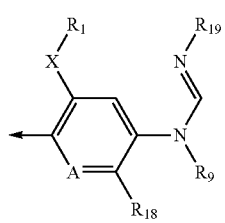
Q7

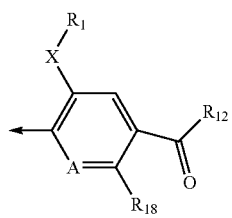
Q9

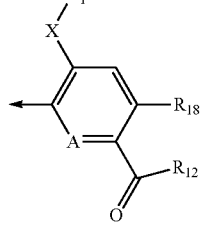
Q10

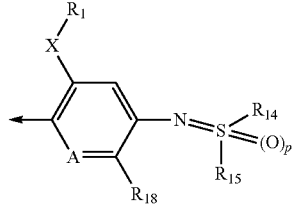
Q11

X is S, SO or $SO_2$; in particular S or $SO_2$;
$R_1$ is $C_1$-$C_3$ alkyl;
A is N or CH;
$R_9$ is hydrogen, $C_1$-$C_6$alkyl, $C_1$-$C_6$haloalkyl, hydroxyl or $C_1$-$C_6$alkoxy; or
$R_9$ is cyclopropylcarbonyl, cyclopropyl, cyclopropyl monosubstituted by cyano, or is $S(O)_2C_1$-$C_2$alkyl;
$R_{10}$ is hydrogen, $C_1$-$C_6$alkyl, $S(O)_2C_1$-$C_2$alkyl, $S(O)_2$cyclopropyl, amino, N—($C_1$-$C_2$alkyl)amino or N—($C_1$-$C_2$alkyl) N-(cyclopropylcarbonyl)amino;
$R_{10}$ is $C_1$-$C_4$alkyl monosubstituted by cyano;
$R_{11}$ is $C_1$-$C_6$alkoxy or cyclopropyl which can be substituted by cyano;
$R_{12}$ is hydroxyl or $C_1$-$C_4$alkyl;
$R_{14}$ is $C_1$-$C_4$ alkyl;
$R_{15}$ is cyclopropyl;
p is 1;

$R_{18}$ is hydrogen, $C_1$-$C_3$ alkyl, halogen, cyclopropyl or cyano and $R_{19}$ is $C_1$-$C_4$alkoxy.

The process according to the invention for preparing compounds of formula (I) is carried out by methods known to those skilled in the art, or described for example in WO 2009/131237, WO 2011/043404, WO 2011/040629, WO 2010/125985, WO 2012/086848, WO 2013/018928, WO 2013/191113, WO 2013/180193 and WO 2013/180194, and comprises reaction of a compound of formula II,

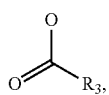
(II)

wherein $R_3$ is selected from the group $Q_{1a}$ to $Q_{14a}$

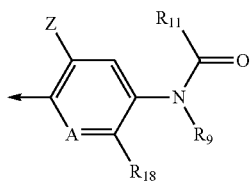
$Q_{1a}$

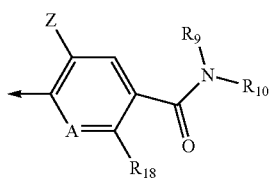
$Q_{2a}$

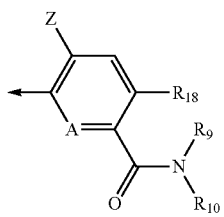
$Q_{3a}$

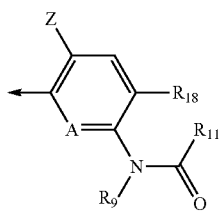
$Q_{4a}$

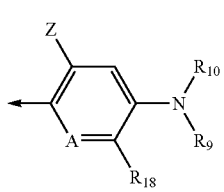
$Q_{5a}$

-continued

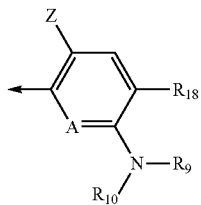
$Q_{6a}$

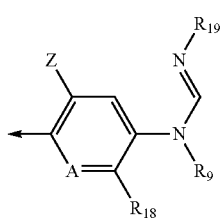
$Q_{7a}$

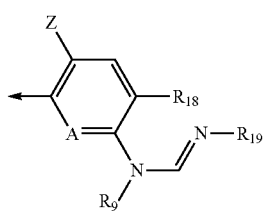
$Q_{8a}$

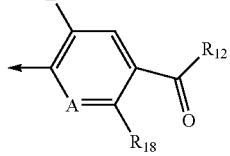
$Q_{9a}$

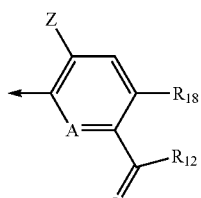
$Q_{10a}$

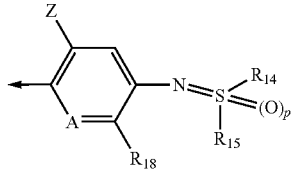
$Q_{11a}$

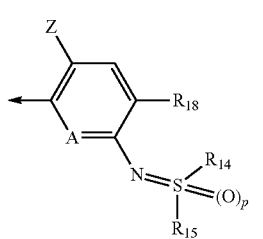
$Q_{12a}$

-continued

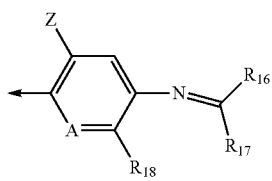

Q13a

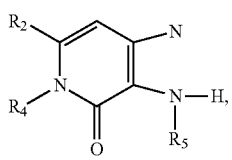

Q14a wherein Z is X—R₁ or a leaving group, for example a halogen, and wherein X, $R_1$, $R_9$, $R_{10}$, $R_{11}$, $R_{12}$, $R_{13}$, $R_{14}$, $R_{15}$, $R_{16}$, $R_{17}$, $R_{18}$, $R_{19}$ and A are as described under formula I above, and wherein the arrow in the radical Q shows the point of attachment to the carbon atom of the carboxyl group in the compound of formula II, with a compound of formula III, (III)

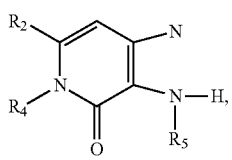

wherein $R_2$, $R_4$ and $R_5$ are as described under formula I above, in the presence of a dehydrating agent, such as for example polyphosphoric acid at temperature between 150° C. to 250° C., to yield compounds of formula Ia, wherein the substituents are as described above and under formula I. Such processes are well known and have been described for example in WO 2008/128968 or WO 2006/003440. The process is summarized in scheme 1 for compounds of formula Ia:

Scheme 1

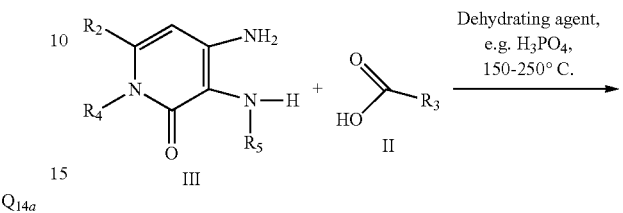

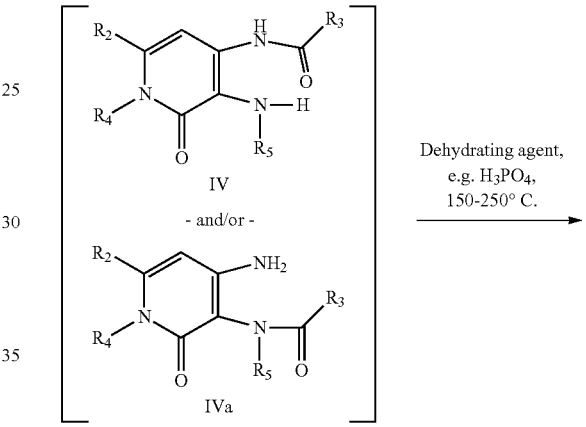

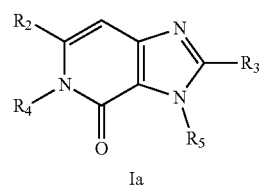

Ia

As can be seen in scheme 1, the formation of compounds of formula Ia occurs through the intermediacy of a compound of formula IV (and/or its position isomer IVa). Intermediate IV or intermediate IVa may form as a pure entity, or intermediates IV and IVa may arise as a mixture of regioisomeric acylation products. It is in many cases advantageous to thus prepare compounds of formula (I) through such intermediates IV/IVa, which may be isolated and optionally purified. This is illustrated for compounds of formula Ia in scheme 2:

Scheme 2

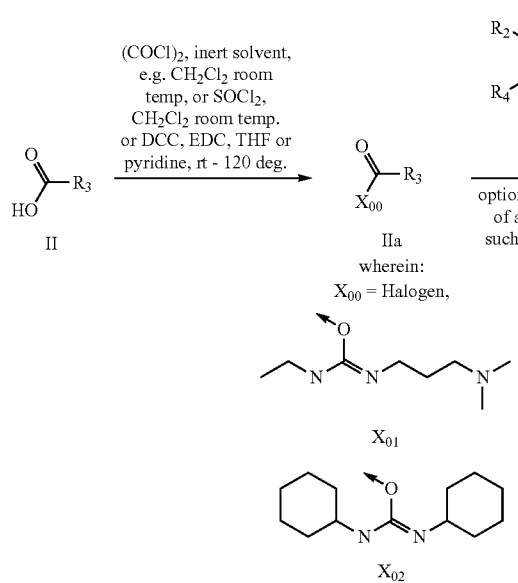
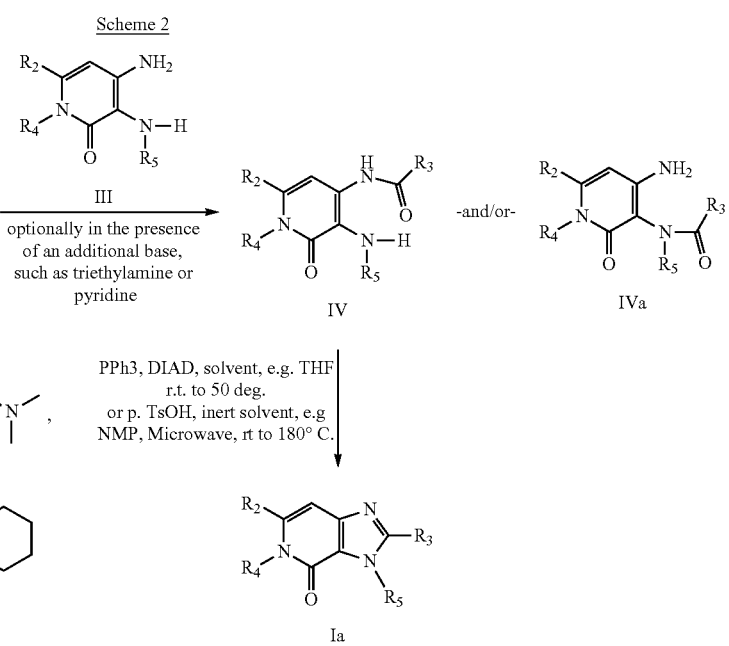

Compounds of the formula IV and/or IVa (or a mixture thereof), or a salt thereof, wherein $R_3$ is as defined above, and wherein $R_2$, $R_4$ and $R_5$ are as described under formula I above, may be prepared by i) activation of compound of formula II, wherein $R_3$ is as defined above, by methods known to those skilled in the art and described in, for example, Tetrahedron, 2005, 61 (46), 10827-10852, to form an activated species IIa, wherein Q is as defined above and wherein $X_{00}$ is halogen, preferably chlorine. For example, compounds IIa where $X_{00}$ is halogen, preferably chlorine, are formed by treatment of II with, for example, oxalyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C. Alternatively, treatment of compounds of formula II with, for example, 1-ethyl-3-(3-dimethylaminopropyl)carbodiimide EDC or dicyclohexyl carbodiimide DCC will generate an activated species IIa, wherein $X_{00}$ is $X_{01}$ or $X_{02}$ respectively, in an inert solvent, such as pyridine or tetrahydrofuran THF, optionally in the presence of a base, such as triethylamine, at temperatures between 25-180° C.; followed by ii) treatment of the activated species IIa with a compound of formula III (or a salt thereof), wherein $R_2$, $R_4$ and $R_5$ are as described under formula I above, optionally in the presence of a base, such as triethylamine or pyridine, in an inert solvents such as dichloromethane, tetrahydrofuran, dioxane or toluene, at temperatures between 0 and 80° C., to form the compounds of formula IV and/or IVa (or a mixture thereof).

Compounds of formula IV and/or IVa (or a mixture thereof) may further be converted into compounds of formula Ia, wherein $R_3$ is as defined above, and wherein $R_2$, $R_4$ and $R_5$ are as described under formula I above, by dehydration, eg. by heating the compounds IV and/or IVa (or a mixture thereof) in the presence of an acid catalyst, such as for example methane sulfonic acid, or para-toluene sulfonic acid TsOH, in an inert solvent such as N-methyl pyrrolidine NMP at temperatures between 25-180° C., preferably 100-170° C., optionally under microwave conditions. Such processes have been described previously, for example, in WO 2010/125985.

Compounds of formula Ia, wherein $R_3$ is as defined above, and wherein Z is a leaving group, for example halogen, preferably fluorine or chlorine, and wherein $R_2$, $R_3$, $R_4$ and $R_5$ are as described under formula I above, can be reacted with compounds of formula V $$R_1\text{—SH} \qquad (V),$$

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula Ib, wherein $R_1$ is as described under formula I above, and in which $R_2$, $R_3$, $R_4$ and $R_5$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Similar chemistry has been previously described, as for example in WO2013/018928. Examples of salts of the compound of formula V include compounds of the formula Va $$R_1\text{—S-M} \qquad (Va),$$

wherein $R_1$ is as defined above and wherein M is, for example, sodium or potassium. This is illustrated for compounds of formula Ib in scheme 3, in the case of $Q_5a$: Identical reaction can be realized with $Q_{1a}$ to $Q_{14a}$.

Scheme 3

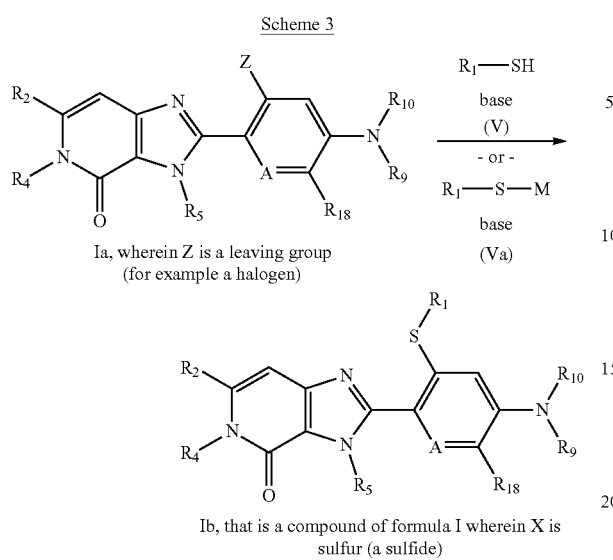

Ia, wherein Z is a leaving group
(for example a halogen)

Ib, that is a compound of formula I wherein X is
sulfur (a sulfide)

Alternatively, this reaction can be carried out in the presence of a palladium catalyst, such as tris(dibenzylideneacetone)dipalladium(0), in the presence of a phosphor ligand, such as xanthphos, in an inert solvent, for example, xylene at temperatures between 100-160° C., preferably 140° C., as described by Perrio et al. in Tetrahedron 2005, 61, 5253-5259.

The subgroup of compounds of formula I, wherein X is SO (sulfoxide) and/or $SO_2$ (sulfone), may be obtained by means of an oxidation reaction of the corresponding sulfide compounds of formula I, wherein X is S (i.e. a compound of formula Ib above), involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds Ib to produce the sulfoxide compounds I (wherein X=SO), and preferably 2 to 2.2 moles of oxidant, relative to 1 mole of the sulfide compounds Ib to produce the sulfone compounds I (wherein X=$SO_2$). Such oxidation reactions are disclosed, for example, in WO 2013/018928.

The sequence to prepare compounds of formula IIIa wherein $R_2$, $R_4$ and $R_5$ are as described under formula I above, from compounds of formula VIII, may involve i. alkylation of compound VIII with $R_6$—$X_{LG}$, wherein $R_6$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula VII, wherein $R_6$, $R_4$ and $R_2$ are as described under formula I above; ii. a reaction of nitration of compound VII in classical conditions, for example, see for example, Advanced Organic Chemistry: Reactions, Mechanisms, and Structure, Fourth Edition by Jerry March, 1992 (Publisher Wiley New York, N.Y.) pages 523-525; and finally iii. a reaction of reduction of compound VI in classical conditions, for example, see for example, Advanced Organic Chemistry: Reactions, Mechanisms, and Structure, Fourth Edition by Jerry March, 1992 (Publisher Wiley New York, N.Y.) p 1216-1217. See scheme 4.

Scheme 4

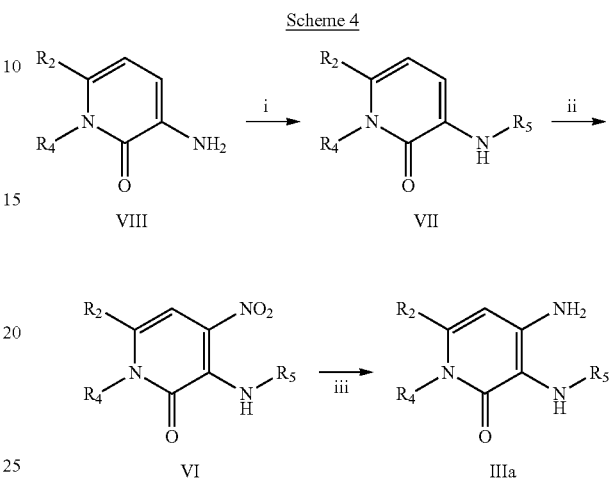

Compounds of formula VIII may be made by methods known to a person skilled in the art, for example Synthesis 2005, No. 8, pp 1269-1278 and Synthesis 2011, No. 7, pp 1149-1156.

Compounds of formula I-2a, wherein Z is X—$R_1$ or a leaving group, for example halogen, and wherein X, $R_1$, $R_4$, $R_6$, A and $R_2$ are as described under formula I above, may be prepared by reaction between compounds of formula II respectively IIa, wherein Z is X—$R_1$ or a leaving group, for example halogen, and wherein X, $R_1$ and A are as described under formula I above, and in which $X_{00}$ is as described above, and compounds of formula IIIa, wherein $R_6$ and $R_2$ are as described under formula I above, under similar conditions as for the preparation of compounds of formula Ia from compounds of formula II/IIa and III described above (see scheme 1 and 2). This is illustrated for compounds of formula IIIa in scheme 5, in the case of $Q_{5a}$: Identical reaction can be realized with $Q_{1a}$ to $Q_{14a}$ or with $Q_1$ to $Q_{14}$.

Scheme 5

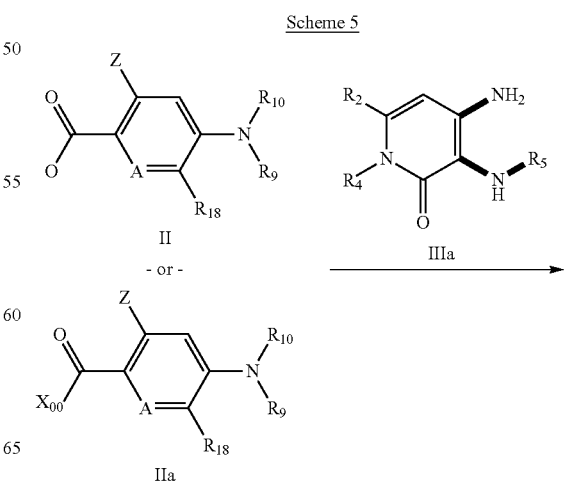

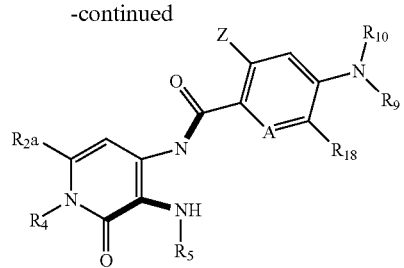

IVa-1

- and/or -

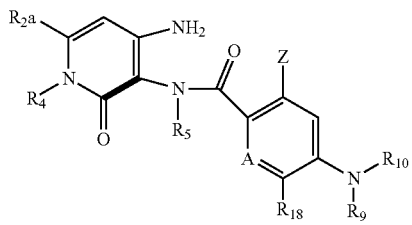

IVa-2

↓

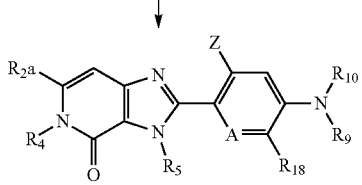

(I-2a)

Compounds of formula II are known or could be synthesised by methods known to those skilled in the art. All reaction described on the next following schemes could be realized on compounds of formula II or precursor under acid or ester form.

Compounds of formula IX, wherein X, $R_2$, $R_4$ and $R_5$ are as defined above, and wherein $Q_b$ is a radical selected from the group consisting of formula $Q_{1b}$ to $Q_{4b}$:

$Q_{1b}$ $Q_{2b}$ $Q_{3b}$

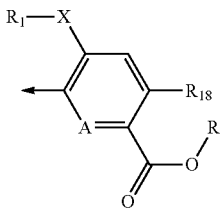

$Q_{4b}$ wherein Y is an leaving group such as a halogen, for example a bromide or a amine protected or not, wherein R is hydrogen or a $C_1$-$C_4$ alkyl group and wherein $R_1$ and $R_{18}$ are as defined in formula I above, may be prepared as described before for Qa analogues or $R_3$ analogues (see scheme 1, 2 and 5). This transformation is illustrated by scheme 6.

Scheme 6

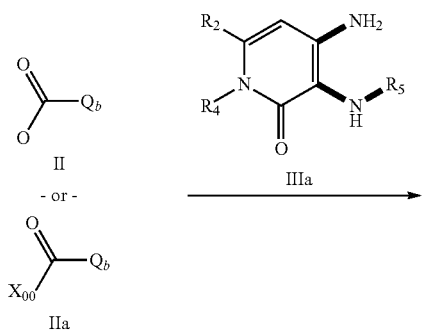

$Q_b$ is selected from $Q_{1b}$ to $Q_{4b}$

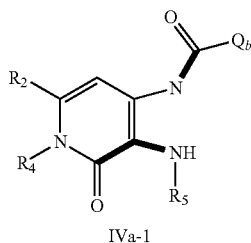

IVa-1

- and/or -

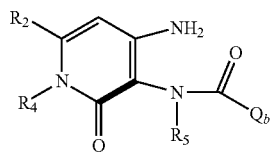

IVa-2

↓

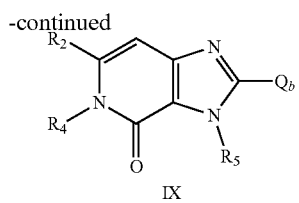

$Q_b$ is selected from $Q_{1b}$ to $Q_{4b}$

Compounds of formula I, wherein X, $R_1$, $R_2$, $R_4$ and $R_5$ are as defined in formula I above and $R_3$ is $Q_1$, $Q_4$, $Q_5$ and $Q_6$, can also be prepared by reacting a compound of formula IX, wherein X, $R_1$, $R_2$, $R_4$ and $R_5$ are as described in formula I and wherein $Q_b$ is a radical $Q_{1b}$ or $Q_{2b}$ by a Buchwald-Hartwig cross coupling, which involves for example, reacting compounds of formula IX, wherein Y is a leaving group, for example, chlorine, bromine or iodine, or an aryl- or alkylsulfonate such as trifluoromethanesulfonate with, for example, compounds of formula Xa or Xb. The reaction can be catalyzed by a palladium based catalyst, for example Palladium acetate, in presence of a base, like cesium carbonate or sodium tert-butoxide, in a solvent or a solvent mixture, like, for example toluene, preferably under inert Alternatively, similar reactions can be carried out in the presence of a copper source such as copper(I) iodide (CuI) or copper(II) trifluoromethanesulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-but oxide. The reaction can be carried out in a suitable solvent such as 1,4-dioxane, N,N-dimethylformamide, dimethyl sulfoxide or N-methylpyrolidinone at a temperature between 100 and 180 degrees centigrade for 15 to 60 minutes under microwave irradiation. See for example US 20140142081, Chemical Communications 2011, 47(31), 8976-8978; Advanced Synthesis & Catalysis 2010, 352(18), 3158-3162.

Alternatively, compounds of formula I, wherein $R_1$, $R_2$, $R_4$, $R_5$ and X are as defined in formula I, can prepared by nucleophile substitution which involves for example, reaction of compounds of formula IXa, wherein Y is a leaving group, for example, fluorine with compounds of formula Xa under basic condition such as potassium carbonate in a solvent such as DMF, see for example Bioorganic & Medicinal Chemistry Letters 2013, 23(6), 1720-1726; WO 2010137349. See scheme 10.

Scheme 10

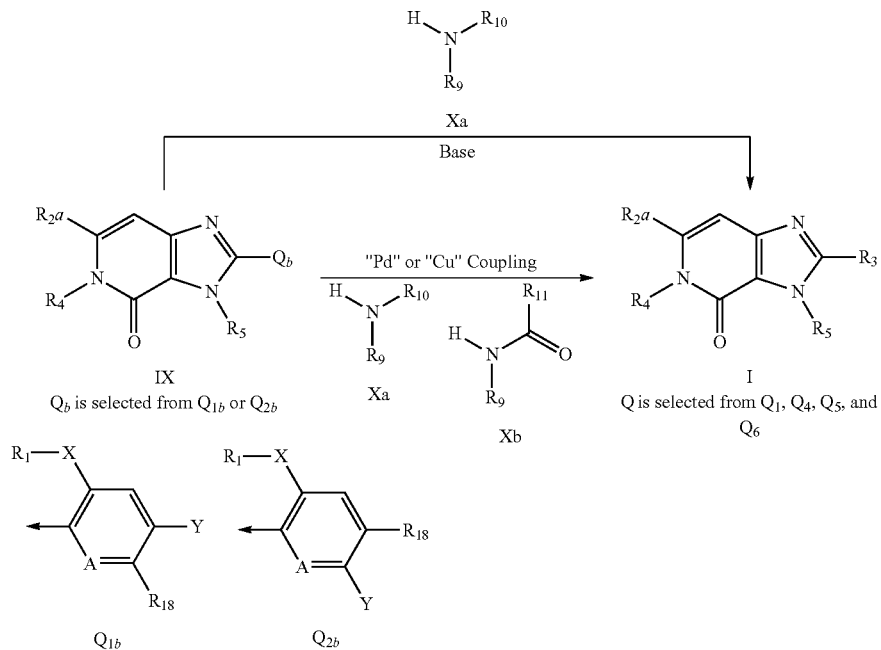

atmosphere and in presence of chelating phosphine such as BINAP or Xamtphos. The reaction temperature can preferentially range from ambient temperature to the boiling point of the reaction mixture. Such Buchwald-Hartwig cross coupling are well known to those skilled in the art, many variation are described in literature and have been reviewed, for example in Strategic Applications of Named Reactions in Organic Synthesis (Kurti, Laszlo; Czako, Barbara; Editors. Ed. ELSEVIER) 2005, p 70 and cited references; Modern Tools for the Synthesis of Complex Bioactive Molecules (Chapter 3: Metal-catalyzed C-heteroatom cross-coupling reactions) 2012, p. 77-109.

Alternatively, compounds of formula IXb wherein X, $R_1$, $R_2$, $R_4$ and $R_{18}$ are as defined in formula I above, can be prepared starting from compounds of formula IX wherein X, $R_1$, $R_2$, $R_4$ and $R_{18}$ are as defined in formula I above and wherein Y is a leaving group such as chloride or bromide, as shown in scheme 11 by substitution of a leaving group (LG) by a azide group coming, for example from sodium azide in a solvent such as N,N-Dimethylformamide or DMSO in presence or not of catalyst such as copper iodine in presence or a ligand such as proline or DMEDA, followed or not by reduction of the azide group in amine under classical reduction condition (see for example: Synthetic Organic Methodology: Comprehensive Organic Transformations. A Guide to Functional Group Preparations, Larock, R. C. 1989 p 409). These reactions can be performed in various organic or aqueous solvents compatible to these conditions, by temperatures from below 0° C. up to the boiling point of the solvent system. This succession of reaction to realize this transformation is well known to those skilled in the art and for example, similar reactions are described in: Medicinal Chemistry Research, 24(1), 171-181; 2015; Tetrahedron Letters, 53(23), 2922-2924; 2012. Alternatively, this reaction could be done in one step and the azide could be reduce in situ under copper catalyst conditions as described in, for example, Journal of Organic Chemistry (2010), 75(14), 4887-4890 and cited references therein.

drofuran, dimethylformamide or toluene could give compounds of formula I wherein X, $R_1$, $R_2$, $R_4$, $R_5$, $R_9$, $R_{10}$, $R_{18}$ and A are as defined in formula I above and wherein $R_3$ is selected from $Q_5$ and $Q_6$ wherein $R_{10}$ is hydrogen. Such reactions can be carried out under well-established methods, described for example, Organic Preparations and Procedures International, 36(4), 347-351; 2004; WO 2004074270 or Tetrahedron, 59(39), 7651-7659; 2003.

Compounds of formula I wherein X, $R_1$, $R_2$, $R_4$, $R_5$, $R_9$, $R_{10}$, $R_{18}$ and A are as defined in formula I above and wherein $R_3$ is selected from $Q_1$ and $Q_4$ can be made by reaction of compounds of formula I wherein X, $R_1$, $R_2$, $R_4$, $R_5$, $R_9$, $R_{10}$, $R_{18}$ and A are as defined in formula I above and wherein $R_3$ is selected from $Q_5$ and $Q_6$ wherein $R_{10}$ is hydrogen with a Scheme 11

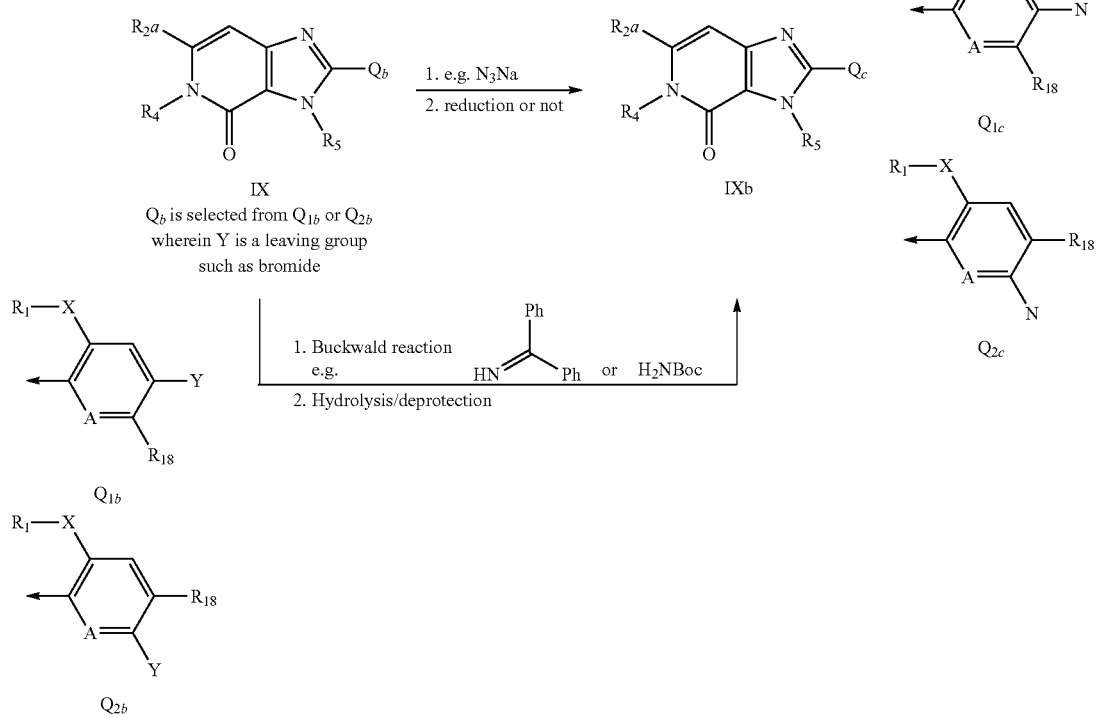

Compounds of formula I wherein X, $R_1$, $R_2$, $R_4$, $R_5$, $R_9$, $R_{10}$, $R_{18}$ and A are as defined in formula I above and wherein $R_3$ is selected from $Q_5$ and $Q_6$, wherein $R_{10}$ is hydrogen, can be made by formation of the N—$R_9$ bond via reductive amination with an aldehyde RxCH(O) or alkylation with $R_9$-$XLG_2$. Reductive amination may be achieved by treatment of the compounds of formula IX with an aldehyde VII and a reducing agent such as sodium cyanoborohydride. Such reactions can be carried out under well-established methods and various conditions could be used, described for example in Synthetic Organic Methodology: Comprehensive Organic Transformations, a Guide to Functional Group Preparations, Larock, R. C. 1989 p 421. Alkylation may be achieved by treatment of the compounds of formula IX with $R_9$-$XLG_2$ wherein $XLG_2$ is chloro, bromo, iodo, mesylate, triflate in presence of a base such as potassium carbonate in a solvent such as dimethylsulfoxide, acetonitrile, tetrahycompound of formula XIII wherein $XLG_1$ is OH, $C_1$-$C_6$alkoxy or Cl, F or Br. When $XLG_1$ is OH such reactions are usually carried out in the presence of a coupling reagent, such as dicyclohexyl-carbo-diimide ("DCC"), N-(3-Dimethylaminopropyl)-N'-ethylcarbodiimide hydrochloride ("EDC") or bis(2-oxo-3-oxazolidinyl)phosphonic chloride ("BOP—Cl"), in the presence of a base, and optionally in the presence of a nucleophilic catalyst, such as hydroxybenzo-triazole ("HOBT"). When $XLG_1$ is Cl, such reactions are usually carried out in the presence of a base, and optionally in the presence of a nucleophilic catalyst for example dimethylaminopyridine. Alternatively, it is possible to conduct the reaction in a biphasic system comprising an organic solvent, preferably ethyl acetate, and an aqueous solvent, preferably a solution of sodium hydrogen carbonate. When $XLG_1$ is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are NN-dimethylacetamide, tetrahydrofuran, dioxane, 1,2-dimethoxyethane, ethyl acetate and toluene. The reaction is carried out at a temperature of from 0 degrees centigrade to 100 degrees centigrade, preferably from 15 degrees centigrade to 30 degrees centigrade, in particular at ambient temperature. Such reactions can be carried out under well-established methods and various conditions could be used, described for example in Synthetic Organic Methodology: Comprehensive Organic Transformations, a Guide to Functional Group Preparations, Larock, R. C. 1989 p 972. Alternatively, the sequence could be reversed and the acetylation could be done first and the alkylation or reductive amination could be done in second to give access to compounds of formula I wherein X, $R_1$, $R_2$, $R_4$, $R_5$, $R_9$, $R_{10}$, $R_{18}$ and A are as defined in formula I above and wherein $R_3$ is selected from $Q_1$ and $Q_4$ wherein $R_9$ is hydrogen, then these compounds could be alkylated to give compounds of formula I wherein X, $R_1$, $R_2$, $R_4$, $R_5$, $R_9$, $R_{10}$, $R_{18}$ and A are as defined in formula I above and wherein $R_3$ is selected from $Q_1$ and $Q_4$. For illustration, see scheme 12.

Compounds of formula I, wherein X, $R_1$, $R_2$, $R_4$, $R_5$, $R_9$, $R_{10}$, $R_{18}$ and A are as defined in formula I above and wherein $R_7$ is selected from $Q_9$ and $Q_{10}$, can be made by esterification from compounds of formula I, wherein X, $R_1$, $R_2$, $R_4$, $R_5$, $R_9$, $R_{10}$, $R_{18}$ and A are as defined in formula I above, and wherein $R_7$ is selected from $Q_9$ and $Q_{10}$ wherein $R_{12}$ is OH. These transformations are well known for persons skilled in the art and are, for example esterification in presence of an alcohol under acidic conditions (see for example: Synthetic Organic Methodology: Comprehensive Organic Transformations. A Guide to Functional Group Preparations, Larock, R. C. 1989 p 966) or for example via an acid halides such as acyl chloride (see for example: Synthetic Organic Methodology: Comprehensive Organic Transformations. A Guide to Functional Group Preparations, Larock, R. C. 1989 p 963) and then reaction with a nucleophile such as, for example $C_1$-$C_6$alkoxyl substituted or not (see for example: Synthetic Organic Methodology: Comprehensive Organic Transformations. A Guide to Functional Group Preparations, Larock, R. C. 1989 p 978). See scheme 13, Transformation E.

Compounds of formula I wherein X, $R_1$, $R_2$, $R_4$, $R_5$, $R_9$, $R_{10}$, $R_{18}$ and A are as defined in formula I above and wherein Scheme 12

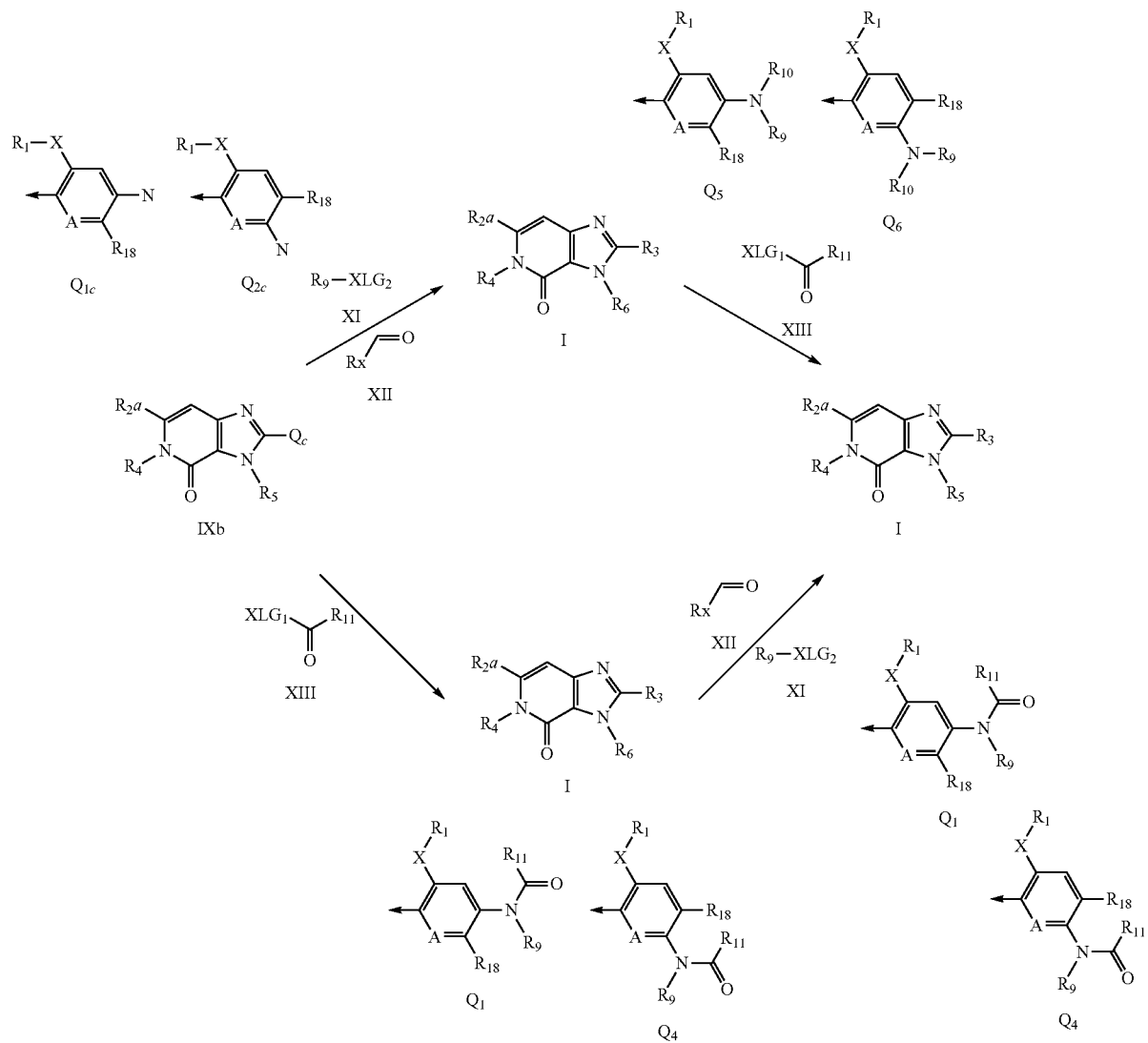

$R_7$ is selected from $Q_9$ and $Q_{10}$ wherein $R_{12}$ is an alkoxy group could be obtained directly from compounds of formula IXc wherein X, $R_1$, $R_2$, $R_4$, $R_5$, $R_9$, $R_{10}$, $R_{18}$ and A are as defined in formula I above and wherein $Q_b$ is selected from $Q_{1b}$ and $Q_{2b}$ wherein Y is cyano by esterification in presence of an alcohol under acidic conditions (see for example: Synthetic Organic Methodology: Comprehensive Organic Transformations. A Guide to Functional Group Preparations, Larock, R. C. 1989 p 993). See scheme 13, Transformation C.

Compounds of formula I wherein X, $R_1$, $R_2$, $R_4$, $R_5$, $R_9$, $R_{10}$, $R_{18}$ and A are as defined in formula I above and wherein $R_7$ is selected from $Q_2$ and $Q_3$, can be made by amide coupling from compound of formula I wherein X, $R_1$, $R_2$, $R_4$, $R_5$, $R_9$, $R_{10}$, $R_{18}$ and A are as defined in formula I above and wherein $R_7$ is selected from $Q_9$ and $Q_{10}$ wherein $R_{12}$ is OH. These transformations are well known for people skilled in the art and are, for example by coupling reaction with an amine group (see for example: Synthetic Organic Methodology: Comprehensive Organic Transformations; A Guide to Functional Group Preparations, Larock, R. C. 1989 p 972-976) or for example via an acid halides such as acyl chloride (see for example: Synthetic Organic Methodology: Comprehensive Organic Transformations; Aa Guide to Functional Group Preparations, Larock, R. C. 1989 p. 963) and then reaction with a nucleophile such as, for example amino group substituted or not $HNR_9R_{10}$ (see for example: Synthetic Organic Methodology: Comprehensive Organic Transformations, A Guide to Functional Group Preparations, Larock, R. C. 1989 p 979). See scheme 13, Transformation F.

Alternatively, Compounds of formula I wherein X, $R_1$, $R_2$, $R_4$, $R_5$, $R_9$, $R_{10}$, $R_{18}$ and A are as defined in formula I above and wherein $R_7$ is selected from $Q_2$ and $Q_3$ could be obtained directly from compounds of formula IXc wherein X, $R_1$, $R_2$, $R_4$, $R_5$, $R_9$, $R_{10}$, $R_{18}$ and A are as defined in formula I above and wherein $Q_b$ is selected from $Q_{1b}$ and $Q_{2b}$ wherein Y is cyano by reaction in presence of an amine ($HNR_9R_{10}$) under various conditions (see for example: Synthetic Organic Methodology: Comprehensive Organic Transformations, A Guide to Functional Group Preparations, Larock, R. C. 1989 p 994). See scheme 13, Transformation B.

Compounds of formula I wherein X, $R_1$, $R_2$, $R_4$, $R_5$, $R_9$, $R_{10}$, $R_{18}$ and A are as defined in formula I above and wherein $R_7$ is selected from $Q_9$ and $Q_{10}$ wherein $R_{12}$ is OH can be made by 1) reaction of compounds of formula IXc wherein X, $R_1$, $R_2$, $R_4$, $R_5$, $R_9$, $R_{10}$, $R_{18}$ and A are as defined in formula I above and wherein $Q_b$ is selected from $Q_{1b}$ and $Q_{2b}$ wherein Y is a leaving group such as bromide with source of cyanide, such as zinc cyanide under or not metal catalysis such as palladium catalyst (see for example: Med. Chem. Commun., 2010, 1, 309-318). 2) by hydrolysis of the cyano group under acidic or basic conditions (see for example: Synthetic Organic Methodology: Comprehensive Organic Transformations: A Guide to Functional Group Preparations, Larock, R. C. 1989 p 993). See scheme 13, Transformation A and D.

Alternatively, Compounds of formula I wherein X, $R_1$, $R_2$, $R_4$, $R_5$, $R_9$, $R_{10}$, $R_{18}$ and A are as defined in formula I above and wherein $R_7$ is selected from $Q_9$ and $Q_{10}$ wherein $R_{12}$ is OH can be made by reaction of compounds of formula I wherein X, $R_1$, $R_2$, $R_4$, $R_5$, $R_9$, $R_{10}$, $R_{18}$ and A are as defined in formula I above and wherein $R_7$ is selected from $Q_9$ and $Q_{10}$ wherein $R_{12}$ is $C_1$-$C_6$ alkoxy under acidic or basic conditions such as, for example sodium hydroxide or lithium hydroxide in a mixture of solvent such as water and tetrahydrofuran. Such are well known for people skilled in the art and are, for example exemplified in Synthetic Organic Methodology: Comprehensive Organic Transformations. A Guide to Functional Group Preparations, Larock, R. C. 1989 p 981. See scheme 13, Transformation Eb.

Alternatively, compounds of formula I wherein X, $R_1$, $R_2$, $R_4$, $R_5$, $R_9$, $R_{10}$, $R_{18}$ and A are as defined in formula I above and wherein $R_7$ is selected from $Q_2$ and $Q_3$ can be made from compounds of formula I wherein X, $R_1$, $R_2$, $R_4$, $R_5$, $R_9$, $R_{10}$, $R_{18}$ and A are as defined in formula I above and wherein $R_7$ is selected from $Q_9$ and $Q_{10}$ wherein $R_{12}$ is $C_1$-$C_6$ alkoxy by reaction with $HNR_9R_{10}$ under various conditions as described in Synthetic Organic Methodology: Comprehensive Organic Transformations: A Guide to Functional Group Preparations, Larock, R. C. 1989 p 987. See scheme 13, Transformation G.

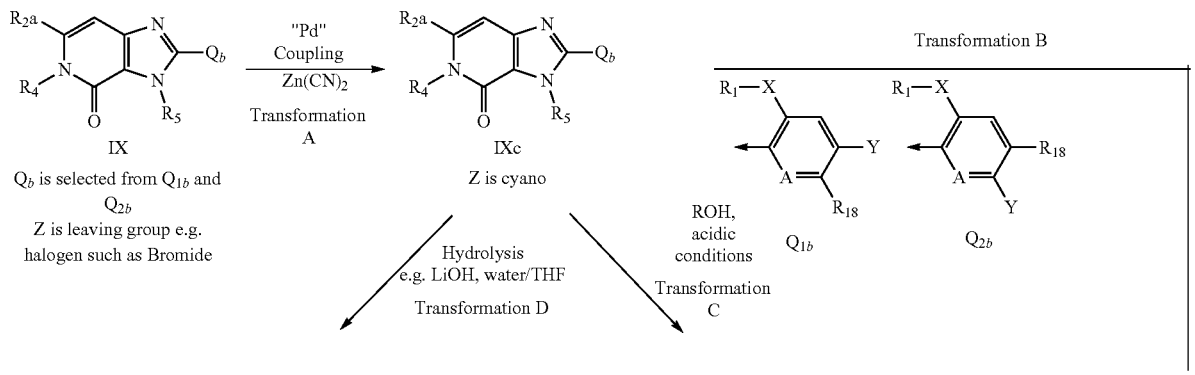

Scheme 13

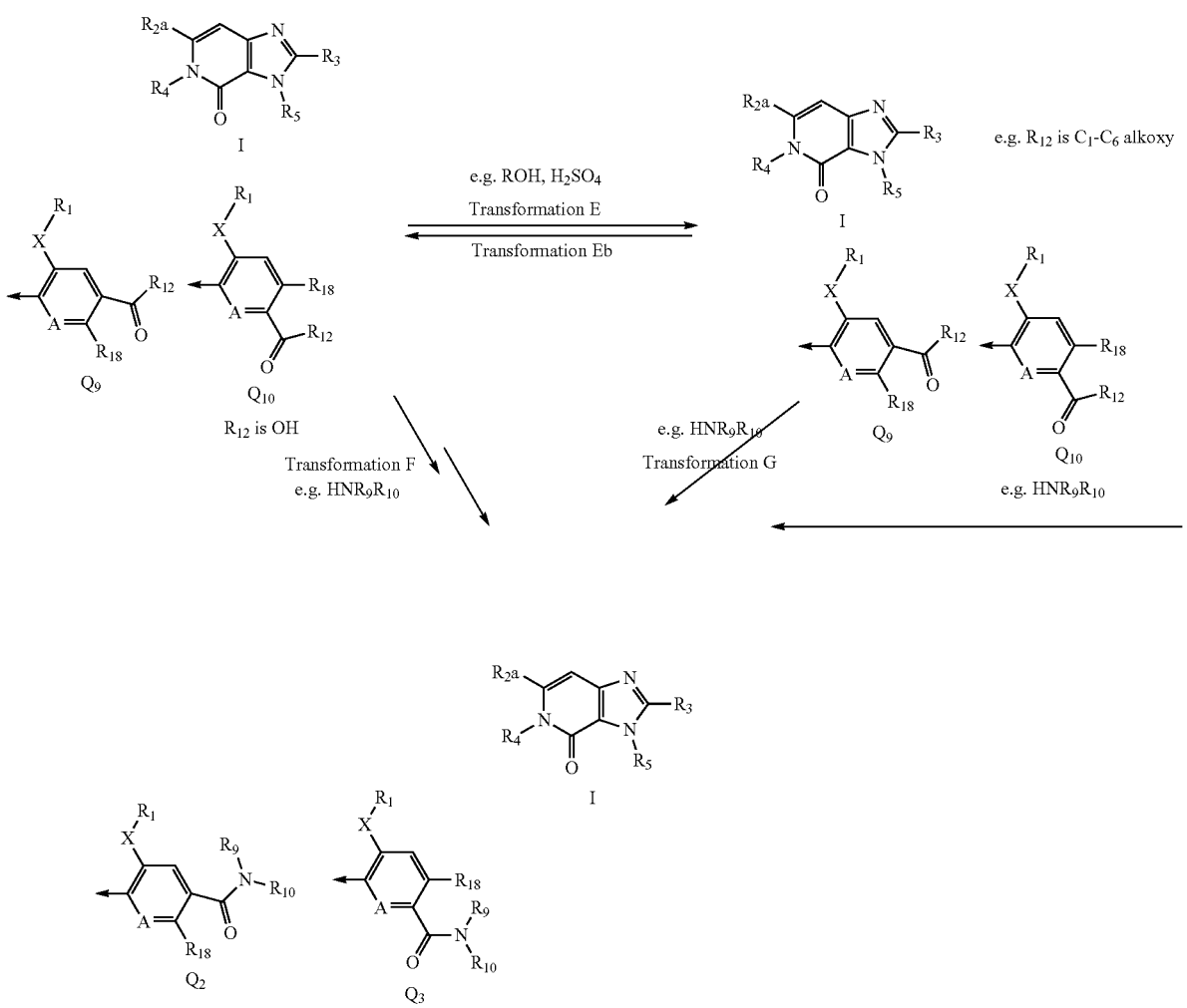

Compounds of formula I, wherein X, $R_1$, $R_2$, $R_4$, $R_5$, $R_9$, $R_{10}$, $R_{18}$ and A are as defined in formula I above and wherein $R_7$ is selected from $Q_9$ and $Q_{10}$ can be made from compounds of formula IXd wherein X, $R_1$, $R_2$, $R_4$, $R_5$, $R_9$, $R_{10}$, $R_{18}$ and A are as defined in formula I above and wherein Qb' is selected from $Q_{1b}'$ and $Q_{2b}'$ wherein $Y_1$ is a group of formula XIV, by oxidation, for example with sodium periodate in solvent such as water. This oxidative scission of Olefins to carbonyl derivatives, either through their ozonides or diols are well known by people skilled in the art and are used widely in organic synthesis, see for example: Synthetic Organic Methodology: Comprehensive Organic Transformations. A Guide to Functional Group Preparations, Larock, R. C. 1989 p 595; Science of Synthesis 2007, p 17-24. This transformation could be made in two steps, via the same type of diol intermediate by 1) transformation of compounds of formula IXd wherein X, $R_1$, $R_2$, $R_4$, $R_5$, $R_9$, $R_{10}$, $R_{18}$ and A are as defined in formula I above and wherein Qb' is selected from $Q_{1b}'$ and $Q_{2b}'$ wherein $Y_1$ is a group of formula XIV to compounds of formula IXd wherein X, $R_1$, $R_2$, $R_4$, $R_5$, $R_9$, $R_{10}$, $R_{18}$ and A are as defined in formula I above and wherein Qb' is selected from $Q_{1b}'$ and $Q_{2b}'$ wherein $Z_1$ is diol analogues XIVa followed by 2) oxidative scission of diols to Aldehydes or ketone. For step 1, see, for example: Curr. Org. Chem., 2004, 8, 1159; Chem. Rev., 1980, 80, 187; Chem. Rev., 1994, 94, 2483. For step 2, see, for example: Organic Letters, 12(7), 1552-1555; 2010; Synlett, (5), 739-742; 2009; Chemistry Letters, (12), 1951-2; 1982; Science of Synthesis 2007, p 17-24; Synthesis, (1), 64-5; 1989 and cited references. If Rc is $C_1$-$C_4$ Alkoxy, hydrolysis of the vinylester function will give compounds of formula I wherein X, $R_1$, $R_2$, $R_4$, $R_5$, $R_9$, $R_{10}$, $R_{18}$ and A are as defined in formula I above and wherein $R_7$ is selected from $Q_9$ and $Q_{10}$. This transformation is well known in literature and could be exemplified by: Journal of Organic Chemistry, 55(10), 3114-8; 1990.

Compounds of formula IXd, wherein X, $R_1$, $R_2$, $R_4$, $R_5$, $R_9$, $R_{10}$, $R_{18}$ and A are as defined in formula I above and wherein Qb' is selected from $Q_{1b}'$ and $Q_{2b}'$ wherein $Y_1$ is a group of formula XIV can be made from compounds of formula IX wherein X, $R_1$, $R_2$, $R_4$, $R_5$, $R_9$, $R_{10}$, $R_{18}$ and A are as defined in formula I above and wherein Qb is selected from $Q_{1b}$ and $Q_{2b}$ wherein Y is leaving group, for example, chlorine, bromine or iodine (preferably bromine), or an aryl- or alkylsulfonate such as trifluoromethanesulfonate, with bispinacol diborane (Bpin)$_2$ under palladium catalysis and a Yb$_1$-Y$_1$ derivative wherein Y$_{b1}$ can be a boron-derived functional group, as for example B(OH)$_2$ or B(OR$_{b2}$)$_2$ wherein R$_{b2}$ can be a C$_1$-C$_6$alkyl group or the two groups OR$_{b2}$ can form together with the boron atom a five- or six-membered ring, as for example a pinacol boronic ester. The reaction can be catalyzed by a palladium based catalyst, for example tetrakis(triphenylphosphine)-palladium(0), bis(triphenylphosphine) palladium(II) dichloride or (1,1'bis(diphenylphosphino)-ferrocene)dichloropalladium-dichloromethane (1:1 complex), in presence of a base, like sodium carbonate or cesium fluoride, in a solvent (such as 1,2-dimethoxyethane, tetrahydrofuran or dioxane) or a solvent mixture, like, for example a mixture of 1,2-dimethoxyethane and water, or of dioxane and water, preferably under inert atmosphere. The reaction temperature can preferentially range from ambient temperature to the boiling point of the reaction mixture, or alternatively heating may be performed under microwave irradiation. This reaction is known as Suzuki cross-coupling. Such Suzuki reactions are well known to those skilled in the art and have been reviewed, for example *J. Orgmet. Chem.* 576, 1999, 147-168 or, Kurti, Laszlo; Czako, Barbara; (Editors) Strategic Applications of Named Reactions in Organic Synthesis (2005) p 448.

Alternatively, compounds of formula IXd, wherein X, R$_1$, R$_2$, R$_4$, R$_5$, R$_9$, R$_{10}$, R$_{18}$ and A are as defined in formula I above and wherein Qb' is selected from $Q_{1b}'$ and $Q_{2b}'$ wherein Y$_1$ is a group of formula XIV can be prepared by a Stille reaction of compounds of formula Yb$_2$—Y$_1$ derivative wherein Y$_{b2}$ is a trialkyl tin derivative, preferably tri-n-butyl tin, with compounds of formula IX wherein X, R$_1$, R$_2$, R$_4$, R$_5$, R$_9$, R$_{10}$, R$_{18}$ and A are as defined in formula I above and wherein Qb is selected from $Q_{1b}$ and $Q_{2b}$ wherein Y is leaving group, for example, chlorine, bromine or iodine (preferably bromine), or an aryl- or alkylsulfonate such as trifluoromethanesulfonate. Such Stille reactions are usually carried out in the presence of a palladium catalyst, for example tetrakis(triphenylphosphine)palladium(0), or (1,1'bis(diphenylphosphino)-ferrocene)dichloropalladium-dichloromethane (1:1 complex), in an inert solvent such as DMF, acetonitrile, or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.*, 2005, 70, 8601-8604, *J. Org. Chem.*, 2009, 74, 5599-5602, and *Angew. Chem. Int. Ed.*, 2004, 43, 1132-1136. Other alternatives are possible such as Heck coupling (see for example: Proceedings (Electrochemical Society) 2006, p 2004-24 or Kurti, Laszlo; Czako, Barbara; (Editors) Strategic Applications of Named Reactions in Organic Synthesis (2005) p 196) or Negishi cross coupling (see for example: or Kurti, Laszlo; Czako, Barbara; (Editors) Strategic Applications of Named Reactions in Organic Synthesis (2005) p 310). See scheme 14.

Scheme 14

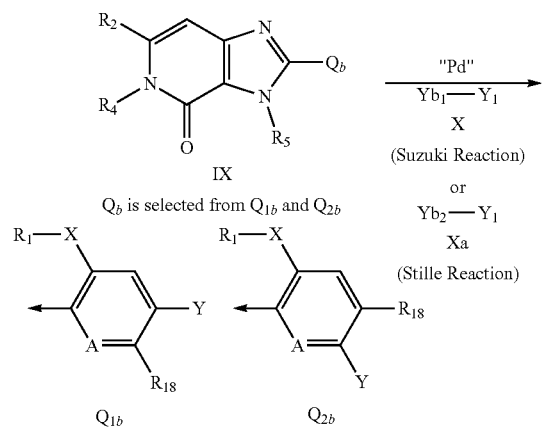

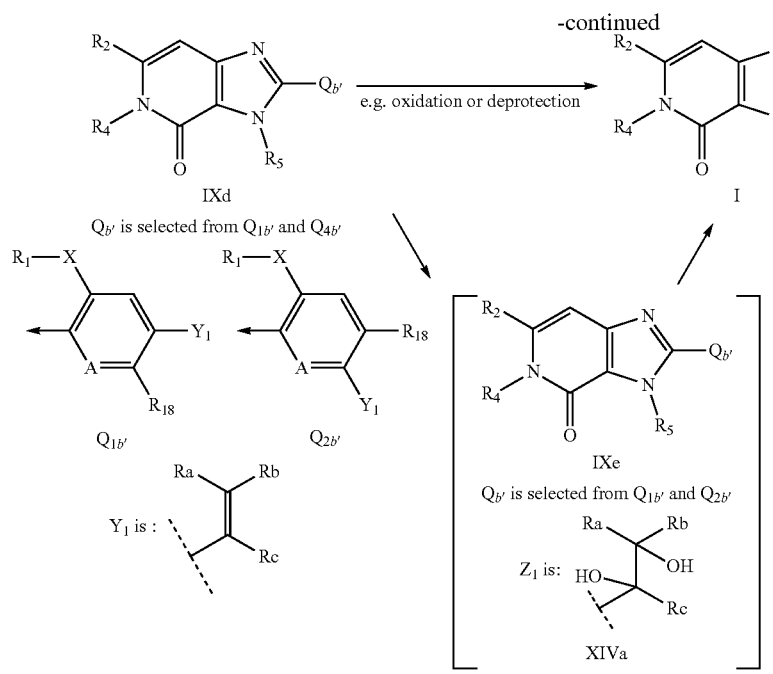

Compounds of formula I wherein X, $R_1$, $R_2$, $R_4$, $R_5$, $R_9$, $R_{10}$, $R_{18}$ and A are as defined in formula I above and wherein $R_7$ is selected from $Q_{13}$ and $Q_{14}$, can prepared (as shown in scheme 15) by reaction of compounds of formula IXb wherein X, $R_1$, $R_2$, $R_4$, $R_5$, $R_9$, $R_{10}$, $R_{18}$ and A are as defined March's Advanced Organic Chemistry: Reactions, Mechanisms, and Structure, 5th Edition;

Smith, Michael B.; March, Jerry p 1185; Tetrahedron: Asymmetry 2008, 19(1), 93-96;

Scheme 15

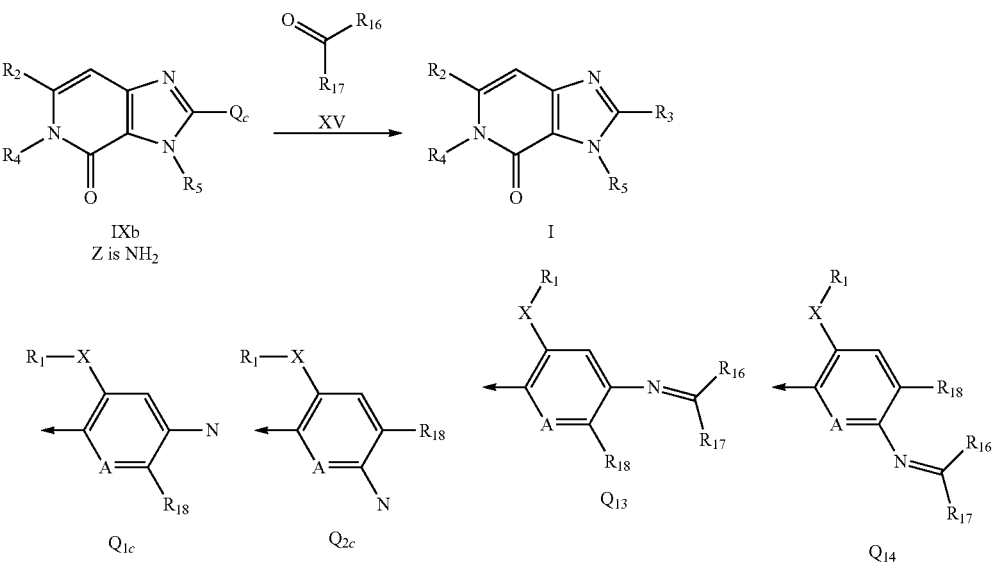

in formula I and where in $Q_c$ is selected from $Q_{1c}$ and $Q_{2c}$, with a compound of formula XV wherein $R_{16}$ and $R_{17}$ are as defined in formula I. Generally, these reactions are possible using a suitable dehydrating agent such as $TiCl_4$ or method such as distillation azeotropic under heating via refluxing the solvent or microwaves. Such reactions can be carried out under well-established methods, described for example, The subgroup of compounds of the formula I wherein G is $-N(=SR_{14}R_{15})$ defined as the sulfilimine I, wherein X, $R_1$, $R_2$, $R_4$, $R_5$, $R_9$, $R_{10}$, $R_{18}$ and A are as defined in formula I, may be prepared by reacting compounds of the compounds of formula IXb wherein X, $R_1$, $R_2$, $R_4$, $R_5$, $R_9$, $R_{10}$, $R_{18}$ and A are as defined in formula I and where in $Q_c$ is selected from $Q_{1c}$ and $Q_{2c}$, under imination reaction conditions (step A, Scheme 16). The particular subgroup of compounds of the formula I wherein X is —N═S(O)$R_{14}R_{15}$ defined as the sulfoximine I, may be obtained by oxidation of the sulfilimine compounds of the formula Ib, as defined above (step B). See scheme 16.

for example, in O. G. Mancheno, C. Bolm, Org. Lett. 2007, 9, 3809-3811. An example of hypochlorite salts being used as oxidant, such as sodium hypochlorite NaOCl, was described in WO 2008/106006.

Scheme 16

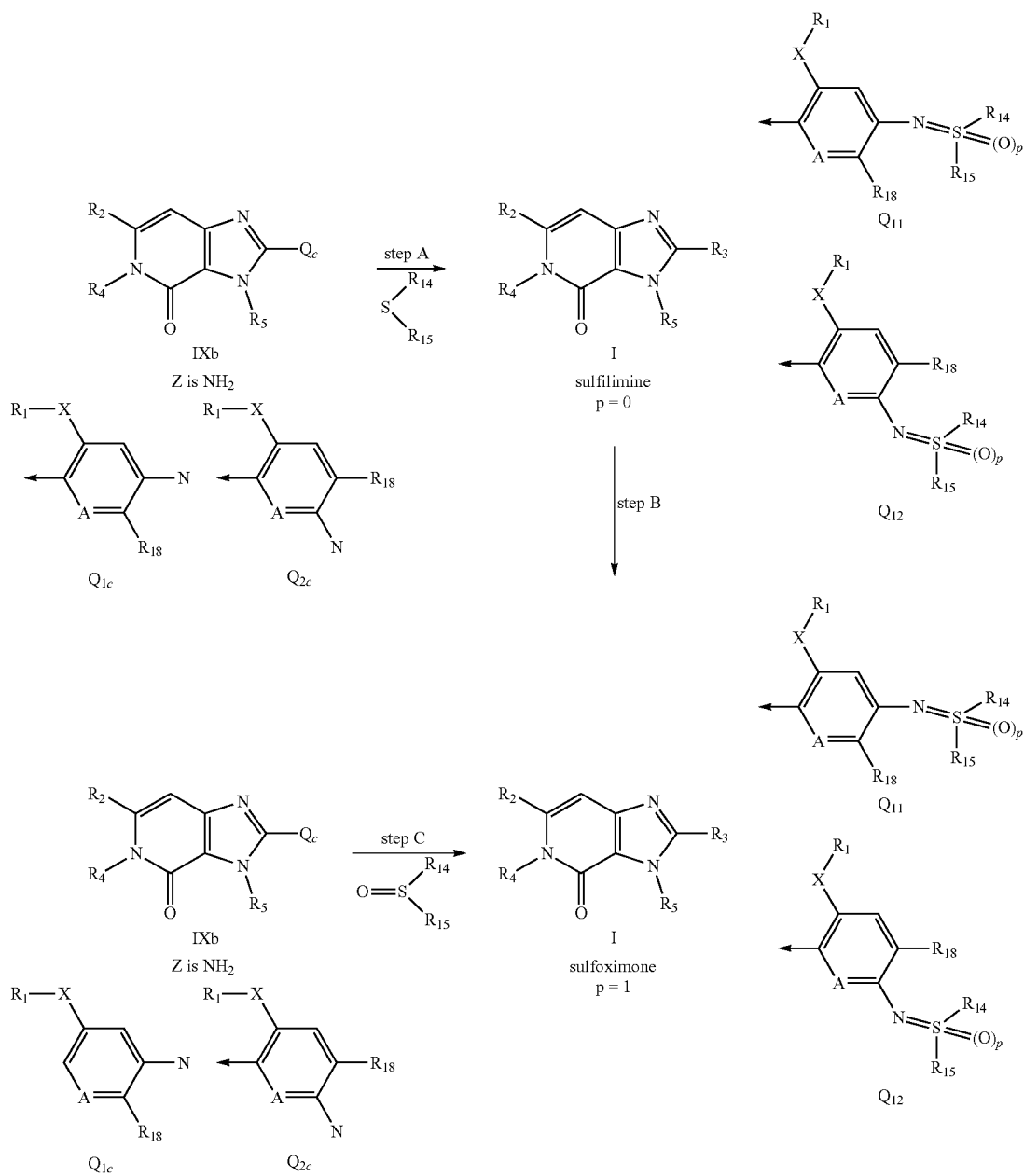

Typical preparation methods and reaction conditions to access the sulfilimines I (step A) or the sulfilimines I (step C), involve $SR_{14}R_{15}$ or $(O)SR_{14}R_{15}$ and an oxidant, for example, PhI(OAc)2 as described in G. Y. Cho, C. Bolm, Tetrahedron Lett. 2005, 46, 8007-8008; or N-bromosuccinimide (NBS) and a base such as sodium or potassium ter-butoxide as described in C. Bolm et al., Synthesis 2010, No 17, 2922-2925. Oxidants such as N-iodosuccinimide (NIS) or iodine may be also used alternatively as described, Typical preparation methods and reaction conditions to access the sulfoximines I (step B) from compounds of formula I (sulfilimines I), wherein X, $R_1$, $R_2$, $R_4$, $R_5$, $R_9$, $R_{10}$, $R_{18}$ and A are classical oxidation reagents such as $KMnO_4$, mCPBA, $NaIO_4/RuO_2$, $H_2O_2$, oxone. Such reactions can be carried out under well-established methods, described for example, in Journal of Organic Chemistry 1979, p 2510; Monatshefte fuer Chemie 1985, 116(10), 1153-64.

Scheme 16b

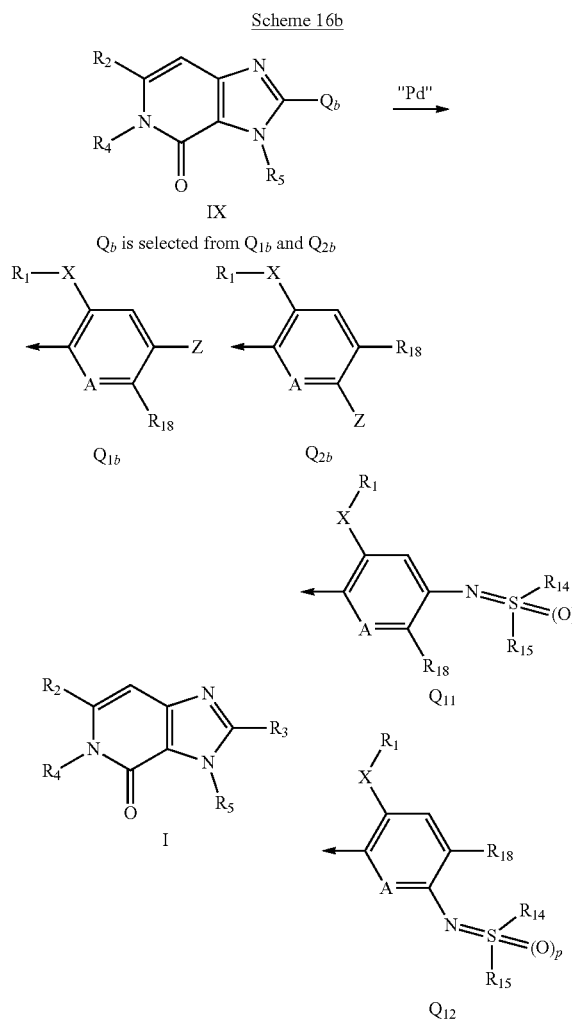

Scheme 17

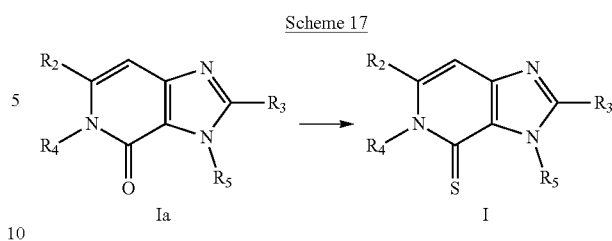

Alternatively, the O of the C(O) can be transformed on S on previews intermediate such as for example, compounds of formula IX, IXc or IXd.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents. The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Alternatively, compounds of formula I wherein $R_3$ is $Q_{11}$ or $Q_{12}$ wherein p is 1, can be prepared (scheme 16b) by reacting compounds of formula I-1, wherein $R_3$ is $Q_{1b}$ or $Q_{2b}$ wherein Z is halogen such as bromide via a palladium coupling. Such reactions are usually carried out in the presence of a palladium catalyst, for example tetrakis(triphenylphosphine)palladium(0) or (1E,4E)-1,5-diphenylpenta-1,4-dien-3-one; palladium, in an inert solvent such as DMF, acetonitrile, or dioxane, optionally in the presence of an additive ligand, such as rac-BINAP or 5-diphenylphosphanyl-9,9-dimethy-xanthen-4-yl)-diphenyl-phosphane, and optionally in the presence of a base such as cesium carbonate.

Examples of these reactions are described, for example, in RSC Advances 20166 (61) p 55710-55714, Tetrahedron Letters 1998 39(32) p 5731-5734 or Journal of Organic Chemistry 2000 65(1) p 169-175.

Compounds of formula I, wherein Y is S, can be prepared (scheme 17) by reacting compounds of formula I-1, wherein Y is O with a reagent that could transfer a sulphur atom such as, for example, the Lawesson's reagent in a solvent such as, for example dimethylformamide or toluene, usually at temperature between 50 to 150° C. This type of transformation is known to a person skilled in the art and are, for example, described in Tetrahedron (2007), 63(48), 11862-11877 or US20120309796.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and herein below, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 10 below can be prepared according to the methods described above. The examples which follow are intended to illustrate the invention and show preferred compounds of formula I.

Table 1: This table discloses the 10 compounds 1.001 to 1.010 of the formula I-1a:

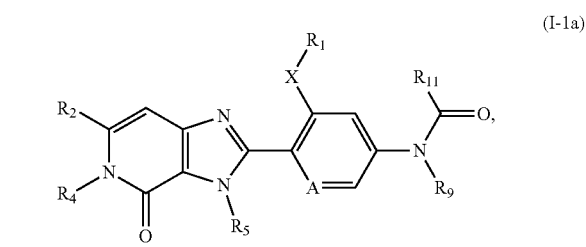

(I-1a)

wherein X is S, $R_4$ is $CH_3$, $R_5$ is $CH_3$, $R_2$ is $CF_3$ and $R_9$, $R_1$, $R_{11}$ and A are as defined below:

TABLE 1

| Comp. No | A | $R_9$ | $R_{11}$ | $R_1$ |
|---|---|---|---|---|
| 1.001 | CH | H | $C_3H_5$ | —$CH_2CH_3$ |
| 1.002 | CH | $CH_3$ | $C_3H_5$ | —$CH_2CH_3$ |
| 1.003 | CH | $SO_2CH_3$ | $C_3H_5$ | —$CH_2CH_3$ |
| 1.004 | CH | $SO_2N(CH_3)_2$ | $C_3H_5$ | —$CH_2CH_3$ |
| 1.005 | CH | H | $CH_3$ | —$CH_2CH_3$ |
| 1.006 | N | H | $C_3H_5$ | —$CH_2CH_3$ |
| 1.007 | N | $CH_3$ | $C_3H_5$ | —$CH_2CH_3$ |
| 1.008 | N | $SO_2CH_3$ | $C_3H_5$ | —$CH_2CH_3$ |
| 1.009 | N | $SO_2N(CH_3)_2$ | $C_3H_5$ | —$CH_2CH_3$ |
| 1.010 | N | H | $CH_3$ | —$CH_2CH_3$ | and the N-oxides of the compounds of Table 1. $C_3H_5$ is cyclopropyl.

Table 2: This table discloses the 10 compounds 2.001 to 2.010 of the formula I-1a, wherein X is SO, and $R_4$ is $CH_3$, $R_5$ is $CH_3$, $R_2$ is $CF_3$ and $R_9$, $R_1$, $R_{11}$ and A are as defined in Table 1.

Table 3: This table discloses the 10 compounds 3.001 to 3.010 of the formula I-1a, wherein X is $SO_2$, and $R_4$ is $CH_3$, $R_5$ is $CH_3$, $R_2$ is $CF_3$ and $R_9$, $R_1$, $R_{11}$ and A are as defined in Table 1.

Table 4: This table discloses the 10 compounds 4.001 to 4.010 of the formula I-2a:

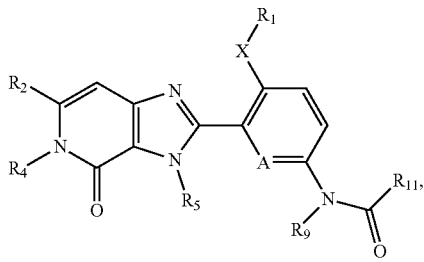

(I-2a)

wherein X is S, $R_4$ is $CH_3$, $R_5$ is $CH_3$, $R_2$ is $CF_3$ and $R_9$, $R_1$, $R_{11}$ and A are as defined below:

TABLE 4

| Comp. No | A | $R_9$ | $R_{11}$ | $R_1$ |
|---|---|---|---|---|
| 4.001 | CH | H | $C_3H_5$ | —$CH_2CH_3$ |
| 4.002 | CH | $CH_3$ | $C_3H_5$ | —$CH_2CH_3$ |
| 4.003 | CH | $SO_2CH_3$ | $C_3H_5$ | —$CH_2CH_3$ |
| 4.004 | CH | $SO_2N(CH_3)_2$ | $C_3H_5$ | —$CH_2CH_3$ |
| 4.005 | CH | H | $CH_3$ | —$CH_2CH_3$ |
| 4.006 | N | H | $C_3H_5$ | —$CH_2CH_3$ |
| 4.007 | N | $CH_3$ | $C_3H_5$ | —$CH_2CH_3$ |
| 4.008 | N | $SO_2CH_3$ | $C_3H_5$ | —$CH_2CH_3$ |
| 4.009 | N | $SO_2N(CH_3)_2$ | $C_3H_5$ | —$CH_2CH_3$ |
| 4.010 | N | H | $CH_3$ | —$CH_2CH_3$ | and the N-oxides of the compounds of Table 4. $C_3H_5$ is cyclopropyl.

Table 5: This table discloses the 10 compounds 5.001 to 5.010 of the formula I-2a, wherein X is SO, and $R_4$ is $CH_3$, $R_5$ is $CH_3$, $R_2$ is $CF_3$ and $R_9$, $R_1$, $R_{11}$ and A are as defined in Table 4.

Table 6: This table discloses the 10 compounds 6.001 to 6.019 of the formula I-2a, wherein X is $SO_2$, and $R_4$ is $CH_3$, $R_5$ is $CH_3$, $R_2$ is $CF_3$ and $R_9$, $R_1$, $R_{11}$ and A are as defined in Table 4.

Table 7: This table discloses the 10 compounds 7.001 to 7.012 of the formula I-3a:

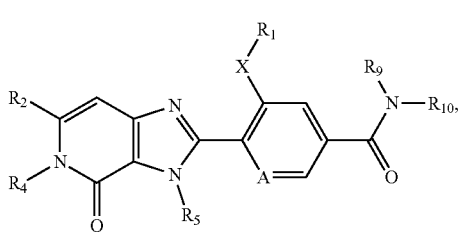

(I-3a)

wherein X is S, $R_4$ is $CH_3$, $R_5$ is $CH_3$, $R_2$ is $CF_3$ and $R_9$, $R_1$, $R_{10}$ and A are as defined below:

TABLE 7

| Comp. No | A | $R_9$ | $R_{10}$ | $R_1$ |
|---|---|---|---|---|
| 7.001 | CH | H | $C_3H_5$ | —$CH_2CH_3$ |
| 7.002 | CH | $CH_3$ | $C_3H_5$ | —$CH_2CH_3$ |
| 7.003 | CH | $SO_2CH_3$ | $C_3H_5$ | —$CH_2CH_3$ |
| 7.004 | CH | H | $CH_3$ | —$CH_2CH_3$ |
| 7.005 | CH | $CH_3$ | $CH_3$ | —$CH_2CH_3$ |
| 7.006 | CH | $SO_2CH_3$ | $CH_3$ | —$CH_2CH_3$ |
| 7.007 | N | H | $C_3H_5$ | —$CH_2CH_3$ |
| 7.008 | N | $CH_3$ | $C_3H_5$ | —$CH_2CH_3$ |
| 7.009 | N | $SO_2CH_3$ | $C_3H_5$ | —$CH_2CH_3$ |
| 7.010 | N | H | $CH_3$ | —$CH_2CH_3$ |
| 7.011 | N | $CH_3$ | $CH_3$ | —$CH_2CH_3$ |
| 7.012 | N | $SO_2CH_3$ | $CH_3$ | —$CH_2CH_3$ | and the N-oxides of the compounds of Table 7. $C_3H_5$ is cyclopropyl.

Table 8: This table discloses the 12 compounds 8.001 to 8.012 of the formula I-3a, wherein X is SO, and $R_4$ is $CH_3$, $R_5$ is $CH_3$, $R_2$ is $CF_3$ and $R_9$, $R_1$, $R_{10}$ and A are as defined in Table 7.

Table 9: This table discloses the 12 compounds 9.001 to 9.012 of the formula I-3a, wherein X is $SO_2$, and $R_4$ is $CH_3$, $R_5$ is $CH_3$, $R_2$ is $CF_3$ and $R_9$, $R_1$, $R_{10}$ and A are as defined in Table 7.

Table 10: This table discloses the 12 compounds 10.001 to 10.012 of the formula I-4a:

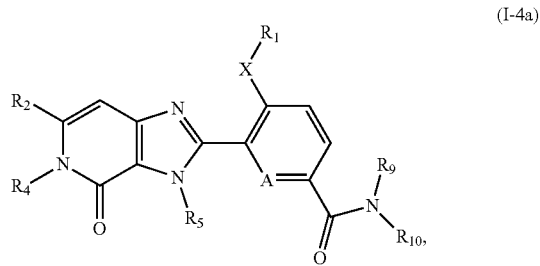

(I-4a)

wherein X is S, $R_4$ is $CH_3$, $R_5$ is $CH_3$, $R_2$ is $CF_3$ and $R_9$, $R_1$, $R_{11}$ and A are as defined below:

TABLE 10

| Comp. No | A | $R_9$ | $R_{10}$ | $R_1$ |
|---|---|---|---|---|
| 10.001 | CH | H | $C_3H_5$ | —$CH_2CH_3$ |
| 10.002 | CH | $CH_3$ | $C_3H_5$ | —$CH_2CH_3$ |
| 10.003 | CH | $SO_2CH_3$ | $C_3H_5$ | —$CH_2CH_3$ |
| 10.004 | CH | H | $CH_3$ | —$CH_2CH_3$ |
| 10.005 | CH | $CH_3$ | $CH_3$ | —$CH_2CH_3$ |
| 10.006 | CH | $SO_2CH_3$ | $CH_3$ | —$CH_2CH_3$ |
| 10.007 | N | H | $C_3H_5$ | —$CH_2CH_3$ |
| 10.008 | N | $CH_3$ | $C_3H_5$ | —$CH_2CH_3$ |
| 10.009 | N | $SO_2CH_3$ | $C_3H_5$ | —$CH_2CH_3$ |
| 10.010 | N | H | $CH_3$ | —$CH_2CH_3$ |
| 10.011 | N | $CH_3$ | $CH_3$ | —$CH_2CH_3$ |
| 10.012 | N | $SO_2CH_3$ | $CH_3$ | —$CH_2CH_3$ | and the N-oxides of the compounds of Table 10. $C_3H_5$ is cyclopropyl.

Table 11: This table discloses the 12 compounds 11.001 to 11.012 of the formula I-4a, wherein X is SO, and $R_4$ is $CH_3$, $R_5$ is $CH_3$, $R_2$ is $CF_3$ and $R_9$, $R_1$, $R_{11}$ and A are as defined in Table 10.

Table 12: This table discloses the 12 compounds 12.001 to 12.012 of the formula I-4a, wherein X is $SO_2$, and $R_4$ is $CH_3$, $R_5$ is $CH_3$, $R_2$ is $CF_3$ and $R_9$, $R_1$, $R_{11}$ and A are as defined in Table 10.

Table 13: This table discloses the 10 compounds 13.001 to 13.010 of the formula I-5a:

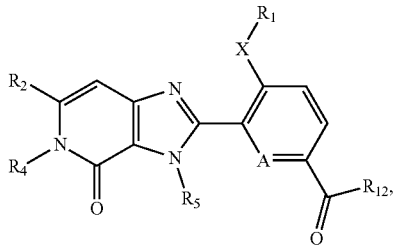

wherein X is S, $R_4$ is $CH_3$, $R_5$ is $CH_3$, $R_2$ is $CF_3$ and $R_1$, $R_{12}$ and A are as defined below:

TABLE 13

| Comp. No | A | $R_{12}$ | $R_1$ |
|---|---|---|---|
| 13.001 | CH | OH | —$CH_2CH_3$ |
| 13.002 | CH | $OCH_3$ | —$CH_2CH_3$ |
| 13.003 | CH | H | —$CH_2CH_3$ |
| 13.004 | CH | $CH_3$ | —$CH_2CH_3$ |
| 13.005 | CH | $OCH_2CH_3$ | —$CH_2CH_3$ |
| 13.006 | N | OH | —$CH_2CH_3$ |
| 13.007 | N | $OCH_3$ | —$CH_2CH_3$ |
| 13.008 | N | H | —$CH_2CH_3$ |
| 13.009 | N | $CH_3$ | —$CH_2CH_3$ |
| 13.010 | N | $OCH_2CH_3$ | —$CH_2CH_3$ | and the N-oxides of the compounds of Table 13.

Table 14: This table discloses the 10 compounds 14.001 to 14.010 of the formula I-5a, wherein X is SO, and $R_4$ is $CH_3$, $R_5$ is $CH_3$, $R_2$ is $CF_3$ and $R_1$, $R_{12}$ and A are as defined in Table 13.

Table 15: This table discloses the 10 compounds 15.001 to 15.010 of the formula I-5a, wherein X is $SO_2$, and $R_4$ is $CH_3$, $R_5$ is $CH_3$, $R_2$ is $CF_3$ and $R_1$, $R_{12}$ and A are as defined in Table 13.

Table 16: This table discloses the 10 compounds 16.001 to 16.010 of the formula I-6a:

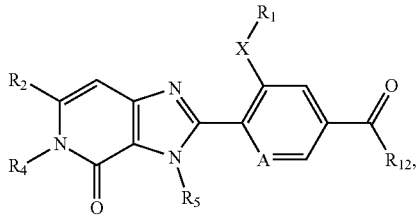

wherein X is S, $R_4$ is $CH_3$, $R_5$ is $CH_3$, $R_2$ is $CF_3$ and $R_9$, $R_1$, $R_{12}$ and A are as defined below:

TABLE 16

| Comp. No | A | $R_{12}$ | $R_1$ |
|---|---|---|---|
| 16.001 | CH | OH | —$CH_2CH_3$ |
| 16.002 | CH | $OCH_3$ | —$CH_2CH_3$ |
| 16.003 | CH | H | —$CH_2CH_3$ |
| 16.004 | CH | $CH_3$ | —$CH_2CH_3$ |
| 16.005 | CH | $OCH_2CH_3$ | —$CH_2CH_3$ |
| 16.006 | N | OH | —$CH_2CH_3$ |
| 16.007 | N | $OCH_3$ | —$CH_2CH_3$ |
| 16.008 | N | H | —$CH_2CH_3$ |
| 16.009 | N | $CH_3$ | —$CH_2CH_3$ |
| 16.010 | N | $OCH_2CH_3$ | —$CH_2CH_3$ | and the N-oxides of the compounds of Table 16.

Table 17: This table discloses the 10 compounds 17.001 to 17.010 of the formula I-6a, wherein X is SO, and $R_4$ is $CH_3$, $R_5$ is $CH_3$, $R_2$ is $CF_3$ and $R_9$, $R_1$, $R_{12}$ and A are as defined in Table 16.

Table 18: This table discloses the 10 compounds 18.001 to 18.010 of the formula I-6a, wherein X is $SO_2$, and $R_4$ is $CH_3$, $R_5$ is $CH_3$, $R_2$ is $CF_3$ and $R_9$, $R_1$, $R_{12}$ and A are as defined in Table 16.

Table 19: This table discloses the 12 compounds 19.001 to 19.012 of the formula I-7a:

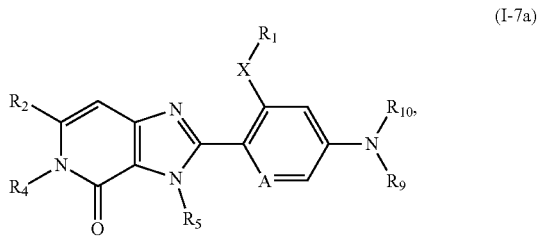

wherein X is S, $R_4$ is $CH_3$, $R_5$ is $CH_3$, $R_2$ is $CF_3$ and $R_9$, $R_1$, $R_{10}$ and A are as defined below:

TABLE 19

| Comp. No | A | $R_9$ | $R_{10}$ | $R_1$ |
|---|---|---|---|---|
| 19.001 | CH | H | $C_3H_5$ | —$CH_2CH_3$ |
| 19.002 | CH | $CH_3$ | $C_3H_5$ | —$CH_2CH_3$ |
| 19.003 | CH | $SO_2CH_3$ | $C_3H_5$ | —$CH_2CH_3$ |
| 19.004 | N | H | $C_3H_5$ | —$CH_2CH_3$ |
| 19.005 | N | $CH_3$ | $C_3H_5$ | —$CH_2CH_3$ |
| 19.006 | N | $SO_2CH_3$ | $C_3H_5$ | —$CH_2CH_3$ |
| 19.007 | CH | H | $CH_3$ | —$CH_2CH_3$ |
| 19.008 | CH | $CH_3$ | $CH_3$ | —$CH_2CH_3$ |
| 19.009 | CH | $SO_2CH_3$ | $CH_3$ | —$CH_2CH_3$ |
| 19.010 | N | H | $CH_3$ | —$CH_2CH_3$ |
| 19.011 | N | $CH_3$ | $CH_3$ | —$CH_2CH_3$ |
| 19.012 | N | $SO_2CH_3$ | $CH_3$ | —$CH_2CH_3$ | and the N-oxides of the compounds of Table 19. $C_3H_5$ is cyclopropyl.

Table 20: This table discloses the 12 compounds 20.001 to 20.012 of the formula I-7a, wherein X is SO, and $R_4$ is $CH_3$, $R_5$ is $CH_3$, $R_2$ is $CF_3$ and $R_9$, $R_1$, $R_{10}$ and A are as defined in Table 19.

Table 21: This table discloses the 12 compounds 21.001 to 21.012 of the formula I-7a, wherein X is $SO_2$, and $R_4$ is $CH_3$, $R_5$ is $CH_3$, $R_2$ is $CF_3$ and $R_9$, $R_1$, $R_{10}$ and A are as defined in Table 19.

Table 22: This table discloses the 12 compounds 22.001 to 22.012 of the formula I-8a:

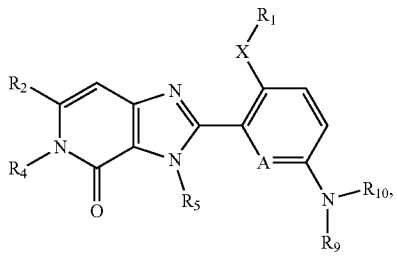

(I-8a)

wherein X is S, $R_4$ is $CH_3$, $R_5$ is $CH_3$, $R_2$ is $CF_3$ and $R_9$, $R_1$, $R_{10}$ and A are as defined below:

TABLE 22

| Comp. No | A | $R_9$ | $R_{10}$ | $R_1$ |
|---|---|---|---|---|
| 22.001 | CH | H | $C_3H_5$ | —$CH_2CH_3$ |
| 22.002 | CH | $CH_3$ | $C_3H_5$ | —$CH_2CH_3$ |
| 22.003 | CH | $SO_2CH_3$ | $C_3H_5$ | —$CH_2CH_3$ |
| 22.004 | N | H | $C_3H_5$ | —$CH_2CH_3$ |
| 22.005 | N | $CH_3$ | $C_3H_5$ | —$CH_2CH_3$ |
| 22.006 | N | $SO_2CH_3$ | $C_3H_5$ | —$CH_2CH_3$ |
| 22.007 | CH | H | $CH_3$ | —$CH_2CH_3$ |
| 22.008 | CH | $CH_3$ | $CH_3$ | —$CH_2CH_3$ |
| 22.009 | CH | $SO_2CH_3$ | $CH_3$ | —$CH_2CH_3$ |
| 22.010 | N | H | $CH_3$ | —$CH_2CH_3$ |
| 22.011 | N | $CH_3$ | $CH_3$ | —$CH_2CH_3$ |
| 22.012 | N | $SO_2CH_3$ | $CH_3$ | —$CH_2CH_3$ | and the N-oxides of the compounds of Table 22. $C_3H_5$ is cyclopropyl.

Table 23: This table discloses the 12 compounds 23.001 to 23.012 of the formula I-8a, wherein X is SO, and $R_4$ is $CH_3$, $R_5$ is $CH_3$, $R_2$ is $CF_3$ and $R_9$, $R_1$, $R_{10}$ and A are as defined in Table 22.

Table 24: This table discloses the 12 compounds 24.001 to 24.012 of the formula I-8a, wherein X is $SO_2$, and $R_4$ is $CH_3$, $R_5$ is $CH_3$, $R_2$ is $CF_3$ and $R_9$, $R_1$, $R_{10}$ and A are as defined in Table 22.

Table 25: This table discloses the 12 compounds 25.001 to 25.012 of the formula I-9a:

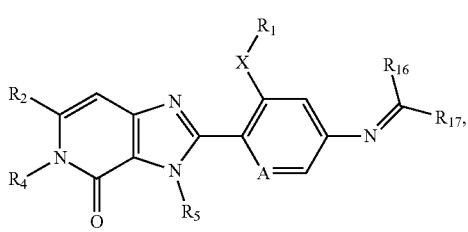

(I-9a)

wherein X is S, $R_4$ is $CH_3$, $R_5$ is $CH_3$, $R_2$ is $CF_3$ and $R_1$, $R_{16}$, $R_{17}$ and A are as defined below:

TABLE 25

| Comp. No | A | $R_{16}$ | $R_{17}$ | $R_1$ |
|---|---|---|---|---|
| 25.001 | CH | H | $C_3H_5$ | —$CH_2CH_3$ |
| 25.002 | CH | $CH_3$ | $C_3H_5$ | —$CH_2CH_3$ |
| 25.003 | CH | H | $CH_3$ | —$CH_2CH_3$ |
| 25.004 | CH | $CH_3$ | $CH_3$ | —$CH_2CH_3$ |
| 25.005 | CH | H | $NHOCH_3$ | —$CH_2CH_3$ |
| 25.006 | CH | $CH_3$ | $NHOCH_3$ | —$CH_2CH_3$ |
| 25.007 | N | H | $C_3H_5$ | —$CH_2CH_3$ |
| 25.008 | N | $CH_3$ | $C_3H_5$ | —$CH_2CH_3$ |
| 25.009 | N | H | $CH_3$ | —$CH_2CH_3$ |
| 25.010 | N | $CH_3$ | $CH_3$ | —$CH_2CH_3$ |
| 25.011 | N | H | $NHOCH_3$ | —$CH_2CH_3$ |
| 25.012 | N | $CH_3$ | $NHOCH_3$ | —$CH_2CH_3$ | and the N-oxides of the compounds of Table 25. $C_3H_5$ is cyclopropyl.

Table 26: This table discloses the 12 compounds 26.001 to 26.012 of the formula I-9a, wherein X is SO, and $R_4$ is $CH_3$, $R_5$ is $CH_3$, $R_2$ is $CF_3$ and $R_1$, $R_{16}$, $R_{17}$ and A are as defined in Table 25.

Table 27: This table discloses the 12 compounds 27.001 to 27.012 of the formula I-9a, wherein X is $SO_2$, and $R_4$ is $CH_3$, $R_5$ is $CH_3$, $R_2$ is $CF_3$ and $R_1$, $R_{16}$, $R_{17}$ and A are as defined in Table 25.

Table 28: This table discloses the 12 compounds 28.001 to 28.012 of the formula I-10a:

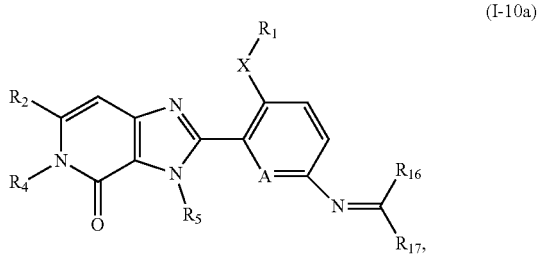

(I-10a)

wherein X is S, $R_4$ is $CH_3$, $R_5$ is $CH_3$, $R_2$ is $CF_3$ and $R_1$, $R_{16}$, $R_{17}$ and A are as defined below:

TABLE 28

| Comp. No | A | $R_{16}$ | $R_{17}$ | $R_1$ |
|---|---|---|---|---|
| 28.001 | CH | H | $C_3H_5$ | —$CH_2CH_3$ |
| 28.002 | CH | $CH_3$ | $C_3H_5$ | —$CH_2CH_3$ |
| 28.003 | CH | H | $CH_3$ | —$CH_2CH_3$ |
| 28.004 | CH | $CH_3$ | $CH_3$ | —$CH_2CH_3$ |
| 28.005 | CH | H | $NHOCH_3$ | —$CH_2CH_3$ |
| 28.006 | CH | $CH_3$ | $NHOCH_3$ | —$CH_2CH_3$ |
| 28.007 | N | H | $C_3H_5$ | —$CH_2CH_3$ |
| 28.008 | N | $CH_3$ | $C_3H_5$ | —$CH_2CH_3$ |
| 28.009 | N | H | $CH_3$ | —$CH_2CH_3$ |
| 28.010 | N | $CH_3$ | $CH_3$ | —$CH_2CH_3$ |
| 28.011 | N | H | $NHOCH_3$ | —$CH_2CH_3$ |
| 28.012 | N | $CH_3$ | $NHOCH_3$ | —$CH_2CH_3$ | and the N-oxides of the compounds of Table 28. $C_3H_5$ is cyclopropyl.

Table 29: This table discloses the 12 compounds 29.001 to 29.012 of the formula I-10a, wherein X is SO, and $R_4$ is $CH_3$, $R_5$ is $CH_3$, $R_2$ is $CF_3$ and $R_1$, $R_{16}$, $R_{17}$ and A are as defined in Table 28.

Table 30: This table discloses the 12 compounds 30.001 to 30.012 of the formula I-10a, wherein X is $SO_2$, and $R_4$ is $CH_3$, $R_5$ is $CH_3$, $R_2$ is $CF_3$ and $R_1$, $R_{16}$, $R_{17}$ and A are as defined in Table 28.

Table 31: This table discloses the 8 compounds 31.001 to 31.008 of the formula I-11a:

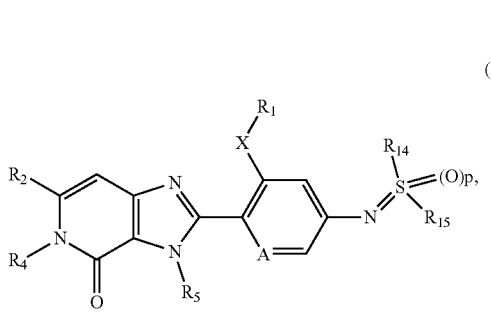

(I-11a)

wherein X is S, $R_4$ is $CH_3$, $R_5$ is $CH_3$, $R_2$ is $CF_3$ and p, $R_1$, $R_{14}$, $R_{15}$ and A are as defined below:

TABLE 31

| Comp. No | A | $R_{14}$ | $R_{15}$ | p | $R_1$ |
|---|---|---|---|---|---|
| 31.001 | CH | $CH_3$ | $C_3H_5$ | 0 | —$CH_2CH_3$ |
| 31.002 | CH | $CH_3$ | $CH_3$ | 0 | —$CH_2CH_3$ |
| 31.003 | CH | $CH_3$ | $C_3H_5$ | 1 | —$CH_2CH_3$ |
| 31.004 | CH | $CH_3$ | $CH_3$ | 1 | —$CH_2CH_3$ |
| 31.005 | N | $CH_3$ | $C_3H_5$ | 0 | —$CH_2CH_3$ |
| 31.006 | N | $CH_3$ | $CH_3$ | 0 | —$CH_2CH_3$ |
| 31.007 | N | $CH_3$ | $C_3H_5$ | 1 | —$CH_2CH_3$ |
| 31.008 | N | $CH_3$ | $CH_3$ | 1 | —$CH_2CH_3$ | and the N-oxides of the compounds of Table 31. $C_3H_5$ is cyclopropyl.

Table 32: This table discloses the 8 compounds 32.001 to 32.008 of the formula I-11a, wherein X is SO, and $R_4$ is $CH_3$, $R_5$ is $CH_3$, $R_2$ is $CF_3$ and p, $R_1$, $R_{14}$, $R_{15}$ and A are as defined in Table 31.

Table 33: This table discloses the 8 compounds 33.001 to 33.008 of the formula I-11a, wherein X is $SO_2$, and $R_4$ is $CH_3$, $R_5$ is $CH_3$, $R_2$ is $CF_3$ and p, $R_1$, $R_{14}$, $R_{15}$ and A are as defined in Table 31.

Table 34: This table discloses the 8 compounds 34.001 to 34.008 of the formula I-12a:

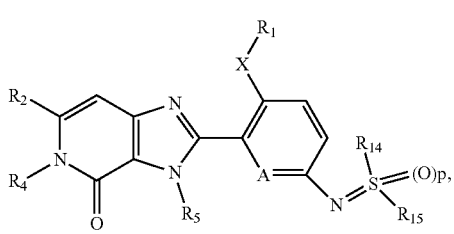

(I-12a)

wherein X is S, $R_4$ is $CH_3$, $R_5$ is $CH_3$, $R_2$ is $CF_3$ and p, $R_1$, $R_{14}$, $R_{15}$ and A are as defined below:

TABLE 34

| Comp. No | A | $R_{14}$ | $R_{15}$ | p | $R_1$ |
|---|---|---|---|---|---|
| 34.001 | CH | $CH_3$ | $C_3H_5$ | 0 | —$CH_2CH_3$ |
| 34.002 | CH | $CH_3$ | $CH_3$ | 0 | —$CH_2CH_3$ |
| 34.003 | CH | $CH_3$ | $C_3H_5$ | 1 | —$CH_2CH_3$ |
| 34.004 | CH | $CH_3$ | $CH_3$ | 1 | —$CH_2CH_3$ |
| 34.005 | N | $CH_3$ | $C_3H_5$ | 0 | —$CH_2CH_3$ |
| 34.006 | N | $CH_3$ | $CH_3$ | 0 | —$CH_2CH_3$ |
| 34.007 | N | $CH_3$ | $C_3H_5$ | 1 | —$CH_2CH_3$ |
| 34.008 | N | $CH_3$ | $CH_3$ | 1 | —$CH_2CH_3$ | and the N-oxides of the compounds of Table 34. $C_3H_5$ is cyclopropyl.

Table 35: This table discloses the 8 compounds 35.001 to 35.008 of the formula I-12a, wherein X is SO, and $R_4$ is $CH_3$, $R_5$ is $CH_3$, $R_2$ is $CF_3$ and p, $R_1$, $R_{14}$, $R_{15}$ and A are as defined in Table 34.

Table 36: This table discloses the 8 compounds 36.001 to 36.008 of the formula I-12a, wherein X is $SO_2$, and $R_4$ is $CH_3$, $R_5$ is $CH_3$, $R_2$ is $CF_3$ and p, $R_1$, $R_{14}$, $R_{15}$ and A are as defined in Table 34.

Table 37: This table discloses the 6 compounds 37.001 to 37.006 of the formula I-13a:

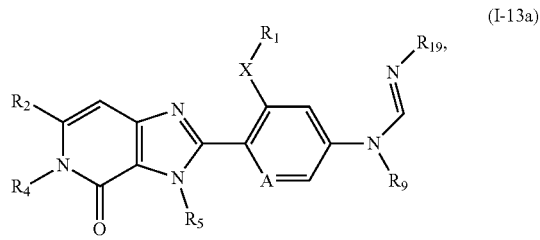

(I-13a)

wherein X is S, $R_4$ is $CH_3$, $R_5$ is $CH_3$, $R_2$ is $CF_3$ and $R_1$, $R_9$, $R_{19}$ and A are as defined below:

TABLE 37

| Comp. No | A | $R_9$ | $R_{19}$ | $R_1$ |
|---|---|---|---|---|
| 37.001 | CH | $CH_3$ | $CH_3$ | —$CH_2CH_3$ |
| 37.002 | CH | $C_3H_5$ | $CH_3$ | —$CH_2CH_3$ |
| 37.003 | CH | $CH_3$ | $C_3H_5$ | —$CH_2CH_3$ |
| 37.004 | N | $CH_3$ | $CH_3$ | —$CH_2CH_3$ |
| 37.005 | N | $C_3H_5$ | $CH_3$ | —$CH_2CH_3$ |
| 37.006 | N | $CH_3$ | $C_3H_5$ | —$CH_2CH_3$ | and the N-oxides of the compounds of Table 37. $C_3H_5$ is cyclopropyl.

Table 38: This table discloses the 6 compounds 38.001 to 38.006 of the formula I-13a, wherein X is SO, and $R_4$ is $CH_3$, $R_5$ is $CH_3$, $R_2$ is $CF_3$ and $R_1$, $R_9$, $R_{19}$ and A are as defined in Table 37.

Table 39: This table discloses the 6 compounds 39.001 to 39.006 of the formula I-13a, wherein X is $SO_2$, and $R_4$ is $CH_3$, $R_5$ is $CH_3$, $R_2$ is $CF_3$ and $R_1$, $R_9$, $R_{19}$ and A are as defined in Table 37.

Table 40: This table discloses the 6 compounds 40.001 to 40.006 of the formula I-14a:

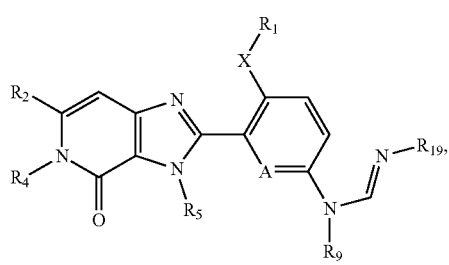

(I-14a)

wherein X is S, $R_4$ is $CH_3$, $R_5$ is $CH_3$, $R_2$ is $CF_3$ and $R_1$, $R_9$, $R_{19}$ and A are as defined below:

TABLE 40

| Comp. No. | A | $R_9$ | $R_{19}$ | $R_1$ |
|---|---|---|---|---|
| 40.001 | CH | $CH_3$ | $CH_3$ | —$CH_2CH_3$ |
| 40.002 | CH | $C_3H_5$ | $CH_3$ | —$CH_2CH_3$ |
| 40.003 | CH | $CH_3$ | $C_3H_5$ | —$CH_2CH_3$ |
| 40.004 | N | $CH_3$ | $CH_3$ | —$CH_2CH_3$ |
| 40.005 | N | $C_3H_5$ | $CH_3$ | —$CH_2CH_3$ |
| 40.006 | N | $CH_3$ | $C_3H_5$ | —$CH_2CH_3$ | and the N-oxides of the compounds of Table 40. $C_3H_5$ is cyclopropyl.

Table 41: This table discloses the 6 compounds 41.001 to 41.006 of the formula I-14a, wherein X is SO, and $R_4$ is $CH_3$, $R_5$ is $CH_3$, $R_2$ is $CF_3$ and $R_1$, $R_9$, $R_{19}$ and A are as defined in Table 40.

Table 42: This table discloses the 6 compounds 42.001 to 42.006 of the formula I-14a, wherein X is $SO_2$, and $R_4$ is $CH_3$, $R_5$ is $CH_3$, $R_2$ is $CF_3$ and $R_1$, $R_9$, $R_{19}$ and A are as defined in Table 40.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,
*Haematopinus* spp., *Linognathus* spp., *Pediculus* spp., *Pemphigus* spp. and *Phylloxera* spp.;

from the order Coleoptera, for example,
*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,
*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,
*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri Mats*, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplo-campa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Grapholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order Thysanura, for example, *Lepisma saccharina*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis*, *Anthemis* spp., *Antirrhinum* spp., *Aster* spp., *Begonia* spp. (e.g. *B. elatior*, *B. semperflorens*, *B. tubéreux*), *Bougainvillea* spp., *Brachycome* spp., *Brassica* spp. (ornamental), *Calceolaria* spp., *Capsicum annuum*, *Catharanthus roseus*, *Canna* spp., *Centaurea* spp., *Chrysanthemum* spp., *Cineraria* spp. (*C. maritime*), *Coreopsis* spp., *Crassula coccinea*, *Cuphea ignea*, *Dahlia* spp., *Delphinium* spp., *Dicentra spectabilis*, *Dorotheantus* spp., *Eustoma grandiflorum*, *Forsythia* spp., *Fuchsia* spp., *Geranium gnaphalium*, *Gerbera* spp., *Gomphrena globosa*, *Heliotropium* spp., *Helianthus* spp., *Hibiscus* spp., *Hortensia* spp., *Hydrangea* spp., *Hypoestes phyllostachya*, *Impatiens* spp. (*I. Walleriana*), *Iresines* spp., *Kalanchoe* spp., *Lantana camara*, *Lavatera trimestris*, *Leonotis leonurus*, *Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum*, *P. Zonale*), *Viola* spp. (pansy), *Petunia* spp., *Phlox* spp., *Plecthranthus* spp., *Poinsettia* spp., *Parthenocissus* spp. (*P. quinquefolia*, *P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola*, *Schizanthus wisetonensis*, *Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum*, *A. cepa*, *A. oschaninii*, *A. Porrum*, *A. ascalonicum*, *A. fistulosum*), *Anthriscus cerefolium*, *Apium graveolus*, *Asparagus officinalis*, *Beta vulgarus*, *Brassica* spp. (*B. Oleracea*, *B. Pekinensis*, *B. rapa*), *Capsicum annuum*, *Cicer arietinum*, *Cichorium endivia*, *Cichorum* spp. (*C. intybus*, *C. endivia*),

*Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba*.

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); Cepaea (*C. hortensis, C. Nemoralis*); ochlodina; *Deroceras* (*D. agrestis, D. empiricorum, D. laeve, D. reticulatum*); *Discus* (*D. rotundatus*); Euomphalia; *Galba* (*G. trunculata*); *Helicelia* (*H. itala, H. obvia*); Helicidae *Helicigona arbustorum*); Helicodiscus; *Helix* (*H. aperta*); *Limax* (*L. cinereoniger, L. flavus, L. marginatus, L. maximus, L. tenellus*); Lymnaea; *Milax* (*M. gagates, M. marginatus, M. sowerbyi*); Opeas; *Pomacea* (*P. canaticulata*); Vallonia and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005/113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |

TABLE B-continued

Examples of native woodborers of economic importance.

| Family | Species | Host or Crop Infested |
| --- | --- | --- |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas. Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattela germanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp.,

*Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate;

sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

| Emulsifiable concentrates: | |
|---|---|
| active ingredient: | 1 to 95%, preferably 60 to 90% |
| surface-active agent: | 1 to 30%, preferably 5 to 20% |
| liquid carrier: | 1 to 80%, preferably 1 to 35% |
| Dusts: | |
| active ingredient: | 0.1 to 10%, preferably 0.1 to 5% |
| solid carrier: | 99.9 to 90%, preferably 99.9 to 99% |

| Suspension concentrates: | |
|---|---|
| active ingredient: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient: | 0.1 to 30%, preferably 0.1 to 15% |
| solid carrier: | 99.5 to 70%, preferably 97 to 85% |

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
| --- | --- | --- | --- |
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
| --- | --- |
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
| --- | --- |
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

| Suspension concentrate | |
| --- | --- |
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
| --- | --- |
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated. Common abbreviations: aq=aqueous, min=minute, h=hour, sat=saturated, RT=retention time, mCPBA=meta-chloroperoxybenzoic acid, MeOH=methanol, EtOH=ethanol, NaHCO$_3$=sodium hydrogen carbonate, Na$_2$CO$_3$=sodium carbonate, HCl=hydrogen chloride, CH$_2$Cl$_2$=dichloromethane, Et$_3$N=triethylamine, DMF=N,N-dimethylformamide. Either one of the LCMS and/or GCMS methods below was used to characterize the compounds. The characteristic LCMS values obtained for each compound were the retention time ("RT", recorded in minutes) and the measured molecular ion (M+H)+.

LCMS and GCMS Methods:

Method A—Standard:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 □m, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

Method B—Standard Long:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 2.7-3.0 min 100% B; Flow (ml/min) 0.85

Method C—Unpolar:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 □m, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 40% B, 60% A; 1.2-1.5 min 100% B; Flow (ml/min) 0.85

Example I1: 4-amino-1-ethyl-3-(methylamino)-6-(trifluoromethyl)pyridin-2-one

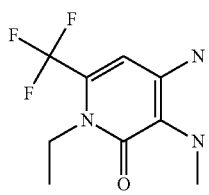 [SMILES: CCn1c(C(F)(F)F)cc(N)c(NC)c1=O]

Step A: 1-ethyl-3-(methylamino)-6-(trifluoromethyl)pyridin-2-one

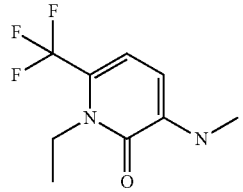

To a solution of 3-amino-1-ethyl-6-(trifluoromethyl)pyridin-2-one (5.00 g, 24.3 mmol, Commercially available or synthesised by analogy with literature, for example, Synthesis 2005, No. 8, pp 1269-1278 and Synthesis 2011, No. 7, pp 1149-1156) in acetonitrile (150 mL) was added formaldehyde (37 mass %) in aqueous solution (14.5 ml, 194 mmol) and acetic acid (6.96 ml, 121 mmol). The resulting suspension stirred for 1 hour, then sodium cyanoborohydride (6.42 g, 97.0 mmol) was added in 5 portions over 3 hours and the mixture was stirred for 18 hours. The solution was diluted with water and extracted with ethyl acetate (3×). The combined organic layer was dried over Sodium sulfate, filtered, concentrated and purified by column chromatography using cyclohexane-ethyl acetate (100-200 silica gel) to give the desired compound as a white solid. $^1$H NMR (400 MHz, CDCl$_3$) δ ppm 6.70 (d, 1H), 6.04 (d, 1H), 5.44 (sb, 1H), 4.15 (q, 2H), 2.85 (s, 3H), 1.32 (t, 3H).

Step B: 1-ethyl-3-(methylamino)-4-nitro-6-(trifluoromethyl)pyridin-2-one

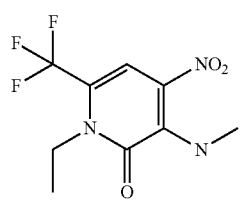 [SMILES: CCn1c(C(F)(F)F)cc([N+](=O)[O-])c(NC)c1=O]

A solution of 1-ethyl-3-(methylamino)-6-(trifluoromethyl)pyridin-2-one (14.3 g, 64.9 mmol) sulfuric acid (195 mL, 356 mmol) was cooled with an ice bath at 0° C. Then, Ice (71.5 g, 397 mmol) and nitric acid (6.30 g, 4.53 mL, 64.9 mmol) were added. After 15 min at 0-10° C., the brown thick solution was poured into iced water. The orange precipitate form was filtrated off, rinsing with water and drying under vacuum to give an orange solid. The water phase was extracted 3 times with ethyl acetate and the orange solid, obtained before, was added to the combinated organic phase. The combinated organic phase was washed with a saturated solution of sodium hydrogenocarbonate, water and brine, dried over magnesium sulfate and concentrated under vacuum to give yield the title compound (4.0 g). The compound was used without extra purification for the next step. LC-MS (Method A): RT 0.98, 276 (M+H+).

Step C: 4-amino-1-ethyl-3-(methylamino)-6-(trifluoromethyl)pyridin-2-one

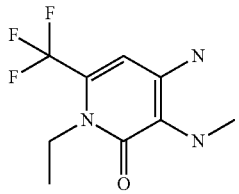 [SMILES: CCn1c(C(F)(F)F)cc(N)c(NC)c1=O]

To a solution of 1-ethyl-3-(methylamino)-4-nitro-6-(trifluoromethyl)pyridin-2-one (12.3 g, 46.4 mmol) in propan-2-ol (500 mL, 6500 mmol) was added tin(II) chloride dihydrate (32.0 g, 167 mmol) followed by hydrogen chloride (50 mL, 610 mmol, 37% aq. solution). The resulting solution was stirred at 70° C. for one hour, and, then allowed to cool down to ambient temperature. The reaction mixture was poured into water, and pH was adjusted to 10-12 with a concentrated aqueous solution of sodium hydroxide (30%).

The aqueous phase was extracted three times with ethyl acetate; the organic phases were combined, dried over magnesium sulfate and concentrated under vacuum. The residue was subjected to column chromatography over silica gel, eluting with ethyl acetate/cyclohexane. The selected fractions were evaporated to yield the title compound (8.43 g). LC-MS (Method A): RT 0.47, 236 (M+H$^+$).

Example I2: Preparation of 5-bromo-3-ethylsulfanyl-pyridine-2-carboxylic Acid

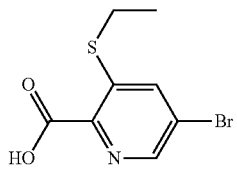

Step A: Preparation of 5-bromo-3-ethylsulfanyl-pyridine-2-carboxylic Acid

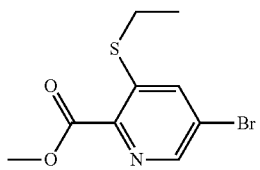

To a solution of methyl 5-bromo-3-chloro-pyridine-2-carboxylate (0.100 g, 0.399 mmol) (commercial product) in tetrahydrofuran, stirred at 0° C., was added ethylsulfanyl-sodium (0.034 g, 1 equiv.). After 1 hour at that temperature, the ice bath was removed and stirring was continued for 20 hours. The reaction mixture was then poured onto water (15 ml) and extracted twice with ethyl acetate. The organic phases were dried over sodium sulfate and the solvent was removed. The residue was submitted to flash chromatography over silica gel and the selected fractions evaporated to yield methyl 5-bromo-3-ethylsulfanyl-pyridine-2-carboxylate as a colorless solid. $^1$H NMR (400 MHz, CDCl$_3$) δ ppm: 8.46 (s, 1H); 7.79 (s, 1H); 4.00 (s, 3H); 2.94 (q, J=7.4 Hz, 2H); 1.42 (t, J=7.4 Hz, 3H).

Step B: Preparation of 5-bromo-3-ethylsulfanyl-pyridine-2-carboxylic Acid

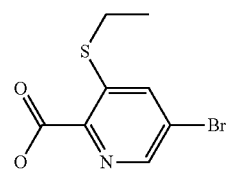

A solution of methyl 5-bromo-3-ethylsulfanyl-pyridine-2-carboxylate (3.900 g, 14.12 mmol) (preparation described here above) in a mixture of methyl alcohol (75 ml) and water (20 ml) stirred at 20° C. was treated with 2N aqueous sodium hydroxide solution (7.04 ml, 1.05 equiv.). The mixture was stirred for two hours, and then most of the alcohol was eliminated under reduced pressure. The residue was then treated with 2N aqueous hydrochloric acid solution and the resulting precipitate was filtered off, washed with water and dried under vacuum. The title compound was obtained as a colorless solid. $^1$H NMR (400 MHz, d6-DMSO) δ ppm: 13.4 (s, 1H); 8.50 (s, 1H); 8.07 (s, 1H); 3.04 (q, 2H); 1.27 (t, 3H).

Example I3: Preparation of 2-(5-bromo-3-ethylsulfonyl-2-pyridyl)-5-ethyl-3-methyl-6-(trifluoromethyl)imidazo[4,5-c]pyridin-4-one

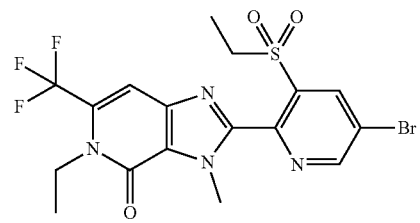 [SMILES: CCn1c(C(F)(F)F)cc2nc(-c3ncc(Br)cc3S(=O)(=O)CC)n(C)c2c1=O]

Step A: Preparation of 5-bromo-N-[1-ethyl-3-(methylamino)-2-oxo-6-(trifluoromethyl)-4-pyridyl]-3-ethylsulfanyl-pyridine-2-carboxamide and N-[4-amino-1-ethyl-2-oxo-6-(trifluoromethyl)-3-pyridyl]-5-bromo-3-ethylsulfanyl-N-methyl-pyridine-2-carboxamide

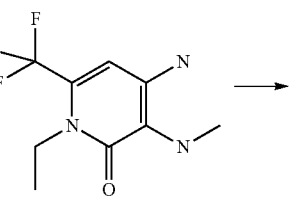

-continued

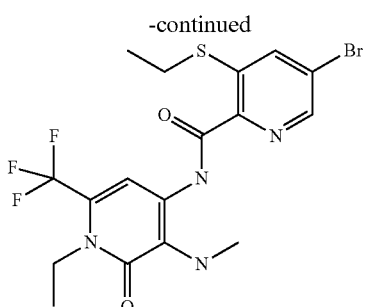

+

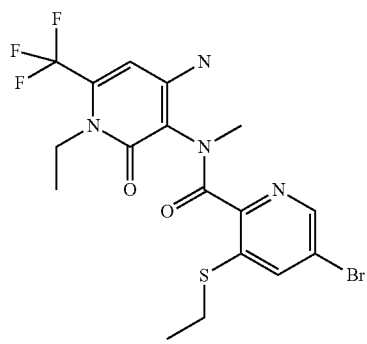

To a suspension of 5-bromo-3-ethylsulfanyl-pyridine-2-carboxylic acid (2.61 g, 9.95 mmol) in dichloromethane (25 ml) was added one drop of N,N-dimethylformamide, followed by oxalyl chloride (2.93 g, 2.01 mL, 22.6 mmol). After the end of gas evolution, the reaction mixture was a pale red solution. The latter was evaporated under reduced pressure at a bath temperature of 60° C. The residue formed dark red crystals of 5-bromo-3-ethylsulfanyl-pyridine-2-carbonyl chloride and the residue was redissolved in a mixture ethyl acetate (20 mL) and dichloromethane (15 mL).

To a solution of 4-amino-1-ethyl-3-(methylamino)-6-(trifluoromethyl)pyridin-2-one (prepared in Example I1, 2.00 g, 9.04 mmol) in ethyl acetate (100 ml) was added N,N-diethylethanamine (2.31 g, 3.18 mL, 22.6 mmol) then the resulting solution was cooled with an ice bath, before slow addition of the previous acid chloride solution. The resulting mixture was stirred 1 hour at 0° C. The solution was neutralized by addition of a saturated aqueous solution of sodium bicarbonate and the product was extracted twice with ethyl acetate. The organic solution was dried over sodium sulfate and evaporated under reduced pressure to yield the crude product. A mixture 70:30 of 5-bromo-N-[1-ethyl-3-(methylamino)-2-oxo-6-(trifluoromethyl)-4-pyridyl]-3-ethylsulfanyl-pyridine-2-carboxamide and N-[4-amino-1-ethyl-2-oxo-6-(trifluoromethyl)-3-pyridyl]-5-bromo-3-ethylsulfanyl-N-methyl-pyridine-2-carboxamide was obtained and used without extra purification for the next step. LC-MS (Method A): RT 0.86, 467.1 (M+H$^+$), 465.1 (M-H$^+$).

Step B: Preparation of 2-(5-bromo-3-ethylsulfonyl-2-pyridyl)-5-ethyl-3-methyl-6-(trifluoromethyl)imidazo[4,5-c]pyridin-4-one

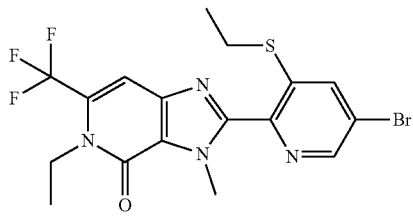 [SMILES: CCSc1cc(Br)cnc1-c1nc2cc(C(F)(F)F)n(CC)c(=O)c2n1C]

To a solution of 5-bromo-N-[1-ethyl-3-(methylamino)-2-oxo-6-(trifluoromethyl)-4-pyridyl]-3-ethylsulfanyl-pyridine-2-carboxamide and N-[4-amino-1-ethyl-2-oxo-6-(trifluoromethyl)-3-pyridyl]-5-bromo-3-ethylsulfanyl-N-methyl-pyridine-2-carboxamide (9.7 g, 20 mmol) in glacial acetic acid (49 mL, 850 mmol) was refluxed for 12 hours. The dark brown solution was allowed to cool down, and was poured into water.

The resulting beige suspension was filtered, washed with water, and solid was redissolved into ethyl acetate (250 mL), dried over Magnesium sulfate and concentrated under vacuum to give 2-(5-bromo-3-ethylsulfanyl-2-pyridyl)-5-ethyl-3-methyl-6-(trifluoromethyl)imidazo[4,5-c]pyridin-4-one. LC-MS (method A): RT 1.14, 462 (M+H). $^1$H NMR (400 MHz, CDCl3) δ ppm 1.37 (m, 6H) 2.95 (m, 2H) 4.20 (s, 3H) 4.25 (s, 2H) 7.36 (s, 1H) 7.86 (d, 1H) 8.56 (d, 1H).

Step C: Preparation of 2-(5-bromo-3-ethylsulfonyl-2-pyridyl)-5-ethyl-3-methyl-6-(trifluoromethyl)imidazo[4,5-c]pyridin-4-one

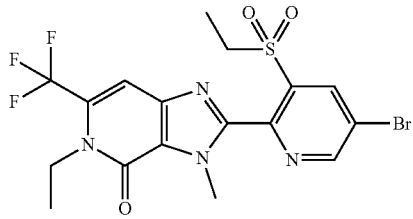 [SMILES: CCn1c(C(F)(F)F)cc2nc(-c3ncc(Br)cc3S(=O)(=O)CC)n(C)c2c1=O]

To a solution of 2-(5-bromo-3-ethylsulfanyl-2-pyridyl)-5-ethyl-3-methyl-6-(trifluoromethyl)imidazo[4,5-c]pyridin-4-one (Prepared in Step B, 6.46 g, 14.0 mmol) in dichloromethane (150 mL, 2330 mmol) was added meta-chloroperbenzoic acid (6.61 g, 28.7 mmol). The yellow solution was stirred at room temperature for an hour. After this time, the reaction mixture was diluted with aqueous sodium thiosulfate solution and extracted with dichloromethane, the combined organic fractions washed with sodium carbonate, dried over magnesium sulfate, and concentrated in vacuo. The crude product was dissolved in dichloromethane and adsorbed on TEFLON BULK SORBENTS, and purified over a silica gel cartridge (TORENT) eluting with heptane/ethyl acetate and then dichloromethane/methanol. This gave the title product as the first eluting product. LC-MS (method A): RT 1.05, 493 (M+H). $^1$H NMR (400 MHz, CDCl$_3$) δ ppm 1.38 (m, 6H) 3.82 (q, 2H) 4.09 (s, 3H) 4.25 (q, 2H) 7.22 (s, 1H) 8.64 (d, 1H) 9.03 (d, 1H).

2-(5-bromo-3-ethylsulfinyl-2-pyridyl)-5-ethyl-3-methyl-6-(trifluoromethyl)imidazo[4,5-c]pyridin-4-one was prepared by using the same protocol with only one equivalent of m-CPBA: $^1$H NMR (400 MHz, CDCl$_3$) δ ppm 8.84 (s, 1H), 8.74 (s, 1H), 7.22 (s, 1H), 4.57 (s, 3H), 4.30 (q, 2H), 3.63 (m, 1H), 3.05 (m, 1H), 1.48-1.308 (m, 6H).

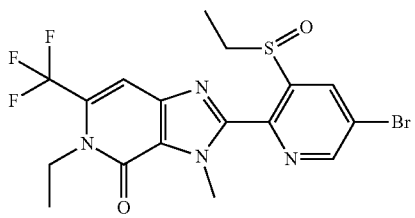 [SMILES: CCn1c(C(F)(F)F)cc2nc(-c3ncc(Br)cc3S(=O)CC)n(C)c2c1=O]

Example I4: 4-amino-1-methyl-3-(methylamino)-6-(trifluoromethyl)pyridin-2-one

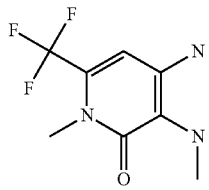

Step A: 1-methyl-3-(methylamino)-6-(trifluoromethyl)pyridin-2-one

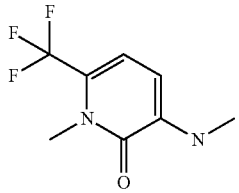

To a solution of 3-amino-1-methyl-6-(trifluoromethyl)pyridin-2-one (1.00 g, 5.20 mmol, Commercially available or synthesized as described for example in Synthesis 2005, No. 8, pp 1269-1278, Synthesis 2011, No. 7, pp 1149-1156) in 1,4-dioxane (62.5 mL, 726 mmol) and pyridine (1.49 mL, 18.2 mmol) under argon was added diacetoxycopper (2.39 g, 13.0 mmol). The mixture was stirred for 15 min before addition of methyl boronic acid (0.803 g, 13.0 mmol). The resulting green/blue suspension was refluxed for 5 hours. After cooling, the solution was filtered through a Celite pad. The dark green solution was concentrated under vacuum and was subjected to column chromatography over silica gel, eluting with ethyl acetate/cyclohexane. The selected fractions were evaporated to yield the title compound (0.71 g). $^1$H NMR (400 MHz, CDCl$_3$) δ ppm 7.27 (s, 1H); 6.72 (d, 1H); 6.04 (d, 2H), 5.46 (bs, 1H), 3.68 (s, 3H), 2.88 (d, 3H).

Step A: Alternative

To a solution of 3-amino-1-methyl-6-(trifluoromethyl)pyridin-2-one (5 g, 26.023 mmol) in acetonitrile (133 g, 169.15 mL,) was added formaldehyde (37 mass %) in aq. solution (16.894 g, 15.60 mL, 208.2 mmol) and acetic acid (7.83 g, 7.46 mL, 130.11 mmol). The reaction was stirred at room temperature for 1 hour then sodium cyanoborohydride (6.89 g, 104.1 mmol) was added in fives portions over 3 hours and the mixture was stirred overnight. The white cloudy solution was extracted with ethyl acetate/water. the organic phase was washed with brine, dried over magnesium sulfate, and concentrated under vacuum. the residue was purified by Flash chromatography to give 1-methyl-3-(methylamino)-6-(trifluoromethyl)pyridin-2-one (4.32 g) as a white solid.

Step B: 1-methyl-3-(methylamino)-4-nitro-6-(trifluoromethyl)pyridin-2-one

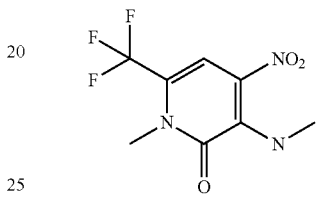

A solution of 1-methyl-3-(methylamino)-6-(trifluoromethyl)pyridin-2-one (4.00 g, 19.4 mmol) sulfuric acid (58.2 mL) was cooled with an ice bath at 0° C. Then, Ice (20.0 g) and nitric acid (1.88 g, 1.35 mL, 19.4 mmol) were added. After 15 min at 0-10° C., the brown thick solution was poured into iced water. The orange precipitate form was filtrated off, rinsing with water and drying under vacuum to give an orange solid. The water phase was extracted 3 times with Ethyl acetate and the orange solid, obtained before, was added to the combinated organic phase. The combinated organic phase was washed with a saturated solution of sodium hydrogen carbonate, water and brine, dried over magnesium sulfate and concentrated under vacuum to give yield the title compound (4.0 g). The compound was used without extra purification for the next step. LC-MS (Method A): RT 0.91, 252 (M+H$^+$), 250 (M–H$^+$).

Step C: 4-amino-1-methyl-3-(methylamino)-6-(trifluoromethyl)pyridin-2-one

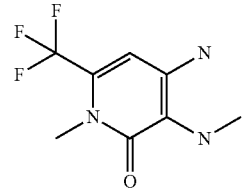

To a solution of 1-methyl-3-(methylamino)-4-nitro-6-(trifluoromethyl)pyridin-2-one (3.0 g, 11.9 mmol) in propan-2-ol (98.1 g, 125 mL, 1620 mmol) was added Tin dichloride (8.24 g, 43.0 mmol) followed by hydrogen chloride (10 mL, 120 mmol, 37%). The resulting solution was stirred at 70° C. for one hour, and, then allowed to cool down to ambient temperature. The reaction mixture was poured into water, and pH was adjusted to 10-12 with a concentrated aqueous solution of sodium hydroxide (30%). The aqueous phase was extracted three times with ethyl acetate; the organic phases were combined, dried over magnesium sulfate and concentrated under vacuum. subjected to column chromatography over silica gel, eluting with ethyl acetate/cyclohexane. The selected fractions were evaporated to yield the title compound (2.15 g). ¹H NMR (400 MHz, CDCl₃) δ ppm 6.30 (s, 1H); 4.15 (bs, 2H), 3.8 (bs, 1H), 3.60 (s, 3H), 2.64 (s, 3H).

Example I5:
6-chloro-3-ethylsulfanyl-pyridine-2-carboxylic Acid

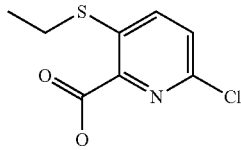

Step A: methyl 3,6-dichloropyridine-2-carboxylate

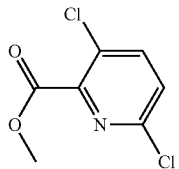

To a suspension of 3,6-dichloropyridine-2-carboxylic acid (22.3 g, 116 mmol) (commercial product) in methanol (223 mL) was added sulfuric acid (12.0 g, 6.55 mL, 116 mmol) at ambient temperature. The resulting mixture was stirred four hours at 65° C. The reaction mixture was concentrated under reduce pressure. The crude was dissolved in dichloromethane and with a saturated solution of sodium hydrogen carbonate solution. Then washed with sodium chloride and the organic layer were dried over magnesium sulfate and concentrated under vacuum. Methyl 3,6-dichloropyridine-2-carboxylate was obtained as a white crystal was obtained. ¹H NMR (400 MHz, CDCl₃) δ ppm 4.00 (s, 3H), 7.42 (d, 1H), 7.76 (d, 1H).

Step B: Preparation of methyl 6-chloro-3-ethylsulfanyl-pyridine-2-carboxylate

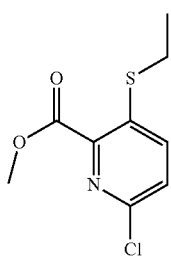

A solution of methyl 3,6-dichloropyridine-2-carboxylate (20 g, 97.073 mmol, commercial compound) in tetrahydrofuran (200 mL) was treated with catalytic quantities of 18-crown-6-ether (ca. 300 mg) followed by sodium ethoxide (9.073 g, 97.073 mmol) in 3 portions. The reaction was the allowed to stir at ambient temperature for 1 hour. LCMS analysis after this time showed consumption of starting materials and the formation of three new products. The reaction mixture was poured on 100 ml saturated ammonium chloride aqueous solution, extracted with 2× 100 ml Ethyl acetate, and the combined organic layers washed with 2× 50 ml saturated aqueous ammonium chloride aqueous solution, 3× 100 ml water, dried over Sodium sulfate, filtered and concentrated in vacuum. The crude product was purified by combi flash chromatography with a column of 220 g and a gradient cyclohexane+0-10% Ethyl acetate. This gave as the first eluting product methyl 3,6-bis(ethylsulfanyl)pyridine-2-carboxylate (Method A, retention time 1.04 mins, (MH+)=258). The second product to elute was methyl 3-chloro-6-ethylsulfanyl-pyridine-2-carboxylate (Method A, retention time 0.99 min, (MH+)=232). The final product to elute was the major product and desired title product, as white crystals. LC-MS (method A): RT 0.88 mins, 232 (MH+). ¹H NMR (400 MHz, chloroform-d) δ ppm 1.40 (t, 3H) 2.95 (q, 2H) 4.00 (s, 3H) 7.41 (d, 1H) 7.66 (d, 1H).

Step C:
6-chloro-3-ethylsulfanyl-pyridine-2-carboxylic Acid

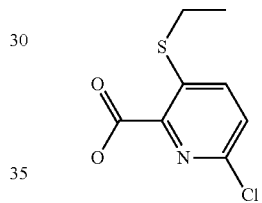

A solution of methyl 6-chloro-3-ethylsulfanyl-pyridine-2-carboxylate (3.900 g, 14.12 mmol) (preparation described here above) in a mixture of methyl alcohol (75 ml) and water (20 ml) stirred at 20° C. was treated with 2N aqueous sodium hydroxide solution (7.04 ml, 1.05 equiv.). The mixture was stirred for two hours, and then most of the alcohol was eliminated under reduced pressure. The residue was then treated with 2N aqueous hydrochloric acid solution and the resulting precipitate was filtered off, washed with water and dried under vacuum. The title compound was obtained as a colorless solid. ¹H NMR (400 MHz, DMSO) δ ppm 1.23 (d, 3H) 2.99 (q, 2H) 7.64 (d, 1H) 7.95 (d, 1H).

Example I6: 2-(6-chloro-3-ethylsulfonyl-2-pyridyl)-3,5-dimethyl-6-(trifluoromethyl)imidazo[4,5-c]pyridin-4-one

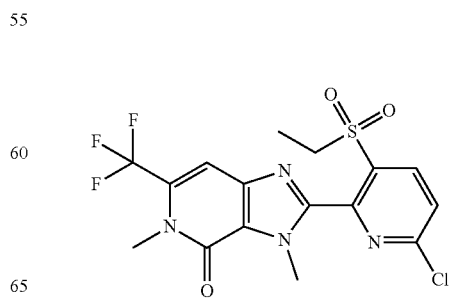

Step A: 6-chloro-3-ethylsulfanyl-N-[1-methyl-3-(methylamino)-2-oxo-6-(trifluoromethyl)-4-pyridyl]pyridine-2-carboxamide and N-[4-amino-1-methyl-2-oxo-6-(trifluoromethyl)-3-pyridyl]-6-chloro-3-ethylsulfanyl-N-methyl-pyridine-2-carboxamide

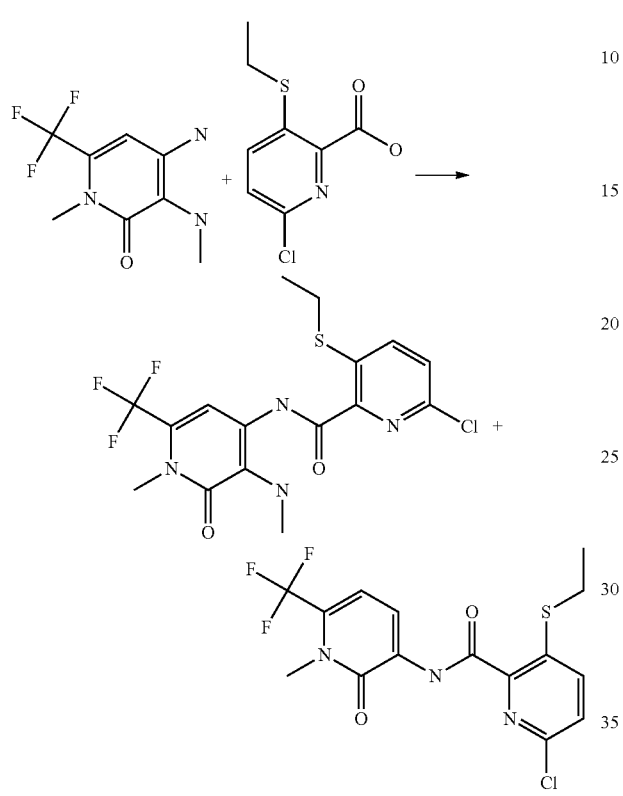

Prepared from intermediate 4-amino-1-methyl-3-(methylamino)-6-(trifluoromethyl)pyridin-2-one and 6-chloro-3-ethylsulfanyl-pyridine-2-carboxylic acid, using a similar protocol as described in Example I3 Step A. LC-MS (Method A): RT 0.86, 421 (M+H$^+$).

Step B: 2-(6-chloro-3-ethylsulfanyl-2-pyridyl)-3,5-dimethyl-6-(trifluoromethyl)imidazo[4,5-c]pyridin-4-one

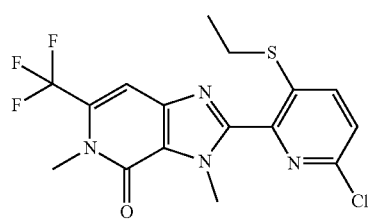 [SMILES: CCSc1ccc(Cl)nc1-c1nc2cc(C(F)(F)F)n(C)c(=O)c2n1C]

Prepared from intermediate 2-(6-chloro-3-ethylsulfanyl-2-pyridyl)-3,5-dimethyl-6-(trifluoromethyl)imidazo[4,5-c]pyridin-4-one, using a similar protocol as described in Example I3 Step B: LC-MS (Method A) RT 1.07, 403 (MH+). $^1$H NMR (400 MHz, CDCl$_3$) δ ppm 1.32 (t, 3H), 2.92 (q, 2H), 3.73 (d, 3H), 4.23 (s, 3H), 7.31 (s, 1H), 7.40 (d, 1H), 7.72 (d, 1H).

Step C: 2-(6-chloro-3-ethylsulfonyl-2-pyridyl)-3,5-dimethyl-6-(trifluoromethyl)imidazo[4,5-c]pyridin-4-one

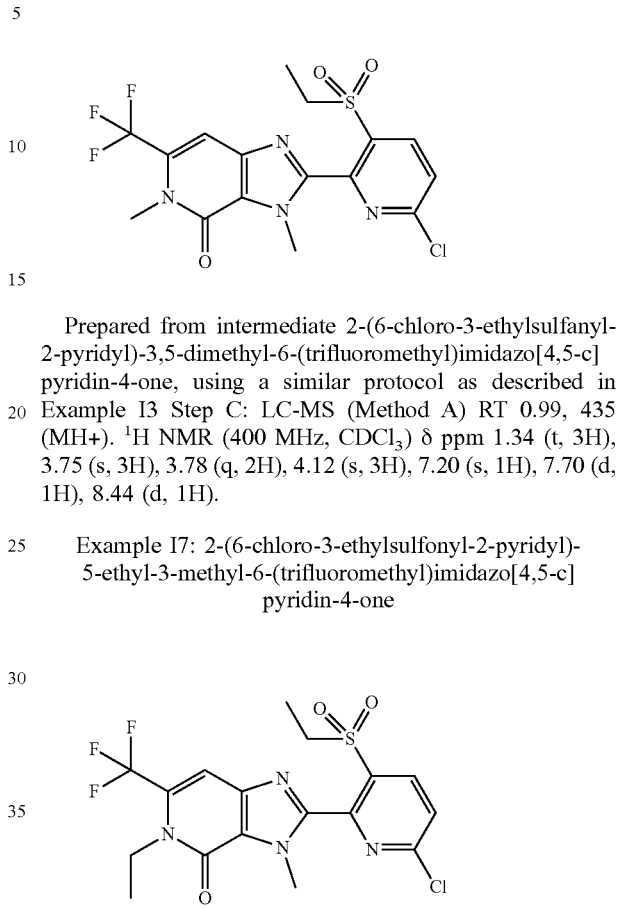

Prepared from intermediate 2-(6-chloro-3-ethylsulfanyl-2-pyridyl)-3,5-dimethyl-6-(trifluoromethyl)imidazo[4,5-c]pyridin-4-one, using a similar protocol as described in Example I3 Step C: LC-MS (Method A) RT 0.99, 435 (MH+). $^1$H NMR (400 MHz, CDCl$_3$) δ ppm 1.34 (t, 3H), 3.75 (s, 3H), 3.78 (q, 2H), 4.12 (s, 3H), 7.20 (s, 1H), 7.70 (d, 1H), 8.44 (d, 1H).

Example I7: 2-(6-chloro-3-ethylsulfonyl-2-pyridyl)-5-ethyl-3-methyl-6-(trifluoromethyl)imidazo[4,5-c]pyridin-4-one

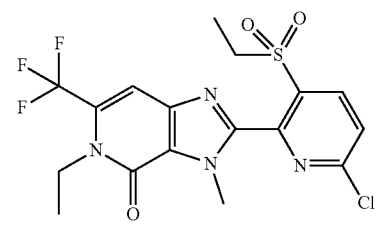 [SMILES: CCS(=O)(=O)c1ccc(Cl)nc1-c1nc2cc(C(F)(F)F)n(C)c(=O)c2n1C]

Step A: 1-ethyl-3-(methylamino)-6-(trifluoromethyl)pyridin-2-one

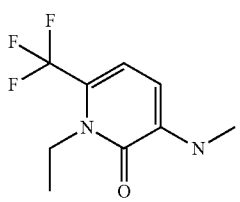

To a solution of 3-amino-1-ethyl-6-(trifluoromethyl)pyridin-2-one (5.00 g, 24.3 mmol, Commercially available or synthesised by analogy with literature, for example, Synthesis 2005, No. 8, pp 1269-1278 and Synthesis 2011, No. 7, pp 1149-1156) in acetonitrile (150 mL) was added formaldehyde (37 mass %) in aqueous solution (14.5 ml, 194 mmol) and acetic acid (6.96 ml, 121 mmol). The resulting suspension stirred for 1 hour, then sodium cyanoborohydride (6.42 g, 97.0 mmol) was added in 5 portions over 3 hours and the mixture was stirred for 18 hours. The solution was diluted with water and extracted with ethyl acetate (3×). The combined organic layer was dried over Sodium sulfate, filtered, concentrated and purified by column chromatography using cyclohexane-ethyl acetate (100-200 silica gel) to give the desired compound as a white solid. $^1$H NMR (400 MHz, CDCl$_3$) δ ppm 6.70 (d, 1H), 6.04 (d, 1H), 5.44 (sb, 1H), 4.15 (q, 2H), 2.85 (s, 3H), 1.32 (t, 3H).

Step B: 1-ethyl-3-(methylamino)-4-nitro-6-(trifluoromethyl)pyridin-2-one

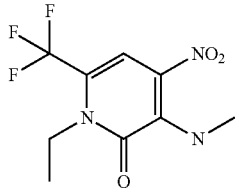 [SMILES: CCn1c(C(F)(F)F)cc([N+](=O)[O-])c(NC)c1=O]

A solution of 1-ethyl-3-(methylamino)-6-(trifluoromethyl)pyridin-2-one (14.3 g, 64.9 mmol) sulfuric acid (195 mL, 3560 mmol) was cooled with an ice bath at 0° C. Then, Ice (71.5 g, 3970 mmol) and nitric acid (6.30 g, 4.53 mL, 64.9 mmol) were added. After 15 min at 0-10° C., the brown thick solution was poured into iced water. The orange precipitate form was filtrated off, rinsing with water and drying under vacuum to give an orange solid. The water phase was extracted 3 times with ethyl acetate and the orange solid, obtained before, was added to the combinated organic phase. The combinated organic phase was washed with a saturated solution of sodium hydrogenocarbonate, water and brine, dried over magnesium sulfate and concentrated under vacuum to give yield the title compound (4.0 g). The compound was used without extra purification for the next step. LC-MS (Method A): RT 0.98, 276 (M+H$^+$).

Step C: 4-amino-1-ethyl-3-(methylamino)-6-(trifluoromethyl)pyridin-2-one

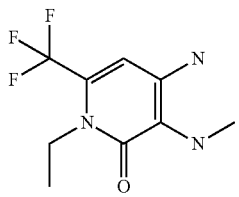 [SMILES: CCn1c(C(F)(F)F)cc(N)c(NC)c1=O]

To a solution of 1-ethyl-3-(methylamino)-4-nitro-6-(trifluoromethyl)pyridin-2-one (12.3 g, 46.4 mmol) in propan-2-ol (500 mL, 6500 mmol) was added tin(II) chloride dihydrate (32.0 g, 167 mmol) followed by hydrogen chloride (50 mL, 610 mmol, 37%). The resulting solution was stirred at 70° C. for one hour, and, then allowed to cool down to ambient temperature. The reaction mixture was poured into water, and pH was adjusted to 10-12 with a concentrated solution of sodium hydroxide (30%).

The aqueous phase was extracted three times with ethyl acetate; the organic phases were combined, dried over magnesium sulfate and concentrated under vacuum. The residue was subjected to column chromatography over silica gel, eluting with ethyl acetate/cyclohexane. The selected fractions were evaporated to yield the title compound (8.43 g). LC-MS (Method A): RT 0.47, 236 (M+H$^+$).

Step D: 6-chloro-N-[1-ethyl-3-(methylamino)-2-oxo-6-(trifluoromethyl)-4-pyridyl]-3-ethylsulfanyl-pyridine-2-carboxamide and N-[4-amino-1-ethyl-2-oxo-6-(trifluoromethyl)-3-pyridyl]-6-chloro-3-ethylsulfanyl-N-methyl-pyridine-2-carboxamide

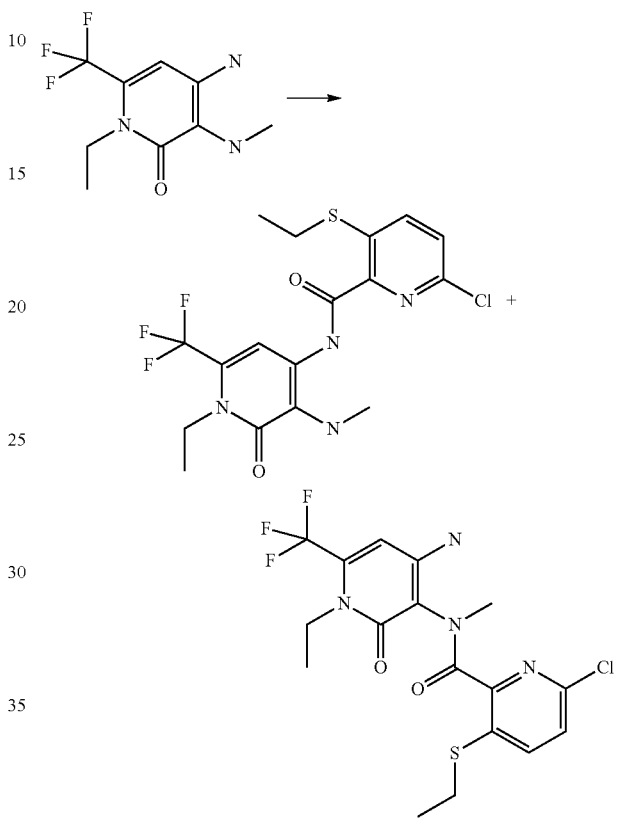

Under argon, 6-chloro-3-ethylsulfanyl-pyridine-2-carboxylic acid (as prepared in Example I5) (4.2 g, 19 mmol) was dissolved in dichloromethane (39 mL) with oxalyl dichloride (5.0 g, 39 mmol) and N,N-dimethylformamide (1 drop). The mixture was stirred for 30 min at room temperature then at reflux for 30 min. Then the solvent was removed and dried under vacuum, 6-chloro-3-ethylsulfanyl-pyridine-2-carbonyl chloride (4.2 g, 18 mmol) was diluted with 5 ml of tetrahydrofuran and a solution of 4-amino-1-ethyl-3-(methylamino)-6-(trifluoromethyl)pyridin-2-one (4.6 g, 20 mmol) in tetrahydrofuran (36 mL) and pyridine (4.2 g, 4.3 mL) was added. The mixture was stirred at reflux for 3 hours, then the brown suspension was poured into a saturated solution of sodium bicarbonate, extracted with ethyl acetate, organic phase was washed with a solution of Hydrogen chloride (1N), brine, dried over MgSO$_4$ and concentrated under vacuum to give a mixture of 6-chloro-N-[1-ethyl-3-(methylamino)-2-oxo-6-(trifluoromethyl)-4-pyridyl]-3-ethylsulfanyl-pyridine-2-carboxamide and N-[4-amino-1-ethyl-2-oxo-6-(trifluoromethyl)-3-pyridyl]-6-chloro-3-ethylsulfanyl-N-methyl-pyridine-2-carboxamide (7 g, 90%) as a brown solid. LC-MS (Method A): RT 0.91, 436 (M+H$^+$), 433 (M−H$^+$).

Step E: 2-(6-chloro-3-ethylsulfanyl-2-pyridyl)-5-ethyl-3-methyl-6-(trifluoromethyl)imidazo[4,5-c]pyridin-4-one

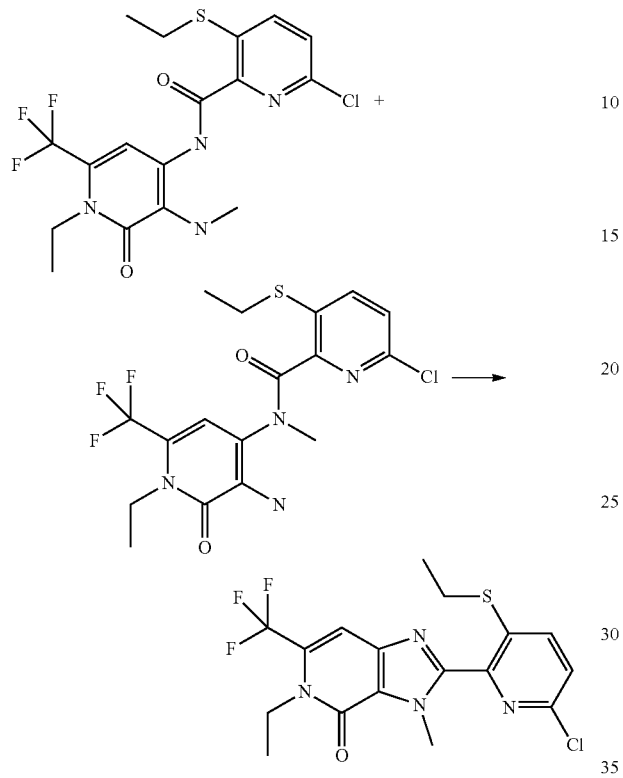

6-chloro-N-[1-ethyl-3-(methylamino)-2-oxo-6-(trifluoromethyl)-4-pyridyl]-3-ethylsulfanyl-pyridine-2-carboxamide and N-[4-amino-1-ethyl-2-oxo-6-(trifluoromethyl)-3-pyridyl]-6-chloro-3-ethylsulfanyl-N-methyl-pyridine-2-carboxamide (7.0 g, 16 mmol) were dissolved in acetic acid (50 mL) and refluxed for 24 hours. The reaction was concentrated under reduced pressure to remove all acetic acid, and then dissolved in dichloromethane and purified by combiflash to give 2-(6-chloro-3-ethylsulfanyl-2-pyridyl)-5-ethyl-3-methyl-6-(trifluoromethyl)imidazo[4,5-c]pyridin-4-one (5 g, 75%) as an slightly yellow solid. $^1$H NMR (400 MHz, CDCl$_3$) δ 7.72 (d, 1H), 7.40 (d, 1H), 7.32 (s, 1H), 4.29-4.21 (m, 5H), 2.93 (q, 2H), 1.42-1.28 (m, 6H).

Step F: 2-(6-chloro-3-ethylsulfonyl-2-pyridyl)-5-ethyl-3-methyl-6-(trifluoromethyl)imidazo[4,5-c]pyridin-4-one

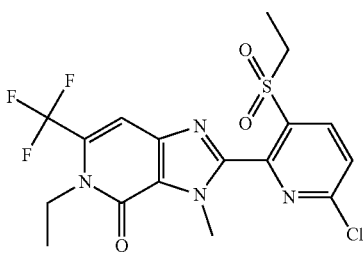 [SMILES: CCn1c(C(F)(F)F)cc2nc(-c3nc(Cl)ccc3S(=O)(=O)CC)n(C)c2c1=O]

To a solution of 2-(6-chloro-3-ethylsulfanyl-2-pyridyl)-5-ethyl-3-methyl-6-(trifluoromethyl)imidazo[4,5-c]pyridin-4-one (4.6 g, 11 mmol) in dichloromethane (50 mL) was added 3-chlorobenzenecarboperoxoic acid (5.2 g, 23 mmol). The mixture was allowed to stand over night at room temperature. It was quenched with a solution of sodium thiosulfate (100 ml) and The reaction was diluted with 1N NaOH (100 ml), extracted with dichloromethane (3×50 ml). Combined organic layer was dried over sodium sulfate, filtered and concentrated under reduced pressure to give 2-(6-chloro-3-ethylsulfonyl-2-pyridyl)-5-ethyl-3-methyl-6-(trifluoromethyl)imidazo[4,5-c]pyridin-4-one (4.6 g, 93%). $^1$H NMR (400 MHz, CDCl$_3$) δ 8.43 (d, 1H), 7.69 (d, 1H), 7.20 (s, 1H), 4.25 (q, 2H), 4.13 (s, 3H), 3.78 (m, 2H), 1.45-1.31 (m, 6H).

Example I8: 4-amino-1-cyclopropyl-3-(methylamino)-6-(trifluoromethyl)pyridin-2-one

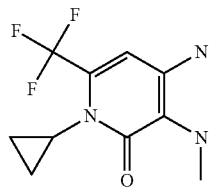 [SMILES: CNc1c(N)cc(C(F)(F)F)n(C2CC2)c1=O]

Step A: 1-cyclopropyl-3-(amino)-6-(trifluoromethyl)pyridin-2-one

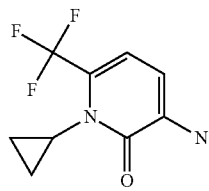 [SMILES: Nc1ccc(C(F)(F)F)n(C2CC2)c1=O]

A sealed bomb was charged with N-[2-oxo-6-(trifluoromethyl)pyran-3-yl]benzamide (commercially available, CAS Registry Number 312615-59-1, 30 g, 105.9 mmol), tetrahydrofuran (132.4 mL, 1620 mmol) and cyclopropylamine (8.24 mL, 116.5 mmol). The mixture was stirred for overnight at 70° C. The sealed vial was cooled and the reaction mixture was dissolved with water and ethyl acetate (250 ml/250 ml). The aqueous phase was extracted with ethyl acetate (3×) and the combined organic layer was dried over sodium sulfate, filtered, concentrated under vacuum. The residue was purified by column chromatography using cyclohexane-ethyl acetate to give the starting material and 23 g of N-[1-cyclopropyl-2-hydroxy-6-oxo-2-(trifluoromethyl)-3H-pyridin-5-yl]benzamide. The N-[1-cyclopropyl-2-hydroxy-6-oxo-2-(trifluoromethyl)-3H-pyridin-5-yl]benzamide was dissolved in hydrogen chloride (563 g, 473.1 mL, 5710 mmol) and the mixture was stirred at 100° C. for Over Night. The precipitate of Benzoic acid was filtered off and the filtrate was basified to pH 7-8 with a solution of sodium hydroxyl conc. Then the water phase was extracted (3×) with AcOEt and the combined organic layers were dried over sodium sulfate, filtered and concentrated under vacuum. The residue was purified by column chromatography using cyclohexane-ethyl acetate to give 12 g of 1-cyclopropyl-3-(amino)-6-(trifluoromethyl)pyridin-2-one. LC-MS (Method A): RT 0.79, 219 (M⁺H⁺). ¹H NMR (400 MHz, CDCl₃) δ ppm 6.59 (d, 1H), 6.33 (d, 1H), 4.60 (sb, 2H), 3.07 (m, 1H), 1.24 (m, 2H), 1.02 (m, 2H).

Step B: 1-cyclopropyl-3-(methylamino)-6-(trifluoromethyl)pyridin-2-one

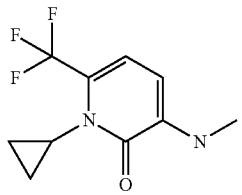 [SMILES: CNc1ccc(C(F)(F)F)n(C2CC2)c1=O]

The 1-cyclopropyl-3-(methylamino)-4-nitro-6-(trifluoromethyl)pyridin-2-one was prepared as for Example I4, step A. LC-MS (Method A): RT 0.93, 233 (M+H⁺).

Step C: 1-cyclopropyl-3-(methylamino)-4-nitro-6-(trifluoromethyl)pyridin-2-one

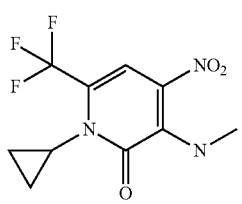 [SMILES: CNc1c([N+](=O)[O-])cc(C(F)(F)F)n(C2CC2)c1=O]

The 1-cyclopropyl-3-(methylamino)-4-nitro-6-(trifluoromethyl)pyridin-2-one was prepared as for Example I2, step C. LC-MS (Method A): RT 0.98, 278 (M+H⁺).

Step D: 4-amino-1-cyclopropyl-3-(methylamino)-6-(trifluoromethyl)pyridin-2-one

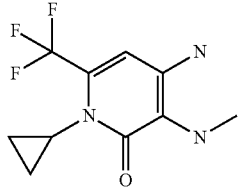 [SMILES: CNc1c(N)cc(C(F)(F)F)n(C2CC2)c1=O]

The 4-amino-1-cyclopropyl-3-(methylamino)-6-(trifluoromethyl)pyridin-2-one was prepared as for Example I2, step D. LC-MS (Method A): RT 0.52, 247 (M+H⁺). Alternatively, the 4-amino-1-cyclopropyl-3-(methylamino)-6-(trifluoromethyl)pyridin-2-one could be prepared via hydrogenation in presence of Pd/C in ethanol using classical reaction. 1H NMR (400 MHz, CDCl3) δ ppm 6.28 (s, 1H), 4.08 (sb, 2H), 3.81 (sb, 1H), 2.97 (m, 1H), 2.63 (s, 3H), 1.18 (m, 2H), 0.98 (m, 2H).

Example I9: 2-(6-chloro-3-ethylsulfonyl-2-pyridyl)-5-cyclopropyl-3-methyl-6-(trifluoromethyl)imidazo[4,5-c]pyridin-4-one

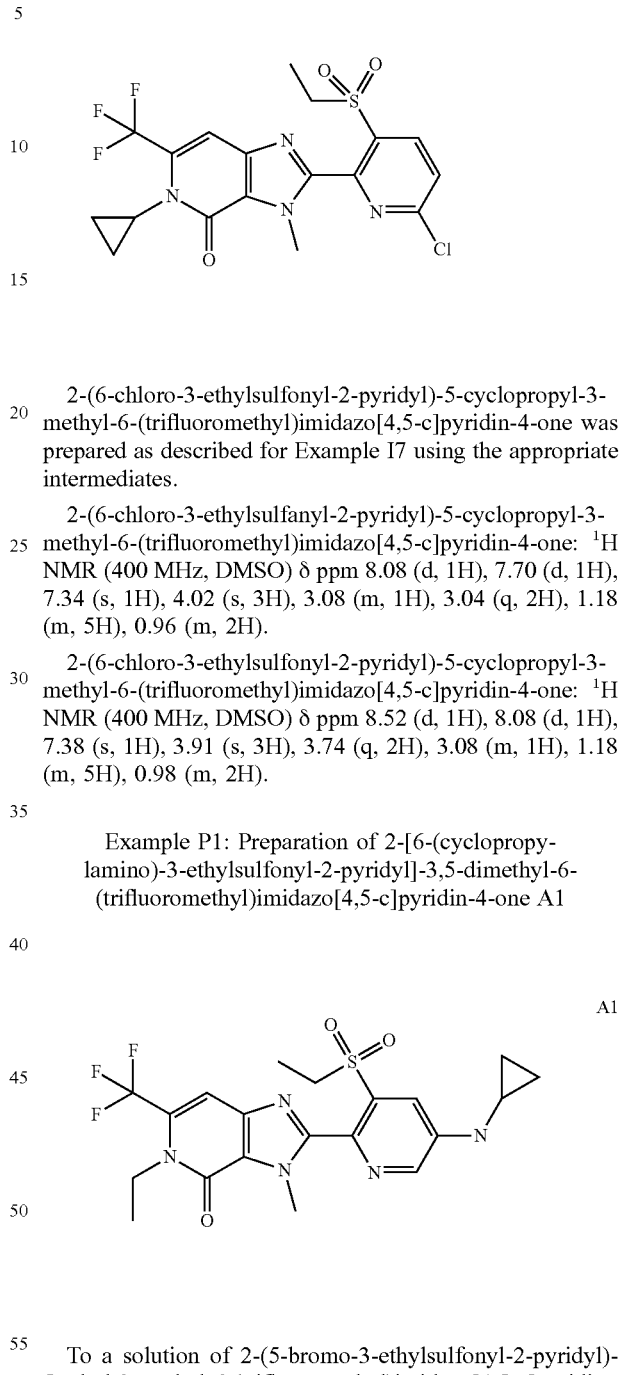

2-(6-chloro-3-ethylsulfonyl-2-pyridyl)-5-cyclopropyl-3-methyl-6-(trifluoromethyl)imidazo[4,5-c]pyridin-4-one was prepared as described for Example I7 using the appropriate intermediates.

2-(6-chloro-3-ethylsulfanyl-2-pyridyl)-5-cyclopropyl-3-methyl-6-(trifluoromethyl)imidazo[4,5-c]pyridin-4-one: ¹H NMR (400 MHz, DMSO) δ ppm 8.08 (d, 1H), 7.70 (d, 1H), 7.34 (s, 1H), 4.02 (s, 3H), 3.08 (m, 1H), 3.04 (q, 2H), 1.18 (m, 5H), 0.96 (m, 2H).

2-(6-chloro-3-ethylsulfonyl-2-pyridyl)-5-cyclopropyl-3-methyl-6-(trifluoromethyl)imidazo[4,5-c]pyridin-4-one: ¹H NMR (400 MHz, DMSO) δ ppm 8.52 (d, 1H), 8.08 (d, 1H), 7.38 (s, 1H), 3.91 (s, 3H), 3.74 (q, 2H), 3.08 (m, 1H), 1.18 (m, 5H), 0.98 (m, 2H).

Example P1: Preparation of 2-[6-(cyclopropylamino)-3-ethylsulfonyl-2-pyridyl]-3,5-dimethyl-6-(trifluoromethyl)imidazo[4,5-c]pyridin-4-one A1

A1

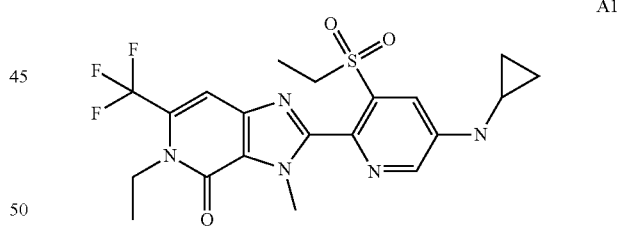

To a solution of 2-(5-bromo-3-ethylsulfonyl-2-pyridyl)-5-ethyl-3-methyl-6-(trifluoromethyl)imidazo[4,5-c]pyridin-4-one (Prepared 13 step C, 500 mg, 1.0136 mmol), cyclopropylamine (63.66 mg, 0.077 mL), cesium carbonate (1155.87 mg, 3.55 mmol) and (5-diphenylphosphanyl-9,9-dimethyl-xanthen-4-yl)-diphenyl-phosphane (30.2438 mg, 0.0507 mmol) in 1,4-dioxane (9.914 g, 9.588 mL, 112 mmol) was added (1E,4E)-1,5-diphenylpenta-1,4-dien-3-one; palladium (9.5349 mg, 0.0101 mmol) under argon atmosphere at room temperature. The mixture was heated at 95° C. stirred for Overnight. The reaction mixture was poured to a mixture of water and ethyl acetate. The organic phase was separated, dried on magnesium sulfate and concentrated under vacuum. The crude product was dissolved in dichloromethane, adsorbed onto TEFLON BULK SORBENTS, and then purified over a silica gel cartridge (Rf200), eluting with dichloromethane/methanol to give the title compound (55.4 mg, 11.6%). LC-MS (Method A) RT 1.00, 470 (MH+) 468 (MH−). $^1$H NMR (400 MHz, CDCl3) δ ppm 0.63 (m, 2H), 0.93 (m, 2H), 1.36 (m, 6H), 2.60 (m, 1H), 3.71 (q, 2H), 4.02 (s, 3H), 4.25 (m, 2H), 7.19 (s, 1H), 7.73 (d, 1H), 8.40 (d, 1H)

Example P2: Preparation of 2-[6-(cyclopropylamino)-3-ethylsulfonyl-2-pyridyl]-3,5-dimethyl-6-(trifluoromethyl)imidazo[4,5-c]pyridin-4-one A2

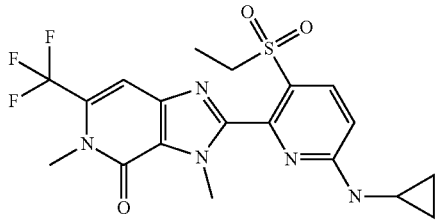

A2

To a solution of 2-(6-chloro-3-ethylsulfonyl-2-pyridyl)-3,5-dimethyl-6-(trifluoromethyl)imidazo[4,5-c]pyridin-4-one (200 mg, 0.46 mmol) and triethylamine (3.0 equiv., 0.194 mL, 0.1410 g) in tetrahydrofuran (1.0 equiv., 2 mL) was added cyclopropylamine (1.5 equiv., 0.0488 mL). The mixture was stirred at 70° C. for 1 h. The reaction was not complete; cyclopropylamine (1.5 equiv., 0.0488 mL, 0.04020 g) was added and stirred overnight at 70° C. to complete conversion. The mixture was diluted with ethyl acetate, washed with water and brine, dried over magnesium sulfate, filtered and evaporated to yield a pale brown solid. LC-MS (Method A) RT 0.95, 456 (MH+) 454 (MH−). $^1$H NMR (400 MHz, CDCl$_3$) δ ppm 0.63 (m, 2H), 0.93 (m, 2H), 1.30 (t, 3H), 3.5 (q, 2H), 3.70 (s, 3H), 4.00 (s, 3H), 5.70 (s, 1H), 6.9 (d, 1H), 8.10 (d, 1H).

Example P3: Preparation of 6-[5-ethyl-3-methyl-4-oxo-6-(trifluoromethyl)imidazo[4,5-c]pyridin-2-yl]-5-ethylsulfonyl-pyridine-3-carboxylic Acid A3

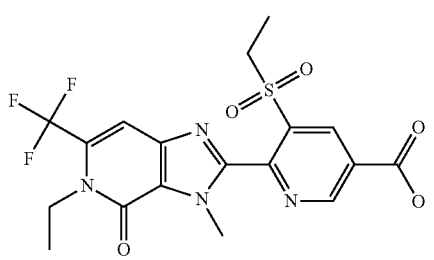

A3

Step A: Preparation of 6-[5-ethyl-3-methyl-4-oxo-6-(trifluoromethyl)imidazo[4,5-c]pyridin-2-yl]-5-ethylsulfonyl-pyridine-3-carbonitrile

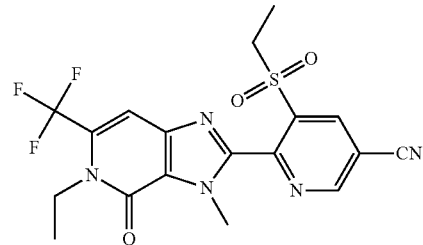 [SMILES: CCn1c(C(F)(F)F)cc2nc(-c3ncc(C#N)cc3S(=O)(=O)CC)n(C)c2c1=O]

2-(5-bromo-3-ethylsulfonyl-2-pyridyl)-5-ethyl-3-methyl-6-(trifluoromethyl)imidazo[4,5-c]pyridin-4-one (Prepared 13 step C, 0.1 g, 0.2 mmol) was dissolved in N,N-dimethyl acetamide (1 mL). To this reaction mixture was added zinc dust (0.02 mmol, 0.002 g) and 1,1-bis(diphenylphosphino)ferrocene (0.008 mmol, 0.004 g) and then purged with N$_2$ gas for 10 min with constant stirring. zinc cyanide (0.1 mmol, 0.01 g) and (1E,4E)-1,5-diphenylpenta-1,4-dien-3-one; palladium (0.004 mmol, 0.004 g) were then added to the above reaction mixture and heated at 130° C. for 1 h. After completion, the reaction mixture was quenched in 2 M NH$_4$OH solution (5 mL), extracted with ethyl acetate (15 mL×3), organic layer was then washed with water (10 ml×3), brine solution, dried and concentrated. The crude was purified by combiflash using 10% Ethyl acetate-Cyclohexane solvent system to give 6-[5-ethyl-3-methyl-4-oxo-6-(trifluoromethyl)imidazo[4,5-c]pyridin-2-yl]-5-ethylsulfonyl-pyridine-3-carbonitrile (0.07 g, 80%). $^1$H NMR (400 MHz, CDCl$_3$) δ ppm 1.38 (m, 6H) 3.91 (m, 2H) 4.16 (s, 3H) 4.26 (m, 2H), 7.21 (s, 1H) 8.78 (d, 1H) 9.19 (d, 1H).

Step B: Preparation of 6-[5-ethyl-3-methyl-4-oxo-6-(trifluoromethyl)imidazo[4,5-c]pyridin-2-yl]-5-ethylsulfonyl-pyridine-3-carboxylic Acid A3

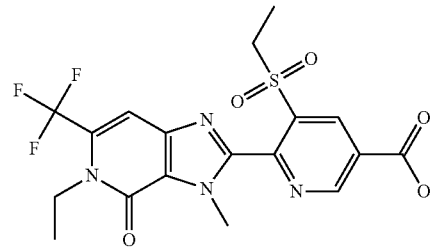

A3

6-[5-ethyl-3-methyl-4-oxo-6-(trifluoromethyl)imidazo[4,5-c]pyridin-2-yl]-5-ethylsulfonyl-pyridine-3-carbonitrile (7 g, 15.93 mmol) in HCl 32% (80 mL) was heated to 60° C. and stirred for 10 hour. After completion, the reaction mixture was cooled to 0°–5° C., treated with NaOH 30% sol. until pH11 and extracted with methyl tert-butyl ether. The water phase was acidified with 10% aqueous HCl to pH4. The solid was filtrated, washed with water and diethyl ether and dried in vacuo to give 6-[5-ethyl-3-methyl-4-oxo-6-(trifluoromethyl)imidazo[4,5-c]pyridin-2-yl]-5-ethylsulfonyl-pyridine-3-carboxylic acid 7 g, 95%). $^1$H NMR (400

MHz, DMSO-d6) δ ppm 1.19 (m, 3H) 1.30 (m, 3H) 3.81 (m, 3H) 3.97 (s, 3H) 4.11-4.23 (m, 2H) 7.47 (s, 1H) 8.81 (d, 1H) 9.48 (d, 1H).

Example P4: Preparation of 6-[5-ethyl-3-methyl-4-oxo-6-(trifluoromethyl)imidazo[4,5-c]pyridin-2-yl]-5-ethylsulfonyl-pyridine-2-carboxylic Acid A4

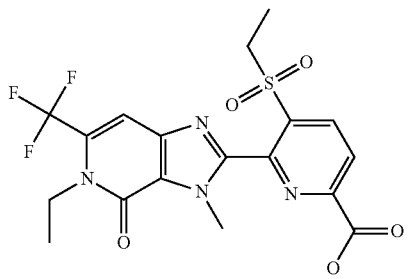

A4

Step A: Preparation of 6-[5-ethyl-3-methyl-4-oxo-6-(trifluoromethyl)imidazo[4,5-c]pyridin-2-yl]-5-ethylsulfonyl-pyridine-2-carbonitrile

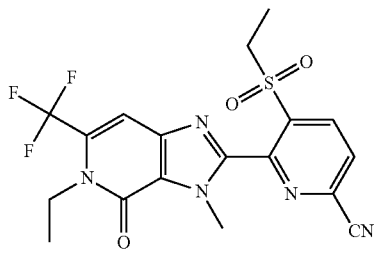 [SMILES: CCn1c(C(F)(F)F)cc2nc(-c3nc(C#N)ccc3S(=O)(=O)CC)n(C)c2c1=O]

2-(6-chloro-3-ethylsulfonyl-2-pyridyl)-5-ethyl-3-methyl-6-(trifluoromethyl)imidazo[4,5-c]pyridin-4-one (11.14 mmol, 5 g) was dissolved in methylsulfinylmethane (40 mL) in a round bottom flask. To this reaction mixture, 1,4-diazabicyclo[2.2.2]octane (0.56 mmol, 0.0625 g, 0.0613 mL) was added at room temperature under nitrogen and stirred for 10 mins. Sodium cyanide (13.37 mmol, 0.655 g) dissolved in water (5 mL) was added to the reaction mixture and heated at 50° C. for 6 hrs. The reaction was quenched with water (100 ml) and diluted with Ethyl acetate (50 ml). Organic layer was separated and the aqueous layer was further extracted with Ethyl acetate (2×50 ml). Combined organic extract was washed with brine, dried over sodium sulfate and concentrated to get crude compound. the purification was done by chromatography and pure compound eluted in 30%-Ethyl acetate/Cyclohexane to give 6-[5-ethyl-3-methyl-4-oxo-6-(trifluoromethyl)imidazo[4,5-c]pyridin-2-yl]-5-ethylsulfonyl-pyridine-2-carbonitrile (7.5 mmol, 3.3 g) in 45% yield. $^1$H NMR (400 MHz, CDCl$_3$) δ ppm 1.36 (m, 6H) 3.85 (m, 2H) 4.15 (s, 3H) 4.23 (m, 2H), 7.21 (s, 1H) 8.05 (d, 1H) 8.68 (d, 1H).

Step B: Preparation of 6-[5-ethyl-3-methyl-4-oxo-6-(trifluoromethyl)imidazo[4,5-c]pyridin-2-yl]-5-ethylsulfonyl-pyridine-2-carboxylic Acid A4

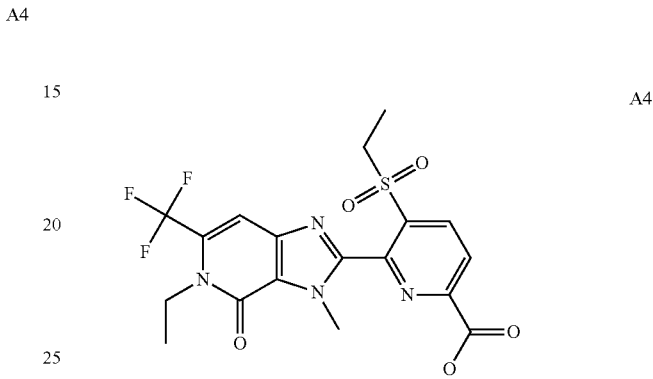

A round bottom flask was charged with 6-[5-ethyl-3-methyl-4-oxo-6-(trifluoromethyl)imidazo[4,5-c]pyridin-2-yl]-5-ethylsulfonyl-pyridine-2-carbonitrile (3.10 mmol, 1.36 g) and concentrated hydrogen chloride (17 mL) was added at room temperature. The reaction was heated at 80° C. for 8 h, then cooled to room temperature and basified till pH 8 with a solution of saturated sodium hydroxide. The aqueous layer was washed with TBME (3×100 ml) to remove non polar impurities. Then, the aqueous layer was acidified till pH-4 when white solid precipitated out. It was then extracted in Ethyl acetate (100 ml). The aqueous layer was further extracted with Ethyl acetate (2×100 ml). Combined organic extract was washed with brine, dried with sodium sulfate, evaporated under vacuum and concentrated to get pure 6-[5-ethyl-3-methyl-4-oxo-6-(trifluoromethyl)imidazo[4,5-c]pyridin-2-yl]-5-ethylsulfonyl-pyridine-2-carboxylic acid (2.8 mmol, 1.3 g) in 92% yield. $^1$H NMR (400 MHz, CDCl$_3$) δ ppm 1.43-1.36 (m, 6H) 3.67 (q, 2H) 3.97 (s, 3H) 4.27 (q, 2H) 7.21 (s, 1H) 8.54 (d, 1H) 8.71 (d, 1H)

Example P5: Preparation of 2-(5-amino-3-ethylsulfonyl-2-pyridyl)-5-ethyl-3-methyl-6-(trifluoromethyl)imidazo[4,5-c]pyridin-4-one A5

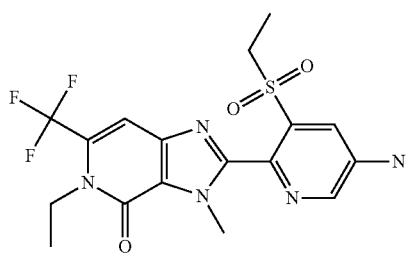

A5

Step A: tert-butyl N-[6-[5-ethyl-3-methyl-4-oxo-6-(trifluoromethyl)imidazo[4,5-c]pyridin-2-yl]-5-ethylsulfonyl-3-pyridyl]carbamate

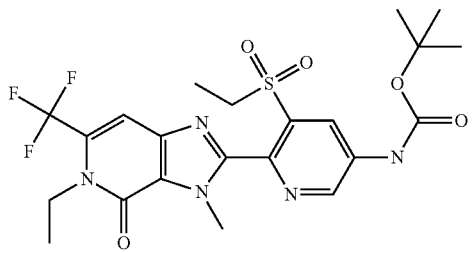 [SMILES: CCn1c(C(F)(F)F)cc2nc(-c3ncc(NC(=O)OC(C)(C)C)cc3S(=O)(=O)CC)n(C)c2c1=O]

2-(5-bromo-3-ethylsulfonyl-2-pyridyl)-5-ethyl-3-methyl-6-(trifluoromethyl)imidazo[4,5-c]pyridin-4-one (Cas: 1879051-82-7) (1 g, 2.027 mmol) was dissolved in anhydrous 1,4-dioxane (10 mL) and cesium carbonate (0.926 g, 2.838 mmol) was added under nitrogen followed by the addition of palladium (II) acetate (0.0137 g, 0.061 mmol) and tert-butyl carbamate (0.2850 g, 2.433 mmol). The reaction mixture was degassed with nitrogen for 15-20 mins, X-PHOS (0.182 mmol, 0.0888 g) was added and the reaction mixture was heated at 110° C. in a preheated oil bath for 14 hours. The solution was filtered through celite bed and washed with Ethyl acetate (20 ml). Organic layer was taken in a separating funnel and washed with water (30 ml), brine, dried over sodium sulfate, filtered and concentrated to get crude product. Column purification done and pure compound eluted in 30% Ethyl acetate/Cyclohexane to give tert-butyl N-[6-[5-ethyl-3-methyl-4-oxo-6-(trifluoromethyl)imidazo[4,5-c]pyridin-2-yl]-5-ethylsulfonyl-3-pyridyl]carbamate (0.893 g, 83%). $^1$H NMR (400 MHz, CDCl$_3$) δ ppm 1.37 (m, 6H) 1.57 (s, 9H) 3.74 (q, 2H) 4.04 (s, 3H) 4.25 (m, 2H) 6.97 (s, 1H) 7.21 (s, 1H) 8.59 (d, 1H) 8.97 (d, 1H).

Step B: 2-(5-amino-3-ethylsulfonyl-2-pyridyl)-5-ethyl-3-methyl-6-(trifluoromethyl)imidazo[4,5-c]pyridin-4-one

A5

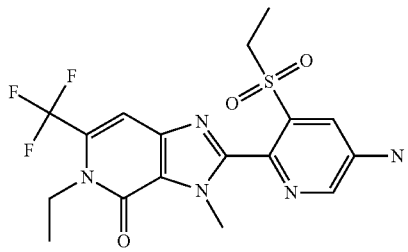

Hydrochloric acid (4M in Dioxane) (1 mL, 4 mmol) was added to a solution of tert-butyl N-[6-[5-ethyl-3-methyl-4-oxo-6-(trifluoromethyl)imidazo[4,5-c]pyridin-2-yl]-5-ethylsulfonyl-3-pyridyl]carbamate (100 mg, 0.1889 mmol) in 1,4-dioxane (1 mL) and the pale yellow solution was stirred at room temperature for overnight and then heated at 50° C. for 6 hours. The reaction was quenched by adding of a saturated aqueous solution of Sodium bicarbonate, and extracted with ethyl acetate. Combined organic layer was evaporated on rotavap and the crude was purified by column chromatography gradient cyclohexane+0-70% Ethyl acetate to give 2-(5-amino-3-ethylsulfonyl-2-pyridyl)-5-ethyl-3-methyl-6-(trifluoromethyl)imidazo[4,5-c]pyridin-4-one (69 mg, 85%). $^1$H NMR (400 MHz, CDCl$_3$) δ ppm 1.33 (t, 3H) 1.38 (t, 3H) 3.71 (q, 2H) 4.01 (s, 3H) 4.24 (q, 2H) 4.47 (br. s., 2H) 7.20 (s, 1H) 7.67 (d, 1H) 8.33 (d, 1H).

Example P6: Preparation of 2-(6-amino-3-ethylsulfonyl-2-pyridyl)-5-ethyl-3-methyl-6-(trifluoromethyl)imidazo[4,5-c]pyridin-4-one A6

(A6)

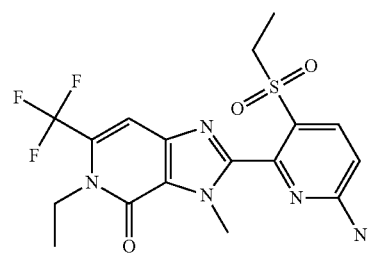

Step A: tert-butyl N-[6-[5-ethyl-3-methyl-4-oxo-6-(trifluoromethyl)imidazo[4,5-c]pyridin-2-yl]-5-ethylsulfonyl-2-pyridyl]carbamate

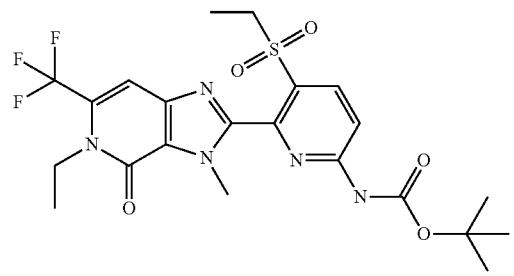 [SMILES: CCn1c(C(F)(F)F)cc2nc(-c3nc(NC(=O)OC(C)(C)C)ccc3S(=O)(=O)CC)n(C)c2c1=O]

In a round bottom flask was added 2-(6-chloro-3-ethylsulfonyl-2-pyridyl)-5-ethyl-3-methyl-6-(trifluoromethyl)imidazo[4,5-c]pyridin-4-one (I7) (15 g, 33.42 mmol), tert-butyl carbamate (4.69 g, 40.11 mmol), cesium carbonate (15.3 g, 46.79 mmol), XPHOS (1.478 g, 3.00 mmol), and 1,4-dioxane (150 mL). The reaction was purged with nitrogen for 10 mins followed by addition of Palladium (II) acetate (237 mg, 1.00 mmol) and then heated at 110° C. for overnight. The reaction was diluted with water (150 ml), extracted with ethyl acetate. The combined organic layers were washed successively with water and brine, dried over Sodium sulfate and concentrated in vacuo. Crude compound was purified by column chromatography gradient cyclohexane+0-30% Ethyl acetate to give tert-butyl N-[6-[5-ethyl-3-methyl-4-oxo-6-(trifluoromethyl)imidazo[4,5-c]pyridin-2-yl]-5-ethylsulfonyl-2-pyridyl]carbamate (14 g, 79%). $^1$H NMR (400 MHz, CDCl$_3$) δ 8.38 (d, 1H), 8.30 (d, 1H), 7.52 (s, 1H), 7.21 (s, 1H), 4.25 (q, 2H), 4.03 (s, 3H), 3.62 (m, 2H), 1.56 (s, 9H), 1.39 (t, 3H), 1.32 (t, 3H).

Step B: 2-(6-amino-3-ethylsulfonyl-2-pyridyl)-5-ethyl-3-methyl-6-(trifluoromethyl)imidazo[4,5-c]pyridin-4-one

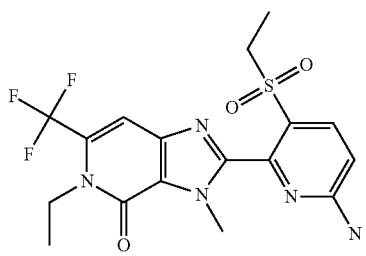

(A6)

To a solution of tert-butyl N-[6-[5-ethyl-3-methyl-4-oxo-6-(trifluoromethyl)imidazo[4,5-c]pyridin-2-yl]-5-ethylsulfonyl-2-pyridyl]carbamate (9.0 g, 17 mmol) in 1,4-dioxane (45 mL) was added 4M Dioxane solution of hydrogen chloride (4 mol/L, 45 mL). The reaction was stirred at 50° C. for 8 hour and then neutralized with saturated aqueous solution of sodium bicarbonate (100 ml) and aqueous layer was extracted with ethyl acetate, combined organic layer was dried over sodium sulfate, filtered and concentrated under reduced pressure. The residue was dried under high-vacuum to give 2-(6-amino-3-ethylsulfonyl-2-pyridyl)-5-ethyl-3-methyl-6-(trifluoromethyl)imidazo[4,5-c]pyridin-4-one (7.0 g, 96%). $^1$H NMR (400 MHz, CDCl$_3$) δ=8.10 (d, 1H), 7.20 (s, 1H), 6.69 (d, 1H), 5.25 (s, 2H), 4.24 (q, 2H), 4.04 (s, 3H), 3.53 (q, 2H), 1.38 (t, 3H), 1.29 (t, 3H).

Example P7: Preparation of N-[6-[5-ethyl-3-methyl-4-oxo-6-(trifluoromethyl)imidazo[4,5-c]pyridin-2-yl]-5-ethylsulfonyl-3-pyridyl]cyclopropanecarboxamide A7

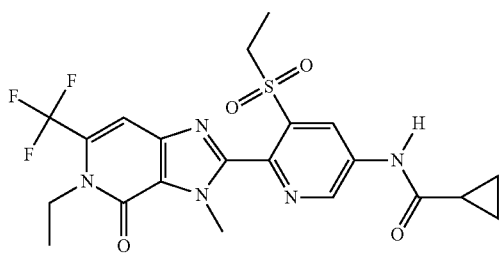

(A7)

In a one neck round bottom flask, 2-(5-amino-3-ethylsulfonyl-2-pyridyl)-5-ethyl-3-methyl-6-(trifluoromethyl)imidazo[4,5-c]pyridin-4-one (300 mg, 0.6986 mmol) was dissolved in dichloromethane (5 mL) and N,N-diethylethanamine (2.096 mmol, 0.30 ml) was added. The mixture was stirred at 0° C. for 5 min, followed by addition of cyclopropane carbonyl chloride (0.8384 mmol, 0.08 ml) dropwise and the mixture was stirring for 3 hours at room temperature. The reaction was quenched by addition of 10 ml of water and additional 15 ml of dichloromethane was added. Organic layer was separated in separating funnel, washed with brine, concentrated and crude was purified by column chromatography gradient cyclohexane+0-40% Ethyl acetate to give N-[6-[5-ethyl-3-methyl-4-oxo-6-(trifluoromethyl)imidazo[4,5-c]pyridin-2-yl]-5-ethylsulfonyl-3-pyridyl]cyclopropanecarboxamide (209 mg, 60%) as a crystalline-white solid. $^1$H NMR (400 MHz, CDCl$_3$) δ=9.32 (s., 1H), 8.63 (d, 1H), 8.33 (brs, 1H), 7.21 (s, 1H), 4.25 (q, 2H), 4.06 (s, 3H), 3.79 (q, 2H), 1.65-1.59 (m, 1H), 1.48-1.32 (m, 6H), 1.22-1.11 (m, 2H), 1.03-0.92 (m, 2H).

Example P8: Preparation of N-[6-[5-ethyl-3-methyl-4-oxo-6-(trifluoromethyl)imidazo[4,5-c]pyridin-2-yl]-5-ethylsulfonyl-2-pyridyl]cyclopropanecarboxamide A8

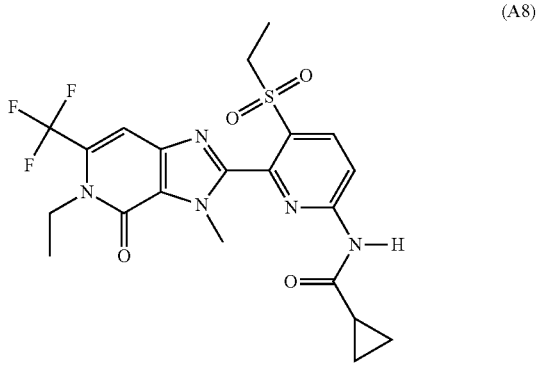 [SMILES: CCn1c(C(F)(F)F)cc2nc(-c3nc(NC(=O)C4CC4)ccc3S(=O)(=O)CC)n(C)c2c1=O]

(A8)

In one neck round bottom flask, 2-(6-amino-3-ethylsulfonyl-2-pyridyl)-5-ethyl-3-methyl-6-(trifluoromethyl)imidazo[4,5-c]pyridin-4-one (300 mg, 0.6986 mmol) was dissolved in dichloromethane (4 mL) and to it was added N,N-diethylethanamine (0.2121 g, 2.096 mmol) and reaction mixture was stirred at 0° C. under ice bath. After 5 min, cyclopropane carbonyl chloride (0.8384 mmol, 0.08764 g) was added dropwise under ice bath and stirred for 6 Hours at room temperature. and the reaction mixture was then quenched by adding 10 ml of water and 15 ml of dichloromethane. Organic and aqueous layer were separated in separating funnel, aqueous layer re-extracted with dichloromethane (2×15 mL). Combined org layer was washed with brine and concentrated under reduced pressure. The crude product was purified by column chromatography gradient cyclohexane+0-50% Ethyl acetate and further with reverse phase column chromatography to give N-[6-[5-ethyl-3-methyl-4-oxo-6-(trifluoromethyl)imidazo[4,5-c]pyridin-2-yl]-5-ethylsulfonyl-2-pyridyl]cyclopropanecarboxamide (71 mg, 10%) as a crystalline-white solid. Mp=103-105° C. $^1$H NMR (400 MHz, CDCl$_3$) δ ppm 0.96-1.01 (m, 2H) 1.16-1.20 (m, 2H) 1.30 (t, 3H) 1.38 (t, 3H) 1.65-1.70 (m, 1H) 3.58 (q, 2H) 4.01 (s, 3H) 4.24 (q, 2H) 7.20 (s, 1H) 8.40 (d, 1H) 8.55 (d, 1H) 8.74 (s, 1H).

Example P9: Preparation of N-[6-[5-ethyl-3-methyl-4-oxo-6-(trifluoromethyl)imidazo[4,5-c]pyridin-2-yl]-5-ethylsulfonyl-3-pyridyl]-N-methyl-cyclopropanecarboxamide A9

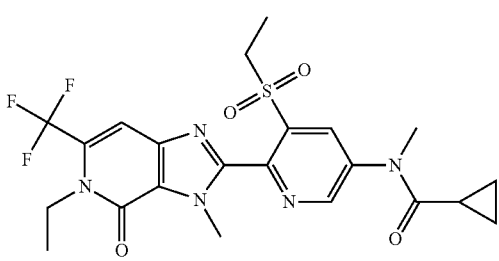

A9

Step A: tert-butyl N-[6-[5-ethyl-3-methyl-4-oxo-6-(trifluoromethyl)imidazo[4,5-c]pyridin-2-yl]-5-ethylsulfonyl-3-pyridyl]carbamate A64

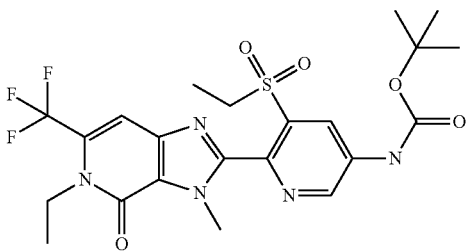 [SMILES: CCn1c(C(F)(F)F)cc2nc(-c3ncc(NC(=O)OC(C)(C)C)cc3S(=O)(=O)CC)n(C)c2c1=O]

2-(5-bromo-3-ethylsulfonyl-2-pyridyl)-5-ethyl-3-methyl-6-(trifluoromethyl)imidazo[4,5-c]pyridin-4-one (Cas: 1879051-82-7) (1 g, 2.027 mmol) was dissolved in anhydrous 1,4-dioxane (10 mL) and to it cesium carbonate (0.926 g, 2.838 mmol) was added under nitrogen followed by the addition of palladium (II) acetate (0.01366 g, 0.06081 mmol) and tert-butyl carbamate (0.2850 g, 2.433 mmol). The reaction mixture was degassed with nitrogen for 15-20 mins, X-PHOS (0.1824 mmol, 0.0888 g) was added and the reaction mixture was heated at 110° C. in a preheated oil bath for 14 hours. The solution was filtered through celite bed and washed with Ethyl acetate (20 ml). Organic layer was washed with water (30 ml), brine, dried over sodium sulfate, filtered and concentrated to get crude product. Column purification was done and pure compound was eluted in 30% Ethyl acetate/Cyclohexane to give tert-butyl N-[6-[5-ethyl-3-methyl-4-oxo-6-(trifluoromethyl)imidazo[4,5-c]pyridin-2-yl]-5-ethylsulfonyl-3-pyridyl]carbamate (0.893 g, 83%). $^1$H NMR (400 MHz, CDCl$_3$) δ ppm 1.37 (m, 6H) 1.57 (s, 9H) 3.74 (q, 2H) 4.04 (s, 3H) 4.25 (m, 2H) 6.97 (s, 1H) 7.21 (s, 1H) 8.59 (d, 1H) 8.97 (d, 1H).

Step B: tert-butyl N-[6-[5-ethyl-3-methyl-4-oxo-6-(trifluoromethyl)imidazo[4,5-c]pyridin-2-yl]-5-ethylsulfonyl-3-pyridyl]-N-methyl-carbamate. A65

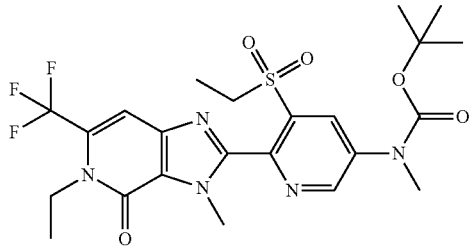 [SMILES: CCn1c(C(F)(F)F)cc2nc(-c3ncc(N(C)C(=O)OC(C)(C)C)cc3S(=O)(=O)CC)n(C)c2c1=O]

To a solution of tert-butyl N-[6-[5-ethyl-3-methyl-4-oxo-6-(trifluoromethyl)imidazo[4,5-c]pyridin-2-yl]-5-ethylsulfonyl-3-pyridyl]carbamate (50 mg, 0.0944 mmol) in N,N-dimethylformamide (1 mL) under N$_2$ at room temperature, dipotassium carbonate (0.5665 mmol, 78 mg) and iodomethane (0.2833 mmol, 0.02 ml) were added. The mixture was stirred at room temperature for 3 hours and then quenched with water. The aqueous phase was extracted in ethyl acetate. Combined organic layer was washed with brine, dried over sodium sulfate and concentrated to give tert-butyl N-[6-[5-ethyl-3-methyl-4-oxo-6-(trifluoromethyl)imidazo[4,5-c]pyridin-2-yl]-5-ethylsulfonyl-3-pyridyl]-N-methyl-carbamate (50 mg, 97%). $^1$H NMR (400 MHz, CDCl$_3$) δ=8.96 (d, 1H), 8.41 (d, 1H), 7.21 (s, 1H), 4.25 (q, 2H), 4.08 (m, 3H), 3.78 (q, 2H), 3.44 (s, 3H), 1.55 (s, 9H), 1.44-1.32 (m, 6H).

Step C: 5-ethyl-2-[3-ethylsulfonyl-5-(methylamino)-2-pyridyl]-3-methyl-6-(trifluoromethyl)imidazo[4,5-c]pyridin-4-one

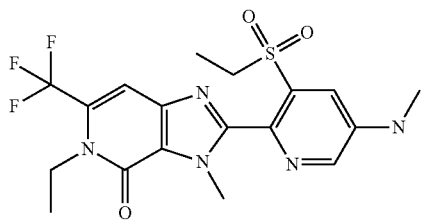 [SMILES: CCn1c(C(F)(F)F)cc2nc(-c3ncc(NC)cc3S(=O)(=O)CC)n(C)c2c1=O]

The hydrochloric acid (4M in Dioxane) (45 mL) was added to a solution of tert-butyl N-[6-[5-ethyl-3-methyl-4-oxo-6-(trifluoromethyl)imidazo[4,5-c]pyridin-2-yl]-5-ethylsulfonyl-3-pyridyl]-N-methyl-carbamate (4.45 g, 8.19 mmol) in 1,4-dioxane (45 mL) and the pale yellow solution was then heated at 50° C. for 9 hour. The reaction was cooled down to 0° C. and quenched by addition of saturated aqueous Sodium bicarbonate solution and 20 ml water. The solution was extracted with 60 ml ethyl acetate, combined organic layer was evaporated on rotavap and crude product was purified by column chromatography gradient cyclohexane+0-70% Ethyl acetate to give 5-ethyl-2-[3-ethylsulfonyl-5-(methylamino)-2-pyridyl]-3-methyl-6-(trifluoromethyl)imidazo[4,5-c]pyridin-4-one (3.2 g, 88%). $^1$H NMR (400 MHz, CDCl$_3$) δ ppm 1.30-1.43 (m, 6H) 3.01 (d, 3H) 3.65-3.77 (m, 2H) 4.01 (s, 3H) 4.24 (q, 2H) 4.56 (br. s., 1H) 7.20 (s, 1H) 7.51 (d, 1H) 8.26 (d, 1H).

Step D: N-[6-[5-ethyl-3-methyl-4-oxo-6-(trifluoromethyl)imidazo[4,5-c]pyridin-2-yl]-5-ethylsulfonyl-3-pyridyl]-N-methyl-cyclopropanecarboxamide A9

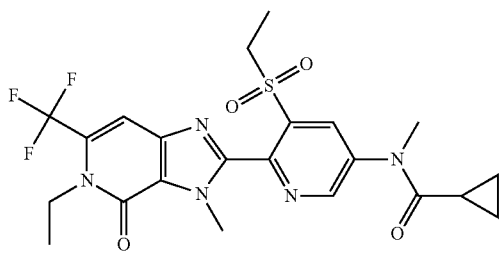

In a 25 ml RB, to a 0° C. cooled solution of 5-ethyl-2-[3-ethylsulfonyl-5-(methylamino)-2-pyridyl]-3-methyl-6-(trifluoromethyl)imidazo[4,5-c]pyridin-4-one (300 mg, 0.6766 mmol) and N,N-diethylethanamine (1.353 mmol) (0.2 ml) in dichloromethane (4 mL) was added cyclopropane carbonyl chloride (1.015 mmol, 0.1 ml). The reaction was slowly allowed to warm to room temperature, stirred for 3 hours. After this mixture was quenched with 10 ml of water and extracted with 15 ml of dichloromethane. Combined dichloromethane layer was evaporated on rotavap to get crude product and purified by column chromatography gradient cyclohexane+0-50% Ethyl acetate to give N-[6-[5-ethyl-3-methyl-4-oxo-6-(trifluoromethyl)imidazo[4,5-c]pyridin-2-yl]-5-ethylsulfonyl-3-pyridyl]-N-methyl-cyclopropanecarboxamide (270 mg, 78%). $^1$H NMR (400 MHz, CDCl$_3$) δ=8.96 (d, 1H), 8.43 (d, 1H), 7.21 (s, 1H), 4.24 (m, 2H), 4.12 (s, 3H), 3.82 (q, 2H), 3.53 (s, 3H), 1.56 (m, 1H), 1.44-1.33 (m, 6H), 1.22-1.15 (m, 2H), 0.94-0.85 (m, 2H).

Example P10: Preparation of N-[6-[5-ethyl-3-methyl-4-oxo-6-(trifluoromethyl)imidazo[4,5-c]pyridin-2-yl]-5-ethylsulfonyl-2-pyridyl]-N-methyl-cyclopropanecarboxamide A10

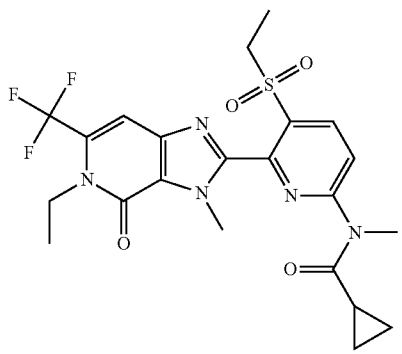

Step A: tert-butyl N-[6-[5-ethyl-3-methyl-4-oxo-6-(trifluoromethyl)imidazo[4,5-c]pyridin-2-yl]-5-ethylsulfonyl-2-pyridyl]carbamate A66

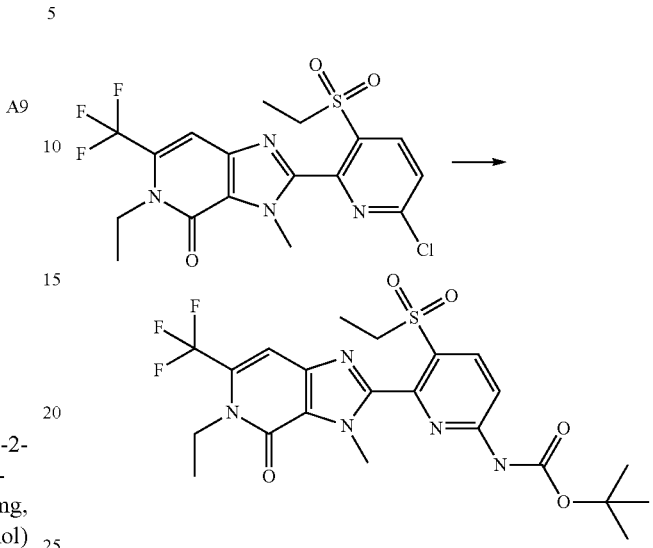

In a round bottom flask was added 2-(6-chloro-3-ethylsulfonyl-2-pyridyl)-5-ethyl-3-methyl-6-(trifluoromethyl)imidazo[4,5-c]pyridin-4-one (I7) (15 g, 33.42 mmol), tert-butyl carbamate (4.69 g, 40.11 mmol), cesium carbonate (15.3 g, 46.79 mmol), XPHOS (1.478 g, 3.00 mmol), and 1,4-dioxane (150 mL). The reaction was purged with nitrogen for 10 mins followed by addition of Palladium (II) acetate (237 mg, 1.00 mmol) and then heated at 110° C. for overnight. The reaction was diluted with water (150 ml), extracted with ethyl acetate. The combined organic layers were washed successively with water and brine, dried over Sodium sulfate and concentrated in vacuo. Crude compound was purified by column chromatography gradient cyclohexane+0-30% Ethyl acetate to give tert-butyl N-[6-[5-ethyl-3-methyl-4-oxo-6-(trifluoromethyl)imidazo[4,5-c]pyridin-2-yl]-5-ethylsulfonyl-2-pyridyl]carbamate (14 g, 79%).

$^1$H NMR (400 MHz, CDCl$_3$) δ 8.38 (d, 1H), 8.30 (d, 1H), 7.52 (s, 1H), 7.21 (s, 1H), 4.25 (q, 2H), 4.03 (s, 3H), 3.62 (m, 2H), 1.56 (s, 9H), 1.39 (t, 3H), 1.32 (t, 3H).

Step B: tert-butyl N-[6-[5-ethyl-3-methyl-4-oxo-6-(trifluoromethyl)imidazo[4,5-c]pyridin-2-yl]-5-ethylsulfonyl-2-pyridyl]-N-methyl-carbamate A67

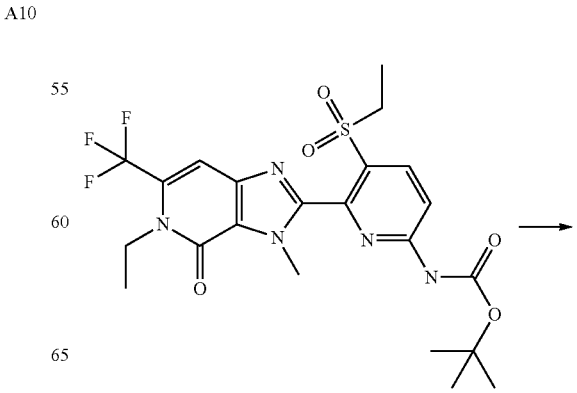

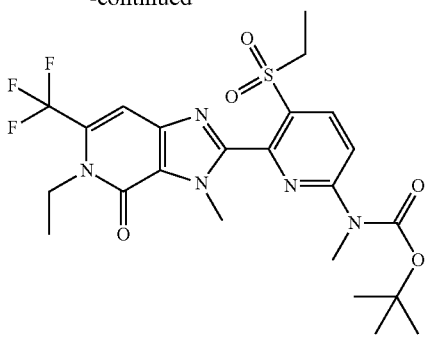

In a 25 ml flask, at 0° C. cooled suspension of sodium hydride (1.700 mmol, 0.06798 g) in tetrahydrofuran (2 mL) was added dropwise a clear solution of tert-butyl N-[6-[5-ethyl-3-methyl-4-oxo-6-(trifluoromethyl)imidazo[4,5-c]pyridin-2-yl]-5-ethylsulfonyl-2-pyridyl]carbamate (600 mg, 1.133 mmol) in tetrahydrofuran (6 ml). The reaction was stirred at 0° C. for 30 mins followed by addition of iodomethane (3.399 mmol, 0.4825 g) (0.22 ml) and N,N-dimethylformamide (1 ml). The reaction mixture was allowed to warm to room temperature over 3 hours and then heated at 40° C. for 15 min. The reaction was neutralized with 2N HCl, diluted with 10 ml water, extracted with ethyl acetate (3×15 ml). Combined organic layer was dried over sodium sulfate, filtered and concentrated under reduced pressure. Crude product was purified by column chromatography gradient cyclohexane+0-30% Ethyl acetate to give tert-butyl N-[6-[5-ethyl-3-methyl-4-oxo-6-(trifluoromethyl)imidazo[4,5-c]pyridin-2-yl]-5-ethylsulfonyl-2-pyridyl]-N-methyl-carbamate (530 mg, 86%). $^1$H NMR (400 MHz, CDCl$_3$) δ ppm 1.29-1.41 (m, 6H) 1.58 (s, 9H) 3.44 (s, 3H) 3.61-3.72 (m, 2H) 4.07 (s, 3H) 4.24 (q, 2H) 7.21 (s, 1H) 8.32 (m, 2H).

Step C: 5-ethyl-2-[3-ethylsulfonyl-6-(methylamino)-2-pyridyl]-3-methyl-6-(trifluoromethyl)imidazo[4,5-c]pyridin-4-one A62

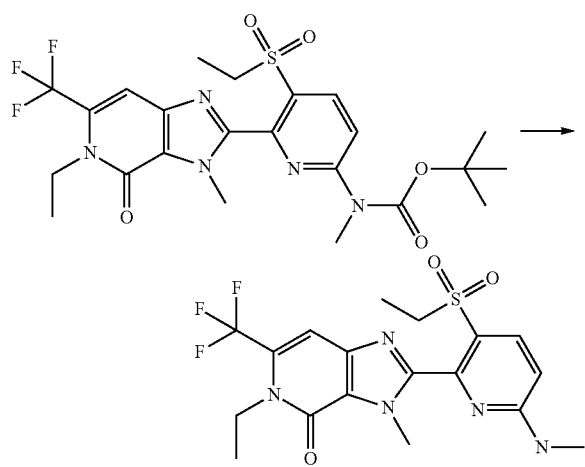

The hydrochloric acid (4M in dioxane) (5 mL, 20 mmol) was added to a solution of tert-butyl N-[6-[5-ethyl-3-methyl-4-oxo-6-(trifluoromethyl)imidazo[4,5-c]pyridin-2-yl]-5-ethylsulfonyl-2-pyridyl]-N-methyl-carbamate (500 mg, 0.9198 mmol) in 1,4-dioxane (5 mL) and the clear solution was then heated at 50° C. for 8 Hours. The reaction went to completion and was cooled to 0° C., quenched with saturated aqueous solution of Sodium bicarbonate and 10 ml water. The aqueous phase was extracted in 20 ml ethyl acetate, combined organic layer was evaporated on rotavap and the crude was purified by Column chromatography gradient cyclohexane+0-70% Ethyl acetate to give 5-ethyl-2-[3-ethylsulfonyl-6-(methylamino)-2-pyridyl]-3-methyl-6-(trifluoromethyl)imidazo[4,5-c]pyridin-4-one (340 mg, 83%). $^1$H NMR (400 MHz, CDCl$_3$) δ ppm 1.26-1.31 (m, 3H) 1.37 (t, 3H) 2.95 (m, 3H) 3.54 (q, 2H) 4.04 (s, 3H) 4.23 (q, 2H) 5.47 (br. s., 1H) 6.56 (d, 1H) 7.20 (s, 1H) 8.04 (d, 1H).

Step D: N-[6-[5-ethyl-3-methyl-4-oxo-6-(trifluoromethyl)imidazo[4,5-c]pyridin-2-yl]-5-ethylsulfonyl-2-pyridyl]-N-methyl-cyclopropanecarboxamide A10

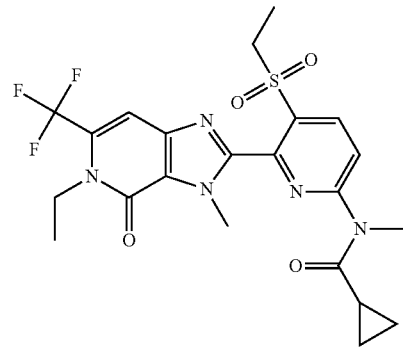

In one neck round bottle flask, 5-ethyl-2-[3-ethylsulfonyl-6-(methylamino)-2-pyridyl]-3-methyl-6-(trifluoromethyl)imidazo[4,5-c]pyridin-4-one (330 mg, 0.7442 mmol) was dissolved in dichloromethane (4 mL) and N,N-diethylethanamine (0.22 ml) was added to it. The mixture was stirred at 0° C. under ice bath and after 5 min cyclopropane carbonyl chloride (1.116 mmol, 0.1167 g) was added dropwise. The reaction was stirred for 40 hours at room temperature. 10 ml Water followed by 15 ml dichloromethane were added to the reaction mixture, organic layer was separated in separating funnel, aqueous layer re-extracted with dichloromethane (2×15 mL). Organic layer was washed with brine, concentrated and crude product was purified by column chromatography gradient cyclohexane+0-40% Ethyl acetate to give N-[6-[5-ethyl-3-methyl-4-oxo-6-(trifluoromethyl)imidazo[4,5-c]pyridin-2-yl]-5-ethylsulfonyl-2-pyridyl]-N-methyl-cyclopropanecarboxamide (140 mg, 77%) as a crystalline-white solid. Mp=177-179° C. $^1$H NMR (400 MHz, CDCl$_3$) δ ppm 0.99 (m, 2H) 1.20-1.24 (m, 2H) 1.35 (t, 3H) 1.40 (t, 3H) 1.98 (m, 1H) 3.65 (s, 3H) 3.70 (q, 2H) 4.09 (s, 3H) 4.26 (m, 2H) 7.22 (s, 1H) 8.13 (d, 1H) 8.38 (d, 1H).

Example P11: Preparation of 2-[5-[cyclopropyl(methyl)amino]-3-ethylsulfonyl-2-pyridyl]-5-ethyl-3-methyl-6-(trifluoromethyl)imidazo[4,5-c]pyridin-4-one A11

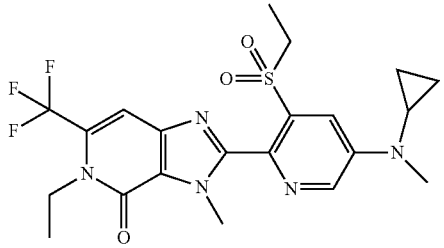

A11

Step A: 2-[5-(cyclopropylamino)-3-ethylsulfonyl-2-pyridyl]-5-ethyl-3-methyl-6-(trifluoromethyl)imidazo[4,5-c]pyridin-4-one

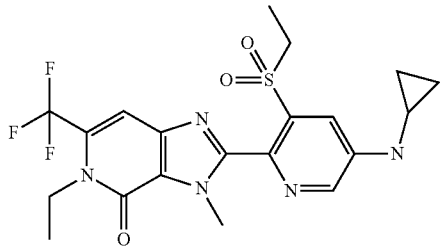 [SMILES: CCn1c(C(F)(F)F)cc2nc(-c3ncc(NC4CC4)cc3S(=O)(=O)CC)n(C)c2c1=O]

2-(5-bromo-3-ethylsulfonyl-2-pyridyl)-5-ethyl-3-methyl-6-(trifluoromethyl)imidazo[4,5-c]pyridin-4-one (Cas: 1879051-82-7) (2.027 mmol, 1 g) was dissolved in anhydrous toluene (10 mL) and to it cesium carbonate (3.041 mmol, 0.992 g) was added under nitrogen. The mixture was purged with nitrogen for 15 mins. tris(dibenzylideneacetone)dipalladium (0) (0.04054 mmol, 0.03750 g), (+/−)-BINAP (0.0811 mmol, 0.0521 g) and cyclopropyl amine (2.433 mmol, 0.1389 g) were successively added to the mixture and it was heated at 110° C. for 16 hours. Pd$_2$(dba)$_3$ (0.01 eq), BINAP (0.02 eq), cesium carbonate (0.75 eq.) and cyclopropylamine (0.6 eq.) were further added to the mixture and heating continued for another 5 hours. The reaction was complete and was filtered through celite bed and the bed was washed with ethyl acetate (20 ml). Organic layer was evaporated and directly subjected to column purification gradient cyclohexane+0-40% Ethyl acetate to give 2-[5-(cyclopropylamino)-3-ethylsulfonyl-2-pyridyl]-5-ethyl-3-methyl-6-(trifluoromethyl)imidazo[4,5-c]pyridin-4-one (0.523 g, 55%). $^1$H NMR (400 MHz, CDCl$_3$) δ ppm 0.62-0.68 (m, 2H) 0.91-0.99 (m, 2H) 1.31-1.42 (m, 6H) 2.57-2.65 (m, 1H) 3.72 (q, 2H) 4.03 (s, 3H) 4.20-4.29 (m, 2H) 4.81 (s, 1H) 7.21 (s, 1H) 7.74 (d, 1H) 8.40 (d, 1H).

Step B: 2-[5-[cyclopropyl(methyl)amino]-3-ethylsulfonyl-2-pyridyl]-5-ethyl-3-methyl-6-(trifluoromethyl)imidazo[4,5-c]pyridin-4-one A11

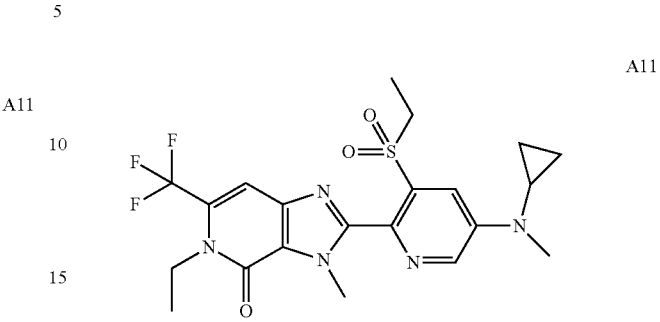

A11

2-[5-(cyclopropylamino)-3-ethylsulfonyl-2-pyridyl]-5-ethyl-3-methyl-6-(trifluoromethyl)imidazo[4,5-c]pyridin-4-one (1.114 mmol, 0.523 g) was dissolved in dry N,N-dimethylformamide (5 mL) and sodium hydride (1.448 mmol, 0.0579 g) was added under nitrogen at 0° C. The mixture was stirred at 0° C. for 10 mins, iodomethane (1.225 mmol, 0.1739 g) was added to the mixture and stirring continued for 2 hours at room temperature. After the completion of the reaction it was quenched in water and diluted with ethyl acetate (10 ml). Organic layer was separated. Aqueous layer was further extracted with ethyl acetate (2×15 ml). Combined organic layer was washed with brine, dried over sodium sulfate and concentrated under vacuum to get crude product. Column purification done in combiflash gradient cyclohexane+0-30% Ethyl acetate to give 2-[5-[cyclopropyl(methyl)amino]-3-ethylsulfonyl-2-pyridyl]-5-ethyl-3-methyl-6-(trifluoromethyl)imidazo[4,5-c]pyridin-4-one A11 (0.2875 mmol, 0.139 g, 25%). $^1$H NMR (400 MHz, CDCl$_3$) δ=8.60 (d, 1H), 7.82 (d, 1H), 7.20 (s, 1H), 4.24 (q, 2H), 4.03 (s, 3H), 3.72 (q, 2H), 3.17 (s, 3H), 2.70 (m, 1H), 1.42-1.31 (m, 6H), 1.09-1.00 (m, 2H), 0.79-0.71 (m, 2H).

Example P12: Preparation of 2-[6-[cyclopropyl(methyl)amino]-3-ethylsulfonyl-2-pyridyl]-5-ethyl-3-methyl-6-(trifluoromethyl)imidazo[4,5-c]pyridin-4-one A12

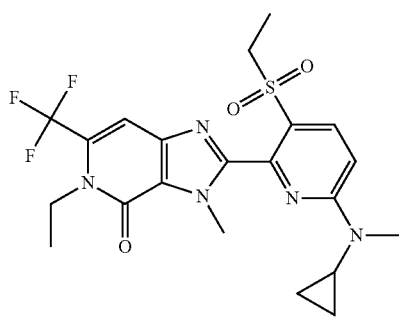

A12

In a microwave vial was added 2-(6-chloro-3-ethylsulfonyl-2-pyridyl)-5-ethyl-3-methyl-6-(trifluoromethyl)imidazo[4,5-c]pyridin-4-one (I7) (235 mg, 0.5236 mmol), dipotassium carbonic acid (1.047 mmol), N-methylcyclopropyl amine hydrochloride (84.50 mg, 0.7854 mmol) and N,N-DIMETHYLFORMAMIDE (3 mL). The reaction was subjected to microwave heating at 130° C. for 1 hour. The reaction was diluted with water (10 ml), extracted with ethyl acetate and combined organic layer was dried over sodium sulfate, concentrated under reduced pressure. The residue was purified by CombiFlash column chromatography gradient cyclohexane+0-50% Ethyl acetate to give 2-[6-[cyclopropyl(methyl)amino]-3-ethylsulfonyl-2-pyridyl]-5-ethyl-3-methyl-6-(trifluoromethyl)imidazo[4,5-c]pyridin-4-one (90 mg, 35%). ¹H NMR (400 MHz, CDCl₃) δ=8.09 (d, 1H), 7.22 (s, 1H), 7.13 (d, 1H), 4.24 (q, 2H), 4.07 (s, 3H), 3.58 (q, 2H), 3.17 (s, 3H), 2.76-2.65 (m, 1H), 1.42-1.35 (m, 3H), 1.31 (t, 3H), 1.06-0.97 (m, 2H), 0.81-0.73 (m, 2H).

Example P13: Preparation of N-[6-[5-ethyl-3-methyl-4-oxo-6-(trifluoromethyl)imidazo[4,5-c]pyridin-2-yl]-5-ethylsulfonyl-3-pyridyl]l-N-methyl-methanesulfonamide A13

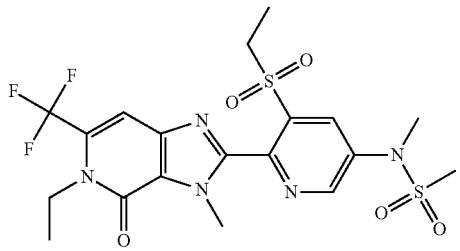

A13

Step A: N-[6-[5-ethyl-3-methyl-4-oxo-6-(trifluoromethyl)imidazo[4,5-c]pyridin-2-yl]-5-ethylsulfonyl-3-pyridyl]-N-methylsulfonyl-methanesulfonamide

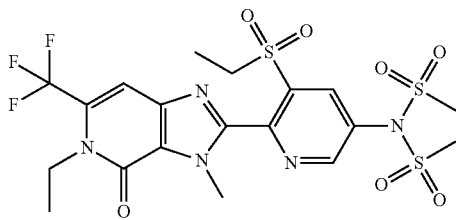 [SMILES: CCn1c(C(F)(F)F)cc2nc(-c3ncc(N(S(C)(=O)=O)S(C)(=O)=O)cc3S(=O)(=O)CC)n(C)c2c1=O]

In a stirring solution of 2-(5-amino-3-ethylsulfonyl-2-pyridyl)-5-ethyl-3-methyl-6-(trifluoromethyl)imidazo[4,5-c]pyridin-4-one A5 (1.5 g, 3.5 mmol) in dichloromethane (15 mL) was added N,N-diethylethanamine (3.145 mmol, 0.93 ml) then was added methane sulfonyl chloride (0.88 g, 7.7 mmol) and reaction was stirred at room temperature for 1 hour. The reaction was washed with sodium bicarbonate solution and dichloromethane layer was concentrated to get crude product which was purified by column chromatography gradient cyclohexane+0-70% Ethyl acetate to give N-[6-[5-ethyl-3-methyl-4-oxo-6-(trifluoromethyl)imidazo[4,5-c]pyridin-2-yl]-5-ethylsulfonyl-3-pyridyl]-N-methylsulfonyl-methanesulfonamide (1.4 g, 68%). Mp=260° C. ¹H NMR (400 MHz, CDCl₃) δ ppm 1.25-1.41 (m, 6H) 3.51 (s, 6H), 3.80 (q, 2H) 4.16 (s, 3H) 4.26 (q, 2H) 7.23 (s, 1H) 8.50 (d, 1H). 8.94 (d, 1H).

Step B: N-[6-[5-ethyl-3-methyl-4-oxo-6-(trifluoromethyl)imidazo[4,5-c]pyridin-2-yl]-5-ethylsulfonyl-3-pyridyl]methanesulfonamide A15

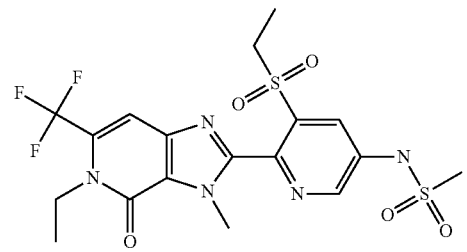

A15

In a stirring solution of N-[6-[5-ethyl-3-methyl-4-oxo-6-(trifluoromethyl)imidazo[4,5-c]pyridin-2-yl]-5-ethylsulfonyl-3-pyridyl]-N-methylsulfonyl-methanesulfonamide (1.3 g, 2.2 mmol) in methanol (20 ml) was added sodium hydroxide (88 mg, 2.2 mmol) dissolved in 4 ml of water and reaction was stirred at room temperature for 1 hour. The reaction was quenched by adding 2N HCl and extracted with Ethyl acetate. Ethyl acetate layer was concentrated and purified by column chromatography gradient cyclohexane+0-70% Ethyl acetate to give N-[6-[5-ethyl-3-methyl-4-oxo-6-(trifluoromethyl)imidazo[4,5-c]pyridin-2-yl]-5-ethylsulfonyl-3-pyridyl]methanesulfonamide (600 mg, 46%). Mp=251-253° C. ¹H NMR (400 MHz, CDCl₃) δ ppm 1.33-1.47 (m, 6H) 3.23 (s, 3H) 3.82 (q, 2H) 4.10 (s, 3H) 4.27 (q, 2H) 7.24 (s, 1H) 8.32 (d, 1H) 8.72 (m, 1H), 8.85 (d, 1H).

Step C: N-[6-[5-ethyl-3-methyl-4-oxo-6-(trifluoromethyl)imidazo[4,5-c]pyridin-2-yl]-5-ethylsulfonyl-3-pyridyl]-N-methyl-methanesulfonamide

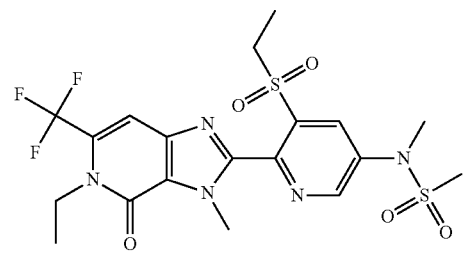

A13

In a stirring solution of N-[6-[5-ethyl-3-methyl-4-oxo-6-(trifluoromethyl)imidazo[4,5-c]pyridin-2-yl]-5-ethylsulfonyl-3-pyridyl]methanesulfonamide (0.3941 mmol, 0.2 g) in dichloromethane (10 mL) was added sodium hydride (0.7882 mmol, 0.0315252 g) at room temperature and to this solution was added methyl iodide (0.7882 mmol, 0.112 g). The reaction was stirred at room temperature for 12 hours and then quenched by addition of water (50 ml). Product was extracted by ethyl acetate, organic layer was concentrated to get crude product and purified by column chromatography gradient cyclohexane+0-70% Ethyl acetate to give N-[6-[5-ethyl-3-methyl-4-oxo-6-(trifluoromethyl)imidazo[4,5-c]pyridin-2-yl]-5-ethylsulfonyl-3-pyridyl]-N-methyl-methanesulfonamide (70 mg, 34%). Mp=223-225° C. ¹H NMR (400 MHz, CDCl₃) δ ppm 1.40 (q, 6H) 3.05 (s, 3H) 3.52 (s, 3H) 3.84 (q, 2H) 4.13 (s, 3H) 4.27 (q, 2H) 7.23 (s, 1H) 8.43 (d, 1H) 9.03 (d, 1H).

Example P14: Preparation of N-[6-[5-ethyl-3-methyl-4-oxo-6-(trifluoromethyl)imidazo[4,5-c]pyridin-2-yl]-5-ethylsulfonyl-3-pyridyl]-N-methyl-methanesulfonamide A14

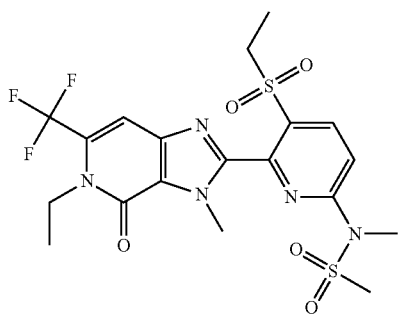

A14

To a solution of sodium hydride (1.034 mmol, 60 mass %) in tetrahydrofuran (2 ml) was added a solution of N-[6-[5-ethyl-3-methyl-4-oxo-6-(trifluoromethyl)imidazo[4,5-c]pyridin-2-yl]-5-ethylsulfonyl-2-pyridyl]methanesulfonamide (Prepared using procedure as descripted in Example I3 Step A and B) (350 mg, 0.6897 mmol) in tetrahydrofuran (3 ml). The reaction was stirred at room temperature for 30 mins. To this was then added iodomethane (2.069 mmol). The reaction was stirred at 50° C. for 5 hours, monitored by TLC. The reaction was neutralized with 2N HCl (10 ml), aqueous layer was extracted with ethyl acetate, combined organic layer was dried over sodium sulfate, concentrated under reduced pressure. Crude product was purified by column chromatography gradient cyclohexane+0-50% Ethyl acetate to give N-[6-[5-ethyl-3-methyl-4-oxo-6-(trifluoromethyl)imidazo[4,5-c]pyridin-2-yl]-5-ethylsulfonyl-3-pyridyl]-N-methyl-methanesulfonamide A14 (170 mg, 47%). ¹H NMR (400 MHz, DMSO) δ=8.44 (d, 1H), 7.71 (d, 1H), 7.22 (s, 1H), 4.26 (q, 2H), 4.11 (s, 3H), 3.73 (q, 2H), 3.52 (s, 3H), 3.19 (s, 3H), 1.38 (m, 6H).

Example P15: Preparation of N-[6-[5-ethyl-3-methyl-4-oxo-6-(trifluoromethyl)imidazo[4,5-c]pyridin-2-yl]-5-ethylsulfonyl-3-pyridyl]methanesulfonamide A15

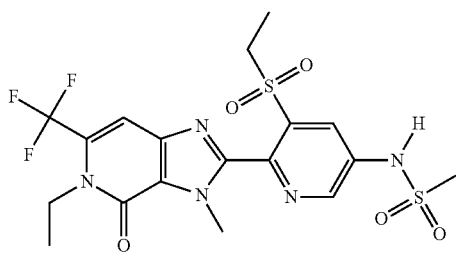

A15

See Example P13 Step A and B.

Example P16: Preparation of N-[6-[5-ethyl-3-methyl-4-oxo-6-(trifluoromethyl)imidazo[4,5-c]pyridin-2-yl]-5-ethylsulfonyl-2-pyridyl]methanesulfonamide A16

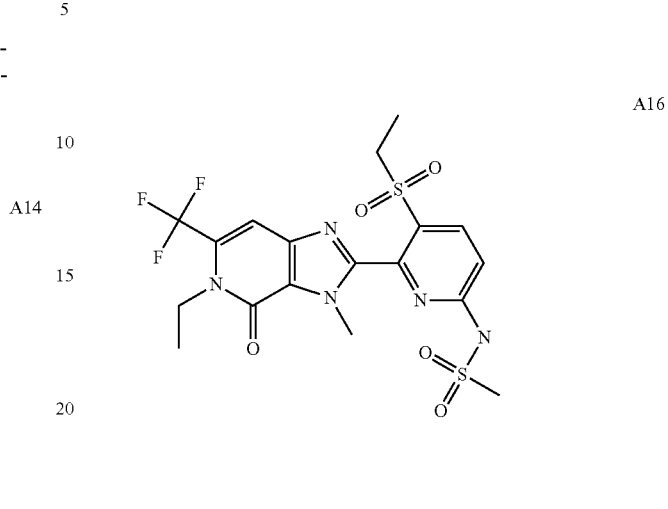

A16

In a microwave vial was taken 2-(6-chloro-3-ethylsulfonyl-2-pyridyl)-5-ethyl-3-methyl-6-(trifluoromethyl)imidazo[4,5-c]pyridin-4-one (600 mg, 1.337 mmol), dipotassium carbonic acid (2.674 mmol, 0.3749 g), methane sulfonamide (2.005 mmol, 0.1907 g) in N,N-dimethylformamide (90.1 mmol, 6.61 g). The reaction was subjected to microwave heating at 150° C. for 1 hour. The reaction was neutralized with 1N HCl (5 ml), diluted with water (10 ml). Aqueous layer was extracted with ethyl acetate. Combined organic layer was dried over sodium sulfate, concentrated under reduced pressure. Crude product was purified by column chromatography gradient cyclohexane+0-30% Ethyl acetate to give N-[6-[5-ethyl-3-methyl-4-oxo-6-(trifluoromethyl)imidazo[4,5-c]pyridin-2-yl]-5-ethylsulfonyl-2-pyridyl]methanesulfonamide (520 mg, 76%). ¹H NMR (400 MHz, CDCl₃) δ 8.43 (d, 1H), 8.15 (br. s., 1H), 7.38 (d, 1H), 7.22 (s, 1H), 4.26 (q, 2H), 4.10 (s, 3H), 3.72 (q, 2H), 3.32 (s, 3H), 1.46-1.31 (m, 6H).

Example P17: Preparation of N-cyclopropyl-6-[5-ethyl-3-methyl-4-oxo-6-(trifluoromethyl)imidazo[4,5-c]pyridin-2-yl]-5-ethylsulfonyl-N-methyl-pyridine-3-carboxamide A17

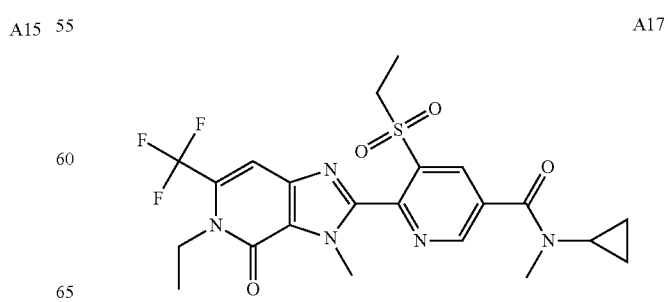

A17

113

Step A: 6-[5-ethyl-3-methyl-4-oxo-6-(trifluoromethyl)imidazo[4,5-c]pyridin-2-yl]-5-ethylsulfonyl-pyridine-3-carbonyl Chloride

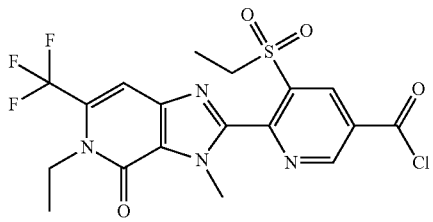 [SMILES: CCn1c(C(F)(F)F)cc2nc(-c3ncc(C(=O)Cl)cc3S(=O)(=O)CC)n(C)c2c1=O]

In a stirring solution of 6-[5-ethyl-3-methyl-4-oxo-6-(trifluoromethyl)imidazo[4,5-c]pyridin-2-yl]-5-ethylsulfonyl-pyridine-3-carboxylic acid (1500 mg, 3.272 mmol) in dichloromethane (20 mL) was added, oxalyl dichloride (6.545 mmol, 0.6 ml) followed by N,N-dimethylformamide and reaction was stirred at ice cold condition for 2 hour. The mixture was concentrated to get 1500 mg crude acid chloride and used immediately for amide coupling.

Step B: N-cyclopropyl-6-[5-ethyl-3-methyl-4-oxo-6-(trifluoromethyl)imidazo[4,5-c]pyridin-2-yl]-5-ethylsulfonyl-N-methyl-pyridine-3-carboxamide A17

A17

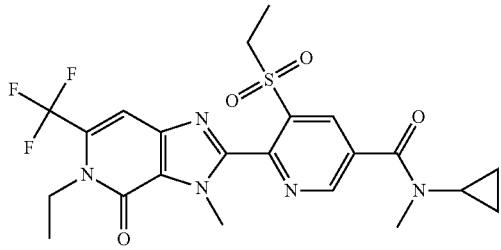

In a stirring solution of 6-[5-ethyl-3-methyl-4-oxo-6-(trifluoromethyl)imidazo[4,5-c]pyridin-2-yl]-5-ethylsulfonyl-pyridine-3-carbonyl chloride (500 mg, 1.048 mmol) in dichloromethane (20 mL) was added N,N-diethylethanamine (4.194 mmol, 0.0.6 ml) then was added HCl salt of N-methylcyclopropyl amine (2.097 mmol, 225 mg) and reaction was stirred at room temperature for 12 hour. The reaction was washed by sodium bicarbonate solution and dichloromethane layer was concentrated to get crude product which was purified by column chromatography gradient cyclohexane+0-70% Ethyl acetate to get N-cyclopropyl-6-[5-ethyl-3-methyl-4-oxo-6-(trifluoromethyl)imidazo[4,5-c]pyridin-2-yl]-5-ethylsulfonyl-N-methyl-pyridine-3-carboxamide (250 mg, 46%). Mp=200-202° C. $^1$H NMR (400 MHz, CDCl$_3$) δ ppm 0.57 (br. s., 2H) 0.78 (br. s., 2H) 1.34-1.47 (m, 6H) 2.90-3.00 (m, 1H) 3.21 (br. s., 3H) 3.83 (m, 2H) 4.12 (s, 3H) 4.27 (q, 2H) 7.23 (s, 1H) 8.66 (br. s., 1H) 9.13 (s, 1H).

114

Example P18: Preparation of N-cyclopropyl-6-[5-ethyl-3-methyl-4-oxo-6-(trifluoromethyl)imidazo[4,5-c]pyridin-2-yl]-5-ethylsulfonyl-N-methyl-pyridine-2-carboxamide A18

A18

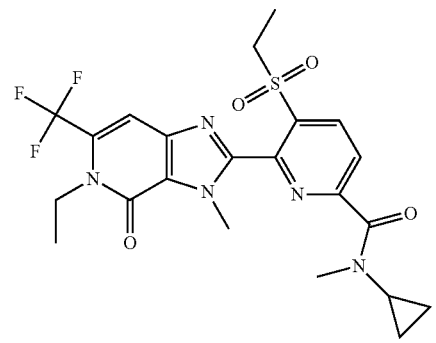

A solution of 6-[5-ethyl-3-methyl-4-oxo-6-(trifluoromethyl)imidazo[45-c]pyridin-2-yl]-5-ethylsulfonyl-pyridine-3-carbonyl chloride (Prepared from 17 using same procedure for Example P17 Step A) dissolved in dry dichloromethane (7 ml) was added dropwise to a mixture of N-methylcyclopropyl amine hydrochloride (1.3089 mmol, 0.1408 g), N,N-diethylethanamine (4.3629 mmol, 0.4415 g, 0.608 mL) and dichloromethane (5 ml) under nitrogen at 0° C. The mixture was stirred at room temperature for 3 hours and then quenched with water (20 ml) and diluted with dichloromethane (20 ml). Organic layer was separated, aqueous layer was further extracted with dichloromethane. Combined Organic extract was washed with brine, dried with sodium sulfate, evaporated under vacuum and concentrated to get crude compound which was purified by column chromatography gradient cyclohexane+0-70% Ethyl acetate to give N-cyclopropyl-6-[5-ethyl-3-methyl-4-oxo-6-(trifluoromethyl)imidazo[4,5-c]pyridin-2-yl]-5-ethylsulfonyl-N-methyl-pyridine-2-carboxamide (0.211 g, 37%). $^1$H NMR (400 MHz, CDCl$_3$) δ=8.59 (d, 1H), 7.90 (d, 1H), 7.21 (s, 1H), 4.25 (q, 2H), 4.05 (s, 3H), 3.74 (q, 2H), 3.19 (s, 3H), 2.99-2.91 (m, 1H), 1.42-1.32 (m, 6H), 0.63-0.53 (m, 2H), 0.51-0.41 (m, 2H).

Example P19: Preparation of N-cyclopropyl-6-[5-ethyl-3-methyl-4-oxo-6-(trifluoromethyl)imidazo[4,5-c]pyridin-2-yl]-5-ethylsulfonyl-pyridine-3-carboxamide A19

A19

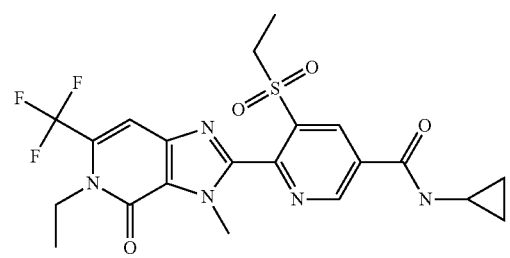

In a stirring solution of 6-[5-ethyl-3-methyl-4-oxo-6-(trifluoromethyl)imidazo[4,5-c]pyridin-2-yl]-5-ethylsulfonyl-pyridine-3-carbonyl chloride (Prepared as described for A17 Step A)

(500 mg, 1.048 mmol) in dichloromethane (5 mL) was added N,N-diethylethanamine (3.145 mmol, 0.6 ml) followed by cyclopropyl amine (2.097 mmol, 0.16 ml) and reaction was stirred at room temperature for 2 hour. The reaction was washed by sodium bicarbonate solution and dichloromethane layer was concentrated to get crude product which was purified by column chromatography gradient cyclohexane+0-70% Ethyl acetate to get N-cyclopropyl-6-[5-ethyl-3-methyl-4-oxo-6-(trifluoromethyl)imidazo[4,5-c]pyridin-2-yl]-5-ethylsulfonyl-pyridine-3-carboxamide (210 mg, 40%). Mp=215-217° C. $^1$H NMR (400 MHz, CDCl$_3$) δ ppm 0.61-0.69 (m, 2H) 0.84-0.93 (m, 2H) 1.26-1.36 (m, 6H) 2.88-2.96 (m, 1H) 3.76 (q, 2H) 4.02 (s, 3H) 4.18 (q, 2H) 6.52 (br. s., 1H) 7.14 (s, 1H) 8.51 (m, 1H) 9.28 (d, 1H).

Example P20: Preparation of N-cyclopropyl-6-[5-ethyl-3-methyl-4-oxo-6-(trifluoromethyl)imidazo[4,5-c]pyridin-2-yl]-5-ethylsulfonyl-pyridine-2-carboxamide A20

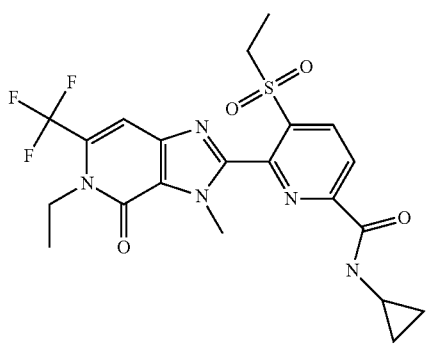

A20

Prepared as described in Example A18 using cyclopropyl amine to give N-cyclopropyl-6-[5-ethyl-3-methyl-4-oxo-6-(trifluoromethyl)imidazo[4,5-c]pyridin-2-yl]-5-ethylsulfonyl-pyridine-2-carboxamide (0.132 g, 60%). $^1$H NMR (400 MHz, CDCl$_3$) δ=8.68-8.64 (m, 1H), 8.59-8.55 (m, 1H), 7.79 (d, J=3.1 Hz, 1H), 7.22 (s, 1H), 4.26 (q, 2H), 4.03 (s, 3H), 3.68 (q, 2H), 2.96 (m, 1H), 1.40 (t, 3H), 1.33 (t, 3H), 0.94-0.87 (m, 2H), 0.68-0.61 (m, 2H)

Example P21: Preparation of N-[6-[5-ethyl-3-methyl-4-oxo-6-(trifluoromethyl)imidazo[4,5-c]pyridin-2-yl]-5-ethylsulfonyl-3-pyridyl]-N-methylsulfonyl-cyclopropanecarboxamide A21

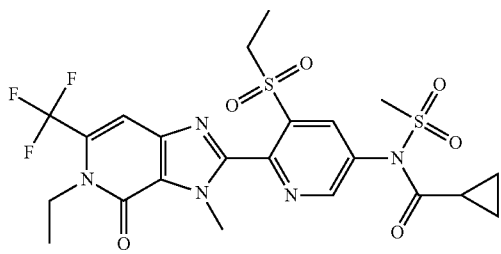

A21

In a stirring solution of N-[6-[5-ethyl-3-methyl-4-oxo-6-(trifluoromethyl)imidazo[4,5-c]pyridin-2-yl]-5-ethylsulfonyl-3-pyridyl]methanesulfonamide A15 (200 mg, 0.3941 mmol) in dichloromethane (15 mL) was added N,N-diethylethanamine (3.145 mmol, 0.11 ml) then was added cyclopropyl carbonyl chloride (0.7882 mmol, 0.0.07 ml) and the reaction was stirred at room temperature for 2 hour. The reaction was washed by sodium bicarbonate solution and dichloromethane layer was concentrated to get crude product which was purified by column chromatography gradient cyclohexane+0-70% Ethyl acetate to give N-[6-[5-ethyl-3-methyl-4-oxo-6-(trifluoromethyl)imidazo[4,5-c]pyridin-2-yl]-5-ethylsulfonyl-3-pyridyl]-N-methylsulfonyl-cyclopropanecarboxamide (130 mg, 57%). Mp: 232-234° C.

$^1$H NMR (400 MHz, CDCl$_3$) δ ppm 1.00-1.06 (m, 2H) 1.33 (m, 2H) 1.41 (m, 7H) 3.56 (s, 3H) 3.90 (q, 2H) 4.18 (s, 3H) 4.27 (q, 2H) 7.23 (s, 1H) 8.51 (d, 1H) 8.97 (d, 1H).

Example P22: Preparation of N'-[6-[5-ethyl-3-methyl-4-oxo-6-(trifluoromethyl)imidazo[4,5-c]pyridin-2-yl]-5-ethylsulfonyl-3-pyridyl]-N,N'-dimethyl-cyclopropanecarbohydrazide A22

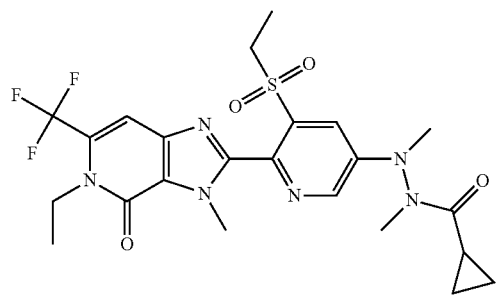

A22

Step A: 2-[5-(2-benzhydrylidenehydrazino)-3-ethylsulfonyl-2-pyridyl]-5-ethyl-3-methyl-6-(trifluoromethyl)imidazo[4,5-c]pyridin-4-one

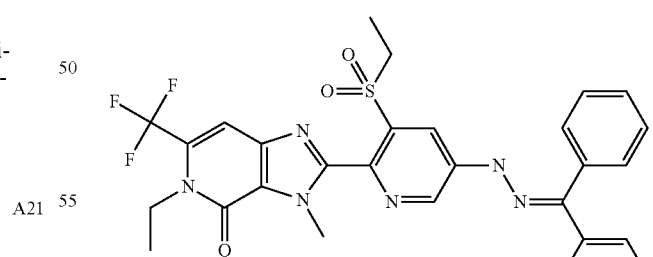

2-(5-bromo-3-ethylsulfonyl-2-pyridyl)-5-ethyl-3-methyl-6-(trifluoromethyl)imidazo[4,5-c]pyridin-4-one (4.054 mmol, 2 g) was dissolved in degassed (20 mins with nitrogen) 2-methylbutan-2-ol (4 mL) and to it sodium hydroxide (5.676 mmol, 0.2270 g) was added under nitrogen in a microwave vial. The mixture was heated at 110° C. In another round flask, palladium (ii) acetate (0.2027 mmol, 0.04553 g) and me-phos (0.4054 mmol, 0.1508 g) were taken together and stirred under nitrogen for 20 mins. This active catalyst was then transferred to the mixture followed by portion wise addition of diphenylmethanone hydrazone (4.054 mmol, 0.7955 g) under nitrogen. The mixture was heated at 110° C. for 5 hours. The mixture was filtered through celite bed and the bed was washed with ethyl acetate (10 ml). Organic layer was evaporated under vacuum and directly subjected to column purification gradient cyclohexane+0-30% Ethyl acetate to give 2-[5-(2-benzhydrylidene hydrazino)-3-ethylsulfonyl-2-pyridyl]-5-ethyl-3-methyl-6-(trifluoromethyl)imidazo[4,5-c]pyridin-4-one (2 g, 81%). $^1$H NMR (400 MHz, CDCl$_3$) δ 8.78 (d, 1H), 8.01 (d, 1H), 7.84 (s, 1H), 7.70-7.60 (m, 5H), 7.42-7.35 (m, 5H), 7.21 (s, 1H), 4.24 (q, 2H), 4.04 (s, 3H), 3.75 (q, 2H), 1.37 (m, 6H).

Step B: 2-[5-[(benzhydrylideneamino)-methyl-amino]-3-ethylsulfonyl-2-pyridyl]-5-ethyl-3-methyl-6-(trifluoromethyl)imidazo[4,5-c]pyridin-4-one

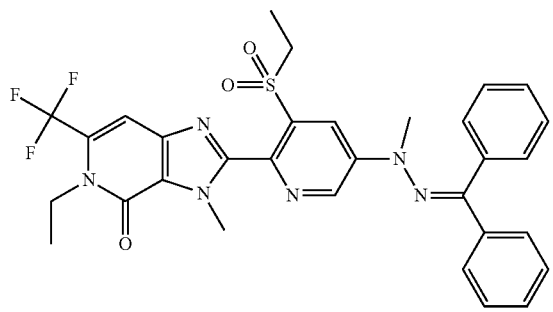 [SMILES: CCn1c(C(F)(F)F)cc2nc(-c3ncc(N(C)N=C(c4ccccc4)c4ccccc4)cc3S(=O)(=O)CC)n(C)c2c1=O]

2-[5-[(benzhydrylideneamino)-methyl-amino]-3-ethylsulfonyl-2-pyridyl]-5-ethyl-3-methyl-6-(trifluoromethyl)imidazo[4,5-c]pyridin-4-one (0.1606 mmol, 0.1 g) was dissolved in dry tetrahydrofuran (1 mL) and to it sodium hydride (0.2465 mmol, 0.009858 g) was added under nitrogen at 0° C. The mixture was stirred at 0° C. for 15 mins and then iodomethane (0.1972 mmol, 0.02799 g) was added. The mixture was stirred at room temperature for 1 hour and then quenched with water and extracted in ethyl acetate (10 ml). Aqueous layer was further extracted in ethyl acetate (2×10 ml), combined organic layer was washed with brine, dried over sodium sulfate, concentrated under vacuum to get crude product which was subjected to column purification gradient cyclohexane+0-50% Ethyl acetate to give 2-[5-[(benzhydrylideneamino)-methyl-amino]-3-ethylsulfonyl-2-pyridyl]-5-ethyl-3-methyl-6-(trifluoromethyl)imidazo[4,5-c]pyridin-4-one (100 mg, 97%). $^1$H NMR (400 MHz, CDCl$_3$) δ=8.75 (d, 1H), 7.92 (d, 1H), 7.68-7.62 (m, 2H), 7.54-7.33 (m, 8H), 7.22 (s, 1H), 4.29-4.21 (m, 2H), 4.06 (s, 3H), 3.76 (q, 2H), 2.99 (s, 3H), 1.38 (m, 8H).

Step C: 2-[5-[amino(methyl)amino]-3-ethylsulfonyl-2-pyridyl]-5-ethyl-3-methyl-6-(trifluoromethyl)imidazo[4,5-c]pyridin-4-one A56

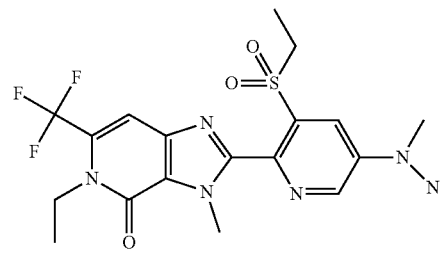

A56

2-[5-[(benzhydrylideneamino)-methyl-amino]-3-ethylsulfonyl-2-pyridyl]-5-ethyl-3-methyl-6-(trifluoromethyl)imidazo[4,5-c]pyridin-4-one (0.2 mmol, 0.1 g) was dissolved in ethanol (0.02 mL) and to it conc. hydrogen chloride (0.176 mL) was added and heated at 50° C. overnight. The mixture was diluted with ethyl acetate (10 ml) and neutralized with sodium hydroxide solution until pH 8. Organic layer separated. Aqueous layer was further extracted with ethyl acetate (2×10 ml). Combined organic layer was washed with brine, dried over sodium sulfate, concentrated under vacuum to get crude product which was subjected to column purification gradient cyclohexane+0-90% Ethyl acetate to give 2-[5-[amino(methyl)amino]-3-ethylsulfonyl-2-pyridyl]-5-ethyl-3-methyl-6-(trifluoromethyl)imidazo[4,5-c]pyridin-4-one (23 mg, 30%).
$^1$H NMR (400 MHz, DMSO) δ=8.57 (d, 1H), 7.86 (d, 1H), 7.39 (s, 1H), 4.93 (s, 2H), 4.15 (m, 2H), 3.87 (s, 3H), 3.70 (m, 2H), 3.26 (s, 3H), 1.29 (t, 3H), 1.15 (t. 3H)

Step D: N'-[6-[5-ethyl-3-methyl-4-oxo-6-(trifluoromethyl)imidazo[4,5-c]pyridin-2-yl]-5-ethylsulfonyl-3-pyridyl]-N'-methyl-cyclopropanecarbohydrazide

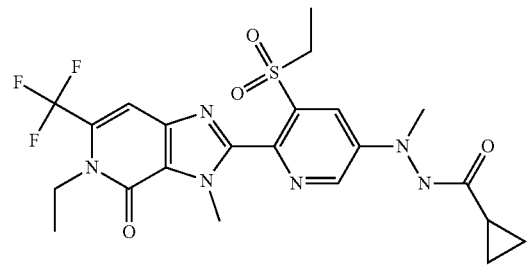 [SMILES: CCn1c(C(F)(F)F)cc2nc(-c3ncc(N(C)NC(=O)C4CC4)cc3S(=O)(=O)CC)n(C)c2c1=O]

In a stirring solution of 2-[5-[amino(methyl)amino]-3-ethylsulfonyl-2-pyridyl]-5-ethyl-3-methyl-6-(trifluoromethyl)imidazo[4,5-c]pyridin-4-one (650 mg, 1.418 mmol) in N,N-dimethylformamide (20 mL) under nitrogen was added N-ethyl-N-isopropyl-propan-2-amine (4.253 mmol, 0.5497 g) followed by cyclopropyl carboxylic acid (1.559 mmol, 0.1343 g) and HATU (2.126 mmol, 0.81 g) and reaction was stirred at that temp for two hours. The mixture was then poured into water and extracted with ethyl acetate. The combined extracts were washed with brine, dried over NaSO₄, filtered and evaporated under reduced pressure to give the crude product. The crude was purified via flash chromatography to give N'-[6-[5-ethyl-3-methyl-4-oxo-6-(trifluoromethyl)imidazo[4,5-c]pyridin-2-yl]-5-ethylsulfonyl-3-pyridyl]-N'-methyl-cyclopropanecarbohydrazide (250 mg, 33%). ¹H NMR (400 MHz, CDCl₃) δ ppm 0.83-0.90 (m, 2H) 0.99-1.04 (m, 2H) 1.23-1.34 (m, 6H) 1.48 (m, 1H) 3.36 (s, 3H) 3.62-3.70 (m, 2H) 3.96 (s, 3H) 4.12-4.22 (m, 2H) 7.16 (s, 1H) 7.63-7.67 (m, 1H) 7.76 (s, 1H) 8.36-8.39 (m, 1H)

Step E: N'-[6-[5-ethyl-3-methyl-4-oxo-6-(trifluoromethyl)imidazo[4,5-c]pyridin-2-yl]-5-ethylsulfonyl-3-pyridyl]-N,N'-dimethyl-cyclopropanecarbohydrazide

A22

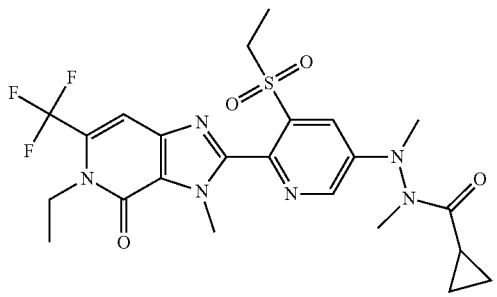

In a stirring solution of N'-[6-[5-ethyl-3-methyl-4-oxo-6-(trifluoromethyl)imidazo[4,5-c]pyridin-2-yl]-5-ethylsulfonyl-3-pyridyl]-N'-methyl-cyclopropanecarbohydrazide (250 mg, 0.4748 mmol) in N,N-dimethylacetamide (5 mL) was added sodium hydride (0.7123 mmol, 60 mass %). The reaction was stirred 15 min and then methyl iodide (0.6648 mmol, 99.5 mass %) was added and the reaction mixture was stirred at room temperature for 8 hour. The reaction mixture was quenched with water and extracted with ethyl acetate. The combined organic layers were washed with water, brine solution, dried with anhydrous sodium sulfate and concentrated under reduced pressure. The residue was purified by column chromatography using ethyl acetate/cyclohexane to get the desired product N'-[6-[5-ethyl-3-methyl-4-oxo-6-(trifluoromethyl)imidazo[4,5-c]pyridin-2-yl]-5-ethylsulfonyl-3-pyridyl]-N,N'-dimethyl-cyclopropane carbohydrazide (47 mg, 18%). ¹H NMR (400 MHz, CHLOROFORM-d) δ ppm 0.66-0.85 (m, 2H) 0.95-1.05 (m, 2H) 1.24-1.36 (m, 6H) 1.82-1.92 (m, 1H) 3.08 (s, 3H) 3.33 (s, 3H) 3.63-3.74 (m, 2H) 3.98 (s, 3H) 4.17 (m, 2H) 7.07 (s, 1H) 7.64 (d, 1H) 8.35 (d, 1H).

Example P23: Preparation of 6-[5-ethyl-3-methyl-4-oxo-6-(trifluoromethyl)imidazo[4,5-c]pyridin-2-yl]-5-ethylsulfonyl-N-methylsulfonyl-pyridine-3-carboxamide A23

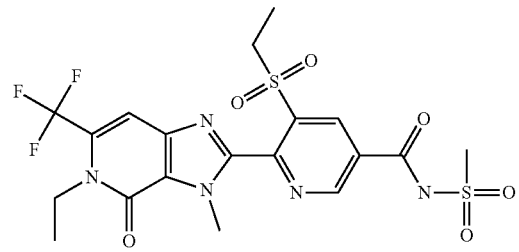

To a −10° C. cooled solution of 6-[5-ethyl-3-methyl-4-oxo-6-(trifluoromethyl)imidazo[4,5-c]pyridin-2-yl]-5-ethylsulfonyl-pyridine-3-carboxylic acid (300 mg, 0.6545 mmol) and methane sulfonamide (0.7853 mmol, 0.07470 g) in pyridine (3 mL) was added phosphorous oxychloride (0.7853 mmol, 0.1204 g) and was stirred at room temperature for 1.5 hours. The reaction was neutralized with 2N HCl (10 ml) and extracted with ethyl acetate. Combined organic layer was dried over sodium sulfate, concentrated under reduced pressure. The crude product was triturated with cyclohexane (10 ml). The solid obtained was purified by reverse phase preparative HPLC to give 6-[5-ethyl-3-methyl-4-oxo-6-(trifluoromethyl)imidazo[4,5-c]pyridin-2-yl]-5-ethylsulfonyl-N-methylsulfonyl-pyridine-3-carboxamide (30 mg, 8.5%). ¹H NMR (400 MHz, CDCl₃) δ=9.49 (d, 1H), 8.98 (d, 1H), 7.22 (s, 1H), 4.26 (q, 2H), 4.14 (s, 3H), 3.93 (q, 2H), 3.53 (s, 3H), 1.45-1.35 (m, 6H).

Example P24: Preparation of 1-[[6-[5-ethyl-3-methyl-4-oxo-6-(trifluoromethyl)imidazo[4,5-c]pyridin-2-yl]-5-ethylsulfonyl-3-pyridyl]amino]cyclopropanecarbonitrile A24

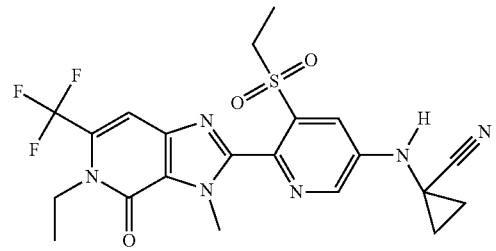

2-(5-bromo-3-ethylsulfonyl-2-pyridyl)-5-ethyl-3-methyl-6-(trifluoromethyl)imidazo[4,5-c]pyridin-4-one (0.6081 mmol, 0.3 g) was dissolved in anhydrous 1,4-dioxane (3 mL) and to it cesium carbonate (0.8514 mmol, 0.278 g) was added under nitrogen followed by palladium (II) acetate (0.0365 mmol, 0.0082 g) and 1-cyanocyclopropyl)ammonium chloride (0.9122 mmol, 0.1082 g). The mixture was purged with nitrogen for 15-20 mins, X-PHOS (0.1095 mmol, 0.05325 g) was then added and the reaction mixture was heated at 110° C. in a preheated oil bath for 26 hours.

The reaction was quenched in water (15 ml) and diluted with ethyl acetate (30 ml). Organic layer was separated and washed with brine, dried over sodium sulfate, filtered and concentrated to get crude product. Crude product was purified by column purification with gradient cyclohexane+0-80% Ethyl acetate to give 1-[[6-[5-ethyl-3-methyl-4-oxo-6-(trifluoromethyl)imidazo[4,5-c]pyridin-2-yl]-5-ethylsulfonyl-3-pyridyl]amino]cyclopropanecarbonitrile (0.079 g, 26%). $^1$H NMR (400 MHz, CDCl$_3$) δ ppm 1.33-1.45 (m, 8H) 1.67-1.80 (m, 2H) 3.77 (q, 2H) 4.05 (s, 3H) 4.25 (q, 2H) 5.46 (s, 1H) 7.21 (s, 1H) 7.86 (d, 1H) 8.53 (d, 1H).

Example P25: Preparation of N-(1-cyanocyclopropyl)-6-[5-ethyl-3-methyl-4-oxo-6-(trifluoromethyl)imidazo[4,5-c]pyridin-2-yl]-5-ethylsulfonyl-pyridine-3-carboxamide A25

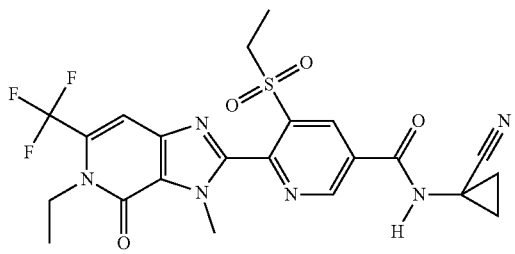

A25

In a stirring solution of 6-[5-ethyl-3-methyl-4-oxo-6-(trifluoromethyl)imidazo[4,5-c]pyridin-2-yl]-5-ethylsulfonyl-pyridine-3-carbonyl chloride (prepared as in example P17 Step A, 500 mg, 1.048 mmol) in dichloromethane (10 mL) was added N,N-diethylethanamine (3.145 mmol, 0.6 ml) followed by 1-aminocyclopropanecarbonitrile (2.097 mmol, 250 mg) and reaction mixture was stirred at room temperature for 2 hour. The mixture was washed with sodium bicarbonate solution and dichloromethane layer was concentrated to get crude product which was purified by column purification with gradient cyclohexane+0-70% Ethyl acetate to give N-(1-cyanocyclopropyl)-6-[5-ethyl-3-methyl-4-oxo-6-(trifluoromethyl)imidazo[4,5-c]pyridin-2-yl]-5-ethylsulfonyl-pyridine-3-carboxamide (330 mg, 60%). Mp=250° C. $^1$H NMR (400 MHz, CDCl$_3$) δ ppm 1.25-1.41 (m, 8H) 1.62 (s, 2H) 3.80 (q, 2H) 4.02 (s, 3H) 4.18 (q, 2H) 7.15 (s, 1H) 7.71 (s, 1H) 8.72 (d, 1H) 9.36 (d, 1H)

Example P26: Preparation of N-[6-[5-ethyl-3-methyl-4-oxo-6-(trifluoromethyl)imidazo[4,5-c]pyridin-2-yl]-5-ethylsulfonyl-3-pyridyl]-N'-methoxy-formamidine A26

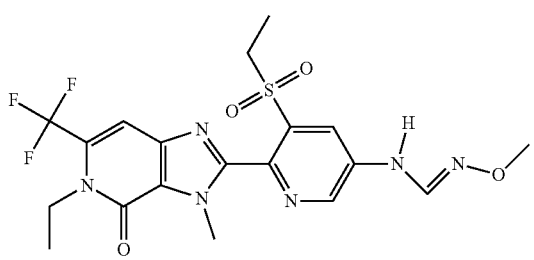

A26

A solution of 2-(5-amino-3-ethylsulfonyl-2-pyridyl)-5-ethyl-3-methyl-6-(trifluoromethyl)imidazo[4,5-c]pyridin-4-one (450 mg, 1.048 mmol), 1,1-dimethoxy-N,N-dimethyl-methanamine (1.258 mmol) in acetonitrile (5 mL) was refluxed for 1 hour. The reaction was concentrated under reduced pressure to obtain N'-[6-[5-ethyl-3-methyl-4-oxo-6-(trifluoromethyl)imidazo[4,5-c]pyridin-2-yl]-5-ethylsulfonyl-3-pyridyl]-N,N-dimethyl-formamidine (400 mg, 0.8256 mmol).

To a solution of N'-[6-[5-ethyl-3-methyl-4-oxo-6-(trifluoromethyl)imidazo[4,5-c]pyridin-2-yl]-5-ethylsulfonyl-3-pyridyl]-N,N-dimethyl-formamidine (400 mg, 0.8256 mmol) in methanol (2 mL) was added O-methyl hydroxylamine hydrochloride (1.258 mmol, 0.1050 g). The reaction was refluxed for 1 hour and monitored by TLC. The reaction was quenched with water (5 ml), extracted with ethyl acetate, combined organic layer was dried over sodium sulfate, concentrated under reduced pressure and was purified by column purification with gradient cyclohexane+0-100% Ethyl acetate to give N-[6-[5-ethyl-3-methyl-4-oxo-6-(trifluoromethyl)imidazo[4,5-c]pyridin-2-yl]-5-ethylsulfonyl-3-pyridyl]-N'-methoxy-formamidine (220 mg, 43%). $^1$H NMR (400 MHz, CDCl$_3$) δ=8.64 (d, 1H), 8.28 (d, 1H), 8.00 (d, 1H), 7.36 (d, 1H), 7.18 (s, 1H), 4.21 (q, 2H), 4.01 (s, 3H), 3.92 (s, 3H), 3.74 (q, 2H), 1.40-1.28 (m, 6H).

Example P27: Preparation of N-[6-[5-ethyl-3-methyl-4-oxo-6-(trifluoromethyl)imidazo[4,5-c]pyridin-2-yl]-5-ethylsulfonyl-3-pyridyl]-N'-methoxy-N-methyl-formamidine A27

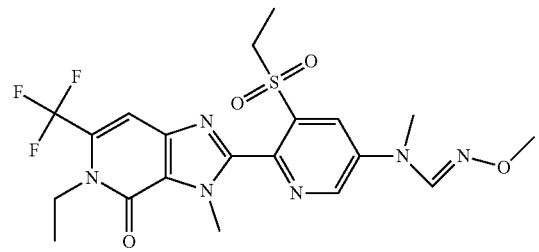

A27

To a solution of N-[6-[5-ethyl-3-methyl-4-oxo-6-(trifluoromethyl)imidazo[4,5-c]pyridin-2-yl]-5-ethylsulfonyl-3-pyridyl]-N'-methoxy-formamidine (300 mg, 0.6166 mmol) in N,N-dimethylformamide (3 mL) was added dipotassium carbonate (129 mg, 0.925 mmol) followed by iodomethane (0.060 ml, 0.925 mmol), The reaction was stirred at room temperature for overnight. The reaction was neutralized with 2N HCl (5 ml), diluted with water (10 ml) and extracted with ethyl acetate. The combined organic layers were washed successively with water and brine, dried over Sodium sulfate and concentrated in vacuo. Crude compound was purified by column chromatography with gradient cyclohexane+0-50% Ethyl acetate_N-[6-[5-ethyl-3-methyl-4-oxo-6-(trifluoromethyl)imidazo[4,5-c]pyridin-2-yl]-5-ethylsulfonyl-3-pyridyl]-N'-methoxy-N-methyl-formamidine (120 mg, 39%). $^1$H NMR (400 MHz, CDCl$_3$) δ=8.70 (d, 1H), 8.45 (s, 1H), 8.04 (d, 1H), 7.21 (s, 1H), 4.25 (q, 2H), 4.06 (s, 3H), 3.85 (s, 3H), 3.77 (m, 2H), 3.46 (s, 3H), 1.44-1.33 (m, 6H).

Example P28: Preparation of N-(cyanomethyl)-6-[5-ethyl-3-methyl-4-oxo-6-(trifluoromethyl)imidazo[4,5-c]pyridin-2-yl]-5-ethylsulfonyl-pyridine-3-carboxamide A28

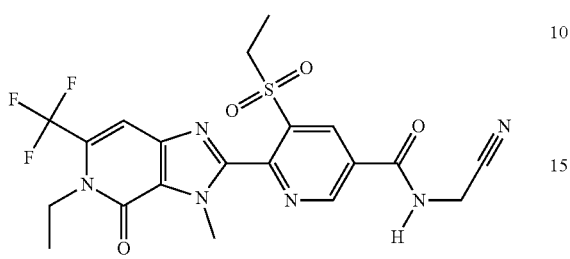

A28

In a stirring solution of 6-[5-ethyl-3-methyl-4-oxo-6-(trifluoromethyl)imidazo[4,5-c]pyridin-2-yl]-5-ethylsulfonyl-pyridine-3-carbonyl chloride (prepared as in example P17 Step A, 500 mg, 1.048 mmol) in dichloromethane (10 mL) was added N,N-diethylethanamine (3.145 mmol, 0.6 ml) then was added HCl salt of 2-aminoacetonitrile (2.097 mmol, 193 mg) and reaction was stirred at room temperature for 2 hour. The reaction was washed with sodium bicarbonate solution and dichloromethane layer was concentrated to get crude product which was purified by column chromatography with gradient cyclohexane+0-70% Ethyl acetate to get N-(cyanomethyl)-6-[5-ethyl-3-methyl-4-oxo-6-(trifluoromethyl)imidazo[4,5-c]pyridin-2-yl]-5-ethylsulfonyl-pyridine-3-carboxamide (250 mg, 48%). Mp=213-215° C. $^1$H NMR (400 MHz, CDCl$_3$) δ ppm 1.26-1.37 (m, 6H) 3.87 (q, 2H) 4.13 (s, 3H) 4.24 (m, 2H) 4.42 (d, 2H) 7.23 (s, 1H) 7.80 (m, 1H) 8.91 (s, 1H) 9.48 (d, 1H).

Example P29: Preparation of N-[6-[5-ethyl-3-methyl-4-oxo-6-(trifluoromethyl)imidazo[4,5-c]pyridin-2-yl]-5-ethylsulfonyl-3-pyridyl]-N-methylsulfonyl-methanesulfonamide A29

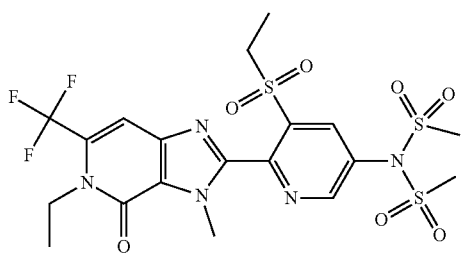

A29

In a stirring solution of 2-(5-amino-3-ethylsulfonyl-2-pyridyl)-5-ethyl-3-methyl-6-(trifluoromethyl)imidazo[4,5-c]pyridin-4-one (1.5 g, 3.5 mmol) in dichloromethane (15 mL) was added N,N-diethylethanamine (3.145 mmol, 0.93 ml) then was added methane sulfonyl chloride (7.7 mmol, 0.0.36 ml) and reaction was stirred at room temperature for 1 hour. NMR confirms the desired product and reaction was washed with sodium bicarbonate solution and dichloromethane layer was concentrated to get crude product which was purified by column chromatography with gradient cyclohexane+0-70% Ethyl acetate to get N-[6-[5-ethyl-3-methyl-4-oxo-6-(trifluoromethyl)imidazo[4,5-c]pyridin-2-yl]-5-ethylsulfonyl-3-pyridyl]-N-methylsulfonyl-methanesulfonamide (1.4 g, 68%). Mp=260° C. $^1$H NMR (400 MHz, CDCl$_3$) δ ppm 1.25-1.41 (m, 6H) 3.51 (s, 6H), 3.80 (q, 2H) 4.16 (s, 3H) 4.26 (m, 2H) 7.23 (s, 1H) 8.50 (d, 1H) 8.94 (d, 1H).

Example P30: Preparation of 2-[6-(cyclopropylamino)-3-ethylsulfonyl-2-pyridyl]-5-ethyl-3-methyl-6-(trifluoromethyl)imidazo[4,5-c]pyridin-4-one A30

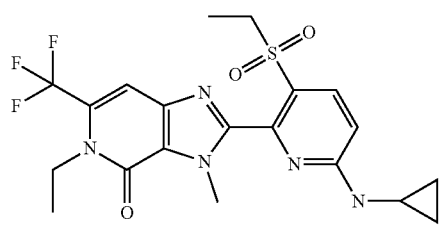

A30

2-(6-chloro-3-ethylsulfonyl-2-pyridyl)-5-ethyl-3-methyl-6-(trifluoromethyl)imidazo[4,5-c]pyridin-4-one (4.456 mmol, 2 g) was dissolved in anhydrous toluene (20 mL) and to it cesium carbonate (6.684 mmol, 2.18 g) was added under nitrogen. The mixture was degassed with nitrogen for 15 mins, tris(dibenzylideneacetone)dipalladium (0) (0.089 mmol, 0.0824 g), (+/−)-BINAP (0.1783 mmol, 0.1144 g) and cyclopropyl amine (5.348 mmol, 0.3053 g, 0.371 mL) were added to the reaction mixture and it was heated at 110° C. for 16 hours. The reaction was diluted with water (30 ml) and extracted with ethyl acetate. The combined organic layers were washed successively with water and brine, dried over Sodium sulfate, filtered and concentrated in vacuum. The crude compound was purified by column chromatography with gradient cyclohexane+0-30% Ethyl acetate to give 2-[6-(cyclopropylamino)-3-ethylsulfonyl-2-pyridyl]-5-ethyl-3-methyl-6-(trifluoromethyl)imidazo[4,5-c]pyridin-4-one (1.2 g, 57%). $^1$H NMR (400 MHz, CDCl$_3$) δ 8.16 (d, 1H), 7.20 (s, 1H), 6.93 (m, 1H), 5.69 (br. s., 1H), 4.23 (m, 2H), 4.03 (s, 3H), 3.53 (q, 2H), 2.63 (m, 1H), 1.43-1.34 (m, 3H), 1.28 (t, 3H), 0.97-0.88 (m, 2H), 0.69-0.61 (m, 2H).

Example P31: Preparation of 2-[5-chloro-6-(cyclopropylamino)-3-ethylsulfonyl-2-pyridyl]-5-ethyl-3-methyl-6-(trifluoromethyl)imidazo[4,5-c]pyridin-4-one A31

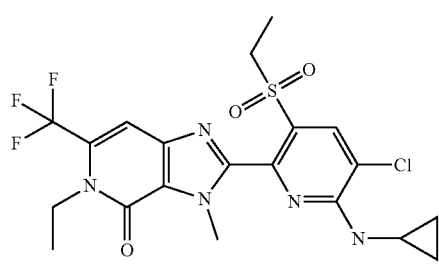

A31

Copper-II-acetate (0.479 g, 2.61 mmol) was added to a solution of 2-(6-amino-5-chloro-3-ethylsulfonyl-2-pyridyl)-

5-ethyl-3-methyl-6-(trifluoromethyl)imidazo[4,5-c]pyridin-4-one A38 (0.303 g, 0.653 mmol) in 1,4-Dioxane (7.83 mL) and Pyridine (0.160 mL) under argon. The mixture was stirred for 5 minutes before addition of Cyclopropylboronic acid (0.234 g, 2.61 mmol). Then, the mixture was heated at reflux for 6 h at 110° C. The mixture was cooled to RT, quenched with a saturated solution of Sodium bicarbonate. The aqueous phase was extracted three times with DCM, washed with aqueous Sodium bicarbonate, dried with sodium sulfate, filtered, and 2 g Isolute was added. After evaporation of the solvent, the residue was purified by chromatography with DCM:EA 0-40% over 12 g silica gel to give the tittle compound (79.8 mg, 24% yield) and the starting material (183.2 mg). $^1$H NMR (400 MHz, CDCl$_3$) δ 8.14 (s, 1H), 7.20 (s, 1H), 5.82 (s.b., 1H), 4.24 (q, 2H), 4.12 (s, 3H), 3.70 (q, 2H), 2.84 (m, 1H), 1.30-1.38 (m, 6H), 0.85 (m, 2H), 0.6 (m, 2H).

Example P32: Preparation of N-[6-[5-ethyl-3-methyl-4-oxo-6-(trifluoromethyl)imidazo[4,5-c]pyridin-2-yl]-5-ethylsulfonyl-2-pyridyl]-N-(2,2,2-trifluoroethyl)cyclopropanecarboxamide A32

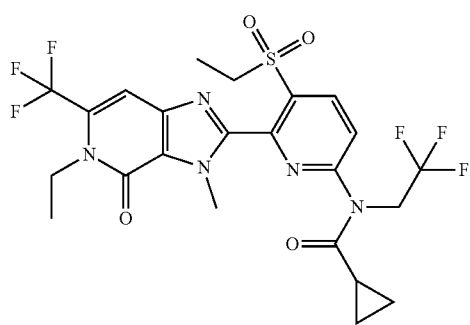

In one neck 25 ml round flask, 5-ethyl-2-[3-ethylsulfonyl-6-(2,2,2-trifluoroethylamino)-2-pyridyl]-3-methyl-6-(trifluoromethyl)imidazo[4,5-c]pyridin-4-one (110 mg, 0.2151 mmol) was dissolved in dichloromethane (2 mL), N,N-diethylethanamine (0.4302 mmol, 0.04353 g) was added. The mixture was stirred at 0° C. under ice bath, after 5 min, cyclopropane carbonyl chloride (0.3226 mmol, 0.03373 g) was added dropwise under ice bath stirred for 8 Hours at room temperature. Then dichloromethane (1 ml), cyclopropane carbonyl chloride (0.04 ml), N,N-diethylethanamine (0.08 ml) and N,N-dimethylpyridin-4-amine (0.2151 mmol, 0.02654 g) was added to reaction mixture and reaction mixture was heated at 50° C. for overnight. Desired product mass was observed, the reaction mixture was quenched in 10 ml of water, added 15 ml dichloromethane, separate organic layer in separating funnel, aqueous layer extracted with 15 ml dichloromethane two times, organic layer washed with brine, concentrated, crude was purified by combiflash to get N-[6-[5-ethyl-3-methyl-4-oxo-6-(trifluoromethyl)imidazo[4,5-c]pyridin-2-yl]-5-ethylsulfonyl-2-pyridyl]-N-(2,2,2-trifluoroethyl)cyclopropanecarboxamide as a yellow gummy mass ((100 mg, 80%). $^1$H NMR (400 MHz, CDCl$_3$) δ ppm 1.02-1.06 (m, 2H) 1.29 (m, 2H) 1.39 (m, 6H) 1.80-1.85 (m, 1H) 3.73 (q, 2H) 4.05 (s, 3H) 4.26 (q, 2H) 4.89 (q, 2H) 7.22 (s, 1H) 7.89 (d, 1H) 8.50 (d, 1H)

Example P33: Preparation of N-[6-[5-ethyl-3-methyl-4-oxo-6-(trifluoromethyl)imidazo[4,5-c]pyridin-2-yl]-5-ethylsulfonyl-2-pyridyl]-N-(2,2,2-trifluoroethyl)cyclopropanecarboxamide A33

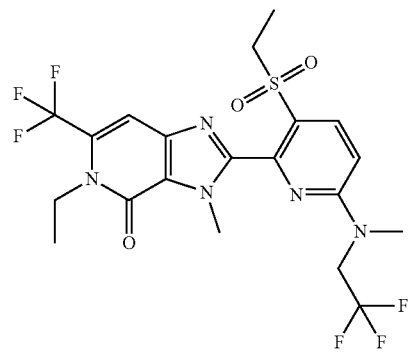

In a 25 ml round flask, to a 0° C. cooled suspension of sodium hydride (0.2738 mmol, 0.01095 g) in N,N-dimethylformamide (0.4 mL) was added dropwise a clear solution of 5-ethyl-2-[3-ethylsulfonyl-6-(2,2,2-trifluoroethylamino)-2-pyridyl]-3-methyl-6-(trifluoromethyl)imidazo[4,5-c]pyridin-4-one (0.1955 mmol, 0.1 g) in N,N-dimethylformamide (0.6 ml). The reaction was stirred at 0° C. for 30 mins, to this was added iodomethane (0.2542 mmol, 0.03608 g), and reaction was stirred at room temperature for 2 hours. After this TLC was checked, LCMS shows product mass, reaction went to completion.

The reaction was quenched in 10 ml of water extracted with ethyl acetate. Combined organic layer was dried over sodium sulfate, filtered, and concentrated under reduced pressure.

The title compound was purified by combiflash silica column chromatography to give N-[6-[5-ethyl-3-methyl-4-oxo-6-(trifluoromethyl)imidazo[4,5-c]pyridin-2-yl]-5-ethylsulfonyl-2-pyridyl]-N-(2,2,2-trifluoroethyl)cyclopropanecarboxamide (99 mg, 96%) Mp=171-173° C. $^1$H NMR (400 MHz, CDCl$_3$) δ ppm 1.32 (t, 3H) 1.40 (t, 3H) 3.27 (s, 3H) 3.62 (q, 2H) 4.03 (s, 3H) 4.25 (q, 2H) 4.37 (q, 2H) 6.83 (d, 1H) 7.21 (s, 1H) 8.22 (d, 1H).

Example P34: Preparation of 5-ethyl-2-[3-ethylsulfonyl-6-(2,2,2-trifluoroethylamino)-2-pyridyl]-3-methyl-6-(trifluoromethyl)imidazo[4,5-c]pyridin-4-one A34

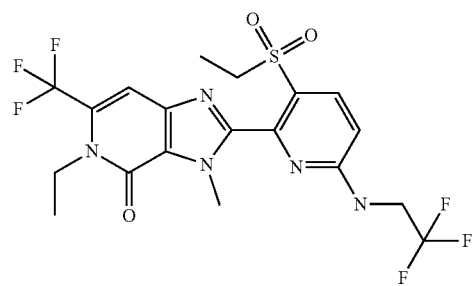

In a 15 ml reaction tube sealed with rubber stopper, 2-(6-chloro-3-ethylsulfonyl-2-pyridyl)-5-ethyl-3-methyl-6-(trifluoromethyl)imidazo[4,5-c]pyridin-4-one (1.114 mmol, 0.5 g) was dissolved in anhydrous toluene (4 ml) and to it cesium carbonate (4.456 mmol, 1.45 g) and 2,2,2-trifluoroethylammonium chloride (1.671 mmol, 0.2265 g) was added under nitrogen. The mixture was degassed with nitrogen for 15 mins, tris(dibenzylideneacetone)dipalladium (0) (0.0223 mmol, 0.0206 g) and (+/−)-BINAP (0.0446 mmol, 0.0286 g) was further added to the reaction mixture and it was heated at 110° C. for 16 hours. The reaction was diluted with water (30 ml), extracted with ethyl acetate, the combined organic layers were washed successively with water and brine, dried over Sodium sulfate and concentrated in vacuo. The title compound was purified by combiflash to give 5-ethyl-2-[3-ethylsulfonyl-6-(2,2,2-trifluoroethylamino)-2-pyridyl]-3-methyl-6-(trifluoromethyl)imidazo[4,5-c]pyridin-4-one (298 mg, 52%) as a white crystalline solid.

$^1$H NMR (400 MHz, CDCl$_3$) 8.13 (d, 1H), 7.21 (s, 1H), 6.75 (d, 1H), 5.62 (t, 1H), 4.24 (q, 2H), 4.20-4.13 (m, 2H), 4.03 (s, 3H), 3.60 (q, 2H), 1.39 (t, 3H), 1.31 (t, 3H).

Example P35: Preparation of N-cyclopropylsulfonyl-6-[5-ethyl-3-methyl-4-oxo-6-(trifluoromethyl)imidazo[4,5-c]pyridin-2-yl]-5-ethylsulfonyl-pyridine-3-carboxamide A35

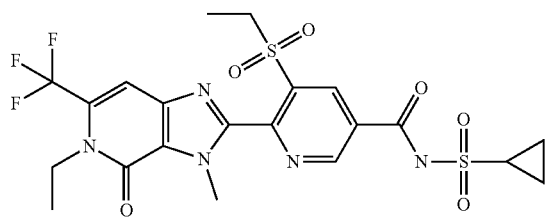

A35

In a stirring solution of dichloromethane (20 mL) was added N,N-diethylethanamine (3.489 mmol) and cyclopropanesulfonamide (1.047 mmol, 0.1268 g). Then in ice cold conditions is added 6-[5-ethyl-3-methyl-4-oxo-6-(trifluoromethyl)imidazo[4,5-c]pyridin-2-yl]-5-ethylsulfonyl-pyridine-3-carbonyl chloride (500 mg, 1.048 mmol) and reaction was stirred at room temperature for 12 hour. The reaction mixture was quenched with water and extracted with ethyl acetate. The combined organic layers were washed with water, brine solution, dried with anhydrous sodium sulfate and concentrated under reduced pressure. The residue was purified by reverse chromatography to get the desired product N-cyclopropylsulfonyl-6-[5-ethyl-3-methyl-4-oxo-6-(trifluoromethyl)imidazo[4,5-c]pyridin-2-yl]-5-ethylsulfonyl-pyridine-3-carboxamide (120 mg, 24%). $^1$H NMR (400 MHz, MeOH-d4) δ ppm 0.85-0.90 (m, 2H) 1.06-1.10 (m, 2H) 1.17-1.23 (m, 4H) 1.26-1.31 (m, 3H) 2.86-3.05 (m, 1H) 3.46-3.65 (m, 2H) 4.09-4.23 (m, 2H) 7.19-7.29 (m, 1H) 8.81-9.01 (m, 1H) 9.31-9.52 (m, 1H).

Example P36: Preparation of N-[6-[5-ethyl-3-methyl-4-oxo-6-(trifluoromethyl)imidazo[4,5-c]pyridin-2-yl]-5-ethylsulfonyl-3-pyridyl]cyclopropanesulfonamide A36

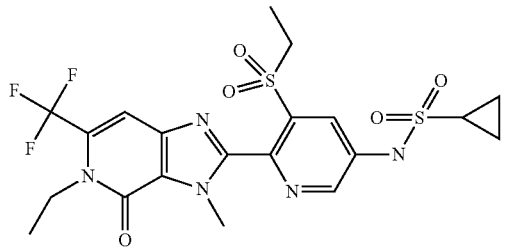

A36

In a stirring solution of pyridine (3.493 mmol, 0.2763 g) under nitrogen was added 2-(5-amino-3-ethylsulfonyl-2-pyridyl)-5-ethyl-3-methyl-6-(trifluoromethyl)imidazo[4,5-c]pyridin-4-one (500 mg, 1.164 mmol) followed by cyclopropane sulfonyl chloride (1.747 mmol, 0.2456 g) and the reaction mixture was stirred at 80° C. for 12 hr. The reaction mixture was quenched with water and extracted with ethyl acetate. The combined organic layers were washed with water, brine solution, dried with anhydrous sodium sulfate, filtered and concentrated under reduced pressure. The residue was purified by column chromatography using ethyl acetate/cyclohexane (6:4) to give N-[6-[5-ethyl-3-methyl-4-oxo-6-(trifluoromethyl)imidazo[4,5-c]pyridin-2-yl]-5-ethylsulfonyl-3-pyridyl]cyclopropanesulfonamide A36 (420 mg, 0.7873 mmol, 67.61% Yield) as a white solid. 1H NMR (400 MHz, CDCl$_3$) δ ppm 1.14-1.22 (m, 2H) 1.36-1.44 (m, 8H) 2.63-2.75 (m, 1H) 3.82 (m, 2H) 4.10 (s, 3H) 4.27 (m, 2H) 7.23 (s, 1H) 7.31 (s, 1H) 8.35 (d, 1H) 8.85 (d, 1H)

Example P37: N-[6-[5-ethyl-3-methyl-4-oxo-6-(trifluoromethyl)imidazo[4,5-c]pyridin-2-yl]-5-ethylsulfonyl-3-pyridyl]-N-methyl-cyclopropanesulfonamide A37

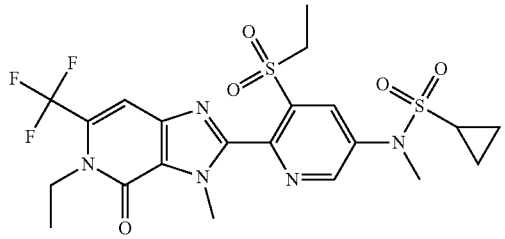

A37

In a stirring solution of tetrahydrofuran (5 mL, 61.6 mmol) was added potassium carbonate (0.3749 mmol, 0.05181 g) followed by N-[6-[5-ethyl-3-methyl-4-oxo-6-(trifluoromethyl)imidazo[4,5-c]pyridin-2-yl]-5-ethylsulfonyl-3-pyridyl]cyclopropanesulfonamide (100 mg, 0.1874 mmol) and The mixture was stirred at room temperature for 2 hr. Then 1 ml of DMF was added and The mixture stirred for 4 hrs.

The mixture was poured in a separating funnel containing Ethyl acetate and water. Organic layer was separated, washed with water and brine, dried over Sodium sulfate, filtered, and concentrated to give crude product which was purified by column chromatography using ethyl acetate/cyclohexane (4:6). $^1$H NMR (400 MHz, CDCl$_3$) δ ppm 1.08-1.16 (m, 2H) 1.23-1.27 (m, 2H) 1.39 (m, 6H) 2.45 (m, 1H) 3.54 (s, 3H) 3.83 (m, 2H) 4.12 (s, 3H) 4.27 (m, 2H) 7.23 (s, 1H) 8.47 (d, 1H) 9.05 (d, 1H)

Example P38: Preparation of 2-(6-amino-5-chloro-3-ethylsulfonyl-2-pyridyl)-5-ethyl-3-methyl-6-(trifluoromethyl)imidazo[4,5-c]pyridin-4-one A38

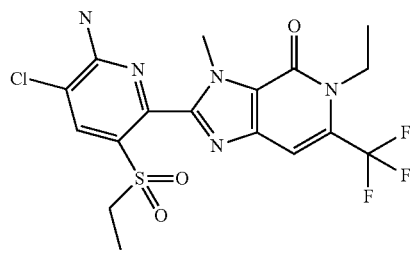

A38

To a 0° C. cooled solution of 2-(6-amino-3-ethylsulfonyl-2-pyridyl)-5-ethyl-3-methyl-6-(trifluoromethyl)imidazo[4,5-c]pyridin-4-one (0.6986 mmol, 0.3 g) in N,N-dimethylformamide (3.0 mL) was added 1-chloropyrrolidine-2,5-dione (0.7685 mmol, 0.1026 g) in two portions. The reaction was stirred at 0° C. for 1 hour, then at room temperature for 4 hours, monitored by TLC. The reaction was diluted with water (10 ml), extracted with ethyl acetate and combined organic layer was dried over sodium sulfate, concentrated under reduced pressure. Crude product was purified by combiflash to afford 2-(6-amino-5-chloro-3-ethylsulfonyl-2-pyridyl)-5-ethyl-3-methyl-6-(trifluoromethyl)imidazo[4,5-c]pyridin-4-one (0.3665 mmol, 0.17 g). $^1$H NMR (400 MHz, CDCl$_3$) δ 8.21 (s, 1H), 7.20 (s, 1H), 5.60 (s, 2H), 4.24 (q, 2H), 4.05 (s, 3H), 3.59 (q, 2H), 1.38 (t, 3H), 1.33 (t, 3H).

Example P39: Preparation of 2-(6-amino-5-bromo-3-ethylsulfonyl-2-pyridyl)-5-ethyl-3-methyl-6-(trifluoromethyl)imidazo[4,5-c]pyridin-4-one A39

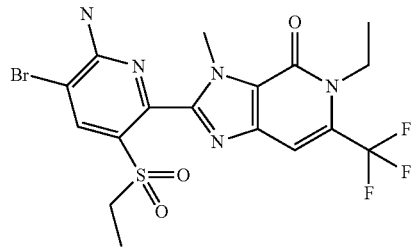

A39

To a 0° C. cooled solution of 2-(6-amino-3-ethylsulfonyl-2-pyridyl)-5-ethyl-3-methyl-6-(trifluoromethyl)imidazo[4,5-c]pyridin-4-one (0.6986 mmol, 0.3 g) in N,N-dimethylformamide (3.0 mL) was added 1-bromopyrrolidine-2,5-dione (0.8384 mmol, 0.1492 g) in two portions. The reaction was stirred at 0° C. for 1 hour, then at room temperature for 4 hours, monitored by TLC. The reaction was diluted with water (10 ml), extracted with ethyl acetate. Combined organic layer was dried over sodium sulfate, concentrated under reduced pressure. Crude product was purified by combiflash to afford 2-(6-amino-5-bromo-3-ethylsulfonyl-2-pyridyl)-5-ethyl-3-methyl-6-(trifluoromethyl)imidazo[4,5-c]pyridin-4-one (0.3935 mmol, 0.2 g) $^1$H NMR (400 MHz, CDCl$_3$) δ 8.37 (s, 1H), 7.21 (s, 1H), 5.64 (s, 2H), 4.24 (q, 2H), 4.05 (s, 3H), 3.59 (q, 2H), 1.42-1.29 (m, 6H).

Example P40: Preparation of N-[3-chloro-6-[5-ethyl-3-methyl-4-oxo-6-(trifluoromethyl)imidazo[4,5-c]pyridin-2-yl]-5-ethylsulfonyl-2-pyridyl]-N-(cyclopropanecarbonyl)cyclopropanecarboxamide A40

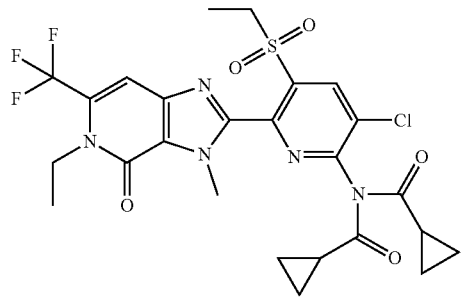 [SMILES: CCn1c(C(F)(F)F)cc2nc(-c3nc(N(C(=O)C4CC4)C(=O)C4CC4)c(Cl)cc3S(=O)(=O)CC)n(C)c2c1=O]

To a flask, 2-(6-amino-5-chloro-3-ethylsulfonyl-2-pyridyl)-5-ethyl-3-methyl-6-(trifluoromethyl)imidazo[4,5-c]pyridin-4-one A38 (0.2 g, 0.431 mmol) was dissolved in dichloromethane (6 mL), then Triethylamine (0.0661 mL) was added to this solution. The solution was cooled to 0° C., and a solution of cyclopropyl carbonyl chloride (0.046 g, 0.04 mL) in dichloromethane (3 mL) was added dropwise at this temperature. The solution was stirred for 15 minutes at 0° C., then at room temperature. After 1 h at room temperature, additional quantities of Triethylamine (0.0661 mL) and cyclopropyl carbonyl chloride (0.04 mL) were added. After 2.5 h at room temperature, additional quantities of Triethylamine (0.0661 mL) and cyclopropyl carbonyl chloride (0.04 mL) were added. After 2 h at room temperature, additional quantities of Triethylamine (0.0661 mL) and cyclopropyl carbonyl chloride (0.04 mL) were added and, finally after 1 h at room temperature, additional Triethylamine (1 mL) and cyclopropyl carbonyl chloride (0.2 mL) were added. The mixture was quenched with a saturated solution of Sodium bicarbonate, and the aqueous phase was extracted twice with dichloromethane. The combinated organic phases were washed with a saturated solution of Sodium bicarbonate, dried with sodium sulfate, filtered. 1.5 g Isolute was added to the filtrate before evaporation of solvent. The residue was purified by chromatography over 12 g silica gel with dichloromethane:ethyl acetate=0-20% to give the title compound in 97% yield. $^1$H NMR (400 MHz, CDCl$_3$) δ 8.64 (s, 1H), 7.18 (s, 1H), 4.24 (q, 2H), 4.10 (s, 3H), 3.88 (q, 2H), 2.0 (m, 2H), 1.30-1.40 (m, 6H), 1.22 (m, 4H), 1.0 (m, 4H).

Example P41: Preparation of N-[3-chloro-6-[5-ethyl-3-methyl-4-oxo-6-(trifluoromethyl)imidazo[4,5-c]pyridin-2-yl]-5-ethylsulfonyl-2-pyridyl]cyclopropanecarboxamide A41

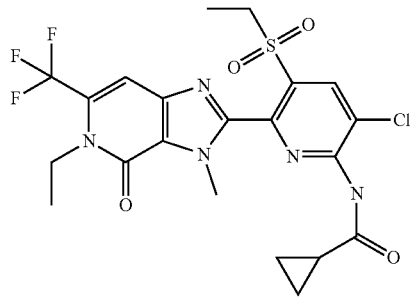 [SMILES: CCn1c(C(F)(F)F)cc2nc(-c3nc(NC(=O)C4CC4)c(Cl)cc3S(=O)(=O)CC)n(C)c2c1=O]

To a colorless solution of N-[3-chloro-6-[5-ethyl-3-methyl-4-oxo-6-(trifluoromethyl)imidazo[4,5-c]pyridin-2-yl]-5-ethylsulfonyl-2-pyridyl]-N-(cyclopropanecarbonyl)cyclopropanecarboxamide A40 (0.14 g, 0.233 mmol) in tetrahydrofuran (14 mL) was added Sodium hydroxide (1N, 2.33 mL, 2.33 mmol). The mixture was stirred 1.5 h at room temperature and the reaction was quenched by addition of 2 ml of a aqueous solution of HCl (1N). The aqueous phase was extracted twice with EA. The combinated organic phases were washed with a saturated solution of Sodium bicarbonate, dried with sodium sulfate, filtered. 1.5 g Isolute was added to the filtrate before evaporation of solvent. The residue was purified by chromatography over 12 g silica gel with cyclohexane:ethyl acetate (0-60%) to give the title compound in 81% yield. $^1$H NMR (400 MHz, CDCl$_3$) δ 8.48 (s, 1H), 8.25 (s, 1H), 7.20 (s, 1H), 4.24 (q, 2H), 4.18 (s, 3H), 3.84 (q, 2H), 2.28 (m, 1H), 1.30-1.40 (m, 6H), 1.22 (m, 2H), 0.96 (m, 2H)

Example P42: Preparation of 2-(6-amino-3-ethylsulfonyl-2-pyridyl)-5-cyclopropyl-3-methyl-6-(trifluoromethyl)imidazo[4,5-c]pyridin-4-one A42

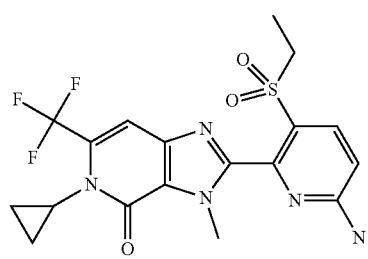

2-(6-amino-3-ethylsulfonyl-2-pyridyl)-5-cyclopropyl-3-methyl-6-(trifluoromethyl)imidazo[4,5-c]pyridin-4-one A42 was prepared by similar reactions as described for Example P6 using the appropriate intermediates via the Tert-butyl N-[6-[5-cyclopropyl-3-methyl-4-oxo-6-(trifluoromethyl)imidazo[4,5-c]pyridin-2-yl]-5-ethylsulfonyl-2-pyridyl]carbamate A63 as intermediate.

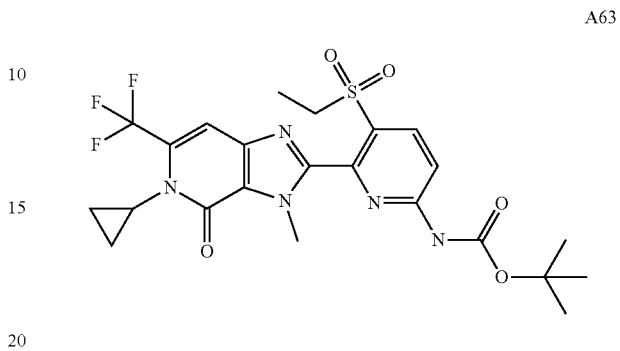

Tert-butyl N-[6-[5-cyclopropyl-3-methyl-4-oxo-6-(trifluoromethyl)imidazo[4,5-c]pyridin-2-yl]-5-ethylsulfonyl-2-pyridyl]carbamate A63: LC-MS (Method A): RT 1.11, 542 (M+H$^+$), 540 (M−H$^+$).

2-(6-amino-3-ethylsulfonyl-2-pyridyl)-5-cyclopropyl-3-methyl-6-(trifluoromethyl)imidazo[4,5-c]pyridin-4-one A42: $^1$H NMR (400 MHz, CDCl$_3$) δ 8.10 (d, 1H), 7.17 (s, 1H), 6.69 (d, 1H), 5.13 (s, 2H), 4.00 (s, 3H), 3.52 (q, 2H), 3.07 (m, 1H), 1.23-1.33 (m, 5H), 1.05 (m, 2H).

Example P43: Preparation of 5-cyclopropyl-2-(3-ethylsulfonyl-6-hydrazino-2-pyridyl)-3-methyl-6-(trifluoromethyl)imidazo[4,5-c]pyridin-4-one A45

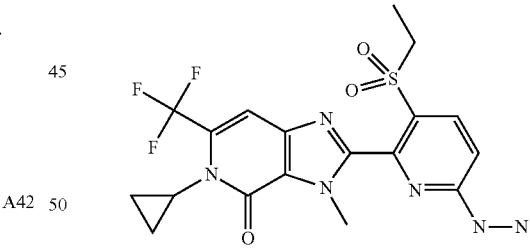

To a flask, Hydrazine hydrate (0.1521 g, 3.04 mmol) was dissolved in tetrahydrofuran (1.823 mL) at room temperature. Then 2-(6-chloro-3-ethylsulfonyl-2-pyridyl)-5-cyclopropyl-3-methyl-6-(trifluoromethyl) imidazo[4,5-c]pyridin-4-one (see example 19, 0.28 g, 0.608 mmol) was added portion wise. The reaction was stirred at room temperature for 2.5 h. 2 g Isolute was added to the reaction, before evaporation of solvent. The residue was purified by chromatography over 12 g silica gel with dichloromethane:ethyl acetate to give the title compound in 80% yield. LC-MS (Method A): RT 0.82, 457 (M+H$^+$), 455 (M−H$^+$).

Example P44: Preparation of 5-cyclopropyl-2-[3-ethylsulfonyl-6-(methoxyamino)-2-pyridyl]-3-methyl-6-(trifluoromethyl)imidazo[4,5-c]pyridin-4-one A46

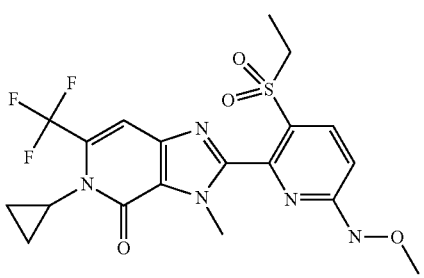

To a vial, 2-(6-chloro-3-ethylsulfonyl-2-pyridyl)-5-cyclopropyl-3-methyl-6-(trifluoromethyl)imidazo[4,5-c]pyridin-4-one (see example 19, 0.25 g, 0.5424 mmol) was dissolved in ethanol (1.2 mL) and tetrahydrofuran (1.2 mL), then o-methyl hydroxylamine hydrochloride (0.093 g, 1.09 mmol) and sodium hydrogenocarbonate (0.0914 g, 1.09 mmol) were added to this solution. The solution was stirred overnight at room temperature and extra o-methyl hydroxylamine hydrochloride (0.093 g, 1.09 mmol) and sodium hydrogenocarbonate (0.0914 g, 1.09 mmol) were added. The solution was stirred overnight at room temperature, then 3 h at 40° C. and additional 20 h at 60° C. Then, two time, o-methyl hydroxylamine hydrochloride (0.093 g, 1.09 mmol) and sodium hydrogenocarbonate (0.0914 g, 1.09 mmol) were added and the reaction was heated at 60° C. for 20 h. Then, two time, o-methyl hydroxylamine hydrochloride (0.093 g, 1.09 mmol) and sodium hydrogenocarbonate (0.0914 g, 1.09 mmol) were added, in addition, extra solvent ethanol (1.2 mL) was added and the reaction was heated at 60° C. for 20 h. Extra o-methyl hydroxylamine hydrochloride (0.093 g, 1.09 mmol) and sodium hydrogenocarbonate (0.0914 g×2) were added and the reaction was at 60° C. for 20 h. The mixture was quenched in dichloromethane and with a saturated solution of Sodium bicarbonate. The aqueous phase was extracted twice with dichloromethane. All of the organic phases were combined, dried with sodium sulfate and filtered. 2 g Isolute was added to the organic phase before evaporation of solvent. The residue was purified by chromatography over 4 g silica gel with dichloromethane:ethyl acetate to give the title compound in 59% yield. $^1$H NMR (400 MHz, CDCl$_3$) δ 8.32 (d, 1H), 7.90 (s, 1H), 7.14 (m, 2H), 3.98 (s, 3H), 3.86 (s, 3H), 3.58 (q, 2H), 3.10 (m, 1H), 1.28 (m, 5H), 1.05 (m, 2H).

Example P45: Preparation of 5-cyclopropyl-2-[3-ethylsulfonyl-6-(hydroxyamino)-2-pyridyl]-3-methyl-6-(trifluoromethyl)imidazo[4,5-c]pyridin-4-one A47

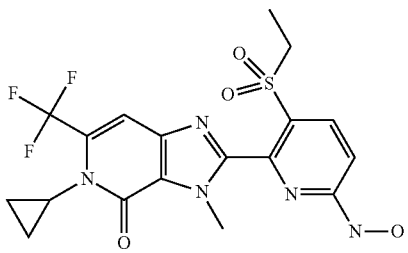 [SMILES: CCS(=O)(=O)c1ccc(NN)nc1-c1nc2cc(C(F)(F)F)n(C3CC3)c(=O)c2n1C]

To a flask, 2-(6-chloro-3-ethylsulfonyl-2-pyridyl)-5-cyclopropyl-3-methyl-6-(trifluoromethyl)imidazo[4,5-c]pyridin-4-one (see example 19, 0.25 g, 0.5424 mmol) was dissolved in DMSO (0.6 mL), then sodium hydrogen carbonate (0.093 g, 1.09 mmol) and hydroxylamine hydrochloride (0.0762 g, 1.09 mmol) were added to this solution. The solution was heated for 1 h at 90° C. The mixture was dissolved in dichloromethane and the organic phase was washed with a saturated solution of Sodium bicarbonate (2×). The combinated aqueous phase was extracted twice with dichloromethane. All of the organic phases were combinated, dried with sodium sulfate and filtered. 1.5 g Isolute was added to the organic phase before evaporation of solvent. The residue was purified by chromatography over 12 g silica gel with dichloromethane:ethyl acetate to give the title compound in 58% yield. $^1$H NMR (400 MHz, CDCl$_3$) δ 8.52 (s, 1H), 8.18 (d, 1H), 7.18 (s, 1H), 7.06 (d, 1H), 3.92 (s, 3H), 3.42 (q, 2H), 3.10 (m, 1H), 1.30 (m, 5H), 1.05 (m, 2H).

Example P46: Preparation of 2-(6-amino-5-cyclopropyl-3-ethylsulfonyl-2-pyridyl)-5-cyclopropyl-3-methyl-6-(trifluoromethyl)imidazo[4,5-c]pyridin-4-one A48

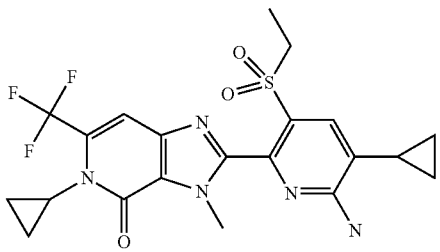 [SMILES: CCS(=O)(=O)c1cc(C2CC2)c(N)nc1-c1nc2cc(C(F)(F)F)n(C3CC3)c(=O)c2n1C]

A solution of 2-(6-amino-5-bromo-3-ethylsulfonyl-2-pyridyl)-5-cyclopropyl-3-methyl-6-(trifluoromethyl)imidazo[4,5-c]pyridin-4-one A44 (preparation described before, 0.13 g, 0.25 mmol) in a mixture of water (1.7 mL) and toluene (1.7 mL) was added potassium phosphate tribasic (0.33 g, 1.50 mmol), cyclopropylboronic acid, (0.081 g, 0.90 mmol) in a vial. The vial was flushed with argon and tetrakis(triphenylphosphine) palladium(0) (0.029 g, 0.025 mmol) was added. The reaction mixture was stirred at reflux for 3.5 hours, then 20 minutes in Microwave at 130° C. Then, cyclopropylboronic acid (0.081 g, 0.90 mmol) and 1,1'-bis(diphenylphosphino)ferrocene-palladium(ii)dichloride dichloromethane complex (0.0215 g, 0.025 mmol) were added and the vial was flushed with argon. The reaction was heated 20 minutes in Microwave at 130° C. The mixture was quenched in dichloromethane and with a 1N solution of sodium hydroxide. The aqueous phase was extracted twice with dichloromethane. All of the organic phases were combinated, watched with a solution of Na₂HCO₃, dried with sodium sulfate and filtered. 1 g Isolute was added to the organic phase before evaporation of solvent. The residue was chromatographed over 4 g silica gel with dichloromethane:ethyl acetate to give the title compound in 32% yield. LC-MS (Method A): RT 0.96, 482 (M+H⁺).

Example P47: Preparation of 2-(6-amino-5-methyl-3-ethylsulfonyl-2-pyridyl)-5-cyclopropyl-3-methyl-6-(trifluoromethyl)imidazo[4,5-c]pyridin-4-one A49

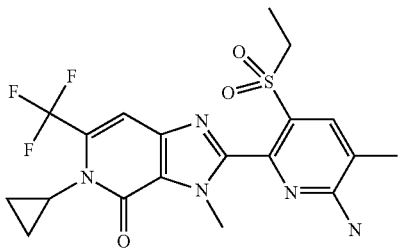 [SMILES: CCS(=O)(=O)c1cc(C)c(N)nc1-c1nc2cc(C(F)(F)F)n(C3CC3)c(=O)c2n1C]

A solution of 2-(6-amino-5-bromo-3-ethylsulfonyl-2-pyridyl)-5-cyclopropyl-3-methyl-6-(trifluoromethyl) imidazo[4,5-c]pyridin-4-one A44 (preparation described before, 0.12 g, 0.23 mmol) in a mixture of water (0.12 mL) and dioxane (1.1 mL) was added potassium carbonate (0.0.095 g, 0.63 mmol), trimethylboroxine (0.030 g, 0.239 mmol) in a vial. The vial was flushed with argon and bis[cyclopentyl(diphenyl)phosphaniumyl]palladium; iron; dihydrochloride (0.0167 g, 0.0228 mmol) was added. The reaction mixture was heated at 100° C. for 3 hours. The mixture was quenched in dichloromethane and with a 1N solution of sodium hydroxide. The aqueous phase was extracted twice with dichloromethane. All of the organic phases were combinated, washed with a solution of Na₂HCO₃, dried with sodium sulfate and filtered. 1.5 g Isolute was added to the organic phase before evaporation of solvent. The residue was purified by chromatography over 4 g silica gel with dichloromethane:ethyl acetate to give the title compound in 76% yield. LC-MS (Method A): RT 0.88, 454 (M−H⁺), 456 (M+H⁺).

Example P48: Preparation of 2-(6-amino-5-cyano-3-ethylsulfonyl-2-pyridyl)-5-cyclopropyl-3-methyl-6-(trifluoromethyl)imidazo[4,5-c]pyridin-4-one A50

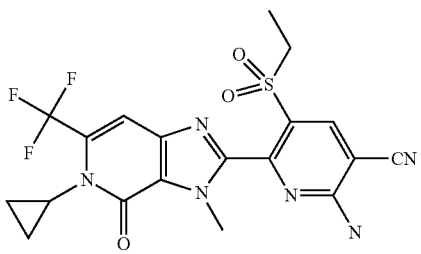 [SMILES: CCS(=O)(=O)c1cc(C#N)c(N)nc1-c1nc2cc(C(F)(F)F)n(C3CC3)c(=O)c2n1C]

A vial was charged with 2-(6-amino-5-bromo-3-ethylsulfonyl-2-pyridyl)-5-cyclopropyl-3-methyl-6-(trifluoromethyl) imidazo[4,5-c]pyridin-4-one A44 (preparation described before, 0.12 g) in dimethylformamide (2.16 mL). To this solution was added Pd₂(dba)₃ (0.010 g), zinc cyanide (0.22 g) and S-Phos (0.011 g). The reaction mixture was purged with N₂ gas for 25 min. Then, the mixture was heated in the microwave 30' at 150° C. The mixture was quenched with ethyl acetate and with a solution of sodium hydroxide (0.1M). The aqueous phase was extracted twice with ethyl acetate. All of the organic phases were combinated, washed with a solution of sodium hydroxide (0.1M), dried with sodium sulfate and filtered. 1 g Isolute was added to the organic phase before evaporation of solvent. The residue was purified by chromatography over 4 g silica gel with dichloromethane:ethyl acetate to give the title compound in 88% yield. LC-MS (Method A): RT 0.92, 465 (M−H⁺), 466 (M+H⁺).

Example P49: Preparation of 5-cyclopropyl-2-[3-ethylsulfonyl-6-(methylamino)-2-pyridyl]-3-methyl-6-(trifluoromethyl)imidazo[4,5-c]pyridin-4-one A51

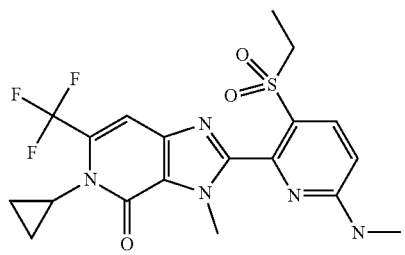 [SMILES: CCS(=O)(=O)c1ccc(NC)nc1-c1nc2cc(C(F)(F)F)n(C3CC3)c(=O)c2n1C]

A flask was charged with 2-(6-chloro-3-ethylsulfonyl-2-pyridyl)-5-cyclopropyl-3-methyl-6-(trifluoromethyl)imidazo[4,5-c]pyridin-4-one (see example 19, 0.25 g, 0.542 mmol) in methylamine (in THF 2M, 2 mL, 4.00 mmol). The reaction was stirred at RT for 1 h. The mixture was quenched in dichloromethane and with a saturated solution of Sodium bicarbonate. The aqueous phase was extracted twice with dichloromethane. All of the organic phases were combinated, dried with sodium sulfate and filtered. The solvent was evaporated to give the title compound in quantitative yield. LC-MS (Method A): RT 0.93, 457 (M+H⁺).

Example P50: Preparation of 1-cyano-N-[6-[5-ethyl-3-methyl-4-oxo-6-(trifluoromethyl)imidazo[4,5-c]pyridin-2-yl]-5-ethylsulfonyl-3-pyridyl]cyclopropanecarboxamide A55

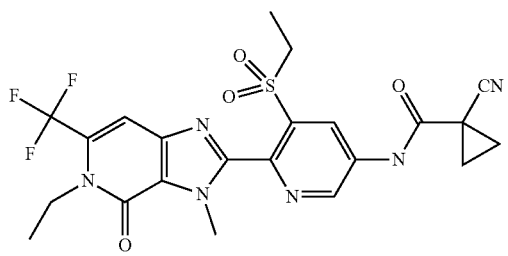 [SMILES: CCn1c(C(F)(F)F)cc2nc(-c3ncc(NC(=O)C4(C#N)CC4)cc3S(=O)(=O)CC)n(C)c2c1=O]

2-(5-amino-3-ethylsulfonyl-2-pyridyl)-5-ethyl-3-methyl-6-(trifluoromethyl)imidazo[4,5-c]pyridin-4-one (100 mg, 0.233 mmol) and 1-cyanocyclopropanecarboxylic acid (26 mg, 0.233 mmol, 1 eq) were dissolved in pyridine (1 ml) at room temperature under nitrogen. The reaction mixture was cooled to −10° C. and phosphorus oxychloride (0.02 ml, 0.279 mmol) was added dropwise under nitrogen. The mixture was stirred at −10° C. and warmed to 0° C. over 30 mins. It was then quenched in water and diluted with Ethyl acetate (10 ml). Organic layer was separated. Aqueous layer was further washed with Ethyl acetate (10 ml). Combined organic extract was washed with brine, dried over sodium sulfate, filtered and concentrated to get crude product which was purified by column chromatography with gradient cyclohexane+0-50% Ethyl acetate to give 1-cyano-N-[6-[5-ethyl-3-methyl-4-oxo-6-(trifluoromethyl)imidazo[4,5-c]pyridin-2-yl]-5-ethylsulfonyl-3-pyridyl]cyclopropanecarboxamide (94 mg) in 79% yield.

1H NMR (400 MHz, CDCl$_3$) δ ppm 1.34-1.45 (m, 6H) 1.74-1.80 (m, 2H) 1.89-1.95 (m, 2H) 3.78 (m, 2H) 4.08 (s, 3H) 4.25 (m, 2H) 7.21 (s, 1H) 8.58 (s, 1H) 8.73 (d, 1H) 9.21 (d, 1H)

Example P51: Preparation of 1-[[6-[5-ethyl-3-methyl-4-oxo-6-(trifluoromethyl)imidazo[4,5-c]pyridin-2-yl]-5-ethylsulfinyl-3-pyridyl]amino]cyclopropanecarbonitrile A57

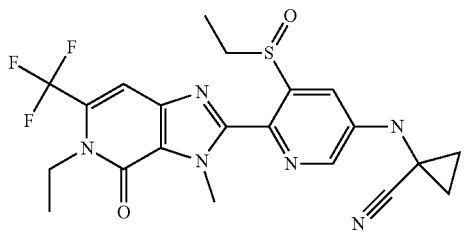

A57

2-(5-bromo-3-ethylsulfinyl-2-pyridyl)-5-ethyl-3-methyl-6-(trifluoromethyl)imidazo[4,5-c]pyridin-4-one (prepared as described in Example I3—step C, 250 mg, 0.5238 mmol) was dissolved in anhydrous 1,4-dioxane (5 mL) and to it cesium carbonate (2.095 mmol, 0.683 g) was added under nitrogen followed by the addition of palladium (II) acetate (0.03143 mmol, 0.00706 g) and (1-cyanocyclopropyl)ammonium chloride (0.7857 mmol, 0.09315 g). The mixture was purged with nitrogen for 15 minutes. X-PHOS (0.09428 mmol, 0.04586 g) was then added and the mixture was heated at 110° C. in a preheated oil bath for 14 hrs. The mixture was filtered through celite bed and bed was washed with Ethyl acetate (20 ml). Organic layer was evaporated and purified by column chromatography using 60% Ethyl acetate/cyclohexane to give 1-[[6-[5-ethyl-3-methyl-4-oxo-6-(trifluoromethyl)imidazo[4,5-c]pyridin-2-yl]-5-ethylsulfinyl-3-pyridyl]amino]cyclopropanecarbonitrile (20 mg, 0.04180 mmol, 8% Yield). $^1$H NMR (400 MHz, CDCl$_3$) δ ppm 1.28-1.34 (m, 2H) 1.37-1.50 (m, 6H) 2.98-3.10 (m, 1H) 3.56-3.67 (m, 1H) 4.23-4.30 (m, 2H) 4.55 (s, 3H) 5.63-5.78 (m, 1H) 7.23 (s, 1H) 8.07 (d, 1H) 8.46 (d, 1H).

Example P52: Preparation of 2-[5-(cyclopropylamino)-3-ethylsulfinyl-2-pyridyl]-5-ethyl-3-methyl-6-(trifluoromethyl)imidazo[4,5-c]pyridin-4-one A58

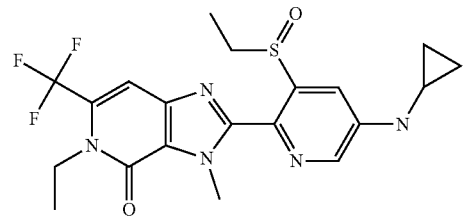

A58

In a 25 ml vial, under nitrogen was taken 2-(5-bromo-3-ethylsulfonyl-2-pyridyl)-5-ethyl-3-methyl-6-(trifluoromethyl)imidazo[4,5-c]pyridin-4-one (220 mg, 0.4460 mmol) in anhydrous toluene (5 mL) and to it cesium carbonate (0.6914 mmol, 0.225 g) was added under nitrogen. The mixture was purged with nitrogen for 5 mins. tris(dibenzylideneacetone)dipalladium (0) (0.009219 mmol, 0.008527 g) and (+/−)-BINAP (0.01844 mmol, 0.01184 g) were added to the above The mixture was purged with nitrogen for 5 min. Cyclopropyl amine (0.5531 mmol, 0.03158 g, 0.0383 mL) was finally added to the above reaction mixture and heated at 110° C. for 16 hrs. The mixture was filtered through celite bed and the bed was washed with Ethyl acetate (20 ml). The mixture was poured in a separating funnel containing Ethyl acetate and water. Organic layer was separated, washed with water and brine, dried over Sodium sulfate, filtered, and concentrated to give crude product which was purified by column chromatography using ethyl acetate/cyclohexane (4:6) to give 2-[5-(cyclopropylamino)-3-ethylsulfinyl-2-pyridyl]-5-ethyl-3-methyl-6-(trifluoromethyl)imidazo[4,5-c]pyridin-4-one (54 mg, 0.1191 mmol, 26% Yield). $^1$H NMR (400 MHz, METHANOL-d4) δ ppm 0.53-0.61 (m, 2H) 0.84-0.94 (m, 2H) 1.38 (m, 6H) 2.57 (m, 1H) 2.92-3.02 (m, 1H) 3.50 (m, 1H) 4.25 (m, 2H) 4.43 (s, 3H) 7.29 (s, 1H) 7.79 (d, 1H) 8.30 (d, 1H)

Example P53: Preparation of N-[6-[5-ethyl-3-methyl-4-oxo-6-(trifluoromethyl)imidazo[4,5-c]pyridin-2-yl]-5-ethylsulfanyl-3-pyridyl]cyclopropanecarboxamide A59

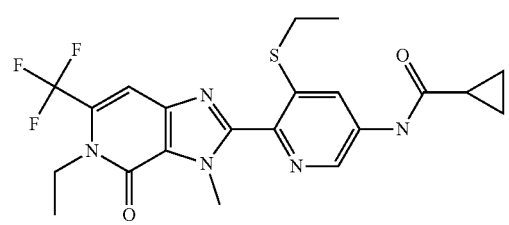

A59

2-(5-amino-3-ethylsulfanyl-2-pyridyl)-5-ethyl-3-methyl-6-(trifluoromethyl)imidazo[4,5-c]pyridin-4-one (See A69, 0.4529 mmol, 0.18 g) was dissolved in dry dichloromethane (2 mL) and to it N,N-diethylethanamine (1.359 mmol, 0.1375 g, 0.189 mL) was added at room temperature under nitrogen. The reaction mixture was cooled to 0° C. and cyclopropane carbonyl chloride (0.4982 mmol, 0.05209 g, 0.04521 mL) was added dropwise under nitrogen. The mixture was stirred at 0° C. to room temperature for 1 h and then quenched in water and diluted with DCM (10 ml). Organic layer was separated. Aqueous layer was further washed with DCM (10 ml). Combined organic extract was washed with brine, dried over sodium sulfate and concentrated to get crude product. Crude compound was purified by column chromatography using 60% Ethyl acetate/Cyclohexane to give N-[6-[5-ethyl-3-methyl-4-oxo-6-(trifluoromethyl)imidazo[4,5-c]pyridin-2-yl]-5-ethylsulfanyl-3-pyridyl]cyclopropanecarboxamide (0.3631 mmol, 0.169 g) in 80% yield. 1H NMR (400 MHz, CDCl$_3$) δ ppm 8.78 (br. s., 1H), 8.44 (d, 1H), 8.37 (s, 1H), 7.33 (s, 1H), 4.26 (m, 2H), 4.15 (s, 3H), 2.95 (m, 2H), 1.75 (m, 1H), 1.42-1.36 (m, 3H), 1.31 (t, 3H), 1.16-1.10 (m, 2H), 0.96-0.90 (m, 2H).

Example P54: Preparation of 2-[6-[cyclopropyl(methyl)sulfoximine]-3-ethylsulfonyl-2-pyridyl]-5-ethyl-3-methyl-6-(trifluoromethyl)imidazo[4,5-c]pyridin-4-one A60

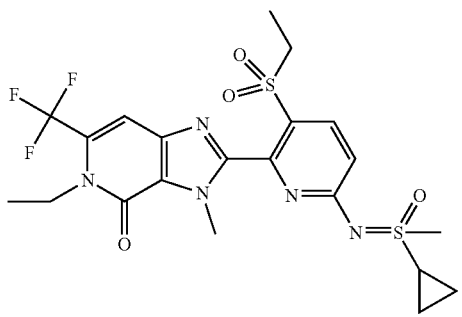

A60

A solution of 2-(6-chloro-3-ethylsulfonyl-2-pyridyl)-5-ethyl-3-methyl-6-(trifluoromethyl)imidazo[4,5-c]pyridin-4-one (0.3 g, 0.7 mmol), Cyclopropyl(methyl)sulfoximine (Commercially available, CAS 1609964-41-1, 0.7 mmol, 0.09 g), dicesium carbonic acid (1 mmol, 0.4 g), and (5-diphenylphosphanyl-9,9-dimethyl-xanthen-4-yl)-diphenyl-phosphane (0.1 mmol, 0.08 g) in 1,4-dioxane (5.0 mL) was purged with nitrogen for 10 min. To this was then added (1E,4E)-1,5-diphenylpenta-1,4-dien-3-one palladium (0.07 mmol, 0.06 g) and reaction mixture was heated in microwave at 110° C. for 60 min. The reaction was diluted with water (10 ml), extracted with ethyl acetate (3×30 ml). Combined organic layer was dried over sodium sulfate, filtered and concentrated under reduced pressure. Crude product was purified by column chromatography using 50% EA-cyclohexane to give 2-[6-[cyclopropyl(methyl)sulfoximine]-3-ethylsulfonyl-2-pyridyl]-5-ethyl-3-methyl-6-(trifluoromethyl)imidazo[4,5-c]pyridin-4-one (120 mg, 30% yield). $^1$H NMR (400 MHz, CDCl$_3$) δ ppm 8.16 (d, 1H), 7.21 (s, 1H), 6.98 (s, 1H), 4.22 (m, 2H), 4.09 (s, 3H), 3.73-3.52 (m, 2H), 3.37 (s, 3H), 2.77-2.65 (m, 1H), 1.50-1.29 (m, 8H), 1.11 (m, 2H)

Example P55: Preparation of 2-[5-[cyclopropyl(methyl)sulfoximine]-3-ethylsulfonyl-2-pyridyl]-5-ethyl-3-methyl-6-(trifluoromethyl)imidazo[4,5-c]pyridin-4-one A61

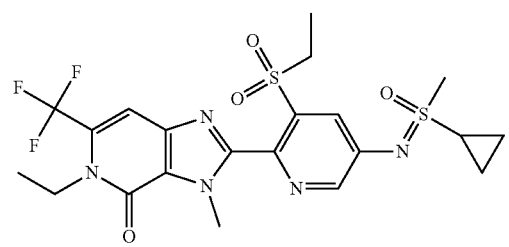

A61

A solution of 2-(5-bromo-3-ethylsulfonyl-2-pyridyl)-5-ethyl-3-methyl-6-(trifluoromethyl)imidazo[4,5-c]pyridin-4-one (0.6081 mmol, 0.3 g), Cyclopropyl(methyl)sulfoximine (Commercially available, CAS 1609964-41-1, 0.6690 mmol, 0.07973 g), dicesium carbonic acid (1.216 mmol, 0.3987 g) and (5-diphenylphosphanyl-9,9-dimethyl-xanthen-4-yl)-diphenyl-phosphane (0.1216 mmol, 0.07255 g) in 1,4-dioxane (5.0 mL) was purged with nitrogen for 10 min. To this was then added (1E,4E)-1,5-diphenylpenta-1,4-dien-3-one; palladium (0.06081 mmol, 0.05569 g) and The mixture was heated in microwave at 110° C. for 60 min. The reaction was diluted with water (10 ml), extracted with ethyl acetate (3×30 ml). Combined organic layer was dried over sodium sulfate, filtered and concentrated under reduced pressure. The crude was purified by combiflash (silica gel, 50% ethyl acetate-cyclohexane) to gave 2-[5-[Cyclopropyl(methyl)sulfoximine]-3-ethylsulfonyl-2-pyridyl]-5-ethyl-3-methyl-6-(trifluoromethyl) imidazo[4,5-c]pyridin-4-one (0.376 mmol, 0.2 g, 62% yield). $^1$H NMR (400 MHz, CDCl$_3$) δ ppm 8.63 (d, 1H), 8.06 (d, 1H), 7.20 (s, 1H), 4.24 (m, 2H), 4.05 (s, 3H), 3.70 (m, 2H), 3.26 (s, 3H), 2.67-2.60 (m, 1H), 1.41-1.32 (m, 6H), 1.31-1.19 (m, 4H).

Example P56: Preparation of 2-(6-acetyl-3-ethylsulfonyl-2-pyridyl)-5-ethyl-3-methyl-6-(trifluoromethyl)imidazo[4,5-c]pyridin-4-one A70

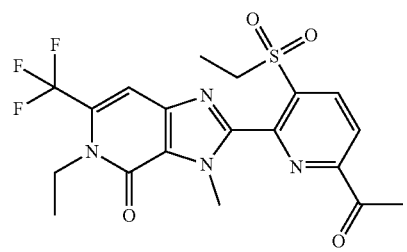

A70

Step A: Preparation of 2-[6-(1-ethoxyvinyl)-3-ethyl-sulfonyl-2-pyridyl]-5-ethyl-3-methyl-6-(trifluoromethyl)imidazo[4,5-c]pyridin-4-one

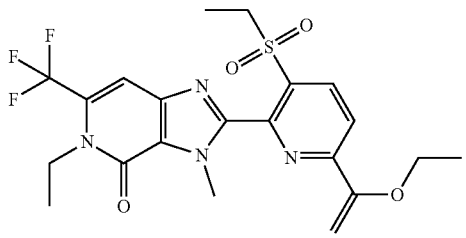 [SMILES: C=C(OCC)c1ccc(S(=O)(=O)CC)c(-c2nc3cc(C(F)(F)F)n(CC)c(=O)c3n2C)n1]

In 30 mL vial, 2-(6-chloro-3-ethylsulfonyl-2-pyridyl)-5-ethyl-3-methyl-6-(trifluoromethyl)imidazo[4,5-c]pyridin-4-one (5.3 mmol, 2400 mg) and tributyl(1-ethoxyvinyl)stannane (5.6 mmol, 2000 mg) were dissolved in 1,4-dioxane (27 mL), then this yellow suspension was degazzed with an nitrogen for 20 minutes. Pd(PPh3)4 (0.27 mmol, 310 mg) was added at room temperature and the suspension was stirred at 80° C. for 2 hr under microwave irradiation. After completion, the reaction was neutralysed with sodium bicarbonate 10% solution (30 ml), and resultant solution was extracted with ehylacetate (20 ml×3). The combined organic layer was washed with aqueous saturated sodium chloride solution (30 ml), dried over anhydrous sodium sulfate, and concentrated of under reduced pressure. The residue was subjected to silica gel column chromatography (30% Ethylacetate hexane and 12 g silica cartage) to obtain tittle compound. This compound was used without any extra purification in the next step.

Step B: Preparation of 2-(6-acetyl-3-ethylsulfonyl-2-pyridyl)-5-ethyl-3-methyl-6-(trifluoromethyl)imidazo[4,5-c]pyridin-4-one A70 a solution of hydrochloride (20 ml) was added to a solution of 2-[6-(1-ethoxyvinyl)-3-ethylsulfonyl-2-pyridyl]-5-ethyl-3-methyl-6-(trifluoromethyl)imidazo[4,5-c]pyridin-4-one (1 mmol, 500 mg) in dichloromethane (30 ml). The reaction was stirred at 50° C. for 2 h. After completion, the reaction was neutralysed with sodium by carbonate 10% solution (30 ml) at 0° C., and resultant solution was extracted with dichloromethane (20 ml×3). The combined organic layer was washed with aqueous saturated sodium chloride solution (30 ml), dried over anhydrous sodium sulfate, and concentrated of under reduced pressure. The residue was subjected to silica gel column chromatography (30% Ethylacetate/hexane and 12 g silica cartage was used) to obtain the desired compound. $^1$H NMR (400 MHz, CDCl3) δ ppm 1.34-1.43 (m, 6H) 2.75 (s, 3H) 3.82 (q, 2H) 4.15 (s, 3H) 4.27 (q, 2H) 7.24 (s, 1H), 8.36 (d, 1H) 8.66 (d, 1H).

TABLE P1

| Examples of compounds of formula (I) | | |
|---|---|---|
| Compound No. | Structures | Analytic Method |
| A1 | | See experimental part above |
| A2 | | See experimental part above |
| A3 | | See experimental part above |

TABLE P1-continued

Examples of compounds of formula (I)

| Compound No. | Structures | Analytic Method |
|---|---|---|
| A4 | 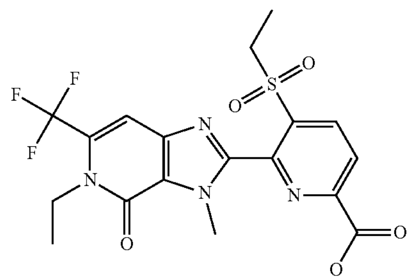 [SMILES: CCn1c(C(F)(F)F)cc2nc(-c3nc(C(=O)O)ccc3S(=O)(=O)CC)n(C)c2c1=O] | See experimental part above |
| A5 | 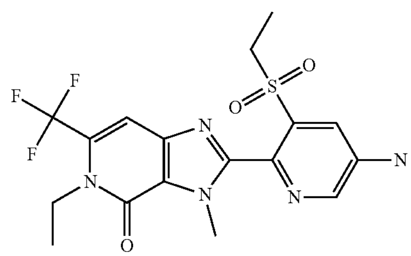 [SMILES: CCn1c(C(F)(F)F)cc2nc(-c3ncc(N)cc3S(=O)(=O)CC)n(C)c2c1=O] | See experimental part above |
| A6 | 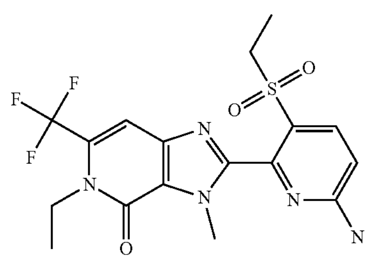 [SMILES: CCn1c(C(F)(F)F)cc2nc(-c3nc(N)ccc3S(=O)(=O)CC)n(C)c2c1=O] | See experimental part above |
| A7 | 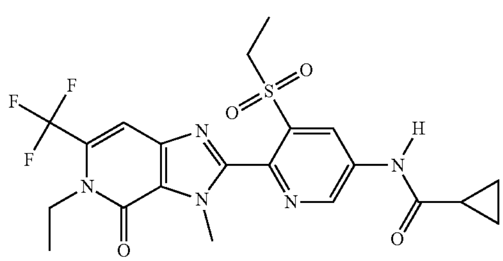 [SMILES: CCn1c(C(F)(F)F)cc2nc(-c3ncc(NC(=O)C4CC4)cc3S(=O)(=O)CC)n(C)c2c1=O] | See experimental part above |
| A8 | 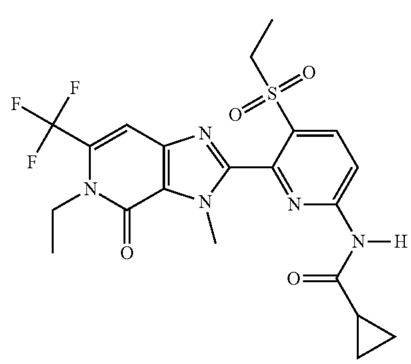 [SMILES: CCn1c(C(F)(F)F)cc2nc(-c3nc(NC(=O)C4CC4)ccc3S(=O)(=O)CC)n(C)c2c1=O] | See experimental part above |

TABLE P1-continued

Examples of compounds of formula (I)

| Compound No. | Structures | Analytic Method |
|---|---|---|
| A9 | 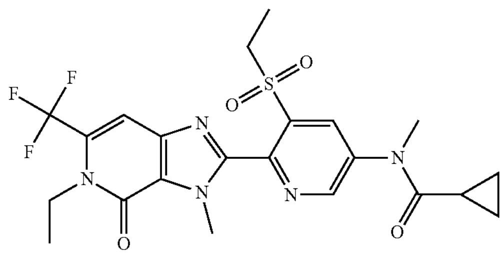 [SMILES: CCn1c(C(F)(F)F)cc2nc(-c3ncc(N(C)C(=O)C4CC4)cc3S(=O)(=O)CC)n(C)c2c1=O] | See experimental part above |
| A10 | 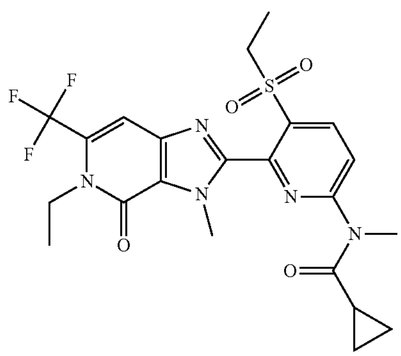 [SMILES: CCn1c(C(F)(F)F)cc2nc(-c3nc(N(C)C(=O)C4CC4)ccc3S(=O)(=O)CC)n(C)c2c1=O] | See experimental part above |
| A11 | 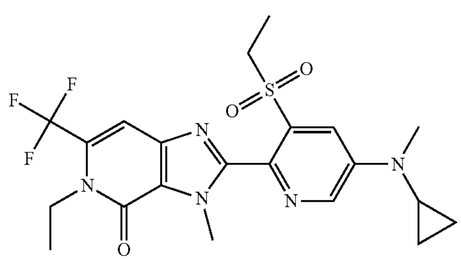 [SMILES: CCn1c(C(F)(F)F)cc2nc(-c3ncc(N(C)C4CC4)cc3S(=O)(=O)CC)n(C)c2c1=O] | See experimental part above |
| A12 | 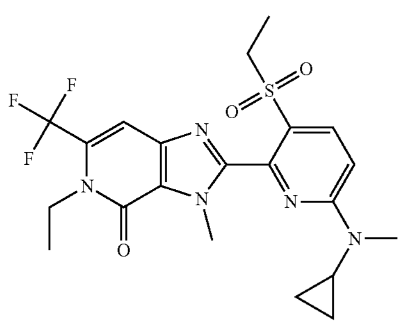 [SMILES: CCn1c(C(F)(F)F)cc2nc(-c3nc(N(C)C4CC4)ccc3S(=O)(=O)CC)n(C)c2c1=O] | See experimental part above |
| A13 | 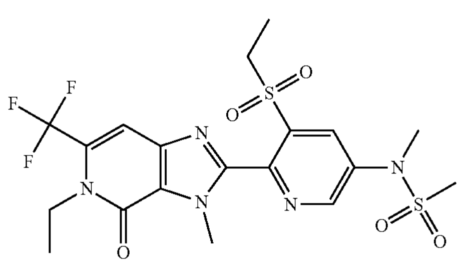 [SMILES: CCn1c(C(F)(F)F)cc2nc(-c3ncc(N(C)S(C)(=O)=O)cc3S(=O)(=O)CC)n(C)c2c1=O] | See experimental part above |

TABLE P1-continued
Examples of compounds of formula (I)
| Compound No. | Structures | Analytic Method |
| --- | --- | --- |
| A14 | 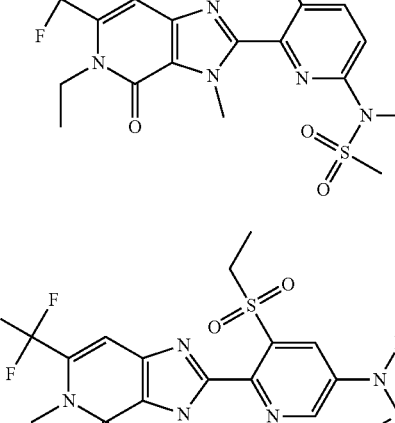 | See experimental part above |
| A15 | 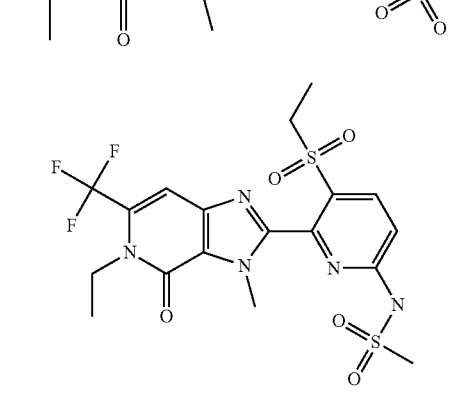 | $^1$H NMR (400 MHz, CDCl$_3$) δ ppm 1.33-1.47 (m, 6 H), 3.23 (s, 3 H), 3.82 (q, 2 H), 4.10 (s, 3 H), 4.27 (q, 2 H), 7.24 (s, 1 H), 8.12 (br. s., 1 H), 8.32 (d, 1 H), 8.85 (d, 1 H). |
| A16 | 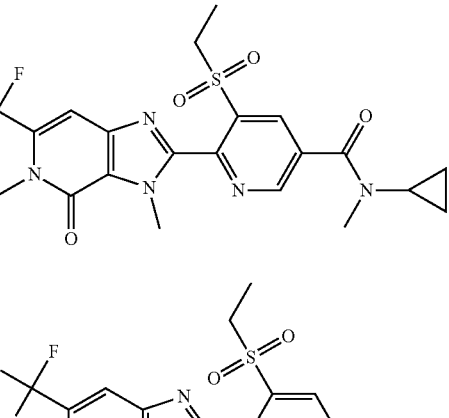 | See experimental part above |
| A17 | 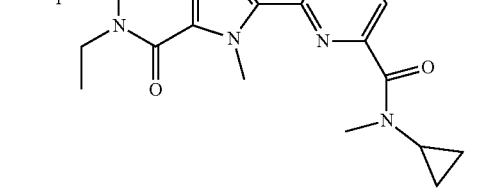 | See experimental part above |
| A18 | 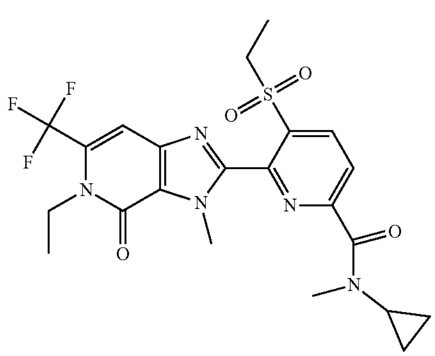 [SMILES: CCn1c(C(F)(F)F)cc2nc(-c3nc(C(=O)N(C)C4CC4)ccc3S(=O)(=O)CC)n(C)c2c1=O] | See experimental part above |

TABLE P1-continued

Examples of compounds of formula (I)

| Compound No. | Structures | Analytic Method |
| --- | --- | --- |
| A19 | 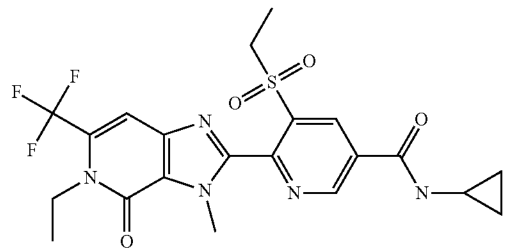 [SMILES: CCn1c(C(F)(F)F)cc2nc(-c3ncc(C(=O)NC4CC4)cc3S(=O)(=O)CC)n(C)c2c1=O] | ¹H NMR (400 MHz, CDCl₃) δ ppm 0.61-0.69 (m, 2 H), 0.84-0.93 (m, 2 H), 1.26-1.36 (m, 6 H), 2.88-2.96 (m, 1 H), 3.76 (q, 2 H), 4.02 (s, 3 H), 4.18 (q, 2 H), 6.52 (br. s., 1 H), 7.14 (s, 1 H), 8.51-8.77 (m, 1 H), 9.28 (d, 1 H). |
| A20 | 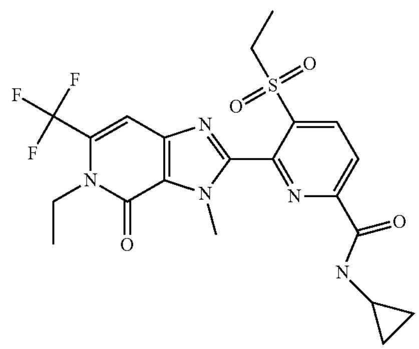 [SMILES: CCn1c(C(F)(F)F)cc2nc(-c3nc(C(=O)NC4CC4)ccc3S(=O)(=O)CC)n(C)c2c1=O] | See experimental part above |
| A21 | 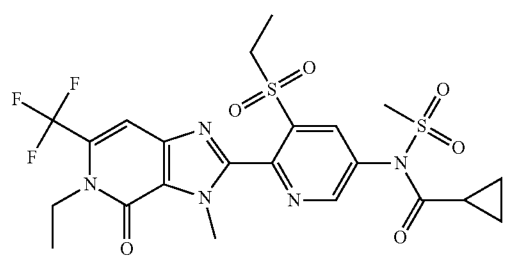 [SMILES: CCn1c(C(F)(F)F)cc2nc(-c3ncc(N(C(=O)C4CC4)S(C)(=O)=O)cc3S(=O)(=O)CC)n(C)c2c1=O] | See experimental part above |
| A22 | 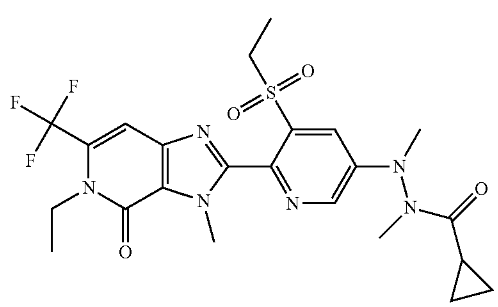 [SMILES: CCn1c(C(F)(F)F)cc2nc(-c3ncc(N(C)N(C)C(=O)C4CC4)cc3S(=O)(=O)CC)n(C)c2c1=O] | See experimental part above |
| A23 | 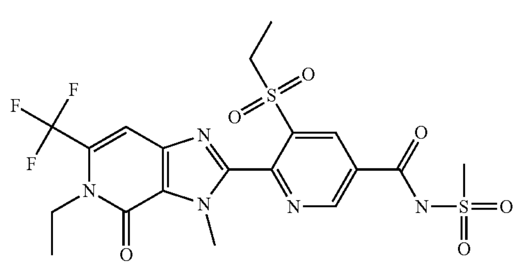 [SMILES: CCn1c(C(F)(F)F)cc2nc(-c3ncc(C(=O)NS(C)(=O)=O)cc3S(=O)(=O)CC)n(C)c2c1=O] | See experimental part above |

TABLE P1-continued

Examples of compounds of formula (I)

| Compound No. | Structures | Analytic Method |
|---|---|---|
| A24 | 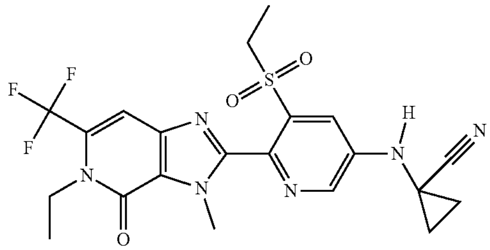 [SMILES: CCn1c(C(F)(F)F)cc2nc(-c3ncc(NC4(C#N)CC4)cc3S(=O)(=O)CC)n(C)c2c1=O] | See experimental part above |
| A25 | 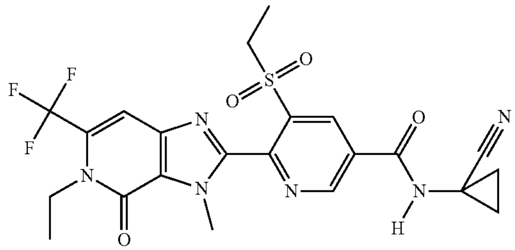 [SMILES: CCn1c(C(F)(F)F)cc2nc(-c3ncc(C(=O)NC4(C#N)CC4)cc3S(=O)(=O)CC)n(C)c2c1=O] | See experimental part above |
| A26 | 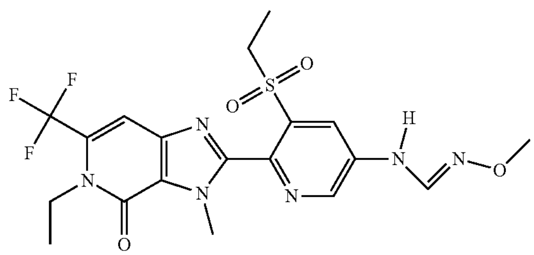 [SMILES: CCn1c(C(F)(F)F)cc2nc(-c3ncc(N/C=N/OC)cc3S(=O)(=O)CC)n(C)c2c1=O] | See experimental part above |
| A27 | 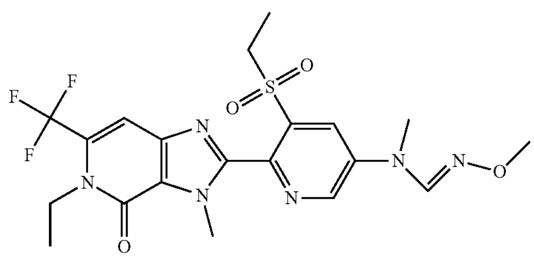 [SMILES: CCn1c(C(F)(F)F)cc2nc(-c3ncc(N(C)/C=N/OC)cc3S(=O)(=O)CC)n(C)c2c1=O] | See experimental part above |
| A28 | 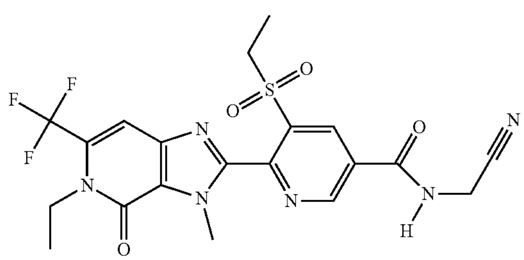 [SMILES: CCn1c(C(F)(F)F)cc2nc(-c3ncc(C(=O)NCC#N)cc3S(=O)(=O)CC)n(C)c2c1=O] | See experimental part above |
| A29 | 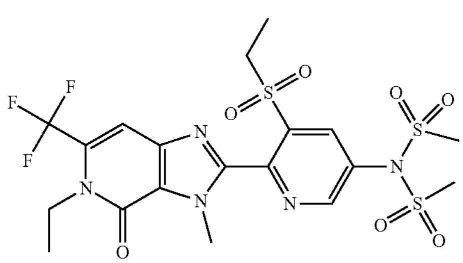 [SMILES: CCn1c(C(F)(F)F)cc2nc(-c3ncc(N(S(C)(=O)=O)S(C)(=O)=O)cc3S(=O)(=O)CC)n(C)c2c1=O] | See experimental part above |

TABLE P1-continued
Examples of compounds of formula (I)
| Compound No. | Structures | Analytic Method |
|---|---|---|
| A30 | 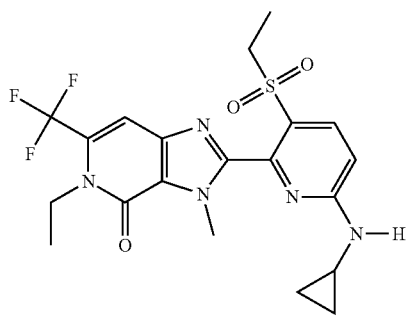 [SMILES: CCn1c(C(F)(F)F)cc2nc(-c3nc(NC4CC4)ccc3S(=O)(=O)CC)n(C)c2c1=O] | See experimental part above |
| A31 | 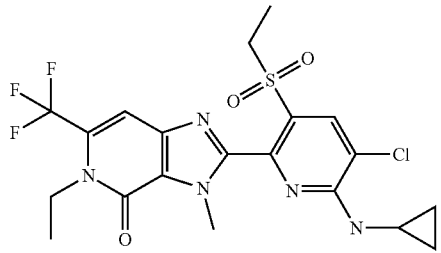 [SMILES: CCn1c(C(F)(F)F)cc2nc(-c3nc(NC4CC4)c(Cl)cc3S(=O)(=O)CC)n(C)c2c1=O] | See experimental part above |
| A32 | 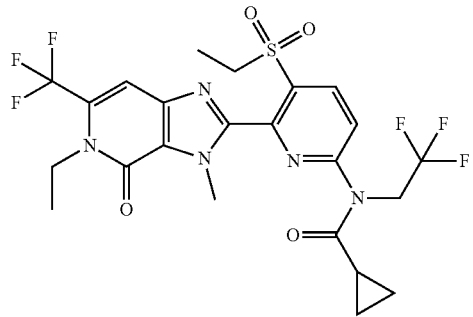 [SMILES: CCn1c(C(F)(F)F)cc2nc(-c3nc(N(CC(F)(F)F)C(=O)C4CC4)ccc3S(=O)(=O)CC)n(C)c2c1=O] | See experimental part above |
| A33 | 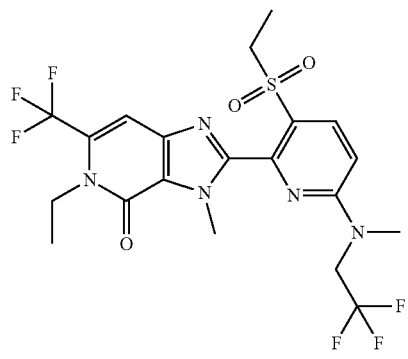 [SMILES: CCn1c(C(F)(F)F)cc2nc(-c3nc(N(C)CC(F)(F)F)ccc3S(=O)(=O)CC)n(C)c2c1=O] | See experimental part above |
| A34 | 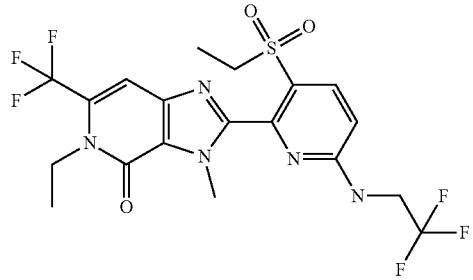 [SMILES: CCn1c(C(F)(F)F)cc2nc(-c3nc(NCC(F)(F)F)ccc3S(=O)(=O)CC)n(C)c2c1=O] | See experimental part above |

TABLE P1-continued
Examples of compounds of formula (I)
| Compound No. | Structures | Analytic Method |
|---|---|---|
| A35 | 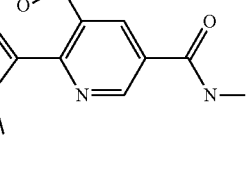 | See experimental part above |
| A36 | 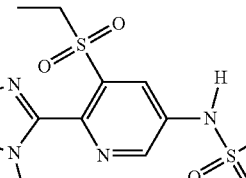 | See experimental part above |
| A37 | 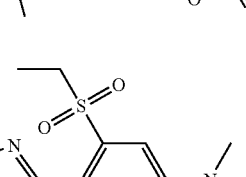 | See experimental part above |
| A38 | 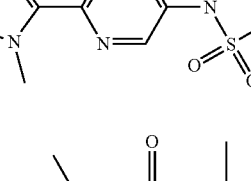 | See experimental part above |
| A39 | 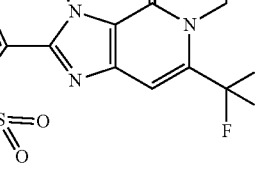 | See experimental part above |
| A40 | 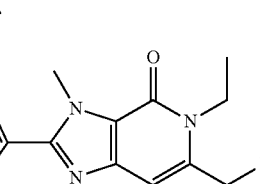 | See experimental part above |

TABLE P1-continued

Examples of compounds of formula (I)

| Compound No. | Structures | Analytic Method |
|---|---|---|
| A41 | 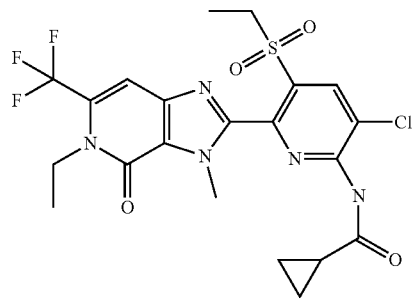 [SMILES: CCn1c(C(F)(F)F)cc2nc(-c3nc(NC(=O)C4CC4)c(Cl)cc3S(=O)(=O)CC)n(C)c2c1=O] | See experimental part above |
| A42 | 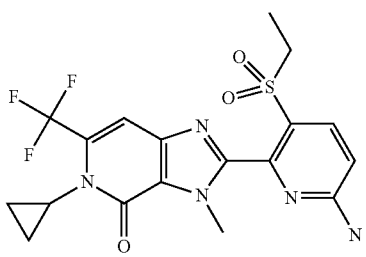 [SMILES: CCS(=O)(=O)c1ccc(N)nc1-c1nc2cc(C(F)(F)F)n(C3CC3)c(=O)c2n1C] | See experimental part above |
| A43 | 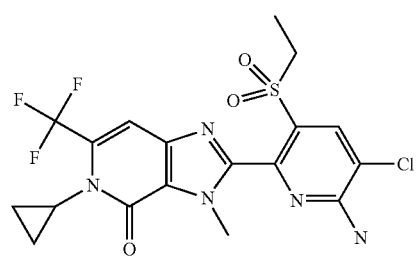 [SMILES: CCS(=O)(=O)c1cc(Cl)c(N)nc1-c1nc2cc(C(F)(F)F)n(C3CC3)c(=O)c2n1C] | 2-(6-amino-5-chloro-3-ethylsulfonyl-2-pyridyl)-5-cyclopropyl-3-methyl-6-(trifluoromethyl)imidazo[4,5-c]pyridin-4-one was synthesised as described example P38: LC-MS (Method A): RT 0.93, 476 (M + H$^+$), 474 (M − H$^+$). |
| A44 | 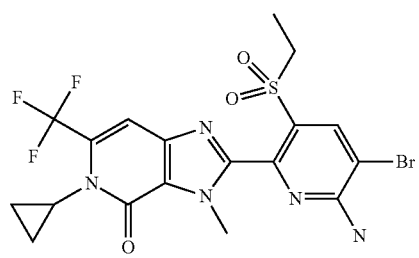 [SMILES: CCS(=O)(=O)c1cc(Br)c(N)nc1-c1nc2cc(C(F)(F)F)n(C3CC3)c(=O)c2n1C] | 2-(6-amino-5-bromo-3-ethylsulfonyl-2-pyridyl)-5-cyclopropyl-3-methyl-6-(trifluoromethyl)imidazo[4,5-c]pyridin-4-one was synthesised as described in example P39: LC-MS (Method A): RT 0.95, 522 (M + H$^+$), 520 (M − H$^+$). |
| A45 | 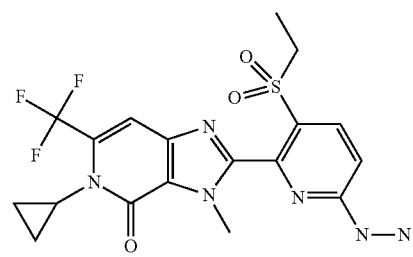 [SMILES: CCS(=O)(=O)c1ccc(NN)nc1-c1nc2cc(C(F)(F)F)n(C3CC3)c(=O)c2n1C] | See experimental part above |

TABLE P1-continued

Examples of compounds of formula (I)

| Compound No. | Structures | Analytic Method |
|---|---|---|
| A46 | 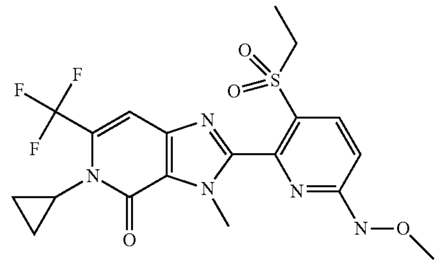 [SMILES: CCS(=O)(=O)c1ccc(NOC)nc1-c1nc2cc(C(F)(F)F)n(C3CC3)c(=O)c2n1C] | See experimental part above |
| A47 | 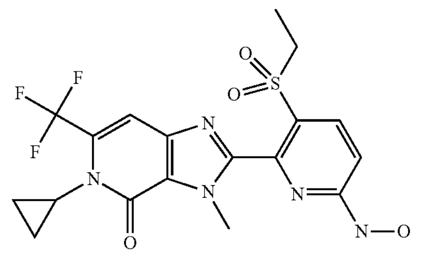 [SMILES: CCS(=O)(=O)c1ccc(NO)nc1-c1nc2cc(C(F)(F)F)n(C3CC3)c(=O)c2n1C] | See experimental part above |
| A48 | 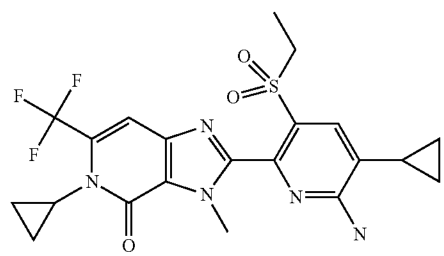 [SMILES: CCS(=O)(=O)c1cc(C2CC2)c(N)nc1-c1nc2cc(C(F)(F)F)n(C3CC3)c(=O)c2n1C] | See experimental part above |
| A49 | 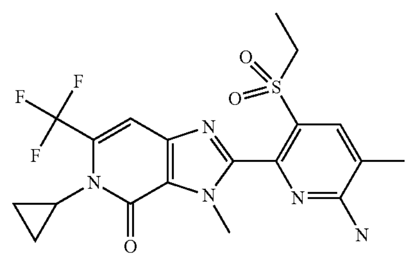 [SMILES: CCS(=O)(=O)c1cc(C)c(N)nc1-c1nc2cc(C(F)(F)F)n(C3CC3)c(=O)c2n1C] | See experimental part above |
| A50 | 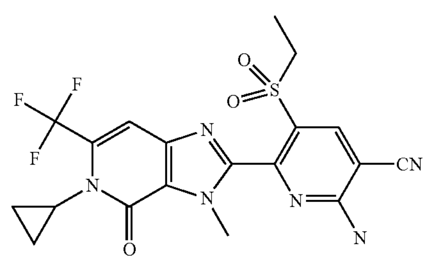 [SMILES: CCS(=O)(=O)c1cc(C#N)c(N)nc1-c1nc2cc(C(F)(F)F)n(C3CC3)c(=O)c2n1C] | See experimental part above |
| A51 | 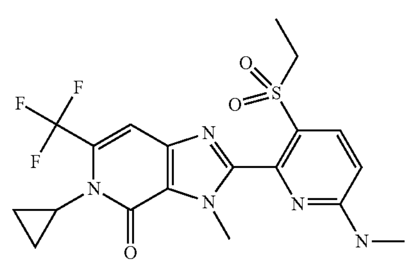 [SMILES: CCS(=O)(=O)c1ccc(NC)nc1-c1nc2cc(C(F)(F)F)n(C3CC3)c(=O)c2n1C] | See experimental part above |

TABLE P1-continued

Examples of compounds of formula (I)

| Compound No. | Structures | Analytic Method |
|---|---|---|
| A52 | 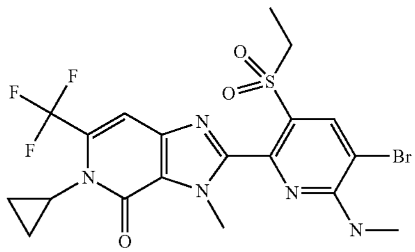 [SMILES: CCS(=O)(=O)c1cc(Br)c(NC)nc1-c1nc2cc(C(F)(F)F)n(C3CC3)c(=O)c2n1C] | 2-[5-bromo-3-ethylsulfonyl-6-(methylamino)-2-pyridyl]-5-cyclopropyl-3-methyl-6-(trifluoromethyl)imidazo[4,5-c]pyridin-4-one was synthesised as described in example P39: LC-MS (Method A): RT 1.05, 536 (M + H⁺), 534 (M − H⁺). |
| A53 | 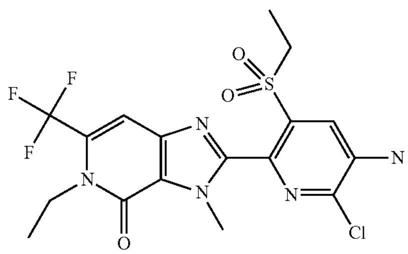 [SMILES: CCn1c(C(F)(F)F)cc2nc(-c3nc(Cl)c(N)cc3S(=O)(=O)CC)n(C)c2c1=O] | 2-(5-amino-6-chloro-3-ethylsulfonyl-2-pyridyl)-5-ethyl-3-methyl-6-(trifluoromethyl)imidazo[4,5-c]pyridin-4-onewas synthesised as described in example P38: $^1$H NMR (400 MHz, CDCl$_3$) δ 7.74 (s, 1H), 7.19 (s, 1H), 4.77 (s, 2H), 4.24 (q, 2H), 4.07 (s, 3H), 3.74 (q, 2H), 1.36 (m, 6H). |
| A54 | 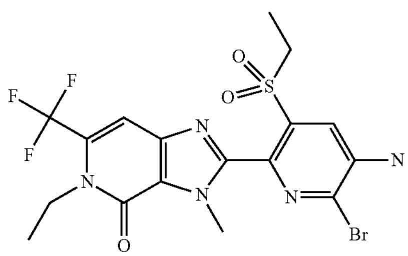 [SMILES: CCn1c(C(F)(F)F)cc2nc(-c3nc(Br)c(N)cc3S(=O)(=O)CC)n(C)c2c1=O] | 2-(5-amino-6-bromo-3-ethylsulfonyl-2-pyridyl)-5-ethyl-3-methyl-6-(trifluoromethyl)imidazo[4,5-c]pyridin-4-onewas synthesised as described in example P39: $^1$H NMR (400 MHz, CDCl$_3$) δ 7.68 (s, 1H), 7.19 (s, 1H), 4.82 (s, 2H), 4.24 (q, 2H), 4.07 (s, 3H), 3.74 (q, 2H), 1.36 (m, 6H). |
| A55 | 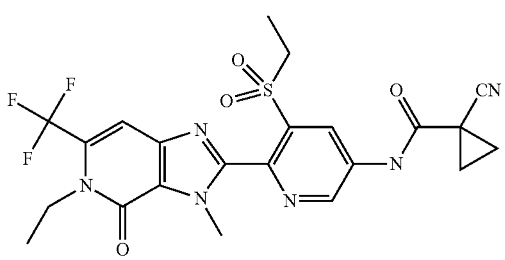 [SMILES: CCn1c(C(F)(F)F)cc2nc(-c3ncc(NC(=O)C4(C#N)CC4)cc3S(=O)(=O)CC)n(C)c2c1=O] | See experimental part above |
| A56 | 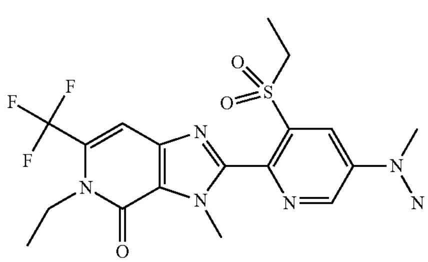 [SMILES: CCn1c(C(F)(F)F)cc2nc(-c3ncc(N(C)N)cc3S(=O)(=O)CC)n(C)c2c1=O] | See experimental part above |
| A57 | 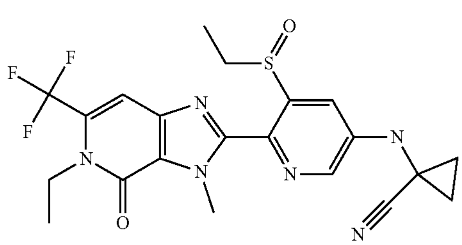 [SMILES: CCn1c(C(F)(F)F)cc2nc(-c3ncc(NC4(C#N)CC4)cc3S(=O)CC)n(C)c2c1=O] | See experimental part above |

TABLE P1-continued
Examples of compounds of formula (I)
| Compound No. | Structures | Analytic Method |
|---|---|---|
| A58 | 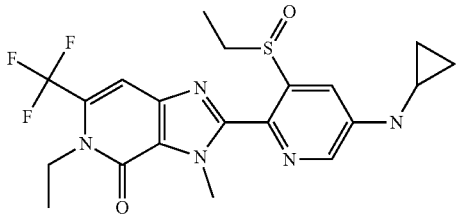 [SMILES: CCn1c(C(F)(F)F)cc2nc(-c3ncc(NC4CC4)cc3S(=O)CC)n(C)c2c1=O] | See experimental part above |
| A59 | 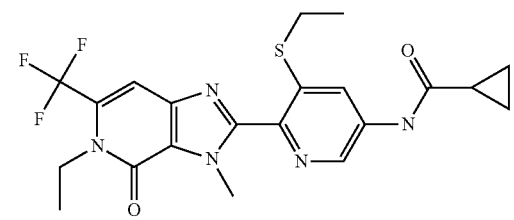 [SMILES: CCSc1cc(NC(=O)C2CC2)cnc1-c1nc2cc(C(F)(F)F)n(CC)c(=O)c2n1C] | See experimental part above |
| A60 | 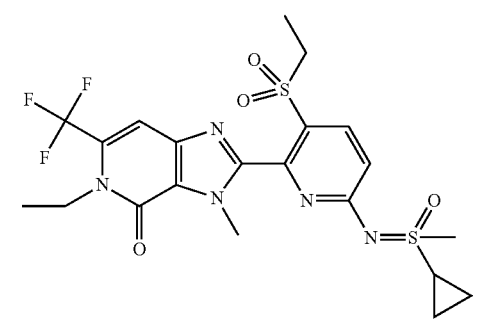 [SMILES: CCn1c(C(F)(F)F)cc2nc(-c3nc(N=S(C)(=O)C4CC4)ccc3S(=O)(=O)CC)n(C)c2c1=O] | See experimental part above |
| A61 | 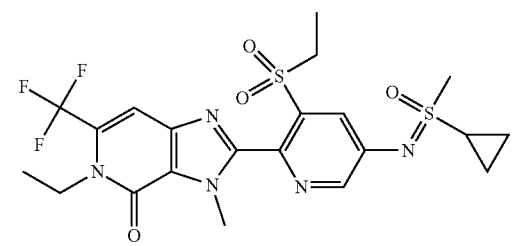 [SMILES: CCn1c(C(F)(F)F)cc2nc(-c3ncc(N=S(C)(=O)C4CC4)cc3S(=O)(=O)CC)n(C)c2c1=O] | See experimental part above |
| A62 | 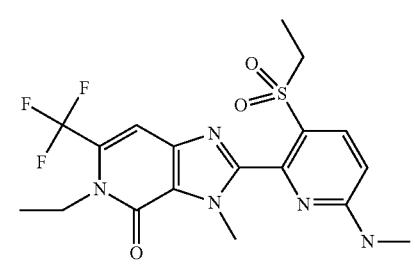 [SMILES: CCn1c(C(F)(F)F)cc2nc(-c3nc(NC)ccc3S(=O)(=O)CC)n(C)c2c1=O] | See experimental part above |
| A63 | 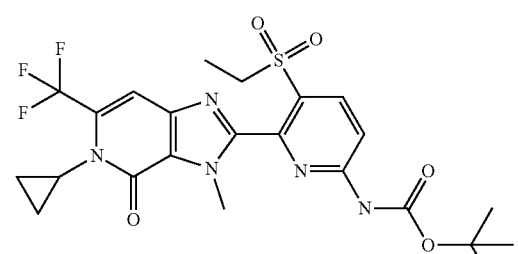 | See experimental part above |

TABLE P1-continued

Examples of compounds of formula (I)

| Compound No. | Structures | Analytic Method |
|---|---|---|
| A64 | 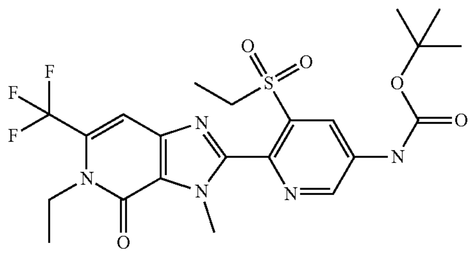 [SMILES: CCn1c(C(F)(F)F)cc2nc(-c3ncc(NC(=O)OC(C)(C)C)cc3S(=O)(=O)CC)n(C)c2c1=O] | See experimental part above |
| A65 | 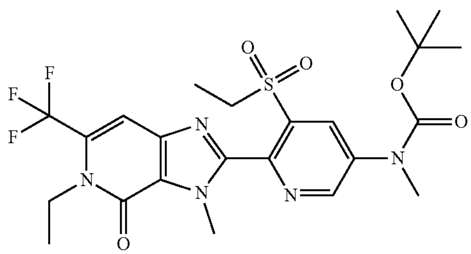 [SMILES: CCn1c(C(F)(F)F)cc2nc(-c3ncc(N(C)C(=O)OC(C)(C)C)cc3S(=O)(=O)CC)n(C)c2c1=O] | See experimental part above |
| A66 | 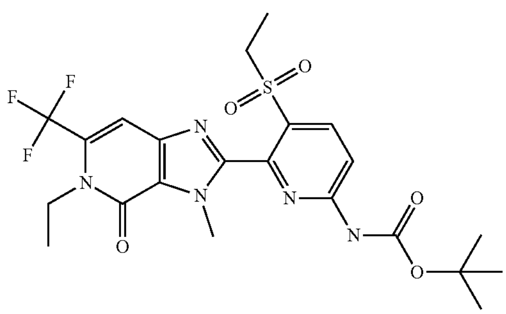 [SMILES: CCn1c(C(F)(F)F)cc2nc(-c3nc(NC(=O)OC(C)(C)C)ccc3S(=O)(=O)CC)n(C)c2c1=O] | See experimental part above |
| A67 | 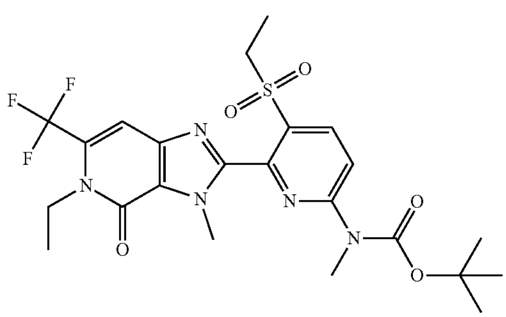 [SMILES: CCn1c(C(F)(F)F)cc2nc(-c3nc(N(C)C(=O)OC(C)(C)C)ccc3S(=O)(=O)CC)n(C)c2c1=O] | See experimental part above |
| A68 | 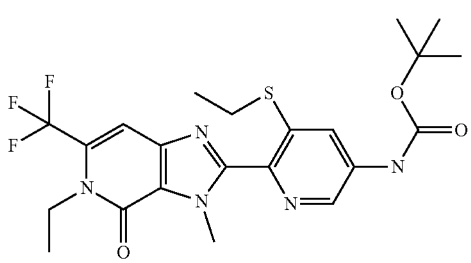 [SMILES: CCSc1cc(NC(=O)OC(C)(C)C)cnc1-c1nc2cc(C(F)(F)F)n(CC)c(=O)c2n1C] | A68 was prepared by analogy with Example P9, step A: $^1$H NMR (400 MHz, CDCl$_3$) δ ppm 1.36 (m, 6H), 1.56 (s, 9 H), 2.98 (q, 2 H), 4.17 (s, 3 H), 4.25 (q, 2 H), 6.80 (s, 1 H), 7.33 (s, 1 H), 8.20 (br. s., 1 H), 8.25 (br. s., 1 H). |

TABLE P1-continued

Examples of compounds of formula (I)

| Compound No. | Structures | Analytic Method |
|---|---|---|
| A69 | 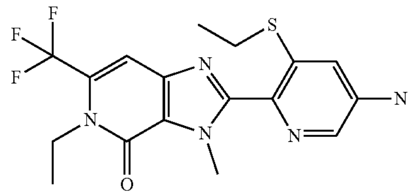 [SMILES: CCSc1cc(N)cnc1-c1nc2cc(C(F)(F)F)n(CC)c(=O)c2n1C] | A69 was prepared by deprotecting A68 using the same protocol that described in step C example P9: $^1$H NMR (400 MHz, CDCl$_3$) δ 7.95 (s, 1H), 7.31 (s, 1H), 6.98 (s, 1H), 4.24 (q, 2H), 4.15 (s, 3H), 2.88 (q, 2H), 1.38 (t, 3H), 1.31 (t, 3H) |
| A70 | 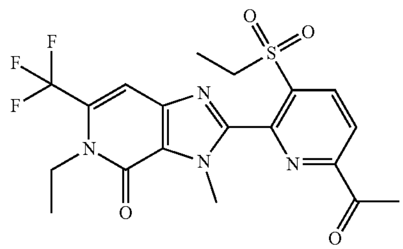 [SMILES: CCn1c(C(F)(F)F)cc2nc(-c3nc(C(C)=O)ccc3S(=O)(=O)CC)n(C)c2c1=O] | See experimental part above |
| A71 | 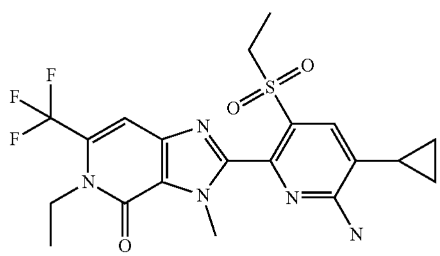 [SMILES: CCn1c(C(F)(F)F)cc2nc(-c3nc(N)c(C4CC4)cc3S(=O)(=O)CC)n(C)c2c1=O] | A71 was prepared using similar protocoles that A48/A50,: $^1$H NMR (400 MHz, CDCl$_3$) δ 0.75 (m, 2 H), 1.08 (m, 2 H), 1.27 (m, 3 H), 1.38 (m, 3 H), 1.70 (m, 1 H), 3.50 (m, 2 H), 4.03 (s, 3 H), 4.23 (m, 2 H), 5.41 (s, 2 H), 7.19 (s, 1 H), 7.90 (s, 1 H). |
| A72 | 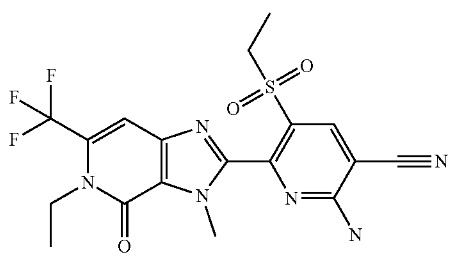 [SMILES: CCn1c(C(F)(F)F)cc2nc(-c3nc(N)c(C#N)cc3S(=O)(=O)CC)n(C)c2c1=O] | A72 was prepared using similar protocoles that A48/A50: $^1$H NMR (400 MHz, CDCl$_3$) δ 1.33-1.43 (m, 6 H), 3.65 (m, 2 H), 4.09 (s, 3 H), 4.23 (m, 2 H), 5.89 (s, 2 H), 7.20 (s, 1 H), 8.46 (s, 1 H). |
| A73 | 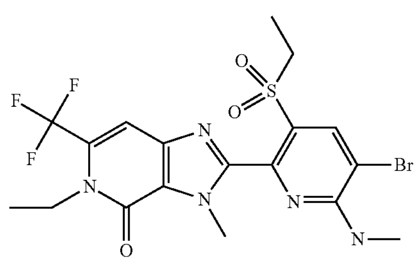 [SMILES: CCn1c(C(F)(F)F)cc2nc(-c3nc(NC)c(Br)cc3S(=O)(=O)CC)n(C)c2c1=O] | A73 was prepared using similar protocoles that A52: $^1$H NMR (400 MHz, CDCl$_3$) δ 1.33 (t, 3 H), 1.40 (m, 3 H), 3.08 (m, 3 H), 3.60-3.67 (m, 2 H), 4.09 (s, 3 H), 4.21-4.27 (m, 2 H), 5.76-5.80 (m, 1 H), 7.21-7.23 (m, 1 H), 8.19-8.32 (m, 1 H). |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 42 and P1 of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fen-pyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure $B_1$ (839)+TX, trimedlure $B_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexane-diol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, Bacillus thuringiensis delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin 1 (696)+TX, cinerin 11 (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin [CCN]+TX, jasmolin 1 (696)+TX, jasmolin 11 (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebucon-azole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoximmethyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphtalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a, 12b-trimethyl-11-oxo-9-(3-pyridinyl)-2H, 11H naphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX; lancotrione [1486617-21-3], florpyrauxifen [943832-81-3], ipfentrifluconazole[1417782-08-1], mefentrifluconazole [1417782-03-6], quinofumelin [861647-84-9], chloroprallethrin [399572-87-3], cyhalodiamide [1262605-53-7], fluazaindolizine [1254304-22-7], fluxametamide [928783-29-3], epsilon-metofluthrin [240494-71-7], epsilon-momfluorothrin [1065124-65-3], pydiflumetofen [1228284-64-7], kappa-bifenthrin [439680-76-9], broflanilide [1207727-04-5], dicloromezotiaz [1263629-39-5], dipymetitrone [16114-35-5], pyraziflumid [942515-63-1] and kappa-tefluthrin [391634-71-2]; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullu-* lans+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, Meloncont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium*

*periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden Insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove peppermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M Oriental Fruit Moth Sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX, Z+TX, Z)-3+TX, 8+TX, 11 Tetradecatrienyl acetate+TX, (Z+TX, Z+TX, E)-7+TX, 11+TX, 13-Hexadecatrienal+TX, (E+TX, Z)-7+TX, 9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (*Aphelinus*-System®)+TX, *Acerophagus papaya*+TX, *Adalia bipunctata* (*Adalia*-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline *cucumeris*®)+TX, *Amblyseius fallacis* (Fallacis®)+TX, *Amblyseius swirskii* (Bugline *swirskii*®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (*Encarsia* Max®+TX, Encarline®+TX, En-Strip®)+TX, *Eretmocerus eremicus* (Enermix®)+

TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, Exhibitline sf®+TX, Scia-rid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator* and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright® 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used. "CAS Reg. No" means the Chemical Abstracts Registry Number.

The active ingredient mixture of the compounds of formula I selected from Tables 1 to 42 with active ingredients described above comprises a compound selected from Tables 1 to 42 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 42 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 42 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1: *Bemisia tabaci* (Cotton White Fly): Feeding/Contact Activity

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation.

The following compounds resulted in at least 80% mortality at an application rate of 200 ppm:

A6, A7, A8, A9, A10, A12, A18, A20, A30, A31, A37, A38, A39, A40, A42, A43, A44, A47, A48, A49, A51, A52, A63, A64, A66 and A71.

Example B2: *Diabrotica balteata* (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:
A1, A2, A5, A6, A8, A10, A11, A12, A24, A26, A30, A31, A32, A33, A34, A37, A38, A39, A40, A41, A42, A43, A44, A45, A46, A47, A48, A49, A50, A51, A52, A53, A54, A56, A57, A58, A59, A63, A66 and A71.

Example B3: *Euschistus heros*(Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation.
The following compounds gave an effect of at least 80% in at least one of the two categories (mortality or growth inhibition) at an application rate of 200 ppm:
A1, A2, A6, A7, A8, A9, A10, A11, A12, A13, A17, A19, A20, A22, A24, A25, A26, A28, A30, A31, A37, A38, A39, A40, A41, A42, A43, A44, A46, A47, A48, A50, A51, A52, A56, A64, A71 and A72.

Example B4: *Frankliniella occidentalis* (Western Flower *Thrips*):Feeding/Contact Activity Sunflower leaf discs were placed on agar in 24-well microtiter plates and sprayed with aqueous test solutions prepared from 10,000 DMSO stock solutions. After drying the leaf discs were infested with a *Frankliniella* population of mixed ages. The samples were assessed for mortality 7 days after infestation.
The following compounds resulted in at least 80% mortality at an application rate of 200 ppm:
A1, A8, A10, A11, A43, A48 and, A50.

Example B5: *Myzus persicae* (Green Peach Aphid):Feeding/Contact Activity

Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.
The following compounds resulted in at least 80% mortality at an application rate of 200 ppm:
A1, A2, A5, A6, A7, A8, A9, A10, A11, A12, A13, A18, A20, A28, A30, A36, A38, A39, A40, A41, A42, A43, A44, A45, A47, A48, A49, A50, A51, A52, A53, A55, A56, A59 and A71.

Example B6: *Myzus persicae* (Green Peach Aphid). Systemic Activity

Roots of pea seedlings infested with an aphid population of mixed ages were placed directly into aqueous test solutions prepared from 10,000 DMSO stock solutions. The samples were assessed for mortality 6 days after placing seedlings into test solutions.
The following compounds resulted in at least 80% mortality at a test rate of 24 ppm:
A2, A6, A7, A9, A10, A17, A18, A19, A20, A22, A28, A30, A42, A43, A45, A47, A48, A49, A50, A51, A55, A71 and A72.

Example B7: *Myzus persicae* (Green Peach Aphid). Intrinsic Activity

Test compounds prepared from 10,000 ppm DMSO stock solutions were applied by pipette into 24-well microtiter plates and mixed with sucrose solution. The plates were closed with a stretched Parafilm. A plastic stencil with 24 holes was placed onto the plate and infested pea seedlings were placed directly on the Parafilm. The infested plate was closed with a gel blotting paper and another plastic stencil and then turned upside down. The samples were assessed for mortality 5 days after infestation.
The following compound resulted in at least 80% mortality at a test rate of 12 ppm:
A59

Example B8: *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.
The following compounds gave an effect of at least 80% in at least one of the two categories (mortality or growth inhibition) at an application rate of 200 ppm:
A1, A2, A5, A6, A7, A8, A9, A10, A11, A12, A13, A17, A18, A19, A20, A22, A24, A26, A27, A28, A30, A31, A32, A33, A34, A37, A38, A39, A40, A41, A42, A43, A44, A45, A46, A47, A48, A49, A50, A51, A52, A53, A54, A55, A56, A57, A59, A63, A64, A66, A70, A71 and A72.

Example B9: *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.
The following compounds resulted in at least 80% control at an application rate of 200 ppm:
A1, A2, A5, A6, A7, A8, A9, A10, A11, A12, A13, A18, A20, A22, A24, A25, A26, A27, A30, A31, A32, A33, A34, A37, A38, A39, A40, A41, A42, A43, A44, A45, A46, A47, A48, A49, A50, A51, A52, A53, A54, A55, A56, A57, A59, A63, A64, A66, A71 and A72.

Example B10: *Spodoptera littoralis* (Egyptian Cotton Leaf Worm)

Test compounds were applied by pipette from 10,000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm:
A2, A6, A8, A9, A10, A11, A20, A26, A31, A38, A39, A40, A41, A42, A43, A44, A45, A50, A51, A52, A53, A56 and A66.

Example B11: *Tetranychus urticae* (Two-Spotted Spider Mite):Feeding/Contact Activity Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:
A1, A2, A4, A1, A13, A19, A24, A30, A32, A34, A42, A48, A64, A66 and A71.

Example B12: *Thrips tabaci* (Onion *Thrips*) Feeding/Contact Activity

Sunflower leaf discs were placed on agar in 24-well microtiter plates and sprayed with aqueous test solutions prepared from 10,000 ppm DMSO stock solutions. After drying the leaf discs were infested with a *thrips* population of mixed ages. The samples were assessed for mortality 6 days after infestation.

The following compounds resulted in at least 80% mortality at an application rate of 200 ppm:
A44 and A52.

Example B13: *Aedes Aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Aedes aegypti* after 48 h and/or 24 h:
A1, A2, A5, A6, A11, A12, A30, A38 and A39.

Example B14: *Anopheles stephensi* (Indian Malaria Mosquito)

Test solutions, at an application rate of 200 ppm in ethanol, were applied to 12 well tissue culture plates. Once the deposits were dry, five, two to five day old adult female *Anopheles stephensi* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Anopheles stephensi* after 48 h and/or 24 h:
A2 and A30.

The invention claimed is:
1. A compound of formula I

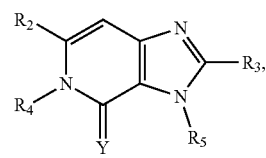

wherein
Y is O or S;
$R_2$ is hydrogen, halogen, $C_1$-$C_6$haloalkyl or $C_1$-$C_6$alkyl; or
$R_2$ is $C_1$-$C_6$haloalkylsulfanyl, $C_1$-$C_6$haloalkylsulfinyl, $C_1$-$C_6$haloalkylsulfonyl, $C_1$-$C_6$alkylsulfanyl, $C_1$-$C_6$alkylsulfinyl, $C_1$-$C_6$alkylsulfonyl, $C_1$-$C_6$alkoxy, $C_1$-$C_6$haloalkoxy, $C_1$-$C_4$haloalkoxy$C_1$-$C_4$alkyl, $C_1$-$C_4$alkoxy$C_1$-$C_4$alkyl, $SF_5$, cyano, $C_3$-$C_6$cycloalkyl$C_1$-$C_4$alkyl or —C(O)$C_1$-$C_6$haloalkyl; or
$R_2$ is $C_3$-$C_6$cycloalkyl which can be mono- or polysubstituted by substituents selected from $R_6$;
$R_4$ is hydrogen, $C_1$-$C_6$alkyl, $C_1$-$C_6$haloalkyl, or is $C_3$-$C_6$cycloalkyl which can be mono- or poly-substituted by $R_{20}$; or is $C_3$-$C_6$cycloalkyl-$C_1$-$C_4$alkyl which can be mono- or polysubstituted by $R_{20}$; or
$R_4$ is $C_1$-$C_4$alkyl substituted by $R_7$; or
$R_4$ is $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_4$alkoxy $C_1$-$C_4$alkyl, $C_1$-$C_6$alkylsulfanyl, $C_1$-$C_4$alkylsulfonyl, $C_1$-$C_6$alkylsulfinyl, $C_1$-$C_6$haloalkylsulfanyl, $C_1$-$C_6$haloalkylsulfonyl, $C_1$-$C_6$haloalkylsulfinyl, amine or hydroxyl; or
$R_4$ is $C_2$-$C_6$alkenyl substituted by $R_7$, or is $C_2$-$C_6$alkynyl substituted by $R_7$;
$R_5$ is hydrogen, $C_1$-$C_6$alkyl, $C_1$-$C_6$haloalkyl or $C_1$-$C_4$alkyl substituted by $C_1$-$C_4$alkylsulfanyl;
$R_6$ and $R_{20}$, independently from each other, are selected from the group consisting of cyano, halogen, $C_1$-$C_6$alkyl and $C_1$-$C_4$haloalkyl;
$R_7$ is cyano, halogen, $C_1$-$C_4$alkylsulfanyl, $C_1$-$C_4$alkylsulfonyl, $C_1$-$C_4$alkylsulfinyl, $C_1$-$C_4$alkoxy, $C_1$-$C_4$alkoxy$C_1$-$C_4$ alkoxy or phenyl which itself can be mono- or polysubstituted by substituents selected from $R_8$;
$R_8$ is halogen, cyano, $C_1$-$C_4$alkyl, $C_1$-$C_4$haloalkyl or $C_1$-$C_4$alkoxy;
$R_3$ is a radical selected from the group consisting of formula $Q_1$, $Q_2$, $Q_3$, $Q_4$, $Q_5$, $Q_6$, $Q_7$, $Q_8$, $Q_9$, $Q_{10}$, $Q_{11}$, $Q_{12}$, $Q_{13}$ and $Q_{14}$;

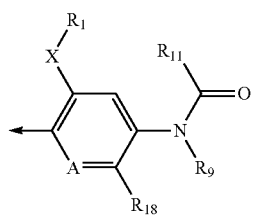

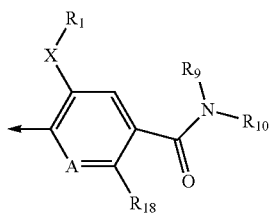
Q2
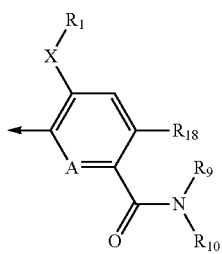
Q3
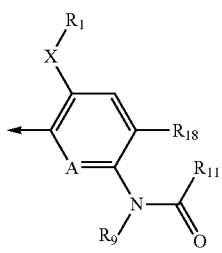
Q4
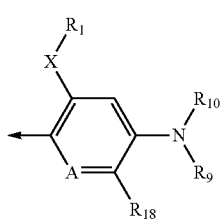
Q5
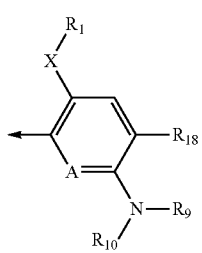
Q6
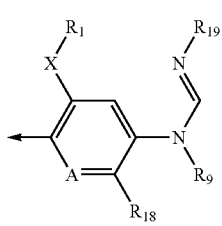
Q7
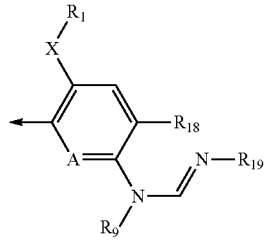
Q8
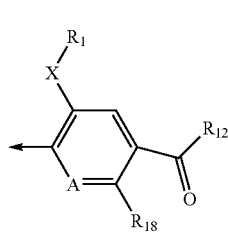
Q9
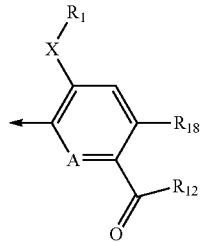
Q10
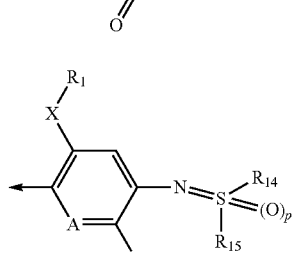
Q11
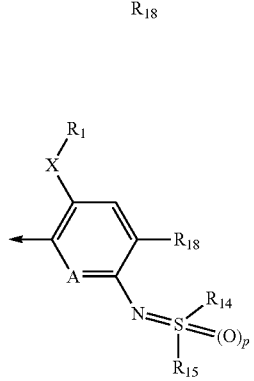
Q12
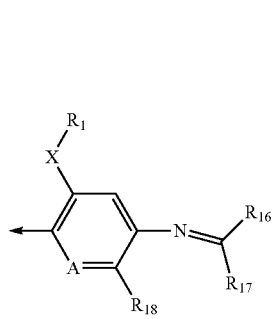
Q13

-continued

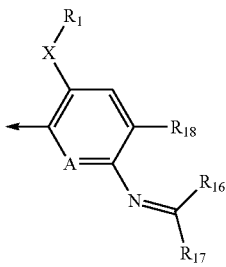

Q14 wherein the arrow denotes the point of attachment to the imidazole ring;
A represents CH or N;
X is S, SO or $SO_2$;
$R_1$ is $C_1$-$C_4$alkyl or $C_1$-$C_4$haloalkyl; or
$R_1$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or
$R_1$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;
$R_9$ is hydrogen, $C_1$-$C_6$alkyl, $C_1$-$C_6$haloalkyl, $C_1$-$C_4$alkoxy$C_1$-$C_4$alkyl, hydroxyl, $C_1$-$C_6$alkoxy or $S(O)m_1R_{21}$; or
$R_9$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or
$R_9$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl; or
$R_9$ is $C_3$-$C_6$ cycloalkylcarbonyl;
$R_{10}$ is hydrogen, $C_1$-$C_6$alkyl, cyano, $C_1$-$C_6$alkoxy, $C_1$-$C_6$haloalkoxy, $C_2$-$C_6$alkynyl, $C_2$-$C_6$alkenyl, amino, NH—CN, N—($C_1$-$C_4$alkyl)amino, N—($C_1$-$C_4$ alkyl)N—($C_1$-$C_4$ alkyl)amino, N—($C_3$-$C_6$cycloalkyl)amino, N—($C_1$-$C_4$alkyl)N—($C_3$-$C_6$cycloalkyl)amino, N—($C_1$-$C_4$alkylcarbonyl)amino, N—($C_1$-$C_4$alkyl)N—($C_1$-$C_4$alkylcarbonyl)amino, N—($C_1$-$C_4$alkyl)N—($C_3$-$C_6$cycloalkylcarbonyl)amino, N—($C_3$-$C_6$cycloalkylcarbonyl)amino, N—($C_1$-$C_4$alkylcarbonyl)N—($C_3$-$C_6$cycloalkyl)amino or —$S(O)mR_{13}$; or
$R_{10}$ is $C_1$-$C_4$alkyl mono- or polysubstituted by substituents independently selected from the group Z; or
$R_{10}$ is a five- to six-membered aromatic or heteroaromatic ring system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five- to six-membered ring system can be mono- or polysubstituted by substituents independently selected from the group V;
$R_{11}$ is hydrogen, $C_1$-$C_6$alkyl, $C_1$-$C_6$alkoxy, $C_1$-$C_6$haloalkoxy, amino, N—$C_1$-$C_4$alkylamino, N—($C_1$-$C_4$ alkyl)N—($C_3$-$C_6$ cycloalkyl)amino, N—($C_3$-$C_6$cycloalkyl)amino or N—($C_1$-$C_4$alkyl)N—($C_1$-$C_4$alkyl)amino; or
$R_{11}$ is $C_1$-$C_4$alkyl mono- or polysubstituted by substituents independently selected from the group Z; or
$R_{11}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or
$R_{11}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl; or
$R_{11}$ is a five- to six-membered aromatic or heteroaromatic ring system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five- to six-membered aromatic or heteroaromatic ring system can be mono- or polysubstituted by substituents independently selected from the group V;
$R_{12}$ is hydrogen, $C_1$-$C_6$ alkyl, $C_1$-$C_6$alkoxy, hydroxy or $C_1$-$C_6$haloalkoxy; or
$R_{12}$ is $C_1$-$C_4$alkyl mono- or polysubstituted by substituents independently selected from the group Z; or
$R_{12}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or
$R_{12}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;
$R_{13}$ is $C_1$-$C_4$alkyl, $C_1$-$C_4$haloalkyl, N—$C_1$-$C_4$alkylamino, N,N—($C_1$-$C_4$ alkyl)$_2$amino or phenyl; said phenyl can be mono- or polysubstituted by substituents selected from the group consisting of halogen, $C_1$-$C_4$alkyl, cyano, $C_1$-$C_4$haloalkyl and $C_1$-$C_4$alkoxy; or
$R_{13}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or
$R_{13}$ is $C_3$-$C_6$cycloalkyl$C_1$-$C_4$alkyl which can be mono- or polysubstituted by substituents selected from the group consisting of halogen, $C_1$-$C_4$haloalkyl, cyano and $C_1$-$C_4$alkyl;
$R_{21}$ is $C_1$-$C_4$alkyl, $C_1$-$C_4$haloalkyl, N—$C_1$-$C_4$alkylamino, N,N—($C_1$-$C_4$ alkyl)$_2$amino or phenyl; said phenyl can be mono- or polysubstituted by substituents selected from the group consisting of halogen, $C_1$-$C_4$alkyl, cyano, $C_1$-$C_4$haloalkyl and $C_1$-$C_4$alkoxy; or
$R_{21}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or
$R_{21}$ is $C_3$-$C_6$cycloalkyl$C_1$-$C_4$alkyl which can be mono- or polysubstituted by substituents selected from the group consisting of halogen, $C_1$-$C_4$haloalkyl, cyano and $C_1$-$C_4$alkyl;
m is 0, 1 or 2;
$m_1$ is 0, 1 or 2;
$R_{14}$ is hydrogen or $C_1$-$C_6$ alkyl;
$R_{15}$ is hydrogen, $C_1$-$C_6$ alkyl, $C_1$-$C_6$alkoxy, $C_1$-$C_6$haloalkoxy, amino, N—$C_1$-$C_4$alkylamino or N,N—($C_1$-$C_4$ alkyl)$_2$amino; or
$R_{15}$ is $C_1$-$C_4$alkyl mono- or polysubstituted by substituents independently selected from the group Z; or $R_{15}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{15}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl;

p is 0 or 1;

$R_{16}$ is hydrogen or $C_1$-$C_6$ alkyl;

$R_{17}$ is hydrogen, $C_1$-$C_6$alkyl, $C_1$-$C_6$haloalkyl, $C_1$-$C_6$alkoxy or $C_1$-$C_6$ haloalkoxy; or $R_{17}$ is amino which can be mono- or disubstituted by substituents selected from the group consisting of cyano, $C_1$-$C_6$alkyl, $C_1$-$C_6$alkoxy, $C_1$-$C_6$haloalkoxy, $C_3$-$C_6$cycloalkyl and $C_3$-$C_6$cycloalkyl-$C_1$-$C_4$alkyl, said $C_3$-$C_6$cycloalkyl and $C_3$-$C_6$cycloalkyl-$C_1$-$C_4$alkyl groups itself can be mono- or polysubstituted by substituents selected from the group consisting of halogen, $C_1$-$C_4$haloalkyl, cyano and $C_1$-$C_4$alkyl; or $R_{17}$ is $C_1$-$C_4$alkyl mono- or polysubstituted by substituents independently selected from Z; or $R_{17}$ is $C_3$-$C_6$cycloalkyl which can be mono- or polysubstituted by substituents selected from the group consisting of halogen, $C_1$-$C_4$haloalkyl, cyano and $C_1$-$C_4$alkyl; or $R_{17}$ is $C_3$-$C_6$cycloalkyl-$C_1$-$C_4$alkyl which can be mono- or polysubstituted by substituents selected from the group consisting of halogen, $C_1$-$C_4$haloalkyl, cyano and $C_1$-$C_4$alkyl; or $R_{17}$ is a five- to six-membered ring aromatic or heteroaromatic ring system, said aromatic or heteroaromatic ring system can contain 1 to 4 hetero atoms selected from the group consisting of nitrogen, oxygen and sulfur, with the proviso that each ring system cannot contain more than 2 oxygen atoms and more than 2 sulfur atoms, said five- to six-membered aromatic or heteroaromatic ring system can be mono- to polysubstituted by substituents independently selected from V;

$R_{18}$ is hydrogen, halogen, amino, cyano, $C_1$-$C_4$alkyl, $C_3$-$C_6$cycloalkyl, $C_1$-$C_4$haloalkyl or $C_3$-$C_6$cycloalkyl substituted by cyano, $C_1$-$C_3$ haloalkyl, $C_1$-$C_3$ alkyl and halogen;

$R_{19}$ is hydrogen, $C_1$-$C_6$alkyl, $C_1$-$C_6$alkoxy, $C_1$-$C_6$haloalkoxy, $C_3$-$C_6$cycloalkyl$C_1$-$C_4$alkyl, $C_3$-$C_6$cycloalkyl;

Z is cyano, halogen, hydroxy, —SH, amino, nitro, $C_1$-$C_4$alkoxy, $C_1$-$C_4$haloalkoxy, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl or phenyl; said phenyl can be mono- or polysubstituted by substituents selected from the group consisting of halogen, $C_1$-$C_4$alkylsulfanyl, $C_1$-$C_4$haloalkylsulfanyl, $C_1$-$C_4$ alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; or Z is pyridyl; said pyridyl can be mono- or polysubstituted by substituents selected from the group consisting of halogen, $C_1$-$C_4$ alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; or Z is pyrimidyl; said pyrimidyl can be mono- or polysubstituted by substituents selected from the group consisting of halogen, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl, $C_1$-$C_4$haloalkylsulfonyl, cyano, $C_1$-$C_4$haloalkyl and $C_1$-$C_4$alkyl; and V is cyano, halogen, $C_1$-$C_4$alkyl, $C_3$-$C_6$ cycloalkyl, $C_1$-$C_4$alkoxy, $C_1$-$C_4$alkoxy$C_1$-$C_4$ alkyl, $C_1$-$C_4$haloalkyl, $C_1$-$C_4$haloalkoxy, $C_1$-$C_4$alkylsulfanyl, $C_1$-$C_4$haloalkylsulfanyl, $C_1$-$C_4$alkylsulfinyl, $C_1$-$C_4$haloalkylsulfinyl, $C_1$-$C_4$alkylsulfonyl or $C_1$-$C_4$haloalkylsulfonyl; and agrochemically acceptable salts, stereoismers, enantiomers, tautomers and N-oxides of the compounds of formula I.

2. A compound of formula I according to claim 1,
wherein Y is O;
X is S, SO or $SO_2$; and
$R_1$ is methyl, ethyl, n-propyl, i-propyl or cyclopropylmethyl.

3. A compound of formula I according to claim 2, wherein $R_4$ is methyl, ethyl, cyclopropyl.

4. A compound of formula I according to claim 2, wherein $R_5$ is methyl.

5. A compound of formula I according to claim 2, wherein A is N;
X is S or $SO_2$;
and $R_1$ is ethyl.

6. A compound of formula I according to claim 2, wherein $R_3$ is selected from the group Q consisting of $Q_1$ to $Q_6$

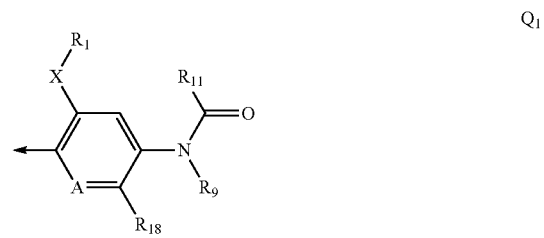

$Q_1$

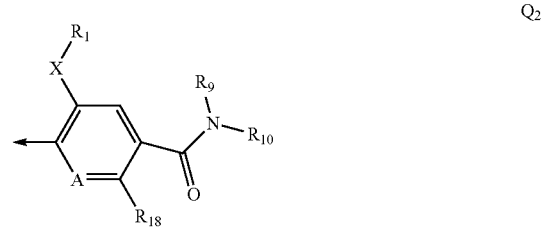

$Q_2$

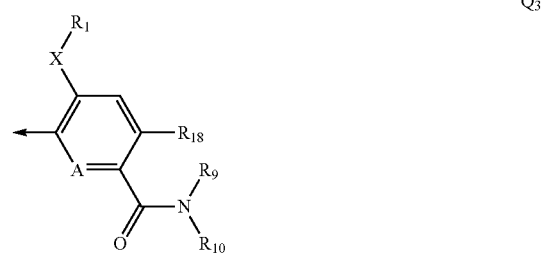

$Q_3$

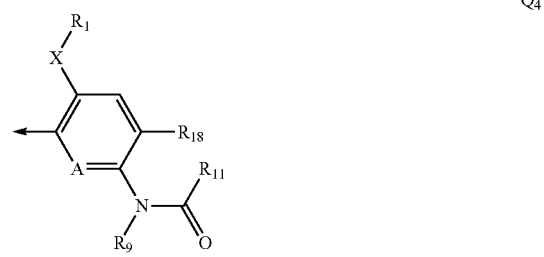

$Q_4$

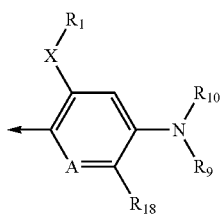

Q5

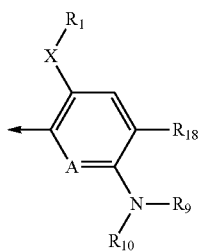

Q6 wherein $R_{18}$ is hydrogen;

X is S, SO or $SO_2$; and $R_1$ is methyl, ethyl, n-propyl, i-propyl or cyclopropylmethyl.

7. A compound of formula I according to claim 2, wherein $R_2$ is $C_1$-$C_4$ haloalkyl;

$R_4$ is $C_1$-$C_4$ alkyl or $C_3$-$C_6$ cycloalkyl;

$R_5$ is $C_1$-$C_4$ alkyl;

$R_3$ is selected from the group consisting of $Q_1$ to $Q_6$

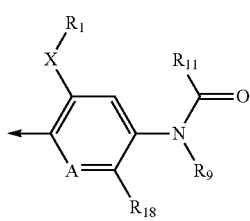

Q1

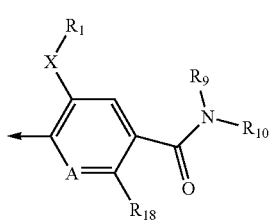

Q2

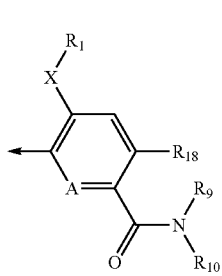

Q3

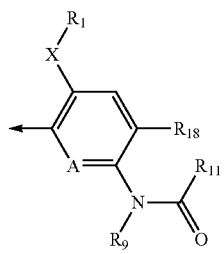

Q4

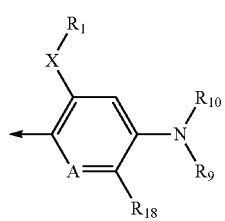

Q5

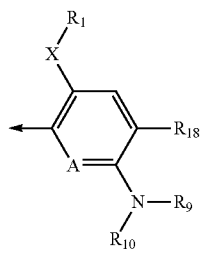

Q6 wherein $R_1$ is $C_1$-$C_4$ alkyl;

X is S, SO or $SO_2$;

$R_{18}$ is hydrogen; and

A is N or CH.

8. A compound of formula I according to claim 2, wherein

A is N or CH;

$R_2$ is $C_1$-$C_4$ haloalkyl;

X is S, SO or $SO_2$;

$R_3$ is selected from the group consisting of $Q_1$ to $Q_6$

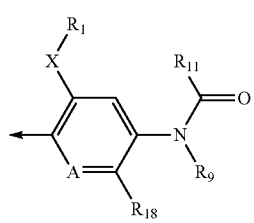

Q1

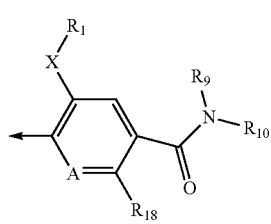

Q2

-continued

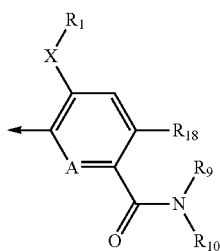

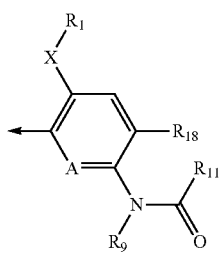

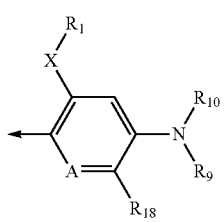

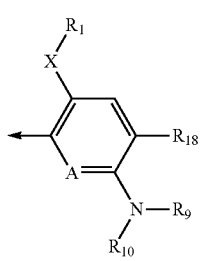

wherein $R_{18}$ is hydrogen;

$R_1$ is $C_1$-$C_4$ alkyl;

$R_4$ is $C_1$-$C_4$ alkyl or $C_3$-$C_6$ cycloalkyl;

$R_5$ is $C_1$-$C_4$ alkyl;

$R_9$ is hydrogen or $C_1$-$C_4$alkyl; or $R_9$ is $C_3$-$C_6$cycloalkyl which can be mono- or polysubstituted by substituents selected from the group consisting of halogen, $C_1$-$C_4$haloalkyl, cyano and $C_1$-$C_4$alkyl;

$R_{10}$ is hydrogen, $C_1$-$C_6$alkyl, cyano, N—($C_1$-$C_4$ alkyl) N—($C_3$-$C_6$cycloalkylcarbonyl)amino, N—$C_3$-$C_6$cycloalkylcarbonylamino or —S(O)$_2$R$_{13}$; or $R_{10}$ is $C_1$-$C_4$alkyl mono- or disubstituted by a group selected from cyano and halogen; or $R_{10}$ is phenyl, pyridinyl or pyrazolyl; said phenyl, pyridinyl or pyrazolyl can be mono to polysubstituted by substituents independently selected from $C_1$-$C_4$haloalkyl and halogen; and $R_{11}$ is $C_1$-$C_4$alkyl, N—$C_1$-$C_4$alkylamino or N,N—($C_1$-$C_4$alkyl)$_2$amino.

9. A compound of formula I according to claim 2, wherein

A is N or CH;

$R_2$ is $C_1$-$C_4$haloalkyl;

X is S, SO or SO$_2$;

$R_3$ is selected from the group consisting of $Q_1$ to $Q_6$ $Q_1$

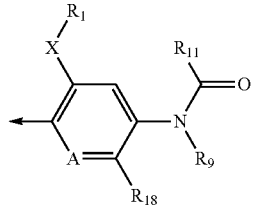

$Q_2$

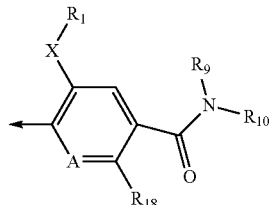

$Q_3$

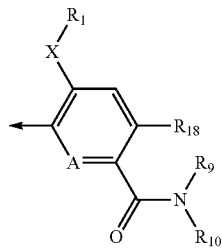

$Q_4$

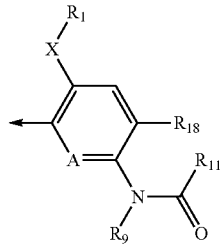

$Q_5$

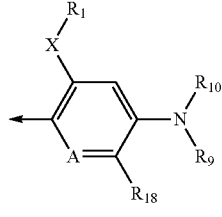

$Q_6$

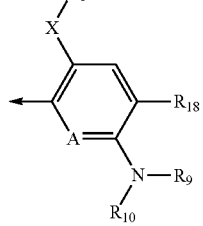

wherein $R_{18}$ is hydrogen;
$R_1$ is $C_1$-$C_4$ alkyl;
$R_4$ is $C_1$-$C_4$ alkyl or $C_3$-$C_6$ cycloalkyl;
$R_5$ is $C_1$-$C_4$ alkyl;
$R_9$ is hydrogen, $C_1$-$C_4$alkyl or $C_3$-$C_6$cycloalkyl;
$R_{10}$ is hydrogen or $C_1$-$C_6$alkyl; and
$R_{11}$ is $C_1$-$C_6$alkyl or $C_3$-$C_6$cycloalkyl, or is $C_1$-$C_6$alkyl or $C_3$-$C_6$cycloalkyl mono- or polysubstituted by substituents selected from the group consisting of halogen, $C_1$-$C_4$haloalkyl, cyano and $C_1$-$C_4$alkyl.

10. A compound of formula I according to claim 2, wherein
Y is O;
$R_2$ is $C_1$-$C_2$ haloalkyl;
$R_4$ is $C_1$-$C_3$ alkyl or cyclopropyl;
$R_5$ is $C_1$-$C_3$ alkyl;
$R_3$ is selected from the group consisting of $Q_1$ to $Q_7$, $Q_9$, $Q_{10}$ and $Q_{11}$

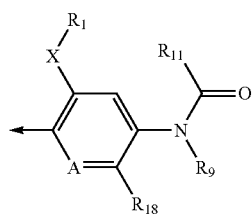
$Q_1$

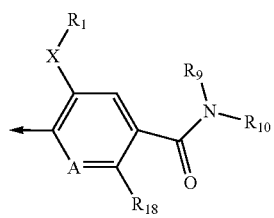
$Q_2$

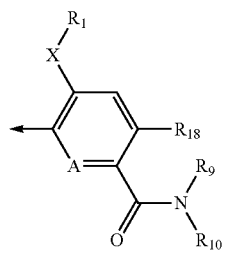
$Q_3$

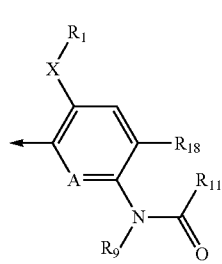
$Q_4$

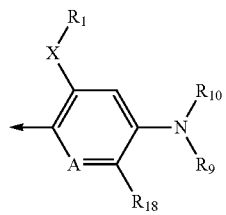
$Q_5$

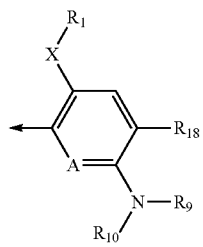
$Q_6$

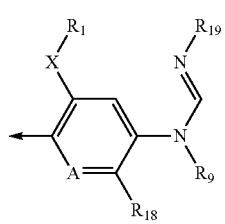
$Q_7$

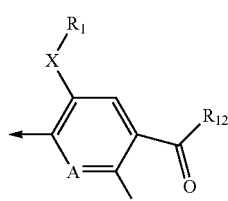
$Q_9$

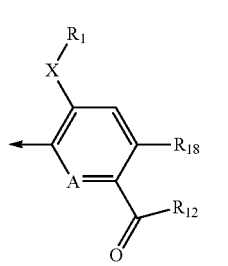
$Q_{10}$

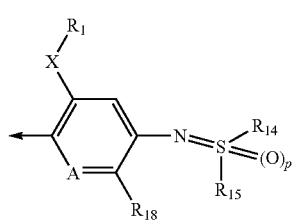
$Q_{11}$

X is S, SO or $SO_2$;
$R_1$ is $C_1$-$C_3$ alkyl;
A is N or CH;
$R_9$ is hydrogen, $C_1$-$C_6$alkyl, $C_1$-$C_6$haloalkyl, hydroxyl or $C_1$-$C_6$alkoxy; or
$R_9$ is cyclopropylcarbonyl, cyclopropyl, cyclopropyl monosubstituted by cyano, or is $S(O)_2C_1$-$C_2$alkyl;
$R_{10}$ is hydrogen, $C_1$-$C_6$alkyl, $S(O)_2C_1$-$C_2$alkyl, $S(O)_2$cyclopropyl, amino, N—($C_1$-$C_2$alkyl)amino or N—($C_1$-$C_2$alkyl)N-(cyclopropylcarbonyl)amino;
$R_{10}$ is $C_1$-$C_4$alkyl monosubstituted by cyano;
$R_{11}$ is $C_1$-$C_6$alkoxy or cyclopropyl which can be substituted by cyano;
$R_{12}$ is hydroxyl and $C_1$-$C_4$ alkyl;
$R_{14}$ is $C_1$-$C_4$ alkyl;
$R_{15}$ is cyclopropyl;
p is 1;

$R_{18}$ is hydrogen, $C_1$-$C_3$ alkyl, halogen, cyclopropyl or cyano and $R_{19}$ is $C_1$-$C_4$alkoxy.

11. A pesticidal composition, which comprises at least one compound of formula I according to claim 1 or a tautomer thereof, in each case in free form or in agrochemically utilizable salt form, as active ingredient and at least one auxiliary.

12. A method for controlling pests, which comprises applying a composition according to claim 11 to the pests or their environment with the exception of a method for treatment of the human or animal body by surgery or therapy and diagnostic methods practised on the human or animal body.

13. A method for the protection of plant propagation material from the attack by pests, which comprises treating the propagation material or a site, where the propagation material is planted, with a composition according to claim 11.

14. A plant propagation material treated with at least one compound of formula I according to claim 1.

* * * * *